US008889638B2

(12) United States Patent (10) Patent No.: US 8,889,638 B2
Cohen et al. (45) Date of Patent: Nov. 18, 2014

(54) STIMULUS-TRIGGERED PRODRUGS

(75) Inventors: Seth M. Cohen, San Marcos, CA (US);
Jody L. Major Jourden, Atlanta, GA
(US)

(73) Assignee: The Regents of the University of California, Oakland, CA (US)

( * ) Notice: Subject to any disclaimer, the term of this patent is extended or adjusted under 35 U.S.C. 154(b) by 72 days.

(21) Appl. No.: 13/166,796

(22) Filed: Jun. 22, 2011

(65) Prior Publication Data

US 2011/0312905 A1 Dec. 22, 2011

Related U.S. Application Data

(60) Provisional application No. 61/357,477, filed on Jun. 22, 2010.

(51) Int. Cl.
*A61K 31/395* (2006.01)
*A61K 31/435* (2006.01)

(52) U.S. Cl.
USPC .......................................................... 514/27

(58) Field of Classification Search
USPC ..................................... 514/27; 536/4.1, 17.4
See application file for complete search history.

(56) References Cited

U.S. PATENT DOCUMENTS

2005/0267102 A1  12/2005  VanZandt et al.

FOREIGN PATENT DOCUMENTS

EP          0126974 A1   12/1984
WO     2006/028523 A2    3/2006

OTHER PUBLICATIONS

Agrawal et al, J. Med. Chem. 2009, 52, 1063-74.*
Howard et al, Bioorganic and Medicinal Chemistry Letters 2001, 11, 59-62.*
Agrawal, Arpita et al., "Zinc-Binding Groups Modulate Selective Inhibition of MMPS", ChemMedChem 3:812-820, 2008.
Al-Muhammed, J. et al., "In-vivo studies on dexamethasone sodium phosphate liposomes", J. Microencapsulation 13(3):293-306, 1996.
Bagshawe, K.D. et al., "First clinical experience with ADEPT", Advanced Drug Delivery Reviews 22:365-367, 1996.
Bagshawe, K. D., "Targeting: The ADEPT Story So Far", Current Drug Targets 10:152-157, 2009.
Blencowe, Christopher A. et al., "Self-immolative linkers in polymeric delivery systems", Polymer Chemistry 2:773-790, 2011.
Bowers, Albert et al., "Total Synthesis and Biological Mode of Action of Largazole: A Potent Class I Histone Deacetylase Inhibitor", Journal of the American Chemical Society 130:11219-11222, 2008.
Chang, Michelle C. Y. et al., "A Selective, Cell-Permeable Optical Probe for Hydrogen Peroxide in Living Cells", Journal of the American Chemical Society 126:15392-15393, 2004.
Charkoudian, Louise K. et al., "A Pro-Chelator Triggered by Hydrogen Peroxide Inhibits Iron-Promoted Hydroxyl Radical Formation", Journal of the American Chemical Society 128:12424-12425, 2006.
Chonn, Arcadio et al., "Recent advances in liposomal drug-delivery systems", Current Opinion in Biotechnology 6:698-708, 1995.
Daniel, Kevin B. et al., "Activation of sulfonate ester based matrix metalloproteinase proinhibitors by hydrogen peroxide", Journal of Biological Inorganic Chemistry 16:313-323, 2011.
De Simone, Giuseppina et al., "Carbonic Anhydrase Inhibitors: Hypoxia-Activatable Sulfonamides Incorporating Disulfide Bonds that Target the Tumor-Associated Isoform IX", Journal of Medicinal Chemistry 49:5544-5551, 2006.
Denny, William A. et al., "Tumor-activated Produgs—A New Approach to Cancer Therapy", Cancer Investigation 22:604-619, 2004.
Dickens, Marina G. et al., "A Prochelator Activated by Hydrogen Peroxide Prevents Metal-Induced Amyloid β Aggregation", ChemBioChem 11:59-62, 2010.
Failes, Timothy W. et al., "Towards bioreductively activated prodrugs: Fe(III) complexes of hydroxamic acids and the MMP inhibitor marimastat", Journal of Inorganic Biochemistry 101:396-403, 2007.
Failes, Timothy W. et al., "Studies of Cobalt (III) Complex of the MMP Inhibitor Marimastat: A Potential Hypoxia-Activated Prodrug", Chemistry A European Journal 13:2974-2982, 2007.
Fernandez, Caridad et al., "Synthesis and biological studies of glycosyl dopamine derivatives as potential antiparkinsonian agents", Carbohydrate Research 327:353-365, 2000.
Fishman, Robert A.,"Brain Edema", The New England Journal of Medicine 293:706-711, 1975.
Fry, Fiona H. et al., "Sensor/ Effector Drug Design with Potential Relevance to Cancer", Current Pharmaceutical Design 12:4479-4499, 2006.
Furumai, Ryohei et al., "FK228 (Depsipeptide) as a Natural Prodrug That Inhibits Class I Histone Deacetylases", Cancer Research 62:4916-4921, 2002.
Gao, Zhi-Hui et al., "Controlled Release of Contraceptive Steroid from Biodegradable and Injectable Gel Formulations: In Vitro Evaluation", Pharmaceutical Research 12(6):857-863, 1995.
Gillies, Robert J. et al., "Causes and Consequences of Increased Glucose Metabolism of Cancers", Journal of Nuclear Medicine 49:24S-42S, 2008.
Haba, Keren et al., "Single-Triggered Trimeric Prodrugs", Angewandte Chemie 44:716-720, 2005.
Haorah, James et al., "Oxidative stress activates protein tyrosine kinase and matrix metalloproteinases leading to blood-brain barrier dysfunction", Journal of Neurochemistry 101:566-576, 2007.
Houston, Todd A. et al., "Painting the Target Around the Arrow: Two-Step Prodrug Therapies from Carbohydrate Chemist's Perspective", Current Drug Delivery 4:264-268, 2007.
Jacobsen, Jennifer A. et al., "To bind zinc or not to bind zinc: An examination of innovative approaches to improved metalloproteinase inhibition", Biochimica et Biophysica Acta 1803:72-94, 2010.

(Continued)

*Primary Examiner* — Ganapathy Krishnan
(74) *Attorney, Agent, or Firm* — Kilpatrick Townsend & Stockton LLP

(57) ABSTRACT

Set forth herein, inter alia, are compositions and methods for treating diseases with prodrugs. Provided herein are prodrug compositions for inhibiting the function of proteins, compositions and methods for treating diseases associated with oxidative compounds, oxidatively-sensitive prodrugs of inhibitors of metalloproteases. and methods of inhibiting metalloproteases using oxidatively-sensitive prodrugs.

7 Claims, 54 Drawing Sheets

(56) References Cited

OTHER PUBLICATIONS

Knight, C. Graham et al., "A novel coumarin-labelled peptide for sensitive continuous assays of the matric metalloproteinases", Federation of European Biochemical Societies 296(3):263-266, 1992.
Kratz, Felix et al., "Prodrug Strategies in Anticancer Chemotherapy", ChemMedChem 3:20-53, 2008.
Kuivila, Henry et al.,"Reaction of Hydrogen Peroxide and Benzeneboronic Acid", Organic and Biological Chemistry 79:5659-5662, 1957.
Lee, Ho Yong et al., "Kinetics of Self-Immolation: Faster Signal Relay over a Longer Linear Distance?" Organic Letters 11(10):2065-2068, 2009.
Lin, Yih-Shyan et al., "Targeting the Delivery of Glycan-Based Paclitaxel Prodrugs to Cancer Cells via Glucose Transporters", Journal of Medicinal Chemistry 51:7428-7441, 2008.
Liu, Kui et al., "Successful ovulation in plasminogen-deficient mice treated with the broad-spectrum matrix metalloproteinase inhibitor galardin", Developmental Biology 295:615-622, 2006.
Lo, Lee-Chiang et al., "Development of highly selective and sensitive probes for hydrogen peroxide", ChemComm Communication 2728-2729, 2003.
Maeda, Hatsuo et al., "Flourescent Probes for Hydrogen Peroxide Based on a Non-Oxidative Mechanism", Angewandte Chemie International Edition 43:2389-2391, 2004.
Maeda, Hatsuo et al., "A Design of Flourescent Probes for Superoxide Based on a Nonredox Mechanism", Journal of the American Chemical Society 127:68-69, 2005.
Major Jourden, Jody L. et al.,"Hydrogen Peroxide Activated Matrix Metalloproteinase Inhibitors: A Prodrug Approach", Angewandte Chemie International Edition 49:6795-6797, 2010.
Major Jourden, Jody L. et al.,"Enzymatic activation of a matrix metalloproteinase inhibitor", ChemComm Communication 46:1241-1243, 2010.
Meyer, Yves et al., "A comparative study of the self-immolation of para-aminobenzylalcohol and hemithioaminal-based linkers in the context of protease-sensitive fluorogenic probes", Organic & Biomolecular Chemistry 8:1777-1780, 2010.
Miller, Evan W. et al.,"Boronate-Based Flourescent Probes for Imagin Cellular Hydrogen Peroxide", Journal of the American Chemical Society 127:16652-16659, 2005.
Miller, Evan W. et al., "Molecular imaging of hydrogen peroxide produced for cell signaling", Nature Chemical Biology 3(5):263-267, 2007.
Mitchell, Mark B. et al., "The synthesis of the glucuronide adduct of Trocade™", Tetrahedron Letters 41:8829-8834, 2000.
Niculescu-Duvaz, I. et al., "Development of prodrugs for ADEPT (antibody-directed enzyme prodrug therapy)", Expert Opinion on Investigational Drugs 3(3):289-308, 1996.
Østergaard, Jesper et al., "Bioreversible Derivatives of Phenol. 2. Reactivity of Carbonate Esters with Fatty Acid-like Structures Towards Hydrolysis in Aqueous Solutions", Molecules 12:2396-2412, 2007.
Ostro, Marc J. et al., "Use of liposomes as injectable-drug delivery systems", American Journal of Hospital Pharmacy 46:1576-1587, 1989.
Perez, Lissette R. et al., "Minding metals: Tailoring multifunctional chelating agents for neurodegenerative disease", Dalton Transactions 39:2177-2187, 2010.
Rao, K. Panduranga, "Recent developments of collagen-based materials for medical applications and drug delivery systems", Journal of Biomaterials Science, Polymer Edition 7(7):623-645, 1995.
Rautio, Jarkko et al., "Prodrugs: design and clinical applications", Nature Reviews Drug Discovery 7:255-270, 2008.
Reid, Tony et al., "Phase II trial of the histone deacetylase inhibitor pivaloyloxymethyl butyrate (Pivanex, AN-9) in advanced non-small cell lung cancer", Lung Cancer 45:381-386, 2004.
Rephaeli, Ada et al., "Prodrugs of Btyric Acide From Bench to Beside: Synthetic Design, Mechanisms of Action, and Clinical Applications", Drug Development Research 50:379-391, 2000.
Schugar, Harvey et al., "Combating Alzheimer's Disease With Multifunctional Molecules Designed for Metal Passivation", Angewandte Chemie International Edition 46:1716-1718, 2007.
Scott, Lauren E. et al., "Altering pyridinone N-substituents to optimize activity as potential prodrugs for Alzheimer's disease", The Royal Society of Chemistry, Dalton Transactions 6364-6367, 2008.
Sella, Eran et al., "Self-immolative dendritic probe for direct detection of tracetone tiperoxide", The Royal Society of Chemistry, ChemComm 5701-5703, 2008.
Simplício, Ana L. et al., "Prodrugs for Amines", Molecules 13:519-547, 2008.
Srikun, Duangkhae et al., "An ICT-Based Approach to Ratiometric Fluorescence Imaging of Hydrogen Peroxide Produced in Living Cells", Journal of the American Chemical Society 130:4596-4597, 2008.
Storr, Tim et al., "Synthesis, Characterization, and Metal Coordinating Ability of Multifunctional Carbohydrate-Containing Compounds for Alzheimer's Therapy", Journal of the American Chemical Society 129:7453-7463, 2007.
Suzuki, Takayoshi et al., "Design, synthesis, and biological activity of folate receptor-targeted prodrugs of thiolate histone deacetylase inhibitors", Bioorganic & Medicinal Chemistry Letters 17:4208-4212, 2007.
Tarasenko, Nataly et al., "Histone deacetylase inhibitors: the anticancer, antimetastatic and antiangiogenic activities of AN-7 are superior to those of the clinically tested AN-9 (Pivanex)", Clinical and Experimental Mestatsis 25:703-716, 2008.
Thomas, Mickaël et al., "Synthesis and biological evaluation of the suberoylanilide hydroxamic acid (SAHA) β-glucuronide and β-galactoside for application in selective prodrug chemotherapy," Biorganic & Medicinal Chemistry Letters 17:983-986, 2007.
Thomas, Mickaël et al., "Synthesis and biological evaluation of glucuronide prodrugs of the histone deacetylase inhibitor CI-994 for application in selective cancer chemotherapy", Bioorganic & Medicinal Chemistry 16:8109-8116, 2008.
Tian, Yu Shun et al., "A Two-Photon Tracer for Glucose Uptake", Angewandte Chemie International Edition 48:8027-8031, 2009.
Tietze, Lutz F. et al., "Highly Selective Compounds for the Antibody-Directed Enzyme Prodrug Therapy of Cancer", Australian Journal of Chemistry 56:841-854, 2003.
Tietze, Lutz F. et al., "Synthesis and Biological Studies of Different Duocarmycin Based Glycosidic Prodrugs for Their Use in the Antibody-Directed Enzyme Prodrug Therapy", 52:537-543, 2009.
Van De Bittner, Genevieve et al., "In vivo imaging of hydrogen peroxide production in a murine tumor model with a chemoselective bioluminescent reporter", Proceedings of the National Academy of Sciences of the United States of America 107(50): 21316-21321, 2010.
Wang, Shusheng et al., "Study on glycosylated prodrugs of toxoflavins for antibody-directed enzyme tumor therapy", Carbohydrate Research 342:1254-1260, 2007.
Wei, Yibin et al., "A novel profluorescent probe for detecting oxidative stress induced by metal and $H_2O_2$ in living cells", ChemComm 46:4472-4474, 2010.
Weinstain, Roy et al., "Activity-Linked Labeling of Enzymes by Self-Immolative Polymers", Bioconjugate Chemistry 20:1783-1791, 2009.
Yang, Yi et al., "Matrix metalloproteinase-mediated disruption of tight junction proteins in cerebral vessels is reversed by synthetic matrix metalloproteinase inhibitor in focal ischemia in rat", Journal of Cerebral Blood Flow & Metabolism 27:697-709, 2007.

* cited by examiner

*Ether Linkage Strategy*

*Ester Linkage Strategy*

*Direct Linkage Strategy*

*Leaving Groups* | *Boronic Ester Protected Compounds*

X = OH, SH or NH₂

4: X=S
5: X=NH

B1

| Compound | $k$ (M$^{-1}$s$^{-1}$) | Compound | $k$ (M$^{-1}$s$^{-1}$) |
|---|---|---|---|
| B1 | 1.12 ± 0.04 | B11 | 5.9 ± 0.2 |
| B2 | 2.7 ± 0.1 | B12 | 3.5 ± 0.3 |
| B3 | 0.031 ± 0.002 | B13 | 2.9 ± 0.1 |
| B10 | 3.1 ± 0.5 | B14 | 4.1 ± 0.2 |

FIGURE 22

| Proinhibitor | IC$_{50}$ | Inhibitor | IC$_{50}$ | Enzyme |
|---|---|---|---|---|
| B17 | >1 mM[a] | 1,2-HOPO-2 | 6.1 µM (± 0.2) | MMP-9 |
| B17 | 17.8 µM (± 1.1) | 1,2-HOPO-2 | 0.053 µM (± 0.01) | MMP-12 |
| B18 | >1 mM[b] | PY-2 | 9.8 µM (± 0.7) | MMP-9 |
| B18 | 12.9 µM (±0.03) | PY-2 | 0.035 µM (± 0.003) | MMP-12 |

FIGURE 45

STIMULUS-TRIGGERED PRODRUGS

STATEMENT AS TO RIGHTS TO INVENTIONS MADE UNDER FEDERALLY SPONSORED RESEARCH AND DEVELOPMENT

This invention was made with government support under grant R01 HL00049-01 awarded by the National Institute of Health. The Government has certain rights in the invention.

CROSS-REFERENCES TO RELATED APPLICATIONS

This application claims the benefit of U.S. Provisional Patent Application 61/357,477, filed Jun. 22, 2010, which is hereby incorporated by reference in its entirety for all purposes.

BACKGROUND OF THE INVENTION

Many therapeutics used to treat diseases, for example cancer, infectious diseases, inflammatory diseases, exhibit toxicity or confer undesirable side effects at doses that limit the amount of the therapeutic that can be safely administered and therefore limit the benefit provided by such therapeutics. It would be preferable if such drugs could be administered in a prodrug form that masked the inherent toxicity of the compounds from healthy tissues, and yet released the fully active drug species at the desired site of action. Such a technology would have the potential to increase the therapeutic window of a variety of drugs, possibly allowing them to be used safely at a more efficacious dose, and with reduced incidence of undesired side-effects for the patient. The use of prodrugs to confer improved properties such as increased bioavailability or aqueous solubility is a well established concept in the art of pharmaceutical research.

Matrix metalloproteinases (MMPs) are a ubiquitous class of zinc(II)-dependent hydrolytic enzymes that have been associated with a wide range of pathologies including cancer, arthritis, heart disease, and stroke.[1-3] Clinical trials of matrix metalloproteinase inhibitors (MMPi) have frequently been hampered by the onset of musculoskeletal syndrome (MSS), which manifests as severe joint pain, and has been attributed to non-specific, systemic inhibition of MMPs and other metalloenzymes.[4,5]

Provided herein are compositions and methods that address these and other problems in the art.

BRIEF SUMMARY OF THE INVENTION

In a first aspect, a method of treating a disease in a patient in need of such treatment is provided. The method includes administering a therapeutically effective amount of an oxidatively-sensitive prodrug to the patient. In an embodiment, the oxidatively-sensitive prodrug includes a drug moiety covalently linked to an oxidatively-sensitive prodrug moiety. In one embodiment, the drug moiety includes a moiety known to be useful for treating the disease for which the prodrug is administered (e.g. the drug moiety is capable of forming a drug known to be useful for treating the disease for which the prodrug is administered).

In a second aspect, a method of inhibiting the activity of a metalloprotein is provided. In one embodiment, the method includes contacting the metalloprotein with a metal binding moiety formed from the reaction of an oxidatively-sensitive prodrug and a reactive oxygen species.

In a third aspect, a compound is provided having the formula:

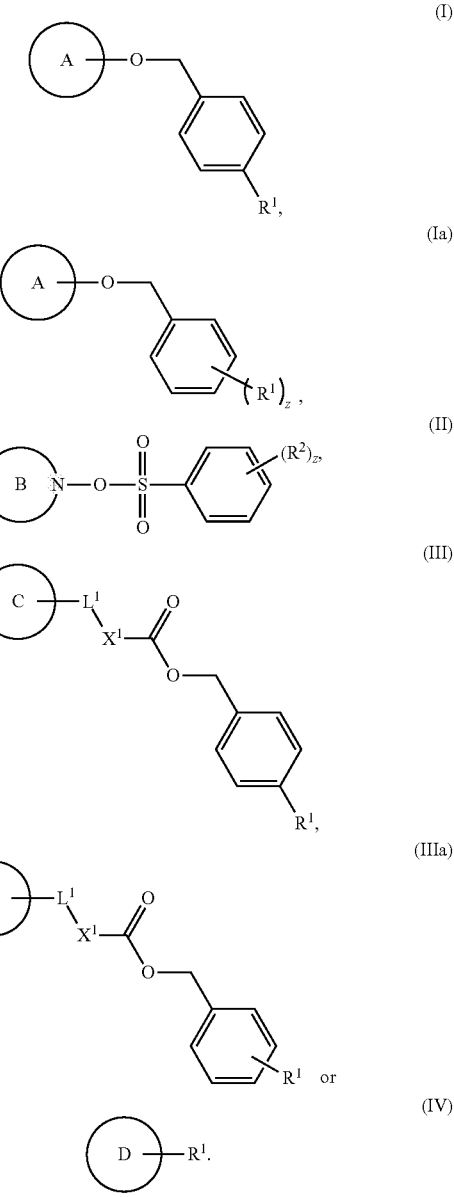

Within formula (I), (Ia), (II), (III), (IIIa) and (IV), A, B, C, and D are independently a drug moiety. $L^1$ is a bond or unsubstituted alkylene. $X^1$ is —NH— or —O—. $R^1$ is independently —B(OH)$_2$, an ROS-reactive boronic ester, hydrogen, halogen, —CN, —SR$^{13B}$, —SO$_2$Cl, —SO$_3$H, —SO$_4$H, —SO$_2$NR$^{7B}$R$^{8B}$, —NHNH$_2$, —ONR$^{7B}$R$^{8B}$, —NHC=(O) NHNH$_2$, —NHC=(O)NR$^{7B}$R$^{8B}$, —N(O)$_m$, —NR$^{7B}$R$^{8B}$, —C(O)R$^{9B}$, —C(O)—OR$^{10B}$, —C(O)NR$^{11B}$R$^{12B}$, —OR$^{13B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl, or peptidomimetic moiety.

$R^{7B}$, $R^{8B}$, $R^{9B}$, $R^{10B}$, $R^{11B}$, $R^{12B}$, and $R^{13B}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl or peptidomimetic moiety.

R$^2$ is independently hydrogen, halogen, —CN, —SR$^{13B}$, —SO$_2$Cl, —SO$_3$H, —SO$_4$H, —SO$_2$NR$^{7B}$R$^{8B}$, —NHNH$_2$, —ONR$^{7B}$R$^{8B}$, —NHC=(O)NHNH$_2$, —NHC=(O)NR$^{7B}$R$^{8B}$, —N(O)$_m$, —NR$^{7B}$R$^{8B}$, —C(O)R$^{9B}$, —C(O)—OR$^{10B}$, C(O)NR$^{11B}$R$^{12B}$, —OR$^{13B}$, substituted or unsubstituted alkyl (e.g. methyl), substituted or unsubstituted heteroalkyl, substituted or unsubstituted cycloalkyl, substituted or unsubstituted heterocycloalkyl, substituted or unsubstituted aryl, substituted or unsubstituted heteroaryl, an electron withdrawing group, peptidyl, or peptidomimetic moiety. The symbol z is an integer from 0 to 5. The symbol m is an integer from 1 to 2.

In another aspect, is a compound having the formula

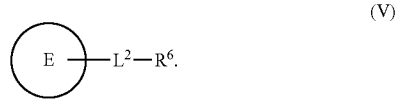

(V)

E is a drug moiety. L$^2$ is independently a bond, —O—, —S—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^6$ is a substituted or unsubstituted carbohydrate moiety.

BRIEF DESCRIPTION OF THE DRAWINGS

FIG. 22. Table 2. Pseudo first-order rate constants calculated with an excess of $H_2O_2$.

FIG. 37. Top. Absorption spectra of B11 (0.05 mM in HEPES buffer (50 mM, pH 7.5)) in the presence of $H_2O_2$ (18 eq) monitored every two minutes for 30 min. The dashed line is the initial spectra and the bold solid line is the final spectra. An authentic sample of 1,2-HOPO (0.05 mM in HEPES buffer (50 mM, pH 7.5)) is shown as a dotted line. Bottom. HPLC traces of compounds 1,2-HOPO, B11 and B11 after reaction with $H_2O_2$ (1.8 eq) for 30 min. Retention times are 4.9 min for 1,2-HOPO and 10.8 min for B11.

Figure 38:
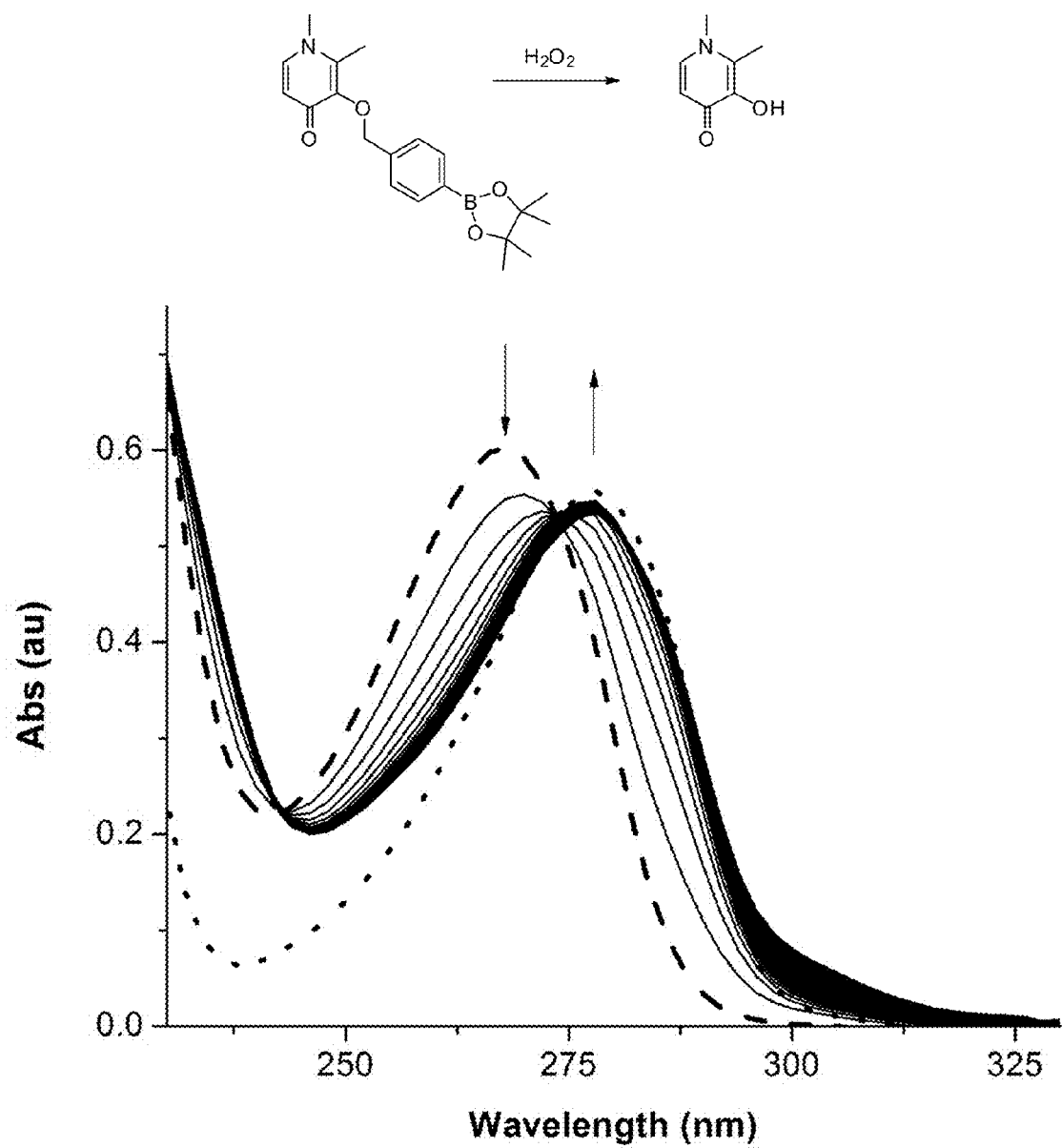

FIG. 38. Absorption spectra of B12 (0.05 mM in HEPES buffer (50 mM, pH 7.5)) in the presence of $H_2O_2$ (18 eq) monitored every two minutes for 1 hr. The dashed line is the initial spectra and the bold solid line is the final spectra. An authentic sample of 3,4-HOPO (0.05 mM in HEPES buffer (50 mM, pH 7.5)) is shown as a dotted line; the arrows indicate the change in absorption over time.

Figure 39:
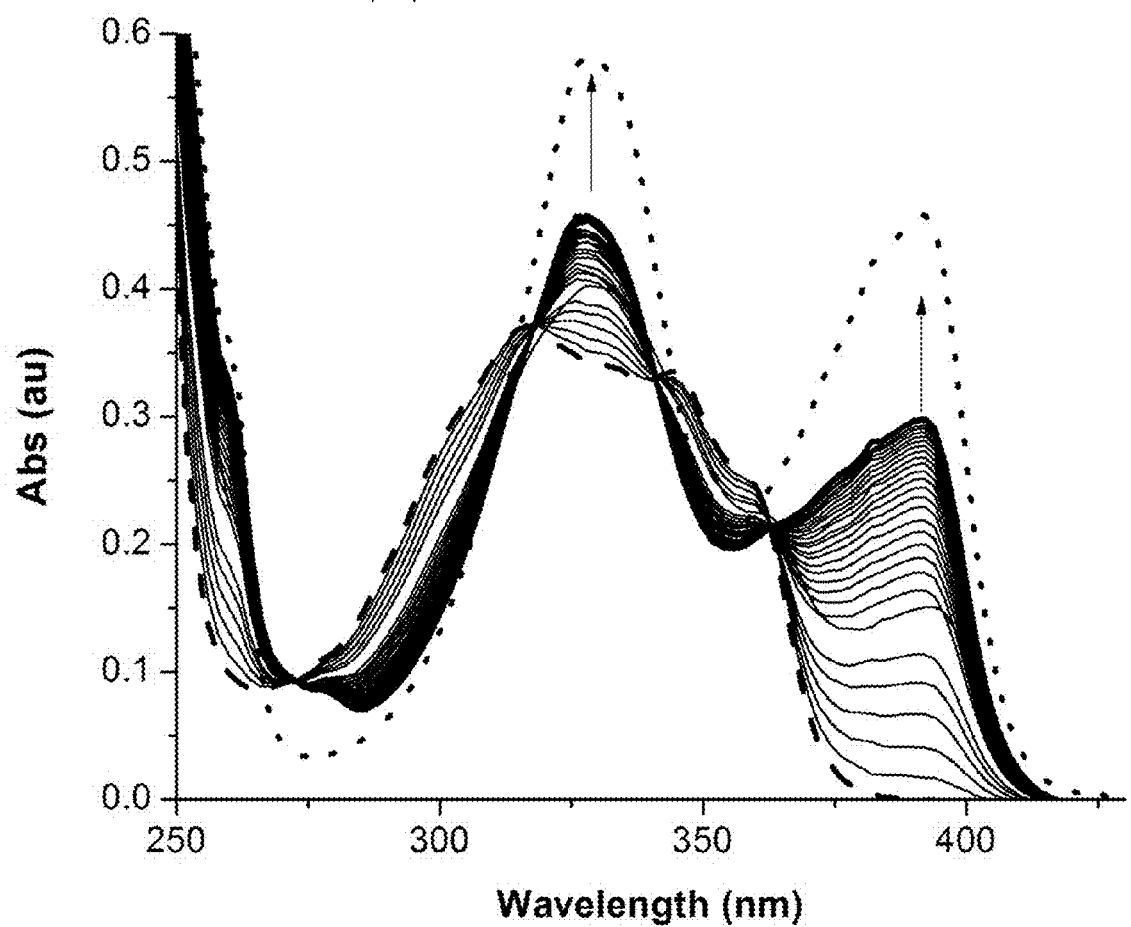

FIG. 39. Absorption spectra of B13 (0.05 mM in HEPES buffer (50 mM, pH 7.5)) in the presence of $H_2O_2$ (5 eq) monitored every two minutes for 1 hr. The dashed line is the initial spectra and the bold solid line is the final spectra. An authentic sample of tropolone (0.05 mM in HEPES buffer (50 mM, pH 7.5)) is shown as a dotted line; the arrow indicates the change in absorption over time.

Figure 40:
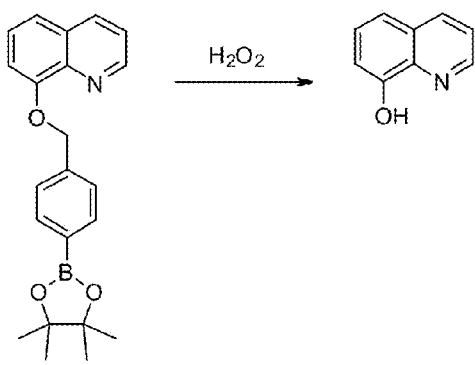
Figure 40:
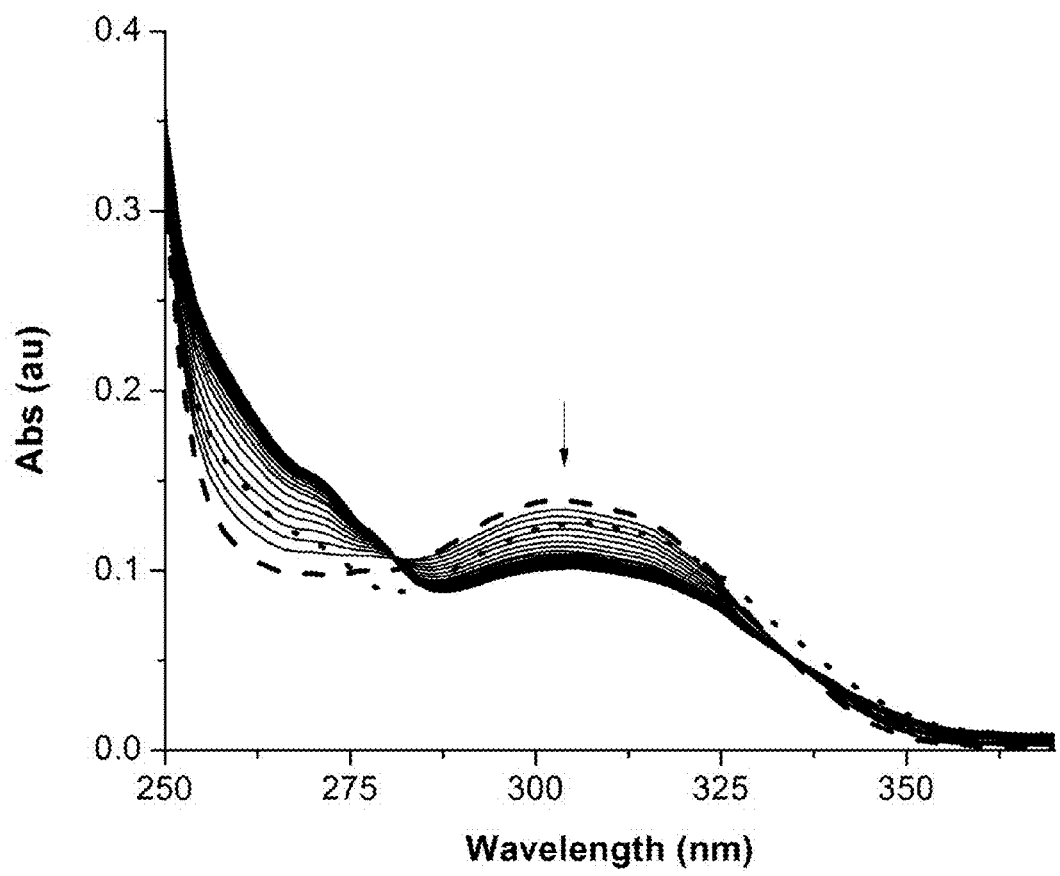

FIG. 40. Absorption spectra of B14 (0.05 mM in HEPES buffer (50 mM, pH 7.5)) in the presence of $H_2O_2$ (18 eq) monitored every two minutes for 1 hr. The dashed line is the initial spectra and the bold solid line is the final spectra. An authentic sample of 8-hydroxy quinoline (0.05 mM in HEPES buffer (50 mM, pH 7.5)) is shown as a dotted line; the arrow indicates the change in absorption over time.

Figure 41:
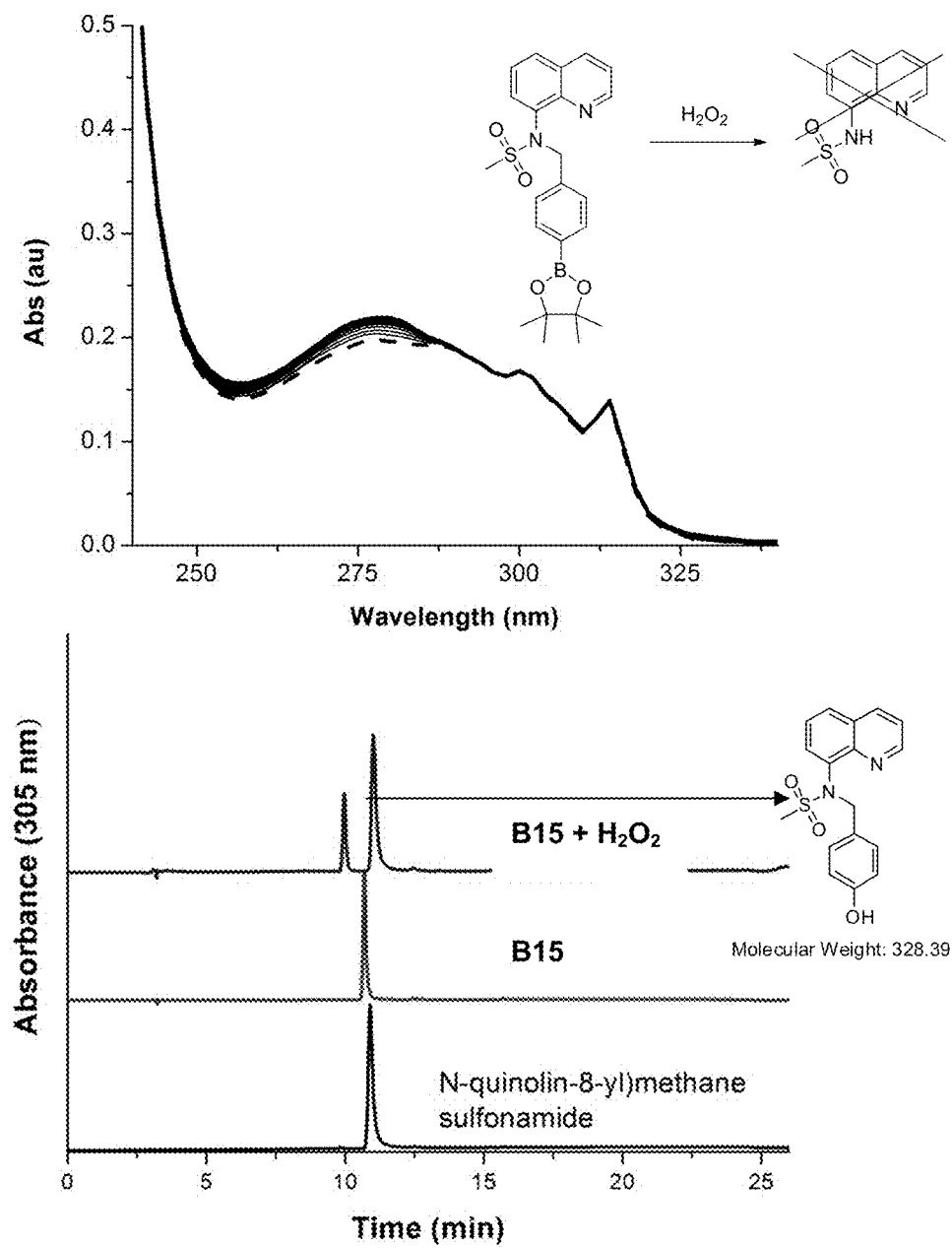

FIG. 41. Top. Absorption spectra of B15 (0.05 mM in HEPES buffer (50 mM, pH 7.5)) in the presence of $H_2O_2$ (18 eq) monitored every two minutes for 1 hr. The dashed line is the initial spectra and the bold solid line is the final spectra. The minimal change in spectra over time indicates that there is no formation of the MBG in the presence of $H_2O_2$. Bottom. HPLC traces of compounds N-(quinolin-8-yl)methanesulfonamide, B15 and B15 after reaction with $H_2O_2$ (18 eq) for 30 min. Retention times are 10.9 min for N-(quinolin-8-yl)methanesulfonamide, 10.7 min for B15, and 9.9 min and 11.0 min for B15 with $H_2O_2$. LC-MS(+) shows an m/z peak of 329.1 at 9.9 min indicative of cleavage of the boronic ester to the phenolic moiety.

Figure 42:
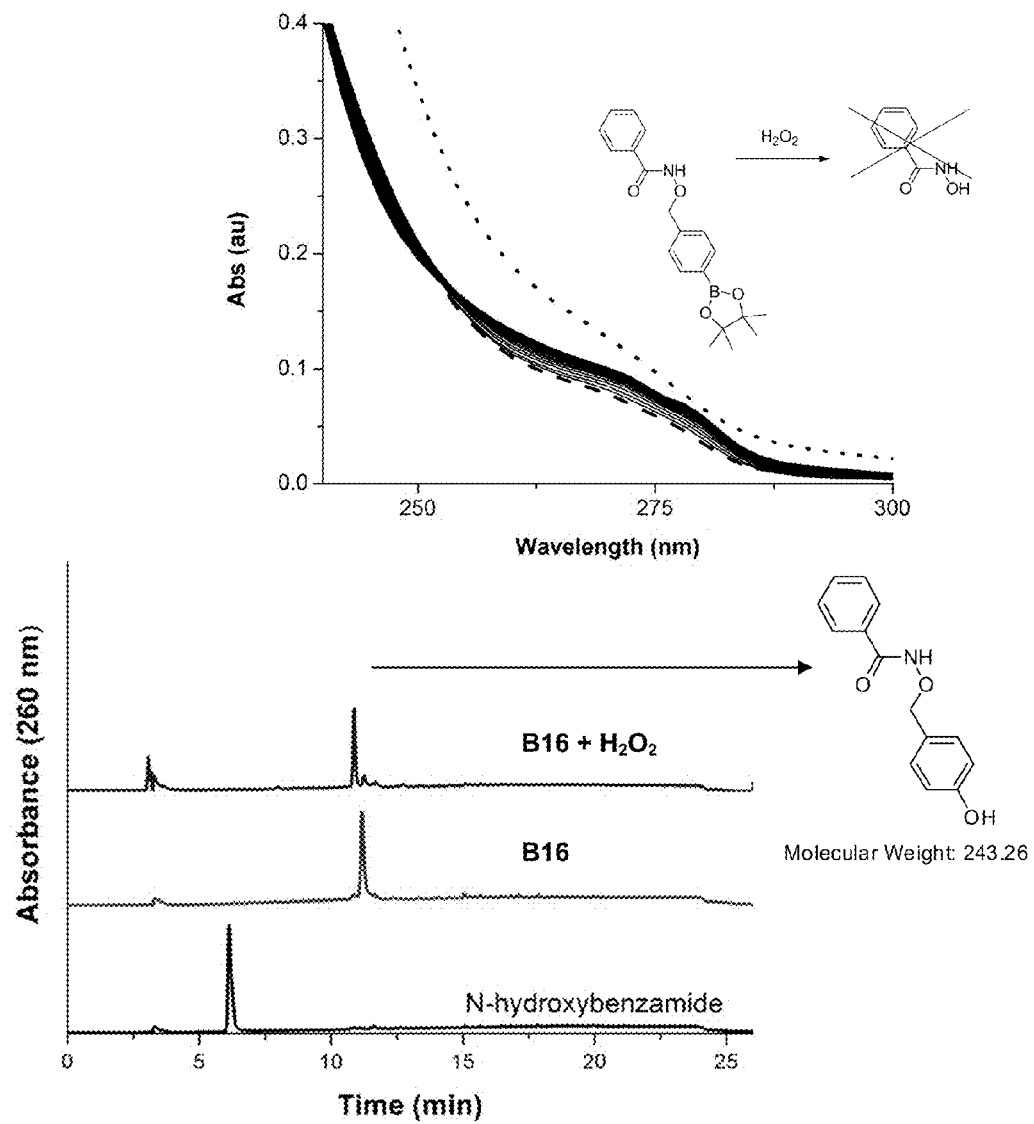

FIG. 42. Top. Absorption spectra of B16 (0.05 mM in HEPES buffer (50 mM, pH 7.5)) in the presence of $H_2O_2$ (18 eq) monitored every two minutes for 1 hr. The dashed line is the initial spectra and the bold solid line is the final spectra. An authentic sample of N-hydroxybenzamide (0.05 mM in HEPES buffer (50 mM, pH 7.5)) is shown as a dotted line. The minimal change in spectra over time indicates that there is no formation of the MBG in the presence of $H_2O_2$. Bottom. HPLC traces of compounds N-hydroxybenzamide, B16 and B16 after reaction with $H_2O_2$ (18 eq) for 2.5 h. Retention times are 6.1 min for N-hydroxybenzamide, 11.2 min for B16, and 10.9 min for B16 with $H_2O_2$. LC-MS(+) shows an m/z peak of 266.1 ([M+Na]$^+$) at 10.9 min indicative of cleavage of the boronic ester to the phenolic moiety.

Figure 43:
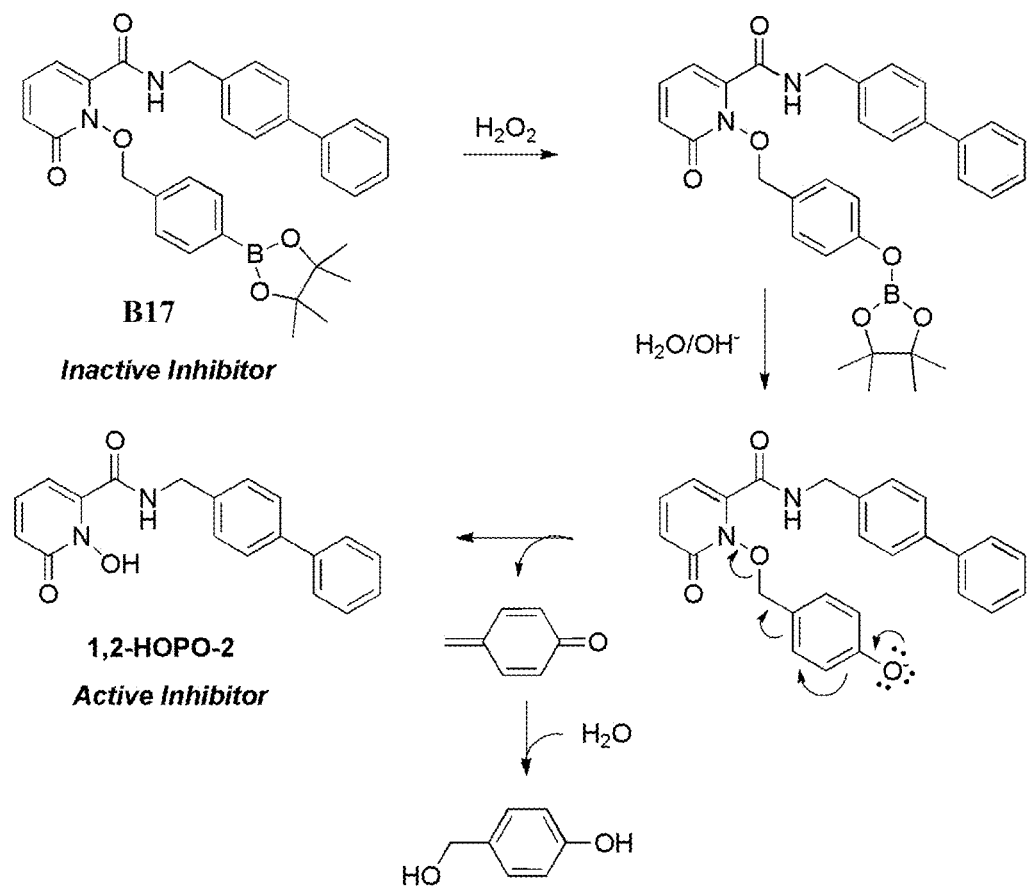

FIG. 43. Release of the active inhibitor 1,2-HOPO-2 in the presence of $H_2O_2$ through a self-immolative linker strategy.

Figure 44:
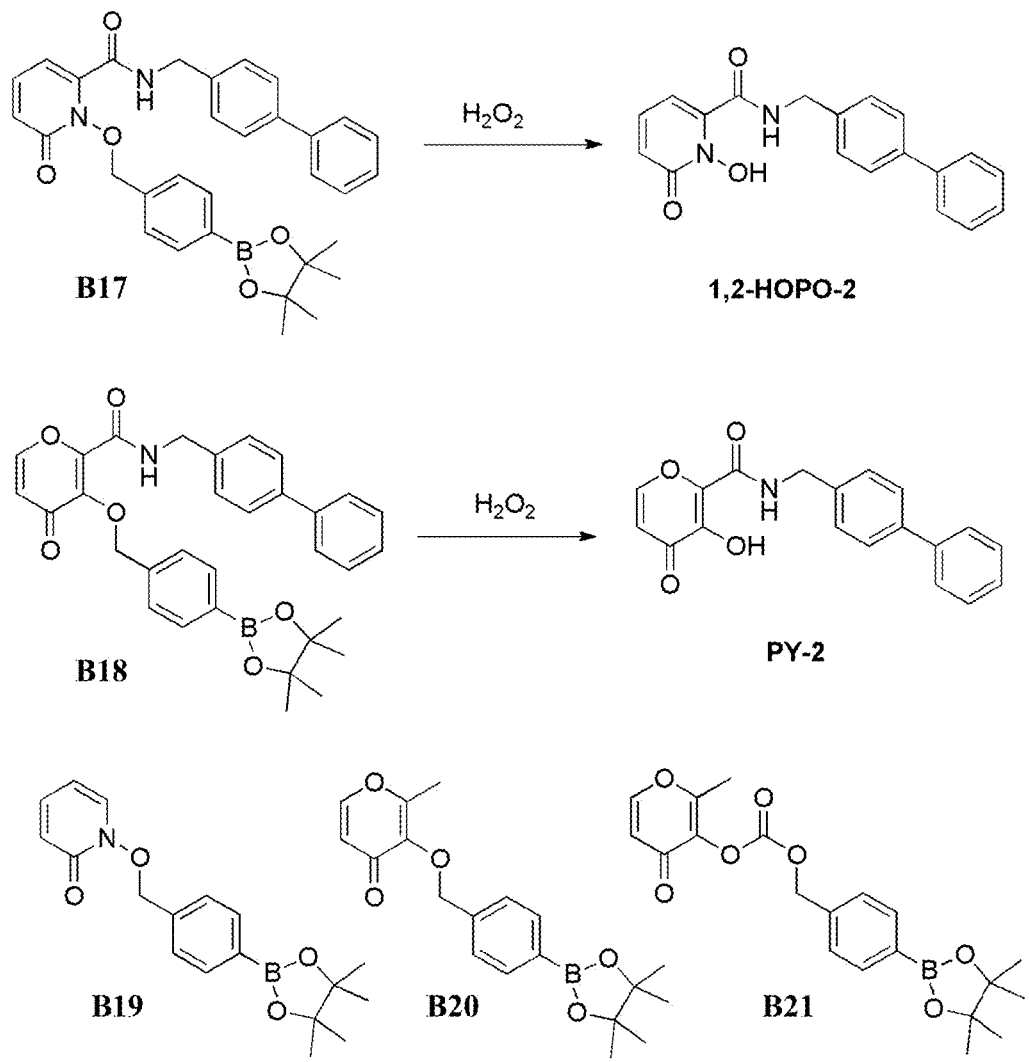

FIG. 44. Structures of proinhibitors B17 and B18 and their active inhibitors 1,2-HOPO-2 and PY-2, respectively, and the protected B19-B21.

FIG. 45. $IC_{50}$ values of proinhibitors and inhibitors against MMP-9 and MMP-12 as measured using a fluorescence based assay. Data are the average of two experiments.

Figure 46:
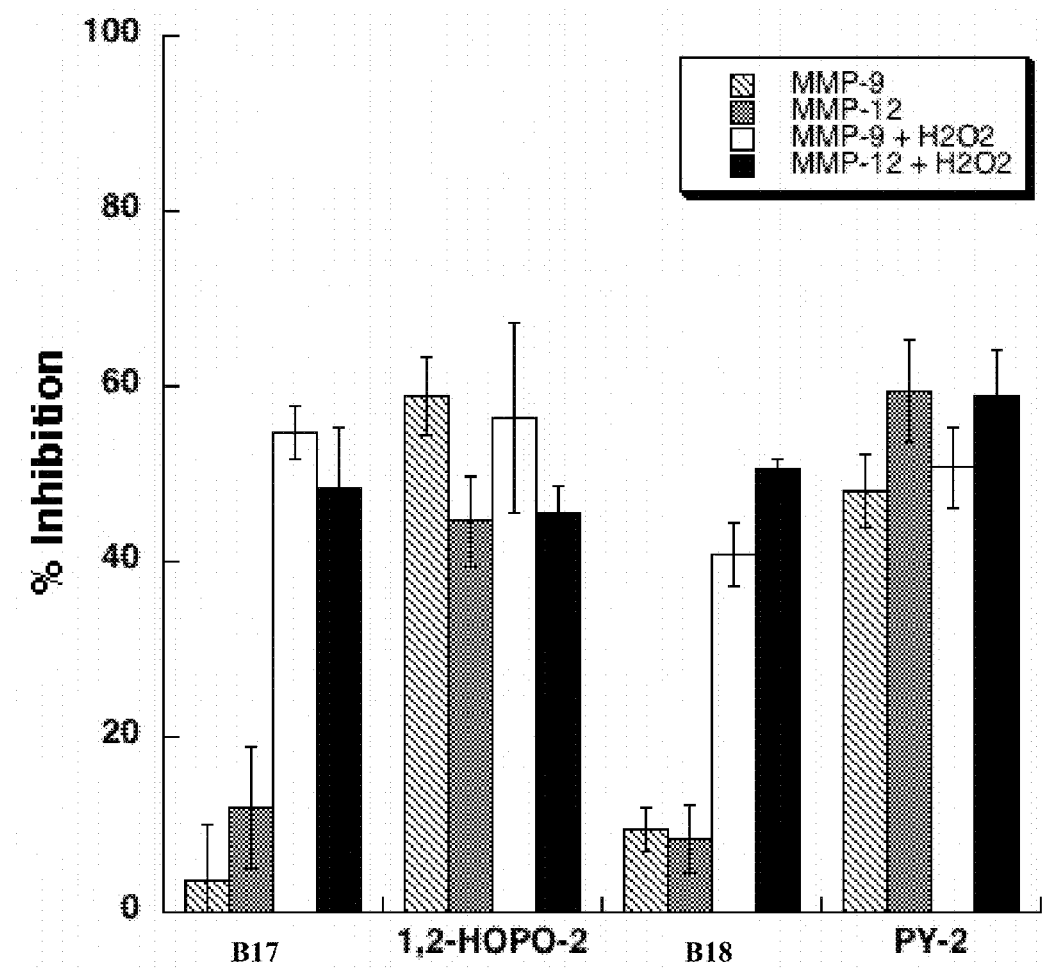

FIG. 46. Percent inhibition of MMP-9 and MMP-12 with proinhibitors B17 and B18 tested at 10 μM for MMP-9 and 50 nM for MMP-12 in the absence and presence of 100 μM $H_2O_2$ after one hour of activation. Data are the average of four experiments.

Figure 47:
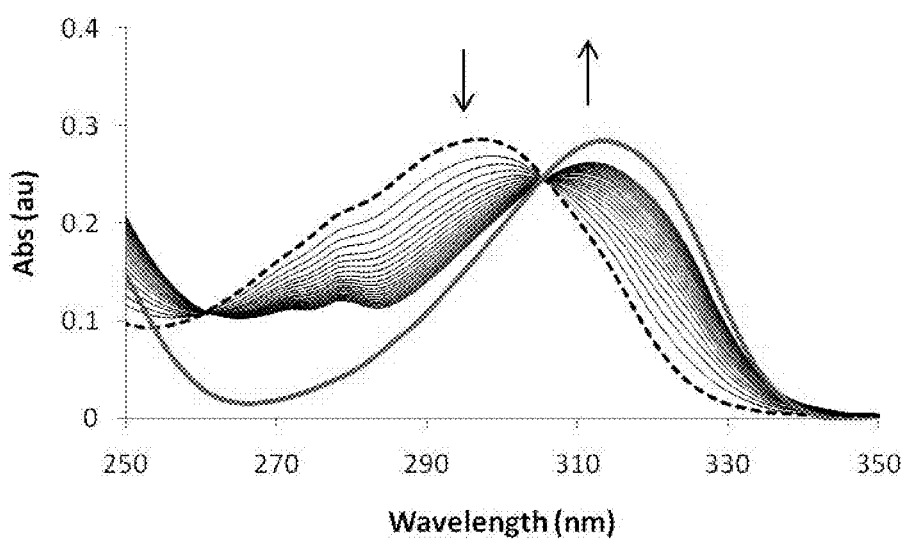

FIG. 47. Absorption spectra of the protected ZBG B19 (0.05 mM in HEPES buffer) in the presence of $H_2O_2$ (0.90 mM) monitored every 2 min for 40 min. The initial spectra is represented by a dashed line and an authentic sample of the ZBG, 2-hydroxypyridine-1-oxide, is shown in light gray; arrows indicate change in spectra over time.

Figure 48:
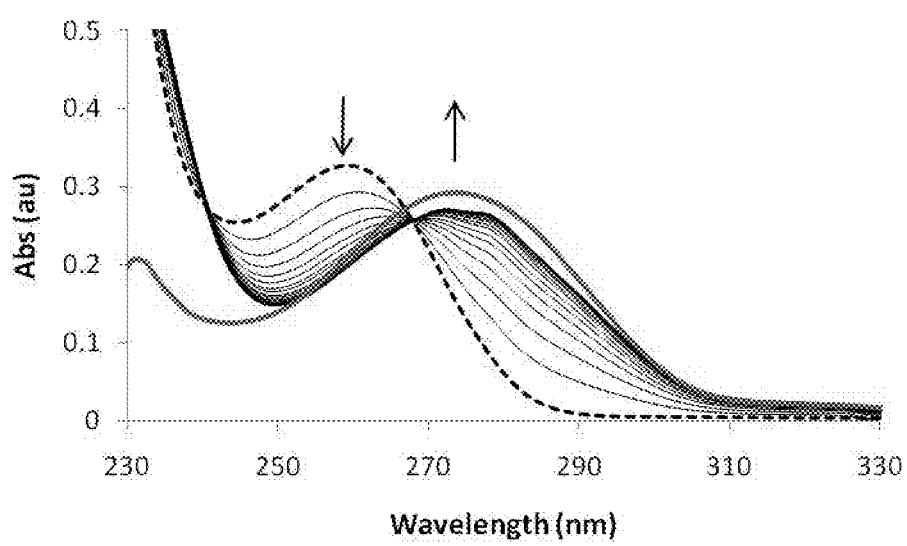

FIG. 48. Absorption spectra of the protected ZBG B20 (0.05 mM in HEPES buffer) in the presence of $H_2O_2$ (0.90 mM) monitored every 2 min for 40 min. The initial spectra is represented by a dashed line and an authentic sample of the ZBG, 3-hydroxy-2-methyl-4H-pyran-4-one (maltol), is shown in light gray; arrows indicate change in spectra over time.

Figure 49:
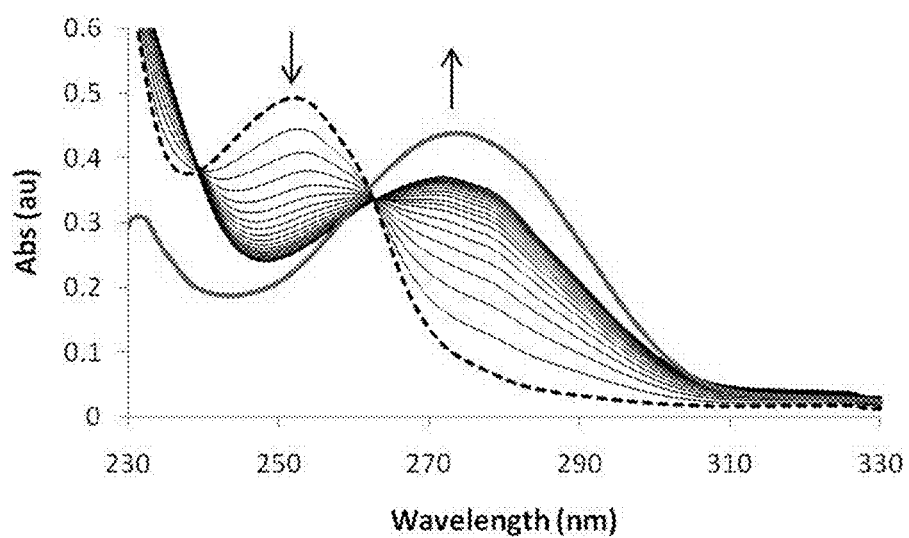

FIG. 49. Absorption spectra of the protected ZBG B21 (0.05 mM in HEPES buffer) in the presence of $H_2O_2$ (0.90 mM) monitored every 2 min for 40 min. The initial spectra is represented by a dashed line and an authentic sample of the ZBG, 3-hydroxy-2-methyl-4H-pyran-4-one (maltol), is shown in light gray; arrows indicate change in spectra over time.

Figure 50:
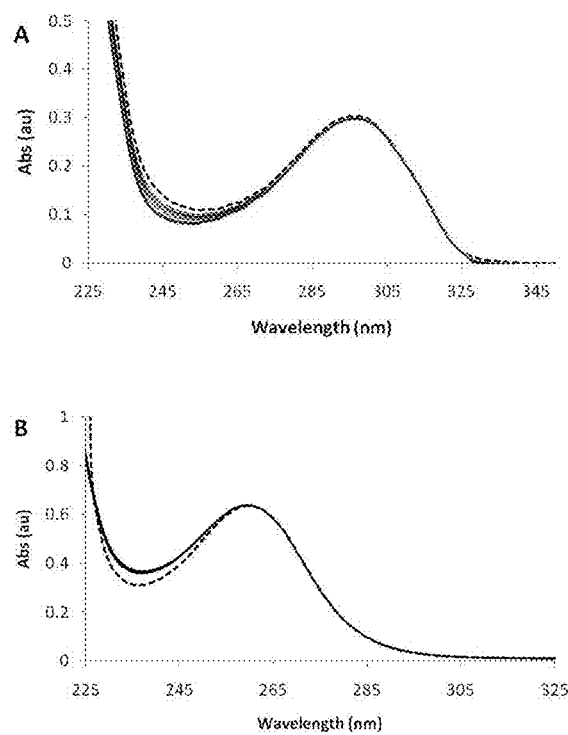

FIG. 50. Absorption spectra of benzyl protected control molecules (0.05 mM in HEPES buffer) in the presence of $H_2O_2$ (0.90 mM) monitored every 5 min for 60 min. The initial spectra of each compound is shown as a dashed line. The overlapping spectra indicate that no cleavage of the protecting group is occurring in the presence of $H_2O_2$.

Figure 51:
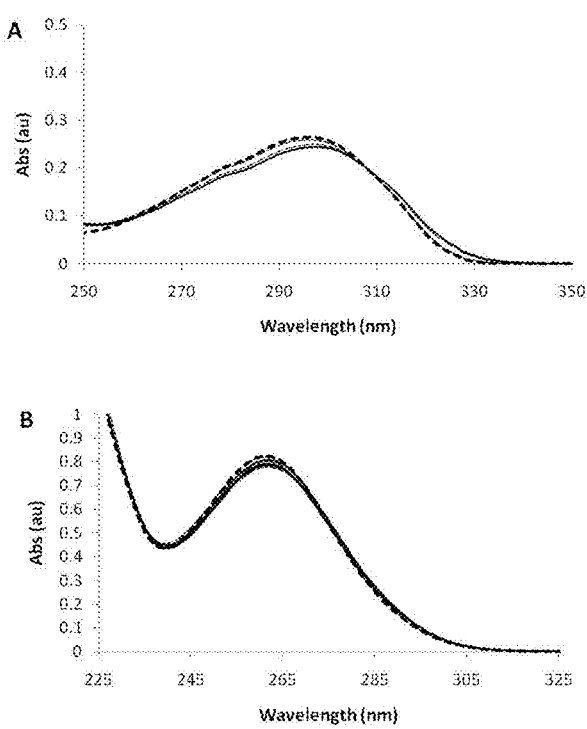

FIG. 51. Absorption spectra of protected ZBGs B19 and B20 (0.05 mM in HEPES, A and B, respectively) in the presence of $KO_2$ (0.10 mM) and catalase (5 U). Spectra were monitored every 3 min for 60 min. The initial spectra of each is shown as a dashed line. The overlapping spectra indicate that compounds B19 and B20 are stable towards $KO_2$.

Figure 52:
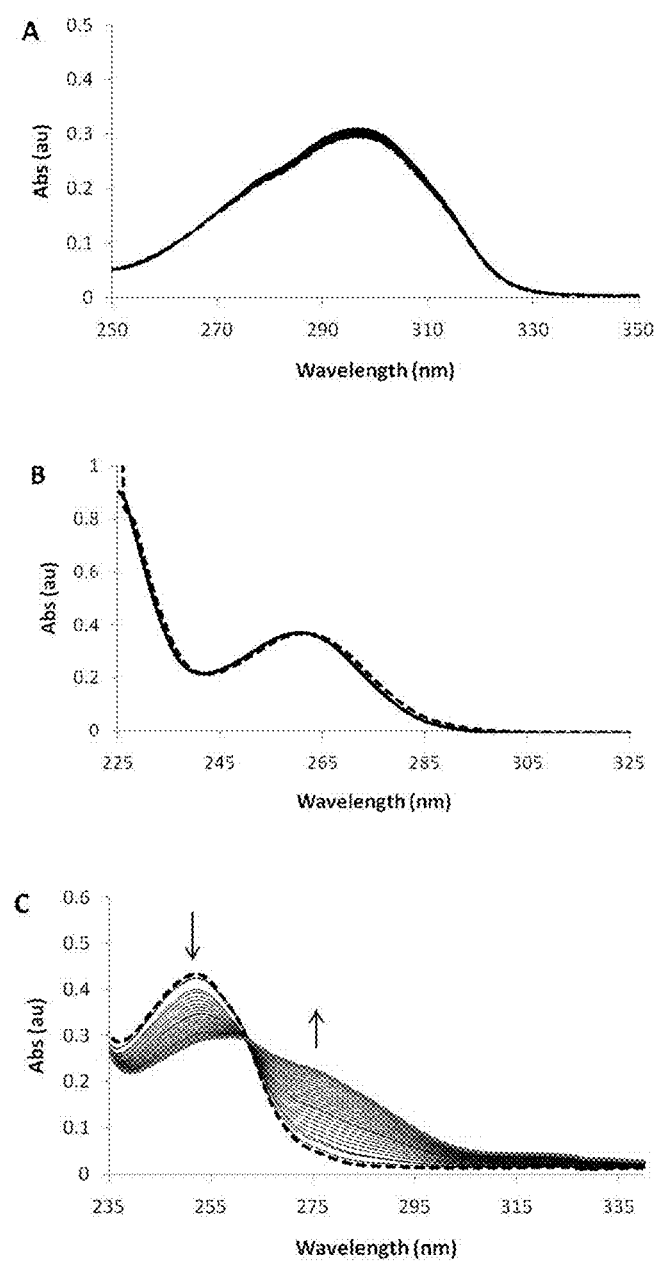

FIG. 52. Absorption spectra of the protected ZBGs at 50 μM in HEPES buffer (B19, panel A; B20, panel B; B21, panel C) monitored over 24 h. Overlapping spectra of compounds B19 and B20 indicate their stability towards hydrolysis while compound B21 shows significant hydrolysis in buffer. The initial spectra of each compound is shown in the dashed line and the final spectra after 24 h is shown for B21 in light gray.

Figure 53:
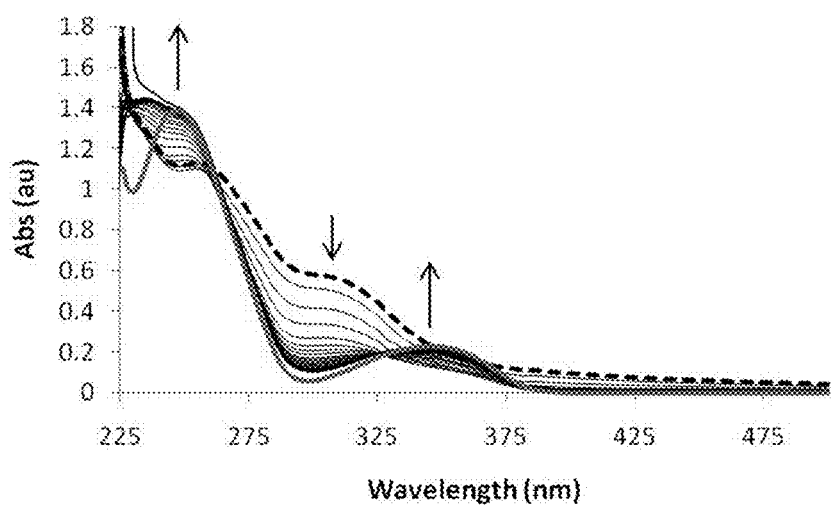

FIG. 53. Absorbance spectra of proinhibitor B17 (0.05 mM in HEPES buffer) in the presence of $H_2O_2$ (0.90 mM) monitored every 2 min for 1 h. The initial spectra is represented by the dashed line and an authentic sample of 1,2-HOPO-2 is represented by the light gray line; arrows indicate change in spectra over time.

Figure 54:
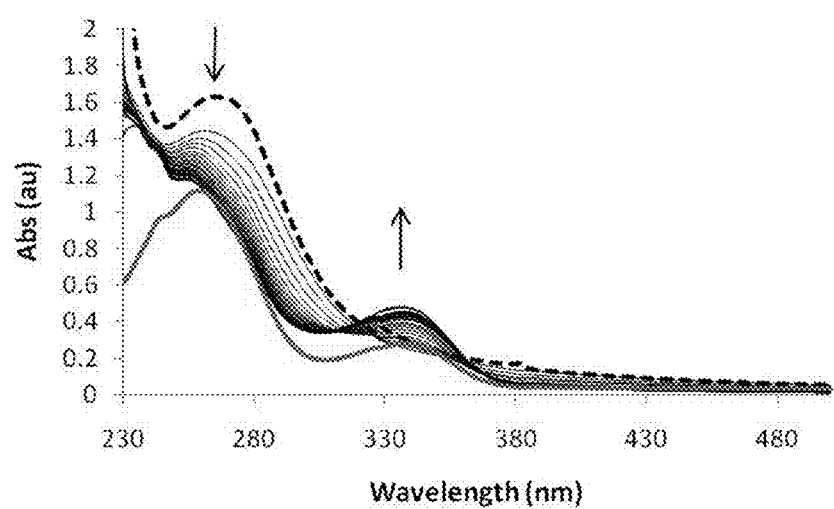

FIG. 54. Absorbance spectra of proinhibitor B18 (0.05 mM in HEPES buffer) in the presence of $H_2O_2$ (0.90 mM) monitored every 2 min for 1 h. The initial spectra is represented by the dashed line and an authentic sample of PY-2 is represented by the light gray line; arrows indicate change in spectra over time.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "or" as used herein should in general be construed non-exclusively. For example, an embodiment of "a formulation including A or B" would typically present an aspect with a formulation including both A and B. "Or" should, however, be construed to exclude those aspects presented that cannot be combined without contradiction.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, consisting of at least one carbon atom and at least one heteroatom selected from the group consisting of B, O, N, P, Si, and S, and wherein the nitrogen and sulfur atoms may optionally be oxidized, and the nitrogen heteroatom may optionally be quaternized. The heteroatom(s) B, O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as B, N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, boronic esters, boronic acids, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, peptidyl, and peptidomimetic moiety, in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro($C_1$-$C_4$)alkoxy, and fluoro($C_1$-$C_4$)alkyl, peptidyl, and peptidomimetic moiety, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, boron (B), oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, peptidyl, peptidomimetic moiety, and (B) alkyl, heteroalkyl, cycloalkyl, heterocycloalkyl, aryl, and heteroaryl, substituted with at least one substituent selected from:
- (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, peptidyl, and peptidomimetic moiety, and
- (ii) alkyl, heteroalkyl, cycloalkyl, heterocycloalkyl, aryl, and heteroaryl, substituted with at least one substituent selected from:
  - (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, peptidyl, and peptidomimetic moiety, and
  - (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, boronic acid, boronic ester, unsubstituted alkyl, unsubstituted heteroalkyl, unsubstituted cycloalkyl, unsubstituted heterocycloalkyl, unsubstituted aryl, and unsubstituted heteroaryl, peptidyl, and peptidomimetic moiety, and
- (iii) boronic acid and boronic ester;

(C) boronic acid and boronic ester.

A "boronic acid", as used herein, means a substituent with the structure —B(OH)$_2$.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. Alternatively, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and/or each substituted or unsubstituted heterocycloalkylene is a substituted or unsubstituted 5 to 7 membered heterocycloalkylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

A "prodrug," as used herein, refers to an inactive pharmacological substance that becomes active upon undergoing a chemical reaction (e.g. metabolization in vivo, bioactivation, enzymatic reaction) or a less active pharmacological substance that becomes more active upon undergoing a chemical reaction. A produg includes a prodrug moiety and a drug moiety (e.g. a metal binding moiety such as a zinc binding moiety). A "prodrug moiety," is a portion of a prodrug that is modified or removed (either partially or wholly) when the prodrug undergoes the chemical reaction (including enzymatic reaction) thereby producing an active drug. The presence of a prodrug moiety is responsible for the inactivity, or reduced activity, of the prodrug. Likewise, the "drug moiety" is a portion of the prodrug that forms, in combination with a chemical moiety (e.g. —OH, or —NH$_2$) produced from the modification or removal of the prodrug moiety, a drug. A "drug" is an active pharmacological substance (e,g, any chemical substance, including organic molecules and inorganic molecules and combinations thereof, useful in the treatment, cure, or prevention of a disease or condition, or used to otherwise enhance the physical or mental well-being of an organism, such as a human). As used herein, the term "drug", "medicine", and "medication" are interchangeable.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " ~~~ " denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "peptide," "polypeptide," and "protein" are used interchangeably herein to refer to a polymer of amino acid residues.

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters as known in the art, for example BLAST or BLAST 2.0. For example, comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, or by computerized implementations of these algorithms (GAP, BESTFIT, FASTA, and TFASTA in the Wisconsin Genetics Software Package, Genetics Computer Group, 575 Science Dr., Madison, Wis.). Thus alignment can be carried out for sequences that have deletions and/or additions, as well as those that have substitutions, as well as naturally occurring, e.g., polymorphic or allelic variants, and man-made variants.

The phrase "substantial sequence identity" or "substantial identity," in the context of two polypeptide sequences, refers to a sequence that has at least 70% identity to a reference sequence. Percent identity can be any integer from 70% to 100%. Two polypeptide sequences that have 100% sequence identity are said to be "identical." A polypeptide sequence is said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above.

The term "expression" includes any step involved in the production of the polypeptide including, but not limited to, transcription, post-transcriptional modification, translation, post-translational modification, and secretion.

An amino acid or peptide is "heterologous" to another sequence with which it is operably linked if the two sequences are not associated in nature.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853). The methods above may be used to synthesize single molecular species for incorporation into a prodrug.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "reactive oxygen species" or "ROS", as used herein, is a molecule comprising a reactive oxygen having unpaired valence shell electrons. Hydrogen peroxide, hydroxyl radical, superoxide anion, and hypochlorous acid are non-limiting examples of reactive oxygen species.

The term "ROS-reactive boronic ester", as used herein, is a boronic ester that is capable of being released from the remainder of the compound upon contacting an ROS (e.g. hydrogen peroxide). The term "boronic ester" is used according to its plain ordinary meaning and refers to a compound formed between a boronic acid and one or more alcohols.

The term "metal binding moiety", as used herein, is a drug moiety that forms an active, or more active, metal binding drug upon modification or removal of the prodrug moiety. A metal binding drug is a drug that is capable of coordinating one or more metal atoms.

The term "zinc binding moiety", as used herein, is a metal binding moiety that forms an active, or more active, zinc binding drug upon modification or removal of the prodrug moiety. A zinc binding drug is a drug that is capable of coordinating one or more zinc atoms. (e.g. a zinc atom necessary for a protein's function).

The term "carbohydrate", as used herein, is used herein according to its plain ordinary meaning and refers to a molecule consisting of carbon, hydrogen and oxygen. "Saccharide" is used interchangeably with "carbohydrate". Carbohydrates include monosaccharides, for example glucose, and ribose, and polysaccharides. A "carbohydrate moiety", as used herein, is a monovalent carbohydrate. A carbohydrate or a carbohydrate moiety may be unsubstituted or it may be substituted with the substituents described herein.

The term "glycosyl moiety", as used herein, is a monovalent monosaccharide.

The term "oxidatively-sensitive prodrug", as used herein, is a prodrug having a prodrug moiety that is modified or removed in the presence of an oxidative compound. An "oxidative compound" is a chemical compound that has the ability to oxidize other substances (e.g. a reactive oxygen species such as hydrogen peroxide).

The term "metalloprotein", as used herein, is a protein that is coordinated to at least one metal atom.

The term "metalloenzyme", as used herein, is a metalloprotein in which the coordinated metal atom participates in a reaction catalyzed by the metalloenzyme.

The term "metalloprotease" or "metalloproteinase", as used herein, is a protease enzyme that coordinates a metal atom in the protease active site and the metal atom, often zinc or cobalt, participates in the reaction catalyzed by the enzyme. Participation by the metal atom may be direct or may be mediated through another atom or molecule, for example the enzyme or a water molecule or another molecule.

The term "matrix metalloprotease" or "matrix metalloproteinase" or "MMP", as used herein, is a metalloprotease of a family of proteases generally capable of degrading extracellular matrix proteins. Certain matrix metalloproteases are also capable of cleaving substrates that are not extracellular matrix proteins.

Examples of matrix metalloproteases include, but are not limited to MMP1, MMP2, MMP3, MMP 7, MMP8, MMP 9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27, or MMP28.

The term "electron withdrawing group", as used herein, is a moiety that draws electrons or electron density to itself from an adjacent chemical moiety or atom.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

II. Compounds

In a first aspect, a compound is provided having the formula:

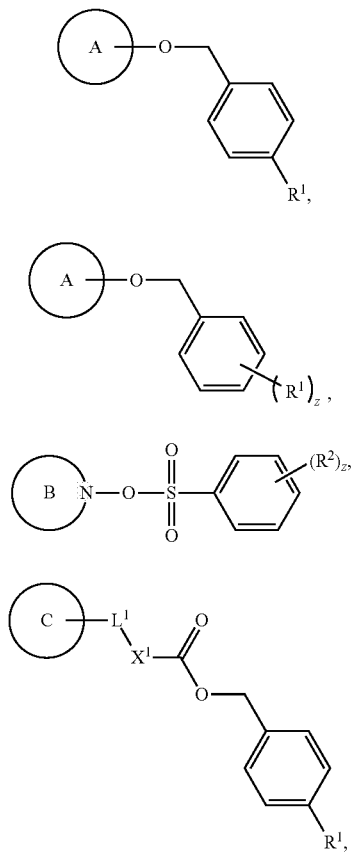

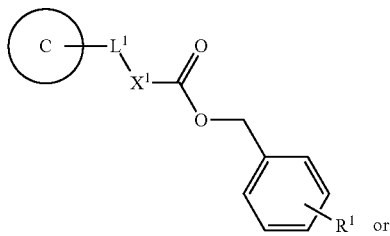

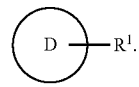

Within formula (I), (Ia), (II), (III), (IIIa) and (IV), A, B, C, and D are independently a drug moiety. $L^1$ is a bond or unsubstituted alkylene. $X^1$ is —NH— or —O—. $R^1$ is independently —B(OH)$_2$, an ROS-reactive boronic ester, hydrogen, halogen, —CN, —SR$^{13B}$, —SO$_2$Cl, —SO$_3$H, —SO$_4$H, —SO$_2$NR$^{7B}$R$^{8B}$, —NHNH$_2$, —ONR$^{7B}$R$^{8B}$, —NHC=(O)NHNH$_2$, —NHC=(O)NR$^{7B}$R$^{8B}$, —N(O)$_m$, —NR$^{7B}$R$^{8B}$, —C(O)R$^{9B}$, —C(O)—OR$^{10B}$, —C(O)NR$^{11B}$R$^{12B}$, —OR$^{13B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl, or peptidomimetic moiety. In some embodiments, $R^1$ is —B(OH)$_2$ or an ROS-reactive boronic ester. In some embodiments, $R^1$ is —B(OH)$_2$. In some embodiments, $R^1$ is an ROS-reactive boronic ester. In some embodiments, $R^1$ is boronic acid pinacol ester. In some embodiments, $L^1$ is a bond. In some embodiments, $L^1$ is an unsubstituted alkylene (e.g. an unsubstituted C$_1$-C$_5$ alkylene such as methylene). In some embodiments, $X^1$ is —NH—. In some embodiments, $X^1$ is —O—. In other embodiments, $X^1$ is —NH— and $L^1$ is an unsubstituted alkylene (e.g. an unsubstituted C$_1$-C$_5$ alkylene such as methylene). Where $X^1$ is —O—, $L^1$ may be a bond.

$R^{7B}$, $R^{8B}$, $R^{9B}$, $R^{10B}$, $R^{11B}$, $R^{12B}$, and $R^{13B}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl or peptidomimetic moiety.

$R^2$ is independently hydrogen, halogen, —CN, —SR$^{13B}$, —SO$_2$Cl, —SO$_3$H, —SO$_4$H, —SO$_2$NR$^{7B}$R$^{8B}$, —NHNH$_2$, —ONR$^{7B}$R$^{8B}$, —NHC=(O)NHNH$_2$, —NHC=(O)NR$^{7B}$R$^{8B}$, —N(O)$_m$, —NR$^{7B}$, R$^{8B}$, —C(O)R$^{9B}$, —C(O)—OR$^{10B}$, C(O)—NR$^{11B}$R$^{12B}$, —OR$^{13B}$, substituted or unsubstituted alkyl (e.g. methyl), substituted or unsubstituted heteroalkyl, substituted or unsubstituted cycloalkyl, substituted or unsubstituted heterocycloalkyl, substituted or unsubstituted aryl, substituted or unsubstituted heteroaryl, an electron withdrawing group, peptidyl, or peptidomimetic moiety. In some embodiments, $R^2$ is independently halogen, —CN, —N(O)$_2$, —COOH, substituted or unsubstituted alkyl (e.g. a substituted or unsubstituted C$_1$-C$_5$ alkyl such as methyl), substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl, peptidomimetic moiety, or an electron withdrawing group. The symbol z is an integer from 0 to 5. The symbol m is an integer from 1 to 2. In some embodiments, z is 1. In another embodiment, z is 2. In a further embodiment, z is 3. In yet another embodiment, z is 4. In a further embodiment, z is 5. In another embodiment, z is 0. In some embodiments, m is 1. In some embodiments, m is 2.

In an embodiment, z is 2 and $R^1$ and $R^2$ are at the ortho and para positions relative to the drug moiety (e.g. drug moiety bonded to the sulfonyl group in the case of $R^2$).

In one embodiment z is 1 and $R^2$ is para-$N(O)_2$. In another embodiment, z is 1 and $R^2$ is para-methyl. In a further embodiment, z is 2 and $R^2$ is ortho-$N(O)_2$ and para-$N(O)_2$. In one embodiment, z is 1 and $R^2$ is para-COOH.

In one embodiment $R^2$ is unsubstituted alkyl. In one embodiment $R^2$ is unsubstituted $C_1$-$C_8$ alkyl. In one embodiment $R^2$ is unsubstituted $C_1$-$C_3$ alkyl. In one embodiment $R^2$ is methyl. In another embodiment, $R^2$ is —$N(O)_2$, methyl or —COOH.

In some embodiments, the compound is an oxidatively-sensitive prodrug that forms a drug upon exposure to an oxidative compound. In some embodiments, the drug moiety is a metal binding moiety. In some embodiments, the metal binding moiety is a zinc binding moiety.

In some embodiments, the drug moiety is capable of forming a drug (in combination with a chemical moiety resulting from the prodrug moiety reaction) following modification or separation of the drug moiety from the oxidatively-sensitive prodrug moiety. In some embodiments, the drug formed from the drug moiety is selected from retinoic acid, retinol, tretinoin, isotretinoin. In some embodiments, the drug is a matrix metalloprotease inhibitor. In some embodiments, the drug is doxycycline, minocycline, a tetracycline, marimastat, BB-2516, cipemastat, Ro-32-3555. In some embodiments, the drug comprises a hydroxamate. In some embodiments, the drug includes a phosphinyl. In some embodiments, the drug is selected from 1,2-hydroxypyridinone, 3-hydroxy-2-methyl-4H-pyran-4-one, 3-hydroxy-1,2-dimethylpyridin-4 (1H)-one, tropolone, methyl salicylate, or 8-hydroxyquinoline.

In some embodiments, A and C are independently

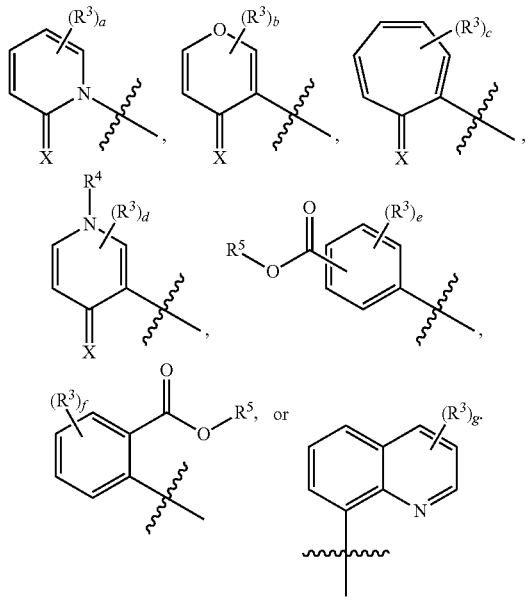

$R^3$ is halogen, —CN, —$SR^{13}$, —$SO_2Cl$, —$SO_3H$, —$SO_4H$, —$SO_2NR^7R^8$, —$NHNH_2$, —$ONR^7R^8$, —NHC=(O) $NHNH_2$, —NHC=(O)$NR^7R^8$, $N(O)_m$, —$NR^7R^8$, —C(O) $R^9$, —C(O)—$OR^{10}$, —C(O)$NR^{11}R^{12}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a peptidyl, or peptidomimetic moiety. In some embodiments, $R^3$ is hydrogen, halogen, —CN, —$SR^{13}$, —$SO_2Cl$, —$SO_3H$, —$SO_4H$, —$SO_2NR^7R^8$, —$NHNH_2$, —$ONR^7R^8$, —NHC= (O)$NHNH_2$, —NHC=(O)$NR^7R^8$, —$N(O)_m$, —$NR^7R^8$, —C(O)$R^9$, —C(O)—$OR^{10}$, —C(O)$NR^{11}R^{12}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In one embodiment, $R^3$ is a substituted or unsubstituted alkylamido.

The symbol m is 1 or 2. In some embodiments, m is 1. In another embodiment, m is 2.

$R^7$, $R^8$, $R^9$, $R^{10}$, $R^{11}$, $R^{12}$, and $R^{13}$ are independently hydrogen, halogen, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl, or peptidomimetic moiety.

In some embodiments, $R^3$ is a peptidyl, peptidyl-substituted alkyl, peptidyl-substituted heteroalkyl, peptidyl-substituted cycloalkyl, peptidyl-substituted heterocycloalkyl, peptidyl-substituted aryl, or peptidyl-substituted heteroaryl. In some embodiments, $R^3$ is a peptidomimetic moiety, peptidomimetic substituted alkyl, peptidomimetic substituted heteroalkyl, peptidomimetic substituted cycloalkyl, peptidomimetic substituted heterocycloalkyl, peptidomimetic substituted aryl, or peptidomimetic substituted heteroaryl.

$R^4$ is hydrogen, halogen, —CN, —OH, —$NH_2$, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —C(O)$R^{9A}$, —C(O)—$OR^{10A}$, —C(O)$NR^{11A}R^{12A}$, —$OR^{13A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted unsubstituted heteroaryl, peptidyl, or peptidomimetic moiety.

$R^{9A}$, $R^{10A}$, $R^{11A}$, $R^{12A}$, and $R^{13A}$ are independently hydrogen, halogen, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl or peptidomimetic moiety.

In some embodiments, $R^4$ is hydrogen, halogen, —C(O) $R^{9A}$, —C(O)—$OR^{10A}$, —C(O)$NR^{11A}$, $R^{12A}$, —$OR^{13A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In some embodiments, $R^{9A}$, $R^{10A}$, $R^{11A}$, $R^{12A}$, and $R^{13A}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^4$ is hydrogen, or substituted or unsubstituted alkyl.

$R^5$ is hydrogen, halogen, —CN, —OH, —NH$_2$, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —C(O)R$^{9A}$, —C(O)—OR$^{10A}$, —C(O)NR$^{11A}$R$^{12A}$, —OR$^{13A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl or peptidomimetic moiety. In some embodiments, $R^5$ is hydrogen, halogen, —C(O)R$^{9A}$, —C(O)—OR$^{10A}$, —C(O)NR$^{11A}$R$^{12A}$, —OR$^{13A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In some embodiments, $R^5$ is hydrogen or substituted or unsubstituted alkyl. In some embodiments, $R^5$ is unsubstituted alkyl. In one embodiment, $R^5$ is unsubstituted $C_1$-$C_8$ alkyl. In one embodiment $R^5$ is unsubstituted $C_1$-$C_3$ alkyl. In one embodiment $R^5$ is methyl.

The symbols a, e, and f are independently an integer from 0 to 4 (e.g. 1 to 4). In further separate embodiments, a is 1. In further separate embodiments, a is 2. In further separate embodiments, a is 3. In further separate embodiments, a is 4. In further separate embodiments, e is 1. In further separate embodiments, e is 2. In further separate embodiments, e is 3. In further separate embodiments, e is 4. In further separate embodiments, f is 1. In further separate embodiments, f is 2. In further separate embodiments, f is 3. In further separate embodiments, f is 4. In some embodiments, a is 0. In some embodiments, e is 0. In some embodiments, f is 0.

The symbols b and d are independently an integer from 0 to 3 (e.g. 1 to 3). In further separate embodiments, b is 1. In further separate embodiments, b is 2. In further separate embodiments, b is 3. In further separate embodiments, d is 1. In further separate embodiments, d is 2. In further separate embodiments, d is 3. The symbol c is an integer from 1 to 5. In further separate embodiments, c is 1. In further separate embodiments, c is 2. In further separate embodiments, c is 3. In further separate embodiments, c is 4. In further separate embodiments, c is 5. In some embodiments, b is 0. In some embodiments, d is 0. In some embodiments, c is 0.

The symbol g is an integer from 0 to 6 (e.g. 1 to 6). In further separate embodiments, g is 1. In further separate embodiments, g is 2. In further separate embodiments, g is 3. In further separate embodiments, g is 4. In further separate embodiments, g is 5. In further separate embodiments, g is 6. In some embodiments, g is 0.

X is =O or =S. In some embodiments X is =O. In some embodiments X is =S. In some embodiments, $L^1$ is a bond. In some embodiments, $L^1$ is unsubstituted alkylene. In some embodiments, $L^1$ is methylene. In some embodiments, $X^1$ is —NH—. In some embodiments, $X^1$ is —O—.

In some embodiments B is:

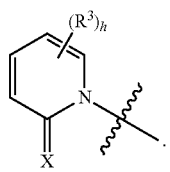

$R^3$ and X are as defined above, including embodiments. The symbol h is an integer from 0 to 4 (e.g. 1 to 4). In further separate embodiments, h is 1. In further separate embodiments, h is 2. In further separate embodiments, h is 3. In further separate embodiments, h is 4. In some embodiments, h is 0.

In one embodiment, C is

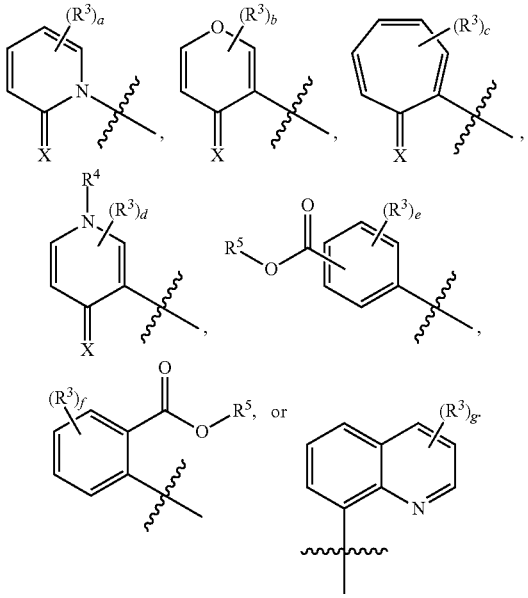

$R^3$, $R^4$, $R^5$, X, a, b, c, d, e, f and g are as defined above, including embodiments.

In some embodiments, D is

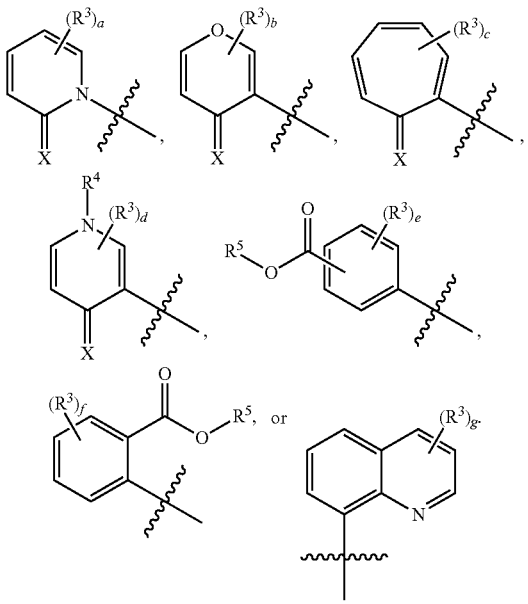

$R^3$, $R^4$, $R^5$, X, a, b, c, d, e, f and g are as defined above, including embodiments.

In any of the above embodiments, $R^3$ may be a peptidyl, peptidomimetic moiety or other suitable moiety for interacting with the protein, metalloprotein, metalloenzyme, or metalloprotease of interest. Suitable backbones for such interactions are known in the art, for example see, Rao G., *Curr Pharm Des.* 2005; 11(3):295-322; Whittaker, et. al. *Chem. Rev.* 1999, 99, 2735-2776; European Patent Application No. 126,974; International Application Publication No. WO 2006/028523 and U.S. Application Publication No. 2005/0267102.

In any of the above embodiments, $R^3$ may be any of the organic radicals derived from the structures shown on Scheme 1 of the Whittaker, et. al. *Chem. Rev.* 1999, 99, 2735-2776, after removal of the C(O)NH(OH) group. In some embodiments, $R^3$ includes a naturally-occurring peptide, a synthetic peptide or a peptide analog (peptidomimetic). Such groups may contain one or more amido moieties (—C(O)NH—), which can be or contain, peptidyl bonds. In some embodiments, $R^3$ includes a peptide of 1 to 20 amino acids of amino acid mimetics In any of the above embodiments, $R^3$ may be biphenylcarbamyl, biphenylcarbamylalkyl, biphenylalkylcarbamyl, biphenylalkylcarbamylalkyl, phenoxyphenylcarbamyl, arylalkylaminoalkyl, biphenylalkylaminoalkyl, arylcarbonylaminoalkyl, arylalkylcarbonylaminoalkyl, biphenyloxyalkylcarbonylaminoalkyl, or phenoxyphenylcarbamylalkyl, wherein, the phenyl or aryl group(s) may be optionally substituted, or a pharmaceutically acceptable salt thereof.

In any of the above embodiments, $R^3$ may be

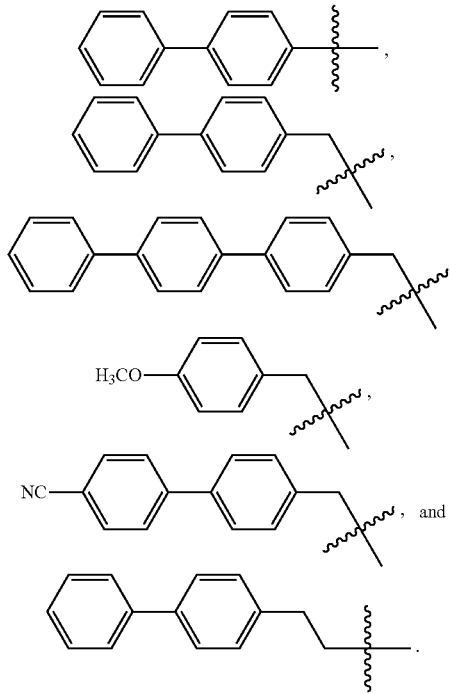

In any of the above embodiments, $R^3$ may be unsubstituted or substituted with one or more substituents, in one embodiment one to five substituents, in another embodiment one, two or three substituents, each independently selected from $Q^1$; where $Q^1$ is hydrogen, halo, pseudohalo, hydroxy, oxo, thia, nitrile, nitro, formyl, mercapto, hydroxycarbonyl, alkyl, haloalkyl, aminoalkyl, diaminoalkyl, alkenyl, alkynyl, cycloalkyl, cycloalkylalkyl, heterocyclyl, heterocyclylalkyl, aryl, heteroaryl, aralkyl, aralkenyl, aralkynyl, alkylcarbonyl, aminocarbonyl, alkoxy, aryloxy, heteroaryloxy, heterocyclyloxy, cycloalkoxy, alkenyloxy, alkynyloxy, aralkoxy, amino, aminoalkyl, alkylamino, arylamino, alkylthio, arylthio, thiocyano, isothiocyano, and each $Q^1$ is independently unsubstituted or substituted with one or more substituents, in one embodiment one, two or three substituents, each independently selected from $Q^2$; each $Q^2$ is independently hydrogen, halo, pseudohalo, hydroxy, oxo, thia, nitrile, nitro, formyl, mercapto, hydroxycarbonyl, alkyl, haloalkyl, aminoalkyl, diaminoalkyl, alkenyl, alkynyl, cycloalkyl, cycloalkylalkyl, heterocyclyl, heterocyclylalkyl, aryl, heteroaryl, aralkyl, aralkenyl, aralkynyl, alkylcarbonyl, aminocarbonyl, alkoxy, aryloxy, heteroaryloxy, heterocyclyloxy, cycloalkoxy, alkenyloxy, alkynyloxy, aralkoxy, amino, aminoalkyl, alkylamino, arylamino, alkylthio, arylthio, thiocyano or isothiocyano.

In another aspect, is a compound having the formula

(V)

E is a drug moiety. $L^2$ is independently a bond, —O—, —S—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^6$ is a substituted or unsubstituted carbohydrate moiety. In one embodiment, E is a metal binding moiety. In a further embodiment, E is a zinc binding moiety. Where $R^6$ is typically attached to the remainder of the compound via a glycosidic bond (e.g. an ether). In some embodiments, where $L^2$ is —O—, $L^2$ serves as the glycosidic bond.

In a further embodiment, $R^6$ is a substituted or unsubstituted glycosyl moiety. In another embodiment, $R^6$ is substituted or unsubstituted hexosyl moiety. In another embodiment, $R^6$ is a substituted or unsubstituted pentosyl moiety. In another embodiment, $R^6$ is a substituted or unsubstituted heptosyl moiety. In another embodiment, $R^6$ is a substituted or unsubstituted monosaccharide moiety. In another embodiment, $R^6$ is a substituted or unsubstituted disaccharide moiety. In another embodiment, $R^6$ is a substituted or unsubstituted polysaccharide moiety. In a further embodiment, $R^6$ is a substituted or unsubstituted glucosyl moiety.

In one embodiment, E is

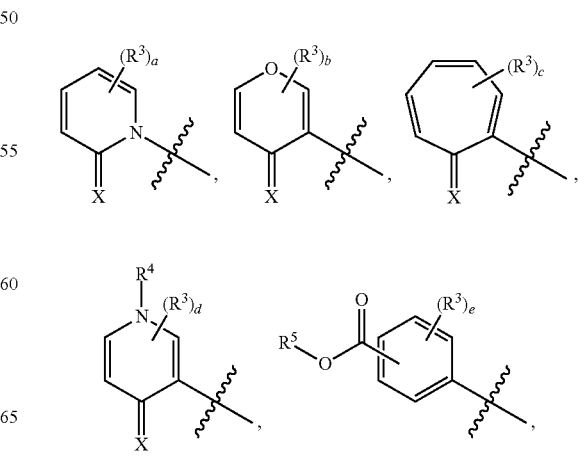

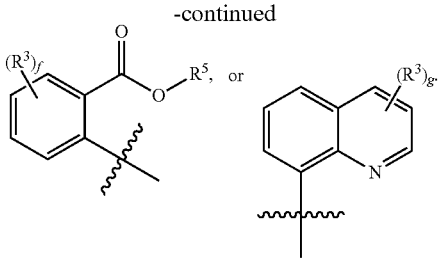

$R^3$, $R^4$, $R^5$, X, a, b, c, d, e, f and g are as defined above, including embodiments.

In some embodiments, the compound is an oxidatively-sensitive prodrug. The oxidatively-sensitive prodrug may be a compound set forth herein (e.g. a compound of formula I, Ia, II, III, IIIa, or IV).

In some embodiments, the compound is an oxidatively-sensitive prodrug that forms a drug upon exposure to an oxidative compound. In one embodiment, A, B, C, D, and E are independently a metal binding moiety. In a further embodiment, the metal binding moiety is a zinc binding moiety. In some embodiments, the compound is an oxidatively-sensitive prodrug that forms a metal binding compound upon exposure to an oxidative compound. In some embodiments, the compound of formula I may form a drug having the formula A-OH. In some embodiments, the compound of formula II may form a drug having the formula B—OH. In some embodiments, the compound of formula III may form a drug having the formula C-$L^1$-$X^1$—H. In some embodiments, the compound of formula IIIa may form a drug having the formula C-$L^1$-$X^1$—H. $L^1$ and $X^1$ are as defined herein, including embodiments. In some embodiments, the compound of formula IV may form a drug having the formula D-OH. In some embodiments, the compound of formula V may form a drug having the formula E-$L^2$-H. $L^2$ is as defined herein, including embodiments.

In another embodiment, the metal binding moiety is attached (e.g. covalently bonded) to a hydroxyl group following reaction of the compound with an ROS. The hydroxylated metal binding moiety that is formed is a metal binding compound or drug. In a further embodiment, the metal binding moiety of formula (III) or (IIIa) in which $X^1$ is —NH—, is attached to an amine group following reaction of the compound with an ROS and the aminated metal binding moiety is a metal binding compound. In another embodiment, the drug moiety is attached to a hydroxyl group following reaction of the compound with an ROS and the hydroxylated drug moiety is a drug that is known to be useful in the treatment of a disease. In a further embodiment, the drug moiety of formula (III) or (IIIa) in which $X^1$ is —NH—, is attached to an amine group following reaction of the compound with an ROS and the aminated drug moiety is a drug known to be useful for the treatment of a disease.

In another embodiment, the ROS-reactive boronic ester is capable of reacting with hydrogen peroxide. Upon reacting, a drug is formed from the compound of formula I, IA, II, III, IIIa, or IV. In another embodiment, the ROS-reactive boronic ester is a boronic acid pinacol ester. In a further embodiment, the ROS-reactive boronic ester has the formula —B($OR^{53}$)($OR^{57}$). $R^{53}$ and $R^{57}$ are independently halogen, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted hetero- cycloalkyl, substituted or unsubstituted aryl, substituted or unsubstituted heteroaryl, peptidyl, or peptidomimetic moiety. In a further embodiment, the ROS-reactive boronic ester has the formula —B($OR^{53}$)($OR^{57}$) wherein $R^{53}$ and $R^{57}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{53}$ and $R^{57}$ form a substituted or unsubstituted cycloalkyl, substituted or unsubstituted heterocycloalkyl, substituted or unsubstituted aryl, or substituted or unsubstituted heteroaryl. In some embodiments, $R^{53}$ and $R^{57}$ form a substituted or unsubstituted fused ring heterocycloalkyl-aryl, substituted or unsubstituted fused ring heterocycloalkyl-heteroaryl, substituted or unsubstituted fused ring heterocycloalkyl-cycloalkyl, or a substituted or unsubstituted fused ring heterocycloalkyl-heterocycloalkyl. In some embodiments, $R^{53}$ and $R^{57}$ form a substituted or unsubstituted heterocycloalkyl or a substituted or unsubstituted heteroaryl ring. In some embodiments, $R^{53}$ and $R^{57}$ form a five membered substituted or unsubstituted heterocycloalkyl or a five membered substituted or unsubstituted heteroaryl ring.

In some embodiments, an ROS-reactive boronic ester comprises the compound of formula (VIII):

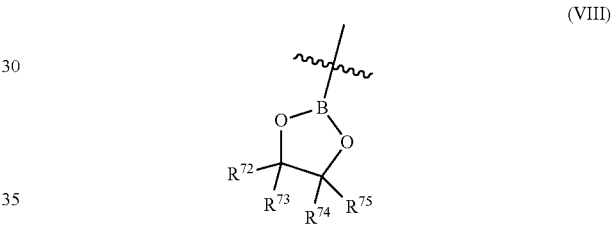

In some embodiments, a boronic ester is a compound of formula (VIII). $R^{72}$, $R^{73}$, $R^{74}$, and $R^{75}$, are independently hydrogen, halogen, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptidyl, or peptidomimetic moiety. In some embodiments, two of $R^{72}$, $R^{73}$, $R^{74}$, and $R^{75}$ form a substituted or unsubstituted cycloalkyl, substituted or unsubstituted heterocycloalkyl, substituted or unsubstituted aryl, or substituted or unsubstituted heteroaryl ring. In some embodiments, the substituted or unsubstituted cycloalkyl, substituted or unsubstituted heterocycloalkyl, substituted or unsubstituted aryl, or substituted or unsubstituted heteroaryl ring is a fused ring. In some embodiments, $R^{72}$ and $R^{73}$ or $R^{74}$ and $R^{75}$ or both pairs of substituents independently form a substituted or unsubstituted cycloalkyl, substituted or unsubstituted heterocycloalkyl, substituted or unsubstituted aryl, or substituted or unsubstituted heteroaryl ring. In some embodiments, $R^{72}$ and $R^{73}$ or $R^{74}$ and $R^{75}$ both independently form a substituted or unsubstituted cycloalkyl, substituted or unsubstituted heterocycloalkyl, substituted or unsubstituted aryl, or substituted or unsubstituted heteroaryl ring and the $R^{72}$ and $R^{73}$ or $R^{74}$ and $R^{75}$ rings are not identical. In some embodiments, $R^{72}$ and $R^{73}$ form a substituted or unsubstituted cycloalkyl, substituted or unsubstituted heterocycloalkyl, substituted or unsubstituted aryl, or substituted or unsubstituted heteroaryl ring and the $R^{72}$ and $R^{73}$ or $R^{74}$ and $R^{75}$ rings are not identical. In another embodiment, the $R^{72}$ and $R^{73}$ or $R^{74}$ and $R^{75}$ rings are identical. In some embodiments, a boronic ester is a boronic acid pinacol ester and $R^{72}$, $R^{73}$, $R^{74}$, and $R^{75}$ are methyl.

In separate embodiments of any aspect herein, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently substituted or unsubstituted $C_1$-$C_5$ alkyl, substituted or unsubstituted 2 to 5 membered heteroalkyl, substituted or unsubstituted $C_3$-$C_6$ cycloalkyl, or substituted, unsubstituted 5 or 6 membered heterocycloalkyl, substituted or unsubstituted aryl, or substituted or unsubstituted heteroaryl.

In some embodiments, a compound of formula (I), (Ia), (II), (III), (IIIa), (IV), or (V) includes one or more peptidyl moieties. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl-substituted alkyl, peptidyl-substituted heteroalkyl, peptidyl-substituted cycloalkyl, peptidyl-substituted heterocycloalkyl, peptidyl-substituted aryl, or peptidyl-substituted heteroaryl. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl. In some embodiments, only one of $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{11B}$, $R^{11B}$, $R^{12B}$, or $R^{13B}$ is or includes a peptidyl or peptidomimetic moiety.

In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{11B}$, $R^{11B}$, $R^{12B}$, or $R^{13B}$ are independently a peptidyl having two amino acids. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 3 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 4 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 5 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 6 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 7 amino acids. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 8 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 9 amino acids. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$$R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 10 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 15 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl having 20 amino acids. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidyl substantially identical to the amino acid sequence of a substrate of a metalloprotease.

In some embodiments, a compound of formula (I), (Ia), (II), (III), (IIIa), (IV), or (V) includes one or more peptidomimetic moieties. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{11B}$, $R^{11B}$, $R^{12B}$, or $R^{13B}$ are independently a peptidomimetic substituted alkyl, peptidomimetic substituted heteroalkyl, peptidomimetic substituted cycloalkyl, peptidomimetic substituted heterocycloalkyl, peptidomimetic substituted aryl, or peptidomimetic substituted heteroaryl. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a peptidomimetic moiety. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a two amino acid peptidomimetic moiety. In some embodiments, $R^{53}$, $R^{57}$, $R^2$, $R^3$, $R^4 R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 3 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{11B}$, $R^{11B}$, $R^{12B}$, or $R^{13B}$ are independently a 4 amino acid peptidomimetic moiety. In some embodiments, R $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 5 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 6 amino acid peptidomimetic moiety. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 7 amino acid peptidomimetic moiety. In some embodiments, $R^{53}$, $R^{57}$, $R^2$, $R^3$, $R^4$, $R^5$, $R^6 R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 8 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 9 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 10 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 15 amino acid peptidomimetic moiety. In some embodiments, $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12B}$, or $R^{13B}$ are independently a 20 amino acid peptidomimetic moiety. In some embodiments $R^{53}$, $R^{57}$, $R^2$, $R^3$, $R^4$, $R^5$, $R^6$, $R^7$, $R^8$, $R^9$, $R^{10}$, $R^{11}$, $R^{12}$, $R^{13}$, $R^{9A}$, $R^{10A}$, $R^{11A}$, $R^{12A}$, $R^{13A}$, $R^{7B}$, $R^{8B}$, $R^{9B}$, $R^{10B}$, $R^{11B}$, $R^{12A}$, or $R^{13B}$ are independently a peptidomimetic moiety substantially identical to the amino acid sequence of a substrate of a metalloprotease.

In some embodiments, $R^1$ is hydrogen, halogen, —CN, —OH, —NH$_2$, —COOH, —CONH$_{25}$—NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{14}$— substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

$R^{14}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

In some embodiments, $R^2$ is hydrogen, halogen, —CN, —OH, —NH$_2$, —COOH, —CONH$_2$5 —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

$R^{17}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

$R^{18}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{19}$-substituted or unsubstituted alkyl, $R^{19}$-substituted or unsubstituted heteroalkyl, $R^{19}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

In some embodiments, $R^3$ is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{21}$-substituted or unsubstituted alkyl, $R^{21}$-substituted or unsubstituted heteroalkyl, $R^{21}$-substituted or unsubstituted cycloalkyl, $R^{21}$ substituted or unsubstituted heterocycloalkyl, $R^{21}$-substituted or unsubstituted aryl, or $R^{21}$-substituted or unsubstituted heteroaryl.

$R^{21}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In some embodiments, $R^4$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{23}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{24}$-substituted or unsubstituted alkyl, $R^{24}$-substituted or unsubstituted heteroalkyl, $R^{24}$-substituted or unsubstituted cycloalkyl, $R^{24}$ substituted or unsubstituted heterocycloalkyl, $R^{24}$-substituted or unsubstituted aryl, or $R^{24}$-substituted or unsubstituted heteroaryl.

$R^{24}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In some embodiments, $R^5$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

$R^{27}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In some embodiments, $R^6$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{29}$— substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

$R^{29}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

$R^{30}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)

NHNH$_2$, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl.

In some embodiments, R$^7$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{32}$-substituted or unsubstituted alkyl, R$^{32}$-substituted or unsubstituted heteroalkyl, R$^{32}$-substituted or unsubstituted cycloalkyl, R$^{32}$-substituted or unsubstituted heterocycloalkyl, R$^{32}$-substituted or unsubstituted aryl, or R$^{32}$-substituted or unsubstituted heteroaryl.

R$^{32}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{33}$-substituted or unsubstituted alkyl, R$^{33}$-substituted or unsubstituted heteroalkyl, R$^{33}$-substituted or unsubstituted cycloalkyl, R$^{33}$ substituted or unsubstituted heterocycloalkyl, R$^{33}$-substituted or unsubstituted aryl, or R$^{33}$-substituted or unsubstituted heteroaryl.

R$^{33}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{34}$-substituted or unsubstituted alkyl, R$^{34}$-substituted or unsubstituted heteroalkyl, R$^{34}$-substituted or unsubstituted cycloalkyl, R$^{34}$-substituted or unsubstituted heterocycloalkyl, R$^{34}$-substituted or unsubstituted aryl, or R$^{34}$-substituted or unsubstituted heteroaryl.

In some embodiments, R$^8$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{35}$-substituted or unsubstituted alkyl, R$^{35}$-substituted or unsubstituted heteroalkyl, R$^{35}$-substituted or unsubstituted cycloalkyl, R$^{35}$-substituted or unsubstituted heterocycloalkyl, R$^{35}$-substituted or unsubstituted aryl, or R$^{35}$-substituted or unsubstituted heteroaryl.

R$^{35}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{36}$-substituted or unsubstituted alkyl, R$^{36}$-substituted or unsubstituted heteroalkyl, R$^{36}$-substituted or unsubstituted cycloalkyl, R$^{36}$ substituted or unsubstituted heterocycloalkyl, R$^{36}$-substituted or unsubstituted aryl, or R$^{36}$-substituted or unsubstituted heteroaryl.

R$^{36}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{37}$-substituted or unsubstituted alkyl, R$^{37}$-substituted or unsubstituted heteroalkyl, R$^{37}$-substituted or unsubstituted cycloalkyl, R$^{37}$-substituted or unsubstituted heterocycloalkyl, R$^{37}$-substituted or unsubstituted aryl, or R$^{37}$-substituted or unsubstituted heteroaryl.

In some embodiments, R$^9$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{38}$-substituted or unsubstituted alkyl, R$^{38}$-substituted or unsubstituted heteroalkyl, R$^{38}$-substituted or unsubstituted cycloalkyl, R$^{38}$-substituted or unsubstituted heterocycloalkyl, R$^{38}$-substituted or unsubstituted aryl, or R$^{38}$-substituted or unsubstituted heteroaryl.

R$^{38}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{39}$-substituted or unsubstituted alkyl, R$^{39}$-substituted or unsubstituted heteroalkyl, R$^{39}$-substituted or unsubstituted cycloalkyl, R$^{39}$ substituted or unsubstituted heterocycloalkyl, R$^{39}$-substituted or unsubstituted aryl, or R$^{39}$-substituted or unsubstituted heteroaryl.

R$^{39}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In some embodiments, R$^{10}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

R$^{41}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{42}$-substituted or unsubstituted alkyl, R$^{42}$-substituted or unsubstituted heteroalkyl, R$^{42}$-substituted or unsubstituted cycloalkyl, R$^{42}$ substituted or unsubstituted heterocycloalkyl, R$^{42}$-substituted or unsubstituted aryl, or R$^{42}$-substituted or unsubstituted heteroaryl.

R$^{42}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl.

In some embodiments, R$^{11}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl.

R$^{44}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{45}$-substituted or unsubstituted alkyl, R$^{45}$-substituted or unsubstituted heteroalkyl, R$^{45}$-substituted or unsubstituted cycloalkyl, R$^{45}$ substituted or unsubstituted heterocycloalkyl, R$^{45}$-substituted or unsubstituted aryl, or R$^{45}$-substituted or unsubstituted heteroaryl.

R$^{45}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

In some embodiments, R$^{12}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

$R^{47}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{48}$-substituted or unsubstituted alkyl, $R^{48}$-substituted or unsubstituted heteroalkyl, $R^{48}$-substituted or unsubstituted cycloalkyl, $R^{48}$ substituted or unsubstituted heterocycloalkyl, $R^{48}$-substituted or unsubstituted aryl, or $R^{48}$-substituted or unsubstituted heteroaryl.

$R^{48}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In some embodiments, $R^{13}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl.

$R^{50}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{51}$-substituted or unsubstituted alkyl, $R^{51}$-substituted or unsubstituted heteroalkyl, $R^{51}$-substituted or unsubstituted cycloalkyl, $R^{51}$ substituted or unsubstituted heterocycloalkyl, $R^{51}$-substituted or unsubstituted aryl, or $R^{51}$-substituted or unsubstituted heteroaryl.

$R^{51}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl.

In a further embodiment, $R^{53}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl.

$R^{54}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

$R^{55}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

In a further embodiment, $R^{57}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

$R^{58}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

$R^{59}$ independently is halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

In some embodiments, $L^2$ is in each instance, independently selected from a bond, —C(O)—, —C(O)N($R^{61}$)—, —C(O)O—, —S(O)$_g$— (i.e. —S—, —S(O)— or —S(O)$_2$), —S(O)$_2$N($R^{61}$)—, —O—, —N($R^{61}$)—, —N($R^{61}$)C(O)N($R^{62}$)—, $R^{63}$-substituted or unsubstituted alkylene, $R^{63}$-substituted or unsubstituted heteroalkylene, $R^{63}$-substituted or unsubstituted cycloalkylene, $R^{63}$-substituted or unsubstituted heterocycloalkylene, $R^{63}$-substituted or unsubstituted arylene, or $R^{63}$-substituted or unsubstituted heteroarylene.

$R^{63}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

$R^{64}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl.

In some embodiments, $R^{61}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

$R^{66}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl.

$R^{67}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl.

In some embodiments, $R^{62}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl.

$R^{69}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl.

$R^{70}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl.

In some embodiments, $R^{16}$, $R^{19}$, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{56}$, $R^{60}$, $R^{65}$, $R^{68}$, and $R^{71}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments of any aspect of the compounds provide herein, a boronic ester is the compound of formula (VIII). $R^{72}$, $R^{73}$, $R^{74}$, and $R^{75}$ are as defined herein.

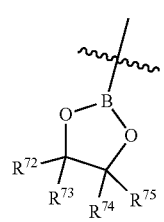

(VIII)

In some embodiments, $R^{72}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{76}$-substituted or unsubstituted alkyl, $R^{76}$-substituted or unsubstituted heteroalkyl, $R^{76}$-substituted or unsubstituted cycloalkyl, $R^{76}$-substituted or unsubstituted heterocycloalkyl, $R^{76}$-substituted or unsubstituted aryl, or $R^{76}$-substituted or unsubstituted heteroaryl.

$R^{76}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{77}$-substituted or unsubstituted alkyl, $R^{77}$-substituted or unsubstituted heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl.

$R^{77}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl.

In some embodiments, $R^{73}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl.

$R^{79}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl.

$R^{80}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl.

In some embodiments, $R^{74}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl.

$R^{82}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{83}$-substituted or unsubstituted alkyl, $R^{83}$-substituted or unsubstituted heteroalkyl, $R^{83}$-substituted or unsubstituted cycloalkyl, $R^{83}$-substituted or unsubstituted heterocycloalkyl, $R^{83}$-substituted or unsubstituted aryl, or $R^{83}$-substituted or unsubstituted heteroaryl.

$R^{83}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{84}$-substituted or unsubstituted alkyl, $R^{84}$-substituted or unsubstituted heteroalkyl, $R^{84}$-substituted or unsubstituted cycloalkyl, $R^{84}$-substituted or unsubstituted heterocycloalkyl, $R^{84}$-substituted or unsubstituted aryl, or $R^{84}$-substituted or unsubstituted heteroaryl.

In some embodiments, $R^{75}$ is independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{85}$-substituted or unsubstituted alkyl, $R^{85}$-substituted or unsubstituted heteroalkyl, $R^{85}$-substituted or unsubstituted cycloalkyl, $R^{85}$- substituted or unsubstituted heterocycloalkyl, $R^{85}$-substituted or unsubstituted aryl, or $R^{85}$-substituted or unsubstituted heteroaryl.

$R^{85}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{86}$-substituted or unsubstituted alkyl, $R^{86}$-substituted or unsubstituted heteroalkyl, $R^{86}$-substituted or unsubstituted cycloalkyl, $R^{86}$-substituted or unsubstituted heterocycloalkyl, $R^{86}$-substituted or unsubstituted aryl, or $R^{86}$-substituted or unsubstituted heteroaryl.

$R^{86}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{87}$-substituted or unsubstituted alkyl, $R^{87}$-substituted or unsubstituted heteroalkyl, $R^{87}$-substituted or unsubstituted cycloalkyl, $R^{87}$-substituted or unsubstituted heterocycloalkyl, $R^{87}$-substituted or unsubstituted aryl, or $R^{87}$-substituted or unsubstituted heteroaryl.

In some embodiments, $R^{78}$, $R^{81}$, $R^{84}$, and $R^{87}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^{9A}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{38A}$-substituted or unsubstituted alkyl, $R^{38A}$-substituted or unsubstituted heteroalkyl, $R^{38A}$-substituted or unsubstituted cycloalkyl, $R^{38A}$-substituted or unsubstituted heterocycloalkyl, $R^{38A}$-substituted or unsubstituted aryl, or $R^{38A}$-substituted or unsubstituted heteroaryl.

$R^{38A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{39A}$-substituted or unsubstituted alkyl, $R^{39A}$-substituted or unsubstituted heteroalkyl, $R^{39A}$-substituted or unsubstituted cycloalkyl, $R^{39A}$-substituted or unsubstituted heterocycloalkyl, $R^{39A}$-substituted or unsubstituted aryl, or $R^{39A}$-substituted or unsubstituted heteroaryl.

$R^{39A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl.

In some embodiments, $R^{10A}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{41A}$-substituted or unsubstituted alkyl, $R^{41A}$-substituted or unsubstituted heteroalkyl, $R^{41A}$-substituted or unsubstituted cycloalkyl, $R^{41A}$-substituted or unsubstituted heterocycloalkyl, $R^{41A}$-substituted or unsubstituted aryl, or $R^{41A}$-substituted or unsubstituted heteroaryl.

$R^{41A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{42A}$-substituted or unsubstituted alkyl, $R^{42A}$-substituted or unsubstituted heteroalkyl, $R^{42A}$-substituted or unsubstituted cycloalkyl, $R^{42A}$-substituted or unsubstituted heterocycloalkyl, $R^{42A}$-substituted or unsubstituted aryl, or $R^{42A}$-substituted or unsubstituted heteroaryl.

$R^{42A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{43A}$-substituted or unsubstituted alkyl, $R^{43A}$-substituted or unsubstituted heteroalkyl, $R^{43A}$-substituted or unsubstituted cycloalkyl, $R^{43A}$-substituted or unsubstituted heterocycloalkyl, $R^{43A}$-substituted or unsubstituted aryl, or $R^{43A}$-substituted or unsubstituted heteroaryl.

In some embodiments, $R^{11A}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{44A}$-substituted or unsubstituted alkyl, $R^{44A}$-substituted or unsubstituted heteroalkyl, $R^{44A}$-substituted or unsubstituted cycloalkyl, $R^{44A}$-substituted or unsubstituted heterocycloalkyl, $R^{44A}$-substituted or unsubstituted aryl, or $R^{44A}$-substituted or unsubstituted heteroaryl.

$R^{44A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{45A}$-substituted or unsubstituted alkyl, $R^{45A}$-substituted or unsubstituted heteroalkyl, $R^{45A}$-substituted or unsubstituted cycloalkyl, $R^{45A}$ substituted or unsubstituted heterocycloalkyl, $R^{45A}$-substituted or unsubstituted aryl, or $R^{45A}$-substituted or unsubstituted heteroaryl.

$R^{45A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{46A}$-substituted or unsubstituted alkyl, $R^{46A}$-substituted or unsubstituted heteroalkyl, $R^{46A}$-substituted or unsubstituted cycloalkyl, $R^{46A}$-substituted or unsubstituted heterocycloalkyl, $R^{46A}$-substituted or unsubstituted aryl, or $R^{46A}$-substituted or unsubstituted heteroaryl.

In some embodiments, $R^{12A}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{47A}$-substituted or unsubstituted alkyl, $R^{47A}$-substituted or unsubstituted heteroalkyl, $R^{47A}$-substituted or unsubstituted cycloalkyl, $R^{47A}$-substituted or unsubstituted heterocycloalkyl, $R^{47A}$-substituted or unsubstituted aryl, or $R^{47A}$-substituted or unsubstituted heteroaryl.

$R^{47A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{48A}$-substituted or unsubstituted alkyl, $R^{48A}$-substituted or unsubstituted heteroalkyl, $R^{48A}$-substituted or unsubstituted cycloalkyl, $R^{48A}$ substituted or unsubstituted heterocycloalkyl, $R^{48A}$-substituted or unsubstituted aryl, or $R^{48A}$-substituted or unsubstituted heteroaryl.

$R^{48A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{49A}$-substituted or unsubstituted alkyl, $R^{49A}$-substituted or unsubstituted heteroalkyl, $R^{49A}$-substituted or unsubstituted cycloalkyl, $R^{49A}$-substituted or unsubstituted heterocycloalkyl, $R^{49A}$-substituted or unsubstituted aryl, or $R^{49A}$-substituted or unsubstituted heteroaryl.

In some embodiments, $R^{13A}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{50A}$-substituted or unsubstituted alkyl, $R^{50A}$-substituted or unsubstituted heteroalkyl, $R^{50A}$-substituted or unsubstituted cycloalkyl, $R^{50A}$-substituted or unsubstituted heterocycloalkyl, $R^{50A}$-substituted or unsubstituted aryl, or $R^{50A}$-substituted or unsubstituted heteroaryl.

$R^{50A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{51A}$-substituted or unsubstituted alkyl, $R^{51A}$-substituted or unsubstituted heteroalkyl, $R^{51A}$-substituted or unsubstituted cycloalkyl, $R^{51A}$ substituted or unsubstituted heterocycloalkyl, $R^{51A}$-substituted or unsubstituted aryl, or $R^{51A}$-substituted or unsubstituted heteroaryl.

$R^{51A}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{52A}$-substituted or unsubstituted alkyl, $R^{52A}$-substituted or unsubstituted heteroalkyl, $R^{52A}$-substituted or unsubstituted cycloalkyl, $R^{52A}$-substituted or unsubstituted heterocycloalkyl, $R^{52A}$-substituted or unsubstituted aryl, or $R^{52A}$-substituted or unsubstituted heteroaryl.

In some embodiments, $R^{40A}$, $R^{43A}$, $R^{46A}$, $R^{49A}$, and $R^{52A}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^{7B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{32B}$-substituted or unsubstituted alkyl, $R^{32B}$-substituted or unsubstituted heteroalkyl, $R^{32B}$-substituted or unsubstituted cycloalkyl, $R^{32B}$-substituted or unsubstituted heterocycloalkyl, $R^{32B}$-substituted or unsubstituted aryl, or $R^{32B}$-substituted or unsubstituted heteroaryl.

$R^{32B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{33B}$-substituted or unsubstituted alkyl, $R^{33B}$-substituted or unsubstituted heteroalkyl, $R^{33B}$-substituted or unsubstituted cycloalkyl, $R^{33B}$ substituted or unsubstituted heterocycloalkyl, $R^{33B}$-substituted or unsubstituted aryl, or $R^{33B}$-substituted or unsubstituted heteroaryl.

$R^{33B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{34B}$-substituted or unsubstituted alkyl, $R^{34B}$-substituted or unsubstituted heteroalkyl, $R^{34B}$-substituted or unsubstituted cycloalkyl, $R^{34B}$-substituted or unsubstituted heterocycloalkyl, $R^{34B}$-substituted or unsubstituted aryl, or $R^{34B}$-substituted or unsubstituted heteroaryl.

In some embodiments, $R^{8B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{35B}$-substituted or unsubstituted alkyl, $R^{35B}$-substituted or unsubstituted heteroalkyl, $R^{35B}$-substituted or unsubstituted cycloalkyl, $R^{35B}$-substituted or unsubstituted heterocycloalkyl, $R^{35B}$-substituted or unsubstituted aryl, or $R^{35B}$-substituted or unsubstituted heteroaryl.

$R^{35B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{36B}$-substituted or unsubstituted alkyl, $R^{36B}$-substituted or unsubstituted heteroalkyl, $R^{36B}$-substituted or unsubstituted cycloalkyl, $R^{36B}$ substituted or unsubstituted heterocycloalkyl, $R^{36B}$-substituted or unsubstituted aryl, or $R^{36B}$-substituted or unsubstituted heteroaryl.

$R^{36B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{37B}$-substituted or unsubstituted alkyl, $R^{37B}$-substituted or unsubstituted heteroalkyl, $R^{37B}$-substituted or unsubstituted cycloalkyl, $R^{37B}$-substituted or unsubstituted heterocycloalkyl, $R^{37B}$-substituted or unsubstituted aryl, or $R^{37B}$-substituted or unsubstituted heteroaryl.

In some embodiments, $R^{9B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{38B}$-substituted or unsubstituted alkyl, $R^{38B}$-substituted or unsubstituted heteroalkyl, $R^{38B}$-substituted or unsubstituted cycloalkyl, $R^{38B}$-substituted or unsubstituted heterocycloalkyl, $R^{38B}$-substituted or unsubstituted aryl, or $R^{38B}$-substituted or unsubstituted heteroaryl.

$R^{38B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{39B}$-substituted or unsubstituted alkyl, $R^{39B}$-substituted or unsubstituted heteroalkyl, $R^{39B}$-substituted or unsubstituted cycloalkyl, $R^{39B}$-substituted or unsubstituted heterocycloalkyl, $R^{39B}$-substituted or unsubstituted aryl, or $R^{39B}$-substituted or unsubstituted heteroaryl.

$R^{39B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{40B}$-substituted or unsubstituted alkyl, $R^{40B}$-substituted or unsubstituted heteroalkyl, $R^{40B}$-substituted or unsubstituted cycloalkyl, $R^{40B}$-substituted or unsubstituted heterocycloalkyl, $R^{40B}$-substituted or unsubstituted aryl, or $R^{40B}$-substituted or unsubstituted heteroaryl.

In some embodiments, $R^{10B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{41B}$-substituted or unsubstituted alkyl, $R^{41B}$-substituted or unsubstituted heteroalkyl, $R^{41B}$-substituted or unsubstituted cycloalkyl, $R^{41B}$-substituted or unsubstituted heterocycloalkyl, $R^{41B}$-substituted or unsubstituted aryl, or $R^{41B}$-substituted or unsubstituted heteroaryl.

$R^{41B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{42B}$-substituted or unsubstituted alkyl, $R^{42B}$-substituted or unsubstituted heteroalkyl, $R^{42B}$-substituted or unsubstituted cycloalkyl, $R^{42B}$-substituted or unsubstituted heterocycloalkyl, $R^{42B}$-substituted or unsubstituted aryl, or $R^{42B}$-substituted or unsubstituted heteroaryl.

$R^{42B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{43B}$-substituted or unsubstituted alkyl, $R^{43B}$-substituted or unsubstituted heteroalkyl, $R^{43B}$-substituted or unsubstituted cycloalkyl, $R^{43B}$-substituted or unsubstituted heterocycloalkyl, $R^{43B}$-substituted or unsubstituted aryl, or $R^{43B}$-substituted or unsubstituted heteroaryl.

In some embodiments, $R^{11B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{44B}$-substituted or unsubstituted alkyl, $R^{44B}$-substituted or unsubstituted heteroalkyl, $R^{44B}$-substituted or unsubstituted cycloalkyl, $R^{44B}$-substituted or unsubstituted heterocycloalkyl, $R^{44B}$-substituted or unsubstituted aryl, or $R^{44B}$-substituted or unsubstituted heteroaryl.

$R^{44B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{45B}$-substituted or unsubstituted alkyl, $R^{45B}$-substituted or unsubstituted heteroalkyl, $R^{45B}$-substituted or unsubstituted cycloalkyl, $R^{45B}$ substituted or unsubstituted heterocycloalkyl, $R^{45B}$-substituted or unsubstituted aryl, or $R^{45B}$-substituted or unsubstituted heteroaryl.

$R^{45B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{46B}$-substituted or unsubstituted alkyl, $R^{46B}$-substituted or unsubstituted heteroalkyl, $R^{46B}$-substituted or unsubstituted cycloalkyl, $R^{46B}$-substituted or unsubstituted heterocycloalkyl, $R^{46B}$-substituted or unsubstituted aryl, or $R^{46B}$-substituted or unsubstituted heteroaryl.

In some embodiments, $R^{12B}$ is hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{47B}$-substituted or unsubstituted alkyl, $R^{47B}$-substituted or unsubstituted heteroalkyl, $R^{47B}$-substituted or unsubstituted cycloalkyl, $R^{47B}$-substituted or unsubstituted heterocycloalkyl, $R^{47B}$-substituted or unsubstituted aryl, or $R^{47B}$-substituted or unsubstituted heteroaryl.

$R^{47B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{40}$-substituted or unsubstituted alkyl, $R^{48B}$-substituted or unsubstituted heteroalkyl, $R^{48B}$-substituted or unsubstituted cycloalkyl, $R^{48B}$ substituted or unsubstituted heterocycloalkyl, $R^{48B}$-substituted or unsubstituted aryl, or $R^{48B}$-substituted or unsubstituted heteroaryl.

$R^{48B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{49B}$-substituted or unsubstituted alkyl, $R^{49B}$-substituted or unsubstituted heteroalkyl, $R^{49B}$-substituted or unsubstituted cycloalkyl, $R^{49B}$-substituted or unsubstituted heterocycloalkyl, $R^{49B}$-substituted or unsubstituted aryl, or $R^{49B}$-substituted or unsubstituted heteroaryl.

In some embodiments, $R^{13B}$ is hydrogen, halogen, —CN, —OH, —NH$_2$, —COOH, —CONH$_{25}$—NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{50B}$-substituted or unsubstituted alkyl, $R^{50B}$-substituted or unsubstituted heteroalkyl, $R^{50B}$-substituted or unsubstituted cycloalkyl, $R^{50B}$-substituted or unsubstituted heterocycloalkyl, $R^{50B}$-substituted or unsubstituted aryl, or $R^{50B}$-substituted or unsubstituted heteroaryl.

$R^{50B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{51B}$-substituted or unsubstituted alkyl, $R^{51B}$-substituted or unsubstituted heteroalkyl, $R^{51B}$-substituted or unsubstituted cycloalkyl, $R^{51B}$ substituted or unsubstituted heterocycloalkyl, $R^{51B}$-substituted or unsubstituted aryl, or $R^{51B}$-substituted or unsubstituted heteroaryl.

$R^{51B}$ is independently halogen, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, $R^{52B}$-substituted or unsubstituted alkyl, $R^{52B}$-substituted or unsubstituted heteroalkyl, $R^{52B}$-substituted or unsubstituted cycloalkyl, $R^{52B}$-substituted or unsubstituted heterocycloalkyl, $R^{52B}$-substituted or unsubstituted aryl, or $R^{52B}$-substituted or unsubstituted heteroaryl.

In some embodiments, $R^{40B}$, $R^{43B}$, $R^{46B}$, $R^{49B}$, and $R^{52B}$ are independently hydrogen, halogen, —CN, —OH, —NH$_2$, —COOH, —CONH$_2$, —NO$_2$, —SH, —SO$_2$Cl, —SO$_3$H, —SO$_4$H, —SO$_2$NH$_{25}$—NHNH$_2$, —ONH$_2$, —NHC═(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is any one or more of the compounds in Table 1 below:

TABLE 1

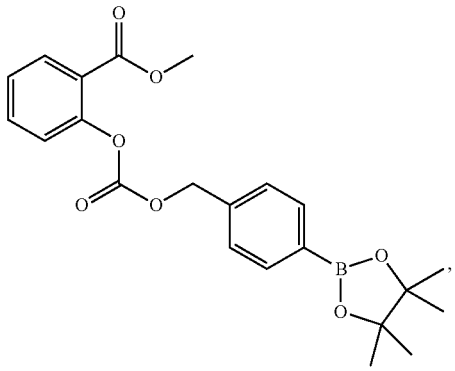 [SMILES: COC(=O)c1ccccc1OC(=O)OCc1ccc(B2OC(C)(C)C(C)(C)O2)cc1]

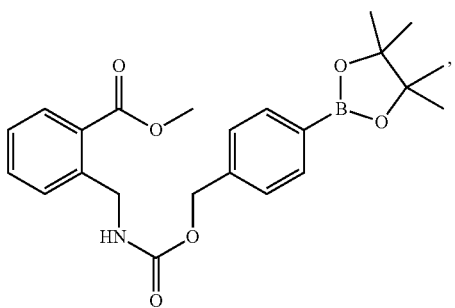 [SMILES: COC(=O)c1ccccc1CNC(=O)OCc1ccc(B2OC(C)(C)C(C)(C)O2)cc1]

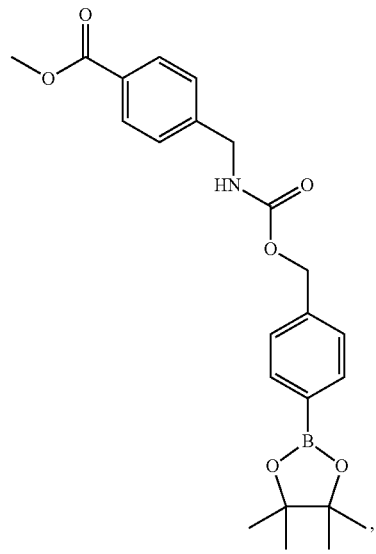

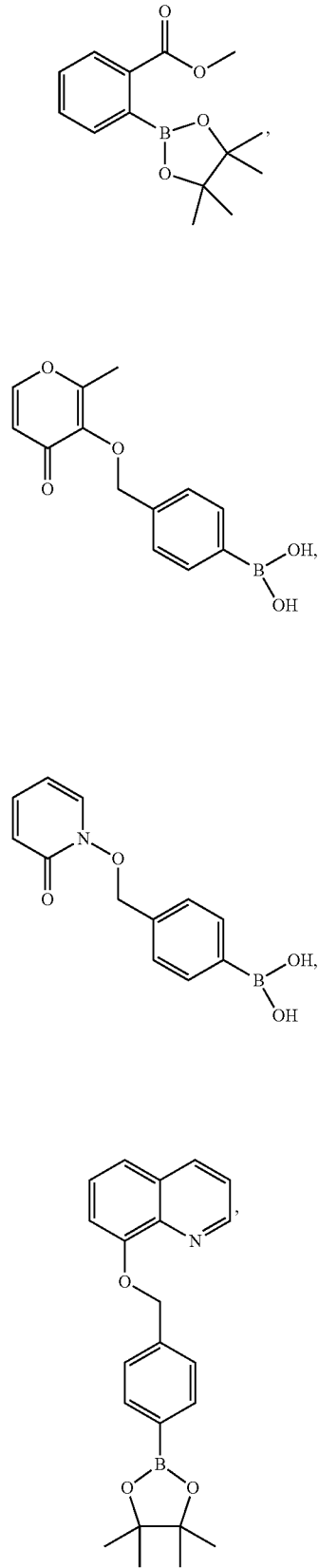
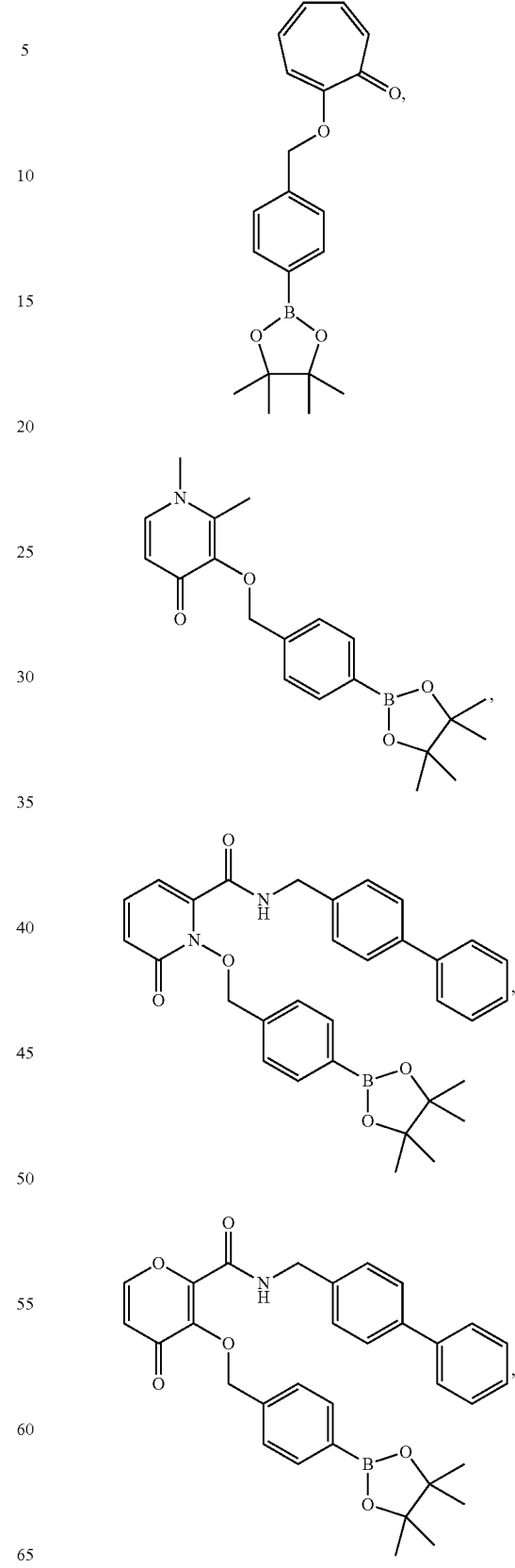

TABLE 1-continued
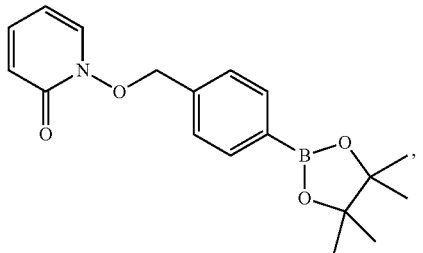 [SMILES: CC1(C)OB(c2ccc(COn3ccccc3=O)cc2)OC1(C)C]
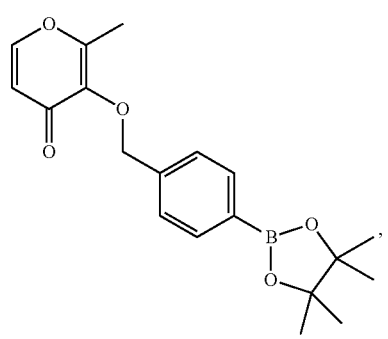 [SMILES: Cc1occc(=O)c1OCc1ccc(B2OC(C)(C)C(C)(C)O2)cc1]
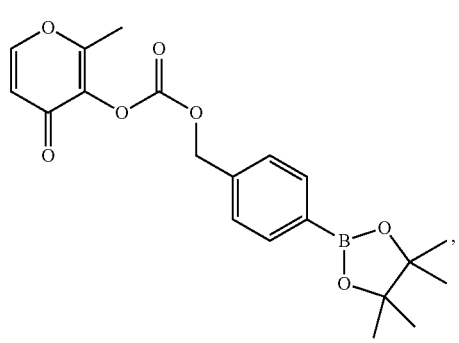 [SMILES: Cc1occc(=O)c1OC(=O)OCc1ccc(B2OC(C)(C)C(C)(C)O2)cc1]
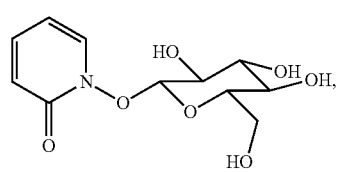 [SMILES: O=c1ccccn1OC1OC(CO)C(O)C(O)C1O]
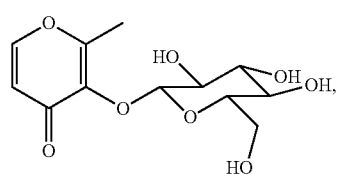 [SMILES: Cc1occc(=O)c1OC1OC(CO)C(O)C(O)C1O]
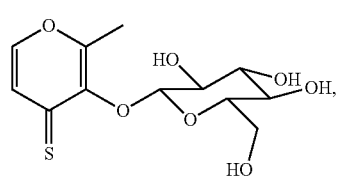 [SMILES: Cc1occc(=S)c1OC1OC(CO)C(O)C(O)C1O]
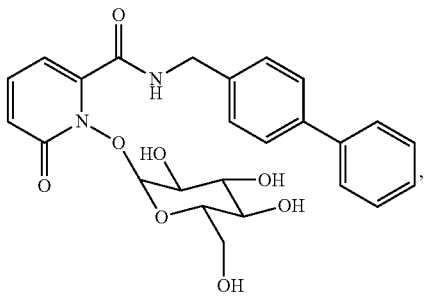 [SMILES: O=C(NCc1ccc(-c2ccccc2)cc1)c1cccc(=O)n1OC1OC(CO)C(O)C(O)C1O]
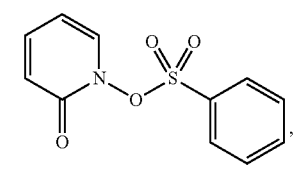 [SMILES: O=c1ccccn1OS(=O)(=O)c1ccccc1]
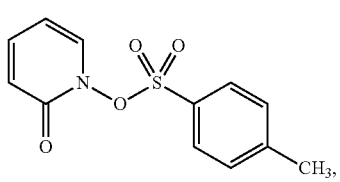 [SMILES: O=c1ccccn1OS(=O)(=O)c1ccc([N+](=O)[O-])cc1]
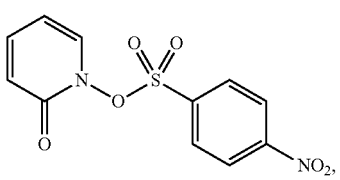
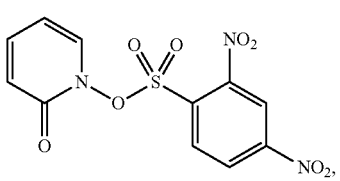 [SMILES: O=c1ccccn1OS(=O)(=O)c1ccc([N+](=O)[O-])cc1[N+](=O)[O-]]
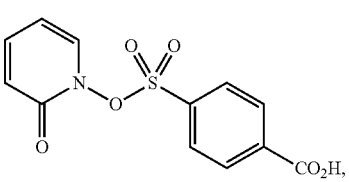 [SMILES: O=C(O)c1ccc(S(=O)(=O)On2ccccc2=O)cc1]
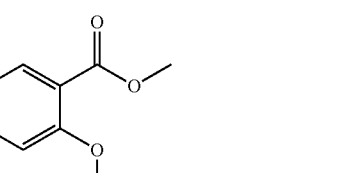
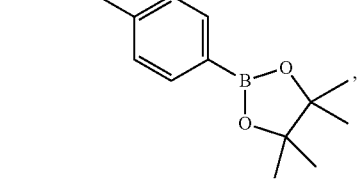

TABLE 1-continued

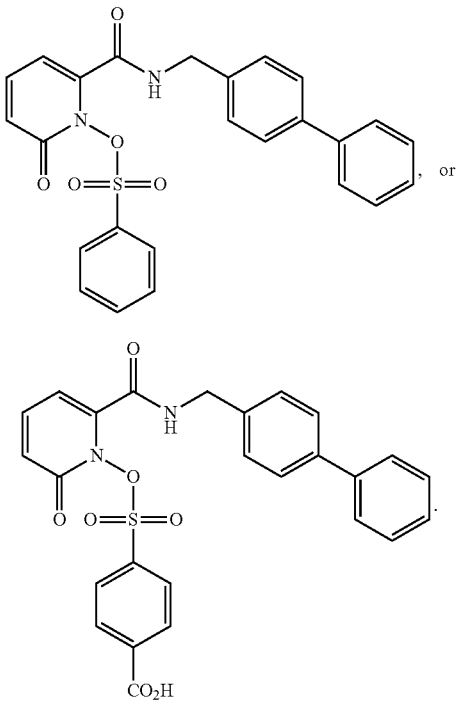

In some embodiments, a compound selected from the compounds listed above may be administered or used in a method selected from any of the methods described herein or included in any pharmaceutical composition provided herein.

III. Methods

In another aspect, a method of treating a disease in a patient in need of such treatment is provided. The method including administering a therapeutically effective amount of an oxidatively-sensitive prodrug to the patient. The oxidatively sensitive prodrug may be a compound of formula I, Ia, II, III, IIIa or IV (including embodiments thereof). In some embodiments, the oxidatively-sensitive prodrug forms a drug upon exposure to an oxidative compound. In some embodiments, the compound of formula I may form a drug having the formula A-OH. In some embodiments, the compound of formula II may form a drug having the formula B—OH. In some embodiments, the compound of formula III may form a drug having the formula C-$L^1$-$X^1$—H. In some embodiments, the compound of formula IIIa may form a drug having the formula C-$L^1$-$X^1$—H. $L^1$ and $X^1$ are as defined herein, including embodiments. In some embodiments, the compound of formula IV may form a drug having the formula D-OH.

In an embodiment, the oxidatively-sensitive prodrug includes a drug moiety covalently linked to an oxidatively-sensitive prodrug moiety. In one embodiment, the drug moiety includes a moiety known to be useful for treating the disease for which the prodrug is administered. In one embodiment, the drug moiety may form a drug known to be useful for treating the disease for which the prodrug is administered in combination with a chemical moiety remaining or formed after the prodrug moiety reacts with an oxidative compound. Known drugs useful in specific diseases are discussed in the Physicians' Desk Reference as being useful for treating the disease (hardcopy (e.g. 2011 Physican's Desk Reference ISBN-13: 9781563637803), electronic (e.g. 2011 PDR on CD-ROM), or online version). In some embodiments, a drug is known to be useful for treating a disease because the drug has been approved by the U.S. FDA, or an equivalent authority in a different country, for use in treating the disease. In another embodiment, following administration of the oxidatively-sensitive prodrug to the patient, the drug moiety forms a drug that is known to be useful for treating the disease for which the oxidatively-sensitive prodrug was administered to the patient. The drug may be known to be useful for a disease because it has been approved to treat that disease by the U.S. FDA or a corresponding authority in a different country. In a further embodiment, the method includes allowing the oxidatively-sensitive prodrug to react with a reactive oxygen species after administering the oxidatively-sensitive prodrug and thereby forming the drug from the drug moiety.

In some embodiments, the oxidatively-sensitive prodrug reacts with a reactive oxygen species at a location within the patient associated with the disease for which the prodrug is administered. In some embodiments, the drug moiety forms the drug primarily at a location associated with the disease. In some embodiments, primarily formed means more drug forms at a location associated with the disease than any other single location within the patient. In some embodiments, the drug forms from the drug moiety at the location associated with the occurrence of a stroke. In some embodiments, the drug forms from the drug moiety at a location of ischemia. In some embodiments, the drug forms from the drug moiety at a location of reperfusion injury. In some embodiments, the drug forms from the drug moiety at a location of stroke. In some embodiments, the drug forms from the drug moiety at a location of arthritis. In some embodiments, the drug forms from the drug moiety at a location of an inflammatory disease. In some embodiments, the drug forms from the drug moiety at a location of rheumatoid arthritis. In some embodiments, the drug forms from the drug moiety at a location of cancer. In some embodiments, the drug forms from the drug moiety at a location where a tumor is located. In some embodiments, the drug forms in the brain. The drug may form near the blood brain barrier.

In some embodiments, the method includes administration of the prodrug within 1 hour of a stroke. In some embodiments, the method includes administration of the prodrug within 2 hours of a stroke. In some embodiments, the method includes administration of the prodrug within 3 hours of a stroke. In some embodiments, the method includes administration of the prodrug within 5 hours of a stroke. In some embodiments, the method includes administration of the prodrug within 12 hours of a stroke. In some embodiments, the method includes administration of the prodrug within 24 hours of a stroke. In some embodiments, the method includes administration of the prodrug within 36 hour of a stroke. In some embodiments, the method includes administration of the prodrug within 48 hours of a stroke.

In some embodiments, the drug formed from the drug moiety of the oxidatively-sensitive prodrug includes or is a metal binding moiety. In some embodiments, the drug includes or is a zinc binding moiety.

In some embodiments, the oxidatively-sensitive prodrug may be a compound set forth herein (e.g. a compound of formula I, Ia, II, III, IIIa, or IV).

In a further embodiment, the method includes an oxidatively-sensitive prodrug, which is a compound of the formula I, Ia, II, III, IIIa, or IV above and embodiments thereof.

In another aspect, a method is provided for inhibiting a metalloprotein (e.g. inhibiting metalloprotein activity). The method may include contacting the metalloprotein with a metal binding moiety formed from the reaction of an oxidatively-sensitive prodrug and an oxidative compound (e.g. a reactive oxygen species). The oxidatively-sensitive prodrug may be a compound of formula I, Ia, II, III, IIIa, or IV (including embodiments thereof). In some embodiments, the oxidatively-sensitive prodrug forms a drug upon exposure to an oxidative compound (e.g. in combination with a chemical moiety as described above). In some embodiments, the compound of formula I may form a drug having the formula A-OH. In some embodiments, the compound of formula II may form a drug having the formula B—OH. In some embodiments, the compound of formula III may form a drug having the formula $C-L^1-X^1$—H. In some embodiments, the compound of formula IIIa may form a drug having the formula $C-L^1-X^1$—H. $L^1$ and $X^1$ are as defined herein, including embodiments. In some embodiments, the compound of formula IV may form a drug having the formula D-OH.

In further embodiments, the metalloprotein is a metalloenzyme. In some embodiments, the metalloprotein is a metalloprotease. In some embodiments, the metalloprotease is a matrix metalloprotease. In some embodiments, the metalloprotease is associated with stroke. In some embodiments, the metalloprotease is associated with breakdown of the blood brain barrier. In some embodiments, the metalloprotease is activated by an ROS. In some embodiments, the metalloprotease is MMP8. In some embodiments, the metalloprotease is MMP9. In some embodiments, the metalloprotease is MMP12. In some embodiments, the metalloprotein is within an organism. In some embodiments, the metalloprotein is within a human. In some embodiments, the metalloprotein is within a mammal. In some embodiments, the metalloprotein is within a cell. In some embodiments, the metalloprotein is in the extracellular matrix of an organism. In some embodiments, the metalloprotein is outside of a cell in an organism. In some embodiments, the metalloprotein is within a reaction vessel. In some embodiments, the reaction vessel is not an organism. In some embodiments, the reaction vessel is plastic, metal, a gel, paper, tissue, glass, an alloy, fiber, or a combination of two or more of the aforementioned substances. In some embodiments, the reaction vessel is inanimate (e.g. not an organism or cell).

In another aspect, a method is provided for inhibiting the activity of a metalloprotein, the method including contacting the metalloprotein with an oxidatively-sensitive prodrug The oxidatively-sensitive prodrug may be a compound of formula I, Ia, II, III, IIIa, or IV (including embodiments thereof). in the presence of an oxidative compound. In some embodiments, the oxidatively-sensitive prodrug forms a drug upon exposure to an oxidative compound. In some embodiments, the compound of formula I may form a drug having the formula A-OH. In some embodiments, the compound of formula II may form a drug having the formula B—OH. In some embodiments, the compound of formula III may form a drug having the formula $C-L^1-X^1$—H. In some embodiments, the compound of formula IIIa may form a drug having the formula $C-L^1-X^1$—H. $L^1$ and $X^1$ are as defined herein, including embodiments. In some embodiments, the compound of formula IV may form a drug having the formula D-OH. In some embodiment, the oxidative compound is an ROS. In some embodiments, the ROS is hydrogen peroxide. In some embodiments, the drug is a metal binding compound. In some embodiments, the metal binding compound is a zinc binding compound.

In some embodiments, a method selected from the methods described herein includes a compound selected from Table 1. In some embodiments, a method of treating a disease in a patient in need of such treatment, includes administering a therapeutically effective amount of an oxidatively-sensitive prodrug to the patient. In some embodiments, the oxidatively-sensitive prodrug is selected from the oxidatively-sensitive prodrugs described herein. In some embodiments, a method of inhibiting the activity of a protein includes contacting the protein with a drug formed from the reaction of an oxidatively-sensitive prodrug and a reactive oxygen species. In some embodiments, the protein is a metal binding protein and the drug is a metal binding compound.

In some embodiments of a method of treating a disease in a patient in need of such treatment, the method includes forming a drug. In some embodiments, a method includes forming a drug from a compound of formula (V). In some embodiments, a method includes forming a drug by contacting a compound of formula (V) with a glycosidase enzyme. In some embodiments, a method includes treating a disease associated with increased expression of one or more glycosidase enzymes.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. The term "treating," and conjugations thereof, include prevention of an injury, pathology, condition, or disease.

An "effective amount" is an amount sufficient to contribute to the treatment, prevention, or reduction of a symptom or symptoms of a disease. An "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a prodrug with a protein, an oxidatively-sensitive prodrug with a protein, an oxidatively-sensitive prodrug with a metalloprotein, an oxidatively-sensitive prodrug with an ROS, a prodrug comprising a carbohydrate moiety and a hydrolase capable of cleaving the bond between the carbohydrate moiety and the non-carbohydrate moiety of the prodrug, a drug with a protein.

As defined herein, the term "inhibition", "inhibit", "inhibiting" and the like in reference to a protein-inhibitor interaction means negatively affecting (e.g. decreasing) the activity or function of the protein (e.g. a metalloprotein, metalloenzyme, metalloprotease) relative to the activity or function of the protein in the absence of the inhibitor. Thus, inhibition includes, at least in part, partially or totally blocking stimulation, decreasing, preventing, or delaying activation, or inactivating, desensitizing, or down-regulating signal transduction or enzymatic activity. Similarly an "inhibitor" is a compound that inhibits metalloenzyme activity, e.g., by binding, partially or totally block stimulation, decrease, prevent, or delay activation, or inactivate, desensitize, or down-regulate signal transduction or enzymatic activity.

"Patient" or "subject in need thereof" refers to a living organism suffering from or prone to a condition that can be treated by administration of a pharmaceutical composition as provided herein. Non-limiting examples include humans, other mammals and other non-mammalian animals.

"Disease" or "condition" refer to a state of being or health status of a patient or subject capable of being treated with the compounds or methods provided herein. In some embodiments, the disease is a disease related to (e.g. caused by) an oxidative compound such as reactive oxygen species (e.g. Alzheimer's disease, Parkinson's disease, osteoporosis, inflammatory diseases, osteoarthritis, rheumatoid arthritis, stroke, aneurysm, brain aneurysm, cerebral aneurysm, brain attack, cerebrovascular accident, ischemia, thrombosis, arterial embolism, hemorrhage, transient ischemic attack, embolism, systemic hypoperfusion, venous thrombosis, arthritis, reperfusion injury, acne, eczema, rosacea, sun damage, or wrinkles.). Examples of diseases, disorders, or conditions include, but are not limited to, cancer, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, migraine headaches, stroke, aneurysm, brain aneurysm, cerebral aneurysm, brain attack, cerebrovascular accident, ischemia, thrombosis, arterial embolism, hemorrhage, transient ischemic attack, anemia, embolism, systemic hypoperfusion, venous thrombosis, arthritis, reperfusion injury, skin diseases or conditions, acne, acne vulgaris, keratosis pilaris, acute, promyelocytic leukemia, baldness, acne rosacea, harlequin ichthyosis, xeroderma pigmentosum, keratoses, neuroblastoma, fibrodysplasia ossificans progressive, eczema, rosacea, sun damage, wrinkles, or cosmetic conditions. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "autoimmune disease" refers to a disease or condition in which a subject's immune system irregularly responds to one or more components (e.g. biomolecule, protein, cell, tissue, organ, etc.) of the subject. In some embodiments, an autoimmune disease is a condition in which the subject's immune system irregularly reacts to one or more components of the subject as if such components were not self. Exemplary autoimmune diseases that may be treated with a compound or method provided herein include Acute Disseminated Encephalomyelitis (ADEM), Acute necrotizing hemorrhagic leukoencephalitis, Addison's disease, Agammaglobulinemia, Asthma, Allergic asthma, Allergic rhinitis, Alopecia areata, Amyloidosis, Ankylosing spondylitis, Anti-GBM/Anti-TBM nephritis, Antiphospholipid syndrome (APS), Arthritis, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Bullous pemphigoid, Cardiomyopathy, Castleman disease, Celiac sprue, Chagas disease, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Graves' disease, Grave's ophthalmopathy, Guillain-Barre syndrome, Hashimoto's encephalitis, Hashimoto's thyroiditis, Hemolytic anemia, Henoch-Schonlein purpura, Herpes gestationis, Hypogammaglobulinemia, Ichthyosis, Idiopathic thrombocytopenic purpura (ITP), IgA nephropathy, IgG4-related sclerosing disease, Immunoregulatory lipoproteins, Inclusion body myositis, Inflammatory bowel disease, Insulin-dependent diabetes (type 1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic, arthritis, Idiopathic pulmonary fibrosis, Pyoderma gangrenous, Pure red cell aplasia, Raynauds phenomenon, Reflex sympathetic dystrophy, Reiter's syndrome, Relapsing polychondritis, Restless legs syndrome, Retroperitoneal Fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, or Wegener's granulomatosis.

As used herein, the term "inflammatory disease" refers to any disease characterized by abnormal inflammation. Exemplary inflammatory diseases that may be treated with a compound or method provided herein include arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, or allergic asthma.

As used herein, the term "cardiovascular disease" refers to a disease or condition affecting the heart or blood vessels. In embodiments, cardiovascular disease includes diseases caused by or exacerbated by atherosclerosis. Exemplary cardiovascular diseases that may be treated with a compound or method provided herein include Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Ischemic heart disease, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, or myocardial infarction. In some embodiments, treating a cardiovascular disease includes treating a condition or symptom caused by a cardiovascular disease. A non-limiting example of such a treatment is treating complications due to a myocardial infarction, after the myocardial infarction has occurred.

As used herein, the term "cancer" refers to all types of cancer, neoplasm or malignant tumors found in mammals, including leukemia, carcinomas and sarcomas. Exemplary cancers that may be treated with a compound or method provided herein include cancer of the brain, breast, cervix, colon, head & neck, liver, kidney, lung, non-small cell lung, melanoma, mesothelioma, ovary, sarcoma, stomach, uterus or Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

In some embodiments, a disease or condition capable of being treated with the compounds or methods provided herein, include reactive oxygen species generating diseases or conditions, or oxidative compound generating diseases or conditions, either of which may include, for example, neurodegeneration, Alzheimer's disease, Parkinson's disease, osteoporosis, frailty, muscle frailty, inflammatory diseases, osteoarthritis, rheumatoid arthritis, asthma and rhinitis, dementia, delirium, cognitive impairment in depressed patients, stroke, aneurysm, brain aneurysm, cerebral aneurysm, brain attack, cerebrovascular accident, ischemia, thrombosis, arterial embolism, hemorrhage, transient ischemic attack, anemia, embolism, systemic hypoperfusion, venous thrombosis, arthritis, and reperfusion injury, acne, eczema, rosacea, sun damage, or wrinkles.

The term "cosmetic condition", as used herein, includes diseases or conditions that may be treated with a compound or method provided herein, including, but not limited to, eczema, rosacea, acne, sun damage, wrinkles, acne vulgaris, keratosis pilaris, acute, promyelocytic leukemia, baldness, acne rosacea, harlequin ichthyosis, xeroderma pigmentosum, or keratoses. The terms "cosmetic condition", "dermatological condition", and "skin condition" are used interchangeably.

IV. Pharmaceutical Compositions

In another aspect, the present invention provides pharmaceutical compositions comprising a compound provided herein (e.g., a compound of formula I, Ia, II, III, IIIa, IV, V, including the reactive oxygen species activatable prodrug, carbohydrate comprising prodrug, boronic acid comprising prodrug, boronic ester comprising prodrug, benzyl ether comprising prodrug, metal binding moiety containing prodrug, zinc binding moiety containing prodrug) in combination with a pharmaceutically acceptable carrier. The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine. and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound provided herein. In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. metalloprotein or metalloprotease), and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., stroke), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

V. Administration

The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The compounds described herein can be used in combination with one another, with other active agents known to be useful in treating a disease associated with generation of reactive oxygen species (e.g. stroke), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

In some embodiments, a pharmaceutical composition as described herein includes a compound selected from the compounds of Table 1.

EXAMPLES

The following examples are offered to illustrate, but not to limit the claimed invention.

Example 1

Exemplary Syntheses Related to Carbohydrate ZBGs s

General Methods.

All chemicals were purchased from commercial suppliers (Aldrich, Alfa Aesar, TCI, or Fisher) and used as is. β-glucosidase (EC 3.2.1.21) from almonds was purchased from Fluka. 1H and 13C NMR spectra were recorded on either a Varian FT-NMR instrument running at 400 MHz or 500 MHz, or a 500 MHz Jeol instrument at the Department of Chemistry and Biochemistry, University of California, San Diego. Mass spectrometry was performed at the Small Molecule Mass Spectrometry Facility in the Department of Chemistry and Biochemistry at the University of California, San Diego. Elemental analysis was performed by NuMega Resonance Labs, San Diego.

1-(2,3,4,6-Tetra-O-acetyl-β-D-glucopyranosyloxy)-pyridin-2(1H)-one (2a)

1-Hydroxypyridine-2(1H)-one (1, 0.50 g, 4.5 mmol) was dissolved in 10 mL of dichloromethane. To this was added 1-bromo-α-D-glucose tetraacetate (0.74 g, 1.8 mmol) and tetrabutylammonium bromide (0.58 g, 1.8 mmol). After heating to 35° C., 10 mL of 1.0 M NaOH was added. The heterogeneous reaction mixture was vigorously stirred for 3 h. After cooling to room temperature, the reaction was diluted with 20 mL of ethyl acetate then washed 2× with 1.0 M NaOH (20 mL) followed by water and brine. The organic layer was dried over $MgSO_4$, filtered, and concentrated for silica gel column purification in 2% MeOH in $CH_2Cl_2$ yielding an off-white solid in 29% yield (0.23 g). $^1$H NMR (500 MHz, $CDCl_3$) δ=7.51 (dd, $J_1$=6.9 Hz, $J_2$=1.8 Hz, 1H), 7.28 (dt, $J_1$=8.6 Hz, $J_2$=2.9 Hz, 1H), 6.60 (dd, $J_1$=9.8 Hz, $J_2$=1.8 Hz, 1H), 6.04 (dt, $J_1$=6.9 Hz, $J_2$=1.7 Hz, 1H), 5.29 (t, J=9.2 Hz, 1H), 5.21 (d, J=8.6 Hz, 1H), 5.16 (t, J=9.8 Hz, 1H), 5.09 (t, J=9.8 Hz, 1H), 4.26 (dd, $J_1$=12.6 Hz, $J_2$=5.2 Hz, 1H, CHCHaHbOAc), 4.09 (dd, $J_1$=12.1H, $J_2$=2.3 Hz, 1H, CHCHaHbOAc), 3.68 (dq, $J_1$=10.3 Hz, $J_2$=2.3 Hz, 1H, CHCHaHbOAc), 2.16 (s, 3H), 2.02 (s, 3H), 2.00 (s, 6H). 13C NMR (125 MHz, CDCl3) δ=170.5, 170.1, 169.9, 169.5, 157.9, 139.3, 137.8, 122.8, 104.3, 103.5, 77.5, 72.3, 69.3, 68.0, 61.4, 20.7. ESI-MS(+): m/z 441.77[M+H]+, 464.06[M+Na]+.

1-Hydroxypyridin-2(1H)-one-β-D-glucopyranoside (2)

2a (0.21 g, 0.48 mmol) was dissolved in 10 mL of dry MeOH. To this was added 0.33 mL (1.42 mmol) of NaOMe (25% in MeOH). The reaction was left stirring for 3 h at room temperature before the addition of ~100 mg cation exchange resin (Biorad AG-50W-X8, H+ form) that was allowed to stir for an additional 10 min. The reaction mixture was filtered and the solvents were evaporated for column purification eluting with 10% MeOH in EtOAc. 2 was collected as a white solid in 50% yield (0.063 g, 0.23 mmol). 1H NMR (500 MHz, CD3OD) δ=7.97 (dd, J1=6.9 Hz, J2=2.3 Hz, 1H), 7.53 (dt, J1=8.6 Hz, 2.3 Hz, 1H), 6.67 (dd, J1=9.2 Hz, J2=1.7 Hz, 1H), 6.34 (dt, J1=6.9 Hz, J2=1.7 Hz, 1H), 4.99 (d, J=8.0 Hz, 1H), 3.81 (dd, J1=12.1 Hz, J2=1.7 Hz, 1H, CHCHaHbOH), 3.68 (dd, J1=12.0 Hz, J2=4.6 Hz, 1H, CHCHaHbOH), 3.44 (t, J=8.6 Hz, 1H), 3.37-3.30 (m, overlapping peaks, 3H). 13C NMR (125 MHz, CD3OD) δ=152.9, 140.6, 138.7, 120.9, 107.4, 106.2, 77.4, 76.2, 72.1, 69.2, 60.8. APCI-MS(+): m/z 273.94 [M+H]+. Anal. calcd for C11H15NO7: C, 48.35; H, 5.53; N, 5.13. Found: C, 47.95; H, 5.90; N, 4.86.

2-Methyl-4H-pyran-4-one-3-(2,3,4,6-tetra-O-acetyl-β-D-glucopyranoside) (4a)

The synthesis of 4a was accomplished following the same procedure as that for 2a using 3-hydroxy-2-methyl-4-pyrone (1.0 g, 7.9 mmol), 1-bromo-α-D-glucose tetraacetate (1.3 g, 3.2 mmol) and tetrabutylammonium bromide (1.02 g, 3.2 mmol) in 20 mL of CH2Cl2 and 20 mL of 1 M NaOH at 35° C. 4a was collected as an off white solid in 28% yield (0.401 g, 0.88 mmol). 1H NMR (500 MHz, CDCl3) δ=7.62 (d, J=5.7 Hz, 1H), 6.32 (d, J=5.8 Hz, 1H), 5.32 (d, J=8.1 Hz, 1H), 5.27 (t, J=9.2 Hz, 1H), 5.16 (t, J=8.0 Hz, 1H), 5.09 (t, J=9.8 Hz, 1H), 4.17 (dd, J1=12.0 Hz, J2=4.6 Hz, 1H, CHCHaHbOAc), 4.10 (dd, J1=12.6H, J2=2.3 Hz, 1H, CHCHaHbOAc), dq (3.63, J1=10.4 Hz, J2=1.7 Hz, 1H, CHCHaHbOAc), 2.29 (s, 3H, ArCH3), 2.11 (s, 3H), 2.02 (s, 3H), 2.01 (s, 3H), 2.00 (s, 3H). 13C NMR (100 MHz, CDCl3) δ=173.6, 170.4, 170.1, 170.0, 169.5, 161.2, 153.7, 141.2, 117.2, 99.3, 72.4, 71.7, 71.2, 68.3, 61.5, 20.8, 20.6, 15.2. ESIMS(+): m/z 457.00 [M+H]+, 479.15 [M+Na]+.

2-Methyl-4H-pyran-4-one-3-β-D-glucopyranoside (4).

The synthesis of 4 was accomplished following the procedure for the synthesis of 2 using 0.15 g (0.33 mmol) of 4a and 0.23 mL (0.99 mmol) of NaOMe (25% in MeOH) in 10 mL of dry MeOH. 4 was collected as a white solid in 95% yield (0.90 g, 0.31 mmol). 1H NMR (500 MHz, CD3OD) δ=7.99 (d, J=5.2 Hz, 1H), 6.43 (d, J=5.7 Hz, 1H), 4.79 (d, J=7.5 Hz, 1H), 3.81 (dd, J1=12.0 Hz, J2=2.3 Hz, 1H, CHCHaHbOH), 3.65 (dd, J1=12.1H, J2=5.2 Hz, 1H, CHCHaHbOH), 3.39 (t, J=9.2 Hz, 1H), 3.36 (t, J=8.6 Hz, 1H), 3.32 (t, J=9.2 Hz, 1H), 3.23 (m, 1H, CHCHaHbOH), 2.45 (s, 3H, ArCH3). 13C NMR (125 MHz, CD3OD) δ=175.9, 163.3, 155.9, 142.3, 116.0, 104.1, 77.2, 76.7, 74.1, 69.7, 61.2, 14.6. ESI-MS(+): m/z 288.85 [M+H]+, 311.03 [M+Na]+. HRMS calcd for C12H16O8Na: 311.0737. Found: 311.0742. Anal. calcd for C12H16O8Na.H2O: C, 43.77; H, 5.51. Found: C, 44.08; H, 5.58.

2-Methyl-4H-pyran-4-thione-3-(2,3,4,6-tetra-O-acetyl-β-D-glucopyranoside) (6a)

4a (0.20 g, 0.43 mmol) was dissolved in 15 mL of benzene and heated to 80° C. To this was added P4S10 (0.07 g, 0.16 mmol) and hexamethyldisilyloxane (0.30 mL, 1.43 mmol). The reaction was heated to reflux for 45 min. After cooling to room temperature the reaction was filtered and concentrated for column purification in 1% MeOH in CH2Cl2 yielding 6a as an orange solid in 83% yield (0.17 g, 0.36 mmol). 1H NMR (500 MHz, CDCl3) δ=7.40 (d, J=5.2 Hz, 1H), 7.15 (d, J=5.2 Hz, 1H), 5.52 (d, J=8.1 Hz, 1H), 5.30 (t, J=9.8 Hz, 1H), 5.24 (t, J=7.5 Hz, 1H), 5.11 (t, J=9.2 Hz, 1H), 4.18 (dd, J1=12.6 Hz, J2=4.6 Hz, 1H, CHCHaHbOAc), 4.12 (dd, J1=12.6H, J2=2.9 Hz, 1H, CHCHaHbOAc), 3.61 (dq, J1=12.1 Hz, J2=2.3 Hz, 1H, CHCHaHbOAc), 2.33 (s, 3H, ArCH3), 2.14 (s, 3H), 2.03 (s, 3H), 2.01 (s, 6H). 13C NMR (125 MHz, CDCl3) δ=193.4, 170.4, 170.1, 170.0, 169.5, 158.3, 149.1, 145.7, 128.9, 98.4, 72.3, 71.7, 71.1, 68.4, 61.4, 21.1, 20.6, 15.8. ESI-MS(+): m/z 472.63 [M+H]+, 494.94 [M+Na]+.

2-Methyl-4H-pyran-4-thione-3-β-D-glucopyranoside (6)

The synthesis of 6 was accomplished following the procedure for the synthesis of 2 using 0.16 g (0.34 mmol) of 6a and 0.23 mL (1.0 mmol) of NaOMe (25% in MeOH) in 10 mL of dry MeOH. 6 was collected as an orange solid in 35% yield (0.035 g, >98% pure by HPLC analysis). 1H NMR (500 MHz, CD3OD) δ=7.76 (d, J=5.2 Hz, 1H), 7.23 (d, J=5.2 Hz, 1H), 5.00 (d, J=8.1 Hz, 1H), 3.82 (dd, J1=12.1 Hz, J2=2.3 Hz, 1H, CHCHaHbOH), 3.64 (dd, J1=12.1 Hz, J2=5.7 Hz, 1H, CHCHaHbOH), 3.47 (t, J=8.1 Hz, 1H), 3.40 (t, J=9.2 Hz, 1H), 3.31 (t, J=9.7 Hz, 1H), 3.21 (dq, J1=9.8 Hz, J2=2.3 Hz, 1H, CHCHaHbOH), 3.12 (s, 3H, ArCH3). 13C NMR (125

MHz, CD3OD) δ=193.7, 159.3, 150.2, 147.3, 127.8, 102.8, 77.0, 76.5, 74.4, 69.6, 67.6, 61.2, 15.2. ESI-MS(+): m/z 304.78 [M+H]+, 326.96 [M+Na]+. HRMS calcd for C12H16O7SNa: 327.0509. Found: 327.0508. Anal. calcd for C12H16O7S.0.5H$_2$O: C, 46.00; H, 5.47; S, 10.23. Found: C, 45.91; H, 5.79; S, 10.78.

N-(Biphenyl-4-ylmethyl)-1-hydroxy-6-oxo-1,6-dihydropyridine-2-carboxamide, 1,2-HOPO-2 (7)

This compound was prepared as previously reported (Agrawal, A.; Romero-Perez, D.; Jacobsen, J. A.; Villareal, F. J.; Cohen, S. M. ChemMedChem, 2008, 3, 812-820). 1H NMR (500 MHz, DMSO-d6) δ=9.32 (t, J=6.3 Hz, 1H, NH), 7.62 (m, 4H), 7.43 (m, 6H), 7.33 (t, J=7.5 Hz, 1H), 6.57 (dd, J1=9.2 Hz, J2=1.7 Hz, 1H), 6.32 (dd, J1=8.6 Hz, J2=1.8 Hz, 1H), 4.45 (d, J=5.7 Hz, 2H, NCH2). APCI-MS(−): m/z 319.09 [M−H]−. Anal. calcd for C19H16N2O3: C, 71.24; H, 5.03; N, 8.74. Found: C, 71.27; H, 5.40; N, 8.84.

N-(Biphenyl-4-ylmethyl)-1-(2,3,4,6-tetra-O-acetyl-β-D-glucopyranosyloxy)-1,6-dihydropyridin-6(1H)-one-2-carboxamide (8a)

In 10 mL of dry DMF was added 7 (0.10 g, 0.31 mmol), Cs2CO3 (0.30 g, 0.94 mmol), and acetobromo-α-D-glucose (0.14 g, 0.34 mmol). The reaction was left stirring at room temperature under N2 for 24 h. Following evaporation of the solvents, the crude product was brought up in EtOAc and washed once each with water and brine. The organic layer was dried over MgSO$_4$, filtered, and concentrated for purification on a silica gel column eluting with 1% MeOH in EtOAc to yield 8a as a white solid in 80% yield (0.16 g, 0.25 mmol). 1H NMR (500 MHz, CDCl3) δ=7.75 (d, J=8.5 Hz, 2H), 7.66 (d, J=8.6 Hz, 2H), 7.56 (d, J=8.0 Hz, 2H), 7.40 (t, J=7.5 Hz, 2H), 7.35 (t, J=5.8 Hz, 1H), 7.30 (t, J=6.3 Hz, 1H), 6.67 (dd, J1=9.2 Hz, J2=1.7 Hz, 1H), 6.56 (dd, J1=6.9 Hz, J2=1.8 Hz, 1H), 5.52 (d, J=8.6 Hz, 1H), 5.14 (t, J=9.5 Hz, 1H), 4.73 (dd, J1=14.4 Hz, J2=6.3 Hz, 1H, NHCHaHbAr), 4.68 (t, J=8.0 Hz, 1H), 4.57 (t, J=10.3 Hz, 1H), 4.55 (dd, J1=8.6 Hz, J2=2.9 Hz, 1H, NHCHaHbAr), 4.31 (dd, J1=12.6 Hz, J2=6.3 Hz, 1H, CHCHaHbOAc), 3.76 (dd, J1=12.6 Hz, J2=2.3 Hz, 1H, CHCHaHbOAc), 3.56 (dq, J1=8.1 Hz, J2=2.3 Hz, 1H, CHCHaHbOAc), 2.09 (s, 3H), 1.98 (s, 3H), 1.94 (s, 3H), 1.62 (s, 3H). 13C NMR (125 MHz, CDCl3) δ=170.9, 169.9, 169.8, 169.4, 159.3, 157.7, 143.3, 140.8, 140.7, 138.7, 136.8, 129.1, 128.8, 127.9, 127.4, 127.2, 124.1, 106.9, 101.1, 72.9, 71.6, 69.5, 68.2, 61.4, 43.8, 20.8, 20.6, 20.0. ESI-MS(+): m/z 650.92 [M+H]+, 673.22 [M+Na]+.

N-(Biphenyl-4-ylmethyl)-6-oxo-1-(β-D-glucopyranosyloxy)-1,6-dihydropyridine-2-carboxamide (8)

8a (0.086 g, 0.13 mmol) was dissolved in dry MeOH (3 mL) in an ice bath. After stirring at 0° C. for 10 min, 30 μL (0.13 mmol) of NaOMe (25% in MeOH) was added. The reaction was stopped after 1 h by the addition of a ~100 mg of cation exchange resin (Biorad AG-50W-X8, H+ form) which was allowed to stir for an additional 10 minutes. The crude product was filtered, concentrated, and purified via silica gel chromatography eluting with 0-1% MeOH in CH2Cl2 yielding a white solid in 79% yield (0.05 g, >93% pure by HPLC analysis). 1H NMR (500 MHz, CD3OD) δ=7.62 (m, 4H), 7.54 (d, J=6.9 Hz, 2H), 7.47 (d, J=8.0 Hz, 2H), 7.40 (t, J=8.0 Hz, 2H), 7.30 (t, J=7.5 Hz, 1H), 6.73 (dd, J1=9.2 Hz, J2=1.7 Hz, 1H), 6.51 (dd, J1=6.9 Hz, J2=1.7 Hz, 1H), 5.01 (d, J=8.0 Hz, 1H), 4.62 (d, J=14.9 Hz, 1H, NHCHaHbAr), 4.45 (d, J=14.9 Hz, 1H, NHCHaHbAr), 3.64 (dd, J1=12.0 Hz, 2.9 Hz, 1H, CHCHaHbOH), 3.37 (m, 2H), 3.28 (t, J=8.6 Hz, 1H), 3.17 (dq, J1=6.3 Hz, J2=2.3 Hz, 1H, CHCHaHbOH), 3.12 (t, J=9.8 Hz, 1H). 13C NMR (125 MHz, CD3OD) δ=161.9, 158.9, 144.6, 140.7, 140.5, 139.7, 136.8, 128.5, 126.9, 126.7, 122.7, 106.6, 105.8, 77.1, 76.3, 72.3, 69.8, 61.1, 47.2. ESIMS (+): m/z 504.97 [M+Na]+. HRMS calcd for C25H26N2O8Na: 505.1581. Found: 505.1576. Anal. calcd for C25H26N2O8.0.5Na.2CH$_3$OH: C, 58.11; H, 6.14; N, 5.02. Found: C, 57.74; H, 6.31; N, 5.10.

Example 2

Exemplary Syntheses Related to Sulfonate Ester ZBGs s

General Procedure for the Synthesis of Sulfonate Ester ZBGs. The ZBG compound was dissolved in pyridine on ice. To this was added the desired sulfonyl chloride. The reaction flask was removed from the ice bath and left stirring overnight under nitrogen while warming to room temperature. The pyridine was removed by rotary evaporation and the resulting oil was redissolved in dichloromethane and washed with 1 M HCl (~30 mL), water, and brine. The organic layer was dried over MgSO$_4$, filtered, and then concentrated via rotary evaporation. The product was purified on a silica gel column eluting with 1% MeOH in CH$_2$Cl$_2$ unless otherwise noted.

2-Oxopyridin-1(2H)-yl benzenesulfonate (PZBG-1a)

2-Hydroxypyridine-1-oxide (1.0 g, 9.1 mmol) was reacted with benzenesulfonyl chloride (1.27 mL, 10.0 mmol) in 75 mL of pyridine to afford PZBG-1a in 77% yield (1.75 g, 7.0 mmol). $^1$H NMR (500 MHz, CDCl$_3$) δ=8.02 (d, J=8.0 Hz, 2H), 7.75 (t, J=8.0 Hz, 1H), 7.59 (m, 3H), 7.28 (dt, J$_1$=6.9 Hz, J$_2$=2.3 Hz, 1H), 6.52 (d, J=9.8 Hz, 1H), 6.15 (t, J=7.5 Hz, 1H). $^{13}$C NMR (100 MHz, CDCl$_3$) δ=157.0, 139.7, 137.1, 136.0, 133.8, 130.0, 129.5, 123.4, 105.4. ESI-MS(+): m/z 252.01 [M+H]+, 273.95 [M+Na]$^+$. Anal. calcd for C$_{11}$H$_9$NO$_4$S: C, 52.58; H, 3.61; N, 5.57. Found: C, 52.21; H, 3.99; N, 5.44.

2-Oxopyridin-1(2H)-yl-4-methylbenzenesulfonate (PZBG-1b). 2-Hydroxypyridine-1-oxide (0.5 g, 4.5 mmol) was reacted with p-toluenesulfonyl chloride (2.57 g, 13.5 mmol) in 40 mL of pyridine to afford PZBG-1b in 89% yield (1.06 g, 4.0 mmol). $^1$H NMR (500 MHz, DMSO-d$_6$) δ=7.82 (d, J=8.6 Hz, 2H), 7.75 (dd, J$_1$=7.5 Hz, J$_2$=1.8 Hz, 1H), 7.49 (d, J=8 Hz, 2H), 7.41 (dt, J$_1$=7.5 Hz, J$_2$=1.7 Hz, 1H), 6.48 (dd, J$_1$=9.2 Hz, J$_2$=1.8 Hz, 1H), 6.21 (dt, J$_1$=7.5 Hz, J$_2$=1.8 Hz, 1H), 2.42 (s, 3H, CH$_3$). $^{13}$C NMR (100 MHz, CDCl$_3$) δ=156.6, 148.9, 141.2, 138.1, 131.1, 130.5, 130.0, 122.9, 106.1, 22.0. ESI-MS(+): m/z 266.10, [M+H]$^+$, 287.99 [M+Na]$^+$. Anal. calcd for C$_{12}$H$_{11}$NO$_4$S: C, 54.33; H, 4.18; N, 5.28. Found: C, 54.24; H, 4.35; N, 5.24.

2-Oxopyridin-1(2H)-yl 4-nitrobenzenesulfonate (PZBG-1c)

2-Hydroxypyridine-1-oxide (0.5 g, 4.5 mmol) was reacted with 4-nitrobenzenesulfonyl chloride (3.0 g, 13.5 mmol) in 40 mL of pyridine to afford PZBG-1c in 92% yield (1.23 g, 4.2 mmol). $^1$H NMR (500 MHz, CDCl$_3$) δ=8.42 (d, J=8.6 Hz, 2H), 8.23 (d, J=9.2 Hz, 2H), 7.65 (dd, J$_1$=7.5 Hz, J$_2$=1.8 Hz, 1H), 7.34 (dt, J$_1$=9.2 Hz, J$_2$=1.7 Hz, 1H), 6.52 (d, J=9.2 Hz, 1H), 6.22 (t, J=7.7 Hz, 1H). $^{13}$C NMR (100 MHz, DMSO) δ=156.6, 152.3, 141.6, 139.4, 138.3, 131.8, 125.6, 122.8, 106.4. ESI-MS(+): m/z 297.28 [M+H]$^+$, 319.02 [M+Na]$^+$.

2-Oxopyridin-1(2H)-yl 2,4-dinitrobenzenesulfonate (PZBG-1d). 2-Hydroxypyridine-1-oxide (0.5 g, 4.5 mmol) was reacted with 2,4-dinitrobenzenesulfonyl chloride (1.32 g, 5.0 mmol) in 40 mL of pyridine to afford PZBG-1d in 31% yield (0.48 g, 1.4 mmol). $^1$H NMR (500 MHz, CDCl$_3$) δ=8.96 (d, J=2.3 Hz, 1H), 8.42 (dd, J$_1$=9.2 Hz, J$_2$=2.3 Hz, 1H), 7.68 (dd, J$_1$=6.9 Hz, J$_2$=1.7 Hz, 1H), 7.50 (dt, J$_1$=7.5 Hz, J$_2$=2.3 Hz, 1H), 7.06 (d, J=8.1 Hz, 1H), 6.82 (dd, J$_1$=9.2 Hz, J$_2$=1.8 Hz, 1H), 6.35 (dt, J$_1$=6.9 Hz, J$_2$=1.8 Hz, 1H). $^{13}$C NMR (100 MHz, CDCl$_3$) δ=157.0, 155.6, 140.5, 135.1, 129.6, 124.0, 122.9, 116.0, 106.6.

4-(((2-Oxopyridin-1(2H)-yl)oxy)sulfonyl)benzoic acid (PZBG-1e). 2-Hydroxypyridine-1-oxide (0.21 g, 1.9 mmol) was reacted with 4-(chlorosulfonyl)benzoic acid (0.62 g, 2.8 mmol) in 5 mL pyridine. The solvent was evaporated, leaving a yellow oil. Addition of 5 mL of dichloromethane followed by the addition of 5 mL of ethyl acetate allowed for precipitation of PZBG-1e in 30% yield (0.17 g, 0.57 mmol). $^1$H NMR (400 MHz, DMSO) δ=8.18 (d, J=8.8 Hz, 2H), 8.08 (d, J=8.4 Hz), 7.88 (dd, J$_1$=7.6 Hz, J$_2$=2 Hz), 7.45 (td, J$_1$=8.2 Hz, J$_2$=2 Hz, 1H), 6.50 (dd, J$_1$=9.2 Hz, J$_2$=1.6 Hz, 1H), 6.26 (td, J$_1$=7 Hz, J$_2$=1.6 Hz, 1H). $^{13}$C NMR (100 MHz, CDCl$_3$) δ=166.5, 156.6, 141.5, 138.2, 137.9, 137.3, 131.2, 130.4, 122.8, 106.2. ESI-MS(−): m/z 294.26[M−H]$^-$. Anal. calcd. for C$_{12}$H$_9$NO$_6$S: C, 48.81; H, 3.07; N, 4.74. Found: C, 48.91; H, 3.37; N, 4.84.

2-Methyl-4-oxo-4H-pyran-3-yl benzenesulfonate (PZBG-2a)

3-Hydroxy-2-methyl-4H-pyran-4-one (1.0 g, 7.9 mmol) was reacted with benzenesulfonyl chloride (3.0 mL, 23.7 mmol) in 75 mL of pyridine to afford PZBG-2a in 71% yield (1.50 g, 5.6 mmol). $^1$H NMR (500 MHz, CDCl$_3$) δ=8.12 (d, J=8.6 Hz, 2H), 7.69 (t, J=7.5 Hz, 1H), 7.65 (d, J=5.8 Hz, 1H), 7.58 (t, J=8.0 Hz, 2H), 6.33 (d, J=5.2 Hz, 1H), 2.46 (s, 3H, CH$_3$). $^{13}$C NMR (100 MHz, CDCl3) δ=172.1, 163.1, 154.3, 138.4, 136.6, 134.7, 129.2, 129.0, 117.7, 16.3. ESI-MS(+): m/z 267.06 [M+H]$^+$, 289.03 [M+Na]$^+$.

2-Methyl-4-oxo-4H-pyran-3-yl 4-methylbenzenesulfonate (PZBG-2b). 3-Hydroxy-2-methyl-4H-pyran-4-one (0.5 g, 4.0 mmol) was reacted with p-toluenesulfonyl chloride (2.27 g, 11.9 mmol) in 40 mL of pyridine to afford PZBG-2b in 64% yield (0.71 g, 2.5 mmol). $^1$H NMR (500 MHz, CDCl$_3$) δ=7.99 (d, J=8 Hz, 2H), 7.64 (d, J=5.8 Hz, 1H), 7.37 (d, J=8 Hz, 2H), 6.34 (d, J=5.8 Hz, 1H), 2.46 (s, 3H, CH$_3$), 2.45 (s, 3H, CH$_3$). $^{13}$C NMR (100 MHz, CDCl$_3$) δ=127.2, 163.2, 154.2, 145.8, 138.4, 133.6, 129.8, 129.0, 117.7, 22.0, 16.3. ESI-MS(+): m/z 281.01 [M+H]$^+$, 303.03 [M+Na]$^+$.

2-Methyl-4-oxo-4H-pyran-3-yl 4-nitrobenzenesulfonate (PZBG-2c). 3-Hydroxy-2-methyl-4H-pyran-4-one (0.5 g, 4.0 mmol) was reacted with 4-nitrobenzenesulfonyl chloride (0.88 g, 4.0 mmol) in 15 mL of pyridine to afford PZBG-2c in 58% yield (0.71 g, 2.3 mmol). $^1$H NMR (500 MHz, CDCl$_3$) δ=8.42 (d, J=9.2 Hz, 2H), 8.31 (d, J=9.2 Hz, 2H), 7.69 (d, J=5.7 Hz, 1H), 6.34 (d, J=5.8 Hz, 1H), 2.53 (s, 3H, CH$_3$). $^{13}$C NMR (100 MHz, CDCl$_3$) δ=171.8, 163.5, 154.6, 151.2, 142.3, 138.6, 130.4, 124.3, 117.6, 16.3. ESI-MS(+): m/z 312.06 [M+H]$^+$.

2-Methyl-4-oxo-4H-pyran-3-yl 2,4-dinitrobenzenesulfonate (PZBG-2d). 3-Hydroxy-2-methyl-4H-pyran-4-one (0.5 g, 4.0 mmol) was reacted with 2,4-dinitrobenzenesulfonyl chloride (1.58 g, 5.9 mmol) in 40 mL of pyridine to afford PZBG-2d in 28% yield (0.39 g, 1.1 mmol). $^1$H NMR (500 MHz, CDCl$_3$) δ=8.72 (d, J=2.3 Hz, 1H), 8.56 (dd, J$_1$=9.2 Hz, J$_2$=2.3 Hz, 1H), 8.44 (d, J=8.6 Hz, 1H), 7.71 (d, J=5.8 Hz, 1H), 6.31 (d, J=5.8 Hz, 1H), 2.53 (s, 3H, CH$_3$). $^{13}$C NMR (100 MHz, CDCl$_3$) δ=171.6, 163.3, 154.9, 139.3, 136.4, 133.8, 126.8, 120.5, 117.5, 16.1. ESI-MS(+): m/z 357.03 [M+H]$^+$, 378.99 [M+Na]$^+$.

1,2-Dimethyl-4-oxo-1,4-dihydropyridin-3-yl benzenesulfonate (PZBG-3a). 3-Hydroxy-1,2-dimethylpyridin-4(1H)-one (0.5 g, 3.6 mmol) was reacted with benzenesulfonyl chloride (0.51 mL, 4.0 mmol) in 40 mL of pyridine to afford PZBG-3a in 43% yield (0.43 g, 1.5 mmol). $^1$H NMR (500 MHz, CDCl$_3$) δ=8.19 (d, J=6.9 Hz, 2H), 7.66 (t, J=7.5 Hz, 1H), 7.57 (t, J=7.5 Hz, 2H), 7.23 (d, J=8 Hz, 1H), 6.34 (d, J=8.1 Hz, 1H), 3.63 (s, 3H, NCH$_3$), 2.49 (s, 3H, CH$_3$). $^{13}$C NMR (100 MHz, CDCl$_3$) δ=171.3, 144.8, 140.7, 139.9, 137.3, 134.3, 129.0, 128.9, 118.3, 41.8, 14.7. ESI-MS(+): m/z 280.09 [M+H]$^+$.

1,2-Dimethyl-4-oxo-1,4-dihydropyridin-3-yl 4-methylbenzenesulfonate (PZBG-3b). 3-Hydroxy-1,2-dimethylpyridin-4(1H)-one (0.2 g, 1.4 mmol) was reacted with p-toluenesulfonyl chloride (0.82 g, 4.3 mmol) in 10 mL of pyridine to afford PZBG-3b in 86% yield (0.35 g, 1.2 mmol). $^1$H NMR (500 MHz, CDCl$_3$) δ=7.99 (d, J=8.4 Hz, 2H), 7.40 (d, J=7.6 Hz, 1H), 7.33 (d, J=8 Hz, 2H), 6.40 (d, J=7.2 Hz, 1H), 3.64 (s, 3H), 2.42 (s, 3H), 2.41 (s, 3H). $^{13}$C NMR (100 MHz, CDCl$_3$) δ=170.71, 145.67, 145.54, 141.48, 134.07, 129.72, 128.96, 126.07, 117.53, 42.25, 22.00, 14.7. ESI-MS(+): m/z 294.05 [M+H]$^+$, 315.97 [M+Na]$^+$.

1,2-Dimethyl-4-oxo-1,4-dihydropyridin-3-yl 4-nitrobenzenesulfonate (PZBG-3c). 3-Hydroxy-1,2-dimethylpyridin-4(1H)-one (0.2 g, 1.5 mmol) was reacted with 4-nitrobenzenesulfonyl chloride (0.488 g, 2.2 mmol) in 10 mL of pyridine to afford PZBG-3c in 50% yield (0.23 g, 0.7 mmol). $^1$H NMR (400 MHz, CDCl$_3$) δ=8.41-8.34 (m, 4H), 7.26 (d, J=7.6 Hz, 1H), 6.33 (d, J=7.6 Hz, 1H), 3.67 (s, 3H), 2.53 (s, 3H). $^{13}$C NMR (100 MHz, CDCl$_3$) δ=170.9, 150.9, 144.9, 143.2, 140.9, 140.1, 130.4, 124.0, 118.4, 41.9, 14.6. ESI-MS(+): m/z 325.11 [M+H]$^+$, 346.96 [M+Na]$^+$.

1,2-Dimethyl-4-oxo-1,4-dihydropyridin-3-yl 2,4-dinitrobenzenesulfonate (PZBG-3d). 3-Hydroxy-1,2-dimethylpyridin-4(1H)-one (0.10 g, 0.73 mmol) was reacted with 2,4-dinitrobenzenesulfonyl chloride (0.3 g, 1.1 mmol) in 10 mL of pyridine to afford PZBG-3d in 23% yield (0.07 g, 0.2 mmol). $^1$H NMR (400 MHz, CDCl$_3$) δ=8.83 (d, J=2.8 Hz 1H), 8.37 (dd, J$_1$=9.6 Hz, J$_2$=2.8 Hz, 1H), 7.82 (d, J=7.6 Hz, 1H), 7.03 (d, J=9.2 Hz, 1H), 6.25 (d, J=7.6 Hz, 1H), 3.68 (s, 3H), 2.31 (s, 3H). $^{13}$C NMR (100 MHz, CDCl$_3$) δ=169.35, 154.98, 144.00, 142.61, 141.42, 140.76, 138.54, 129.69, 122.24, 118.15, 116.78, 59.63, 13.29.

7-Oxocyclohepta-1,3,5-trien-1-yl benzenesulfonate (PZBG-4a). 2-Hydroxycyclohepta-2,4,6-trienone (0.2 g, 1.7 mmol) was reacted with benzenesulfonyl chloride (0.63 mL, 4.9 mmol) in 5 mL of pyridine to afford PZBG-4a in 76% yield (0.33 g, 1.3 mmol). $^1$H NMR (400 MHz, DMSO) δ=7.95 (d, J=7.6 Hz, 2H), 7.80 (t, J=7.6 Hz, 1H), 7.67 (t, J=8 Hz, 2H), 7.43-7.37 (m, 2H), 7.25 (t, J=8.4 Hz, 1H), 7.14-7.09 (m, 2H). $^{13}$C NMR (100 MHz, CDCl$_3$) δ=179.24, 154.79, 141.19, 138.21, 136.37, 136.33, 135.57, 131.96, 130.92, 130.27, 128.76. ESI-MS(+): m/z 262.97 [M+H]$^+$, 279.72 [M+NH$_4$]$^+$, 284.99 [M+Na]$^+$.

7-Oxocyclohepta-1,3,5-trien-1-yl 4-methylbenzenesulfonate (PZBG-4b). 2-Hydroxycyclohepta-2,4,6-trienone (0.2 g, 1.7 mmol) was reacted with p-toluenesulfonyl chloride (0.41 g, 2.0 mmol) in 10 mL of pyridine to afford PZBG-4b in 63% Yield (0.04 g, 0.1 mmol). $^1$H NMR (400 MHz, CDCl$_3$) δ=7.92 (d, J=8.4 Hz, 2H), 7.46 (d, J=9.2 Hz, 1H), 7.35 (d, J=8.4 Hz, 2H), 7.26-7.16 (m, 2H), 7.13-7.06 (m, 1H), 6.98 (t, J=10 Hz, 1H), 2.45 (s, 3H). $^{13}$C (125 MHz, CDCl$_3$) δ=179.41, 155.15, 145.50, 141.23, 136.32, 134.61, 133.41, 130.81, 130.00, 129.60, 128.59, 21.78. ESI-MS(+): m/z 277.21 [M+H]$^+$, 293.99 [M+NH$_4$]$^+$.

7-Oxocyclohepta-1,3,5-trien-1-yl 4-nitrobenzenesulfonate (PZBG-4c). 2-Hydroxycyclohepta-2,4,6-trienone (0.2 g, 1.7 mmol) was reacted with 4-nitrobenzenesulfonyl chloride (1.1 g, 4.9 mmol) in 5 mL of pyridine. Addition of 10 mL of water allowed for precipitation of PZBG-4c in 71% yield (0.38 g, 1.2 mmol) without the need for further purification. $^1$H NMR (400 MHz, DMSO) δ=8.45 (d, J=8.8 Hz, 2H), 8.22 (d, J=8.8 Hz, 2H), 7.52 (d, J=9.2 Hz, 1H), 7.46 (dd, J$_1$=10.2 Hz, J$_2$=3.6 Hz, 1H), 7.31 (dd, J$_1$=9.8 Hz, J$_2$=2 Hz, 1H), 7.15 (dd, J$_1$=10.6 Hz, J$_2$=3.6 Hz, 1H). $^{13}$C (100 MHz, CDCl$_3$) δ=179.09, 154.86, 151.50, 141.95, 141.27, 138.59, 136.87, 132.06, 131.48, 130.42, 125.42. ESI-MS(+): m/z 308.01 [M+H]$^+$, 324.73 [M+NH$_4$]$^+$ 7-Oxocyclohepta-1,3,5-trien-1-yl 2,4-dinitrobenzenesulfonate (PZBG-4d). 2-Hydroxycyclohepta-2,4,6-trienone (0.2 g, 1.7 mmol) was reacted with 2,4-dinitrobenzenesulfonyl chloride (0.54 g, 2.0 mmol) in 10 mL of pyridine to afford PZBG-4d in 6% Yield (0.04 g, 0.1 mmol). $^1$H NMR (400 MHz, DMSO) δ=9.00 (d, J=2.4 Hz 1H), 8.66 (dd, J$_1$=8.8 Hz, J$_2$=2.4 Hz, 1H), 8.38 (d, J=8.8 Hz 1H), 7.66 (d, J=9.6 Hz 1H), 7.50 (td, J$_1$=8.4 Hz, J$_2$=3.6 Hz, J$_3$=1.2 Hz, 1H), 7.35 (td, J$_1$=8.4 Hz, J$_2$=2.4 Hz, 1H), 7.20-7.15 (m, 2H). $^{13}$C (125 MHz, DMSO) δ=178.71, 155.30, 151.20, 147.90, 140.96, 138.83, 137.10, 134.58, 133.22, 131.93, 131.55, 127.92, 121.11. ESI-MS(+): m/z 353.15 [M+H]$^+$, 375.11 [M+Na]$^+$.

6-(([1,1'-Biphenyl]-4-ylmethyl)carbamoyl)-2-Oxopyridin-1(2H)-yl benzenesulfonate (1a). 1,2-HOPO-2 was prepared as previously reported [38]. In a 10 mL round bottom flask was dissolved 0.05 g (0.16 mmol) of 1,2-HOPO-2 in 3 mL of pyridine. To this was added 60 µL (0.5 mmol) of benzenesulfonyl chloride. The reaction was left stirring under N$_2$ at room temperature overnight. After 16 h, the solvent was evaporated to leave an orange oil which was dissolved in CH$_2$Cl$_2$ and washed once with 1 M HCl then brine. The organic layer was dried over MgSO$_4$, filtered and concentrated. Product was purified on a silica gel column eluting with 1% MeOH with CH$_2$Cl$_2$ to afford 1a in 67% yield (0.05 g, 0.1 mmol). $^1$H NMR (400 MHz, CDCl$_3$) δ=8.01 (d, J=7.6 Hz, 2H), 7.76 (t, J=7.6 Hz, 1H), 7.61 (m, 6H), 7.47 (m, 4H), 7.38-7.31 (m, 2H), 6.62 (d, J=8.0 Hz, 1H), 6.57 (d, J=6.4 Hz, 1H), 4.63 (d, J=5.2 Hz, 2H). $^{13}$C (100 MHz, CDCl$_3$) δ=159.2, 157.0, 142.7, 141.2, 140.8, 138.9, 136.0, 134.5, 129.9, 129.5, 129.1, 128.9, 127.8, 127.7, 127.3, 125.2, 107.6, 44.5. ESI-MS(+): m/z 461.13 [M+H]$^+$, 483.13 [M+Na]$^+$. Anal. calcd for C$_{25}$H$_{20}$N$_2$O$_5$S.0.5H$_2$O: C, 63.95; H, 4.51; N, 5.99. Found: C, 63.68; H, 5.14; N, 5.99.

4-(((6-(([1,1'-Biphenyl]-4-ylmethyl)carbamoyl)-2-Oxopyridin-1(2H)yl)oxy)sulfonyl)benzoic acid (1b). 1,2-HOPO-2 (0.20 g, 0.6 mmol) was dissolved in 5 mL of pyridine. To this was added 4-(chlorosulfonyl)benzoic acid (0.21 g, 1.0 mmol). The reaction was allowed to proceed overnight at room temperature. The solvent was evaporated and to the remaining oil was added 5 mL of dichloromethane followed by 5 mL of ethyl acetate, allowing for precipitation. The solid white product was filtered and collected in 14% yield (0.04 g, 0.08 mmol). $^1$H NMR (400 MHz, DMSO) δ=9.36 (t, J=5.6 Hz, 1H, NH), 8.18 (d, J=8.8 Hz, 2H), 8.06 (d, J=8.8 Hz, 2H), 7.66-7.61 (m, 4H), 7.53 (dd, J$_1$=7.8 Hz, J$_2$=2.8 Hz, 1H), 7.45 (t, J=7.6 Hz, 2H), 7.38-7.33 (m, 3H), 6.67 (dd, J$_1$=9.2 Hz, J$_2$=1.6 Hz, 1H), 6.47 (dd, J$_1$=6.4 Hz, J$_2$=1.2 Hz, 1H), 4.27 (d, J=5.6 Hz, 2H). $^{13}$C NMR (100 MHz, DMSO) δ=166.55, 159.45, 156.86, 143.21, 140.61, 140.54, 139.68, 138.26, 138.02, 137.61, 130.97, 130.09, 129.62, 128.73, 128.08, 127.33, 127.28, 124.19, 107.11, 43.05. ESI-MS(−): m/z 502.89 [M−H]$^+$. Anal. calcd for C$_{26}$H$_{20}$N$_2$O$_7$S. 0.25 HCl: C, 60.80; H, 3.97; N, 5.45. Found: C, 60.92; H, 4.30; N, 5.73.

2-(([1,1'-Biphenyl]-4-ylmethyl)carbamoyl)-4-oxo-4H-pyran-3-yl benzenesulfonate (2a). PY-2 was prepared as previously reported [38]. In a 50 mL round bottom flask was dissolved 0.20 g (0.6 mmol) of PY-2 in 15 mL of pyridine. To this was added 240 µL (1.8 mmol) of benzenesulfonyl chloride. The reaction was left stirring under N$_2$ at room temperature overnight. After 16 h, the solvent was evaporated to leave a red oil which was dissolved in CH$_2$Cl$_2$ and washed once with 1 M HCl then brine. The organic layer was dried over MgSO$_4$, filtered and concentrated. Product was precipitated from MeOH to afford 2a in 12% yield (0.03 g, 0.07 mmol). $^1$H NMR (400 MHz, CDCl$_3$) δ=8.10 (d, J=8.4 Hz, 2H), 7.80 (d, J=5.6 Hz, 1H), 7.71 (t, J=7.6 Hz, 1H), 7.61 (m, 6H), 7.47-7.36 (m, 6H), 6.47 (d, J=6.0 Hz, 1H), 4.67 (d, J=6.0 Hz, 2H). $^{13}$C NMR (100 MHz, CDCl$_3$) δ=172.7, 157.3, 154.8, 151.3, 141.2, 140.8, 139.2, 136.0, 135.8, 135.2, 129.3, 129.2, 129.1, 128.9, 127.8, 127.7, 127.3, 118.4, 44.3. ESI-MS(+): m/z 461.98 [M+H]$^+$, 484.02 [M+Na]$^+$.

Example 3

Exemplary Syntheses Related to Boronic Ester Compounds

Figure 18:
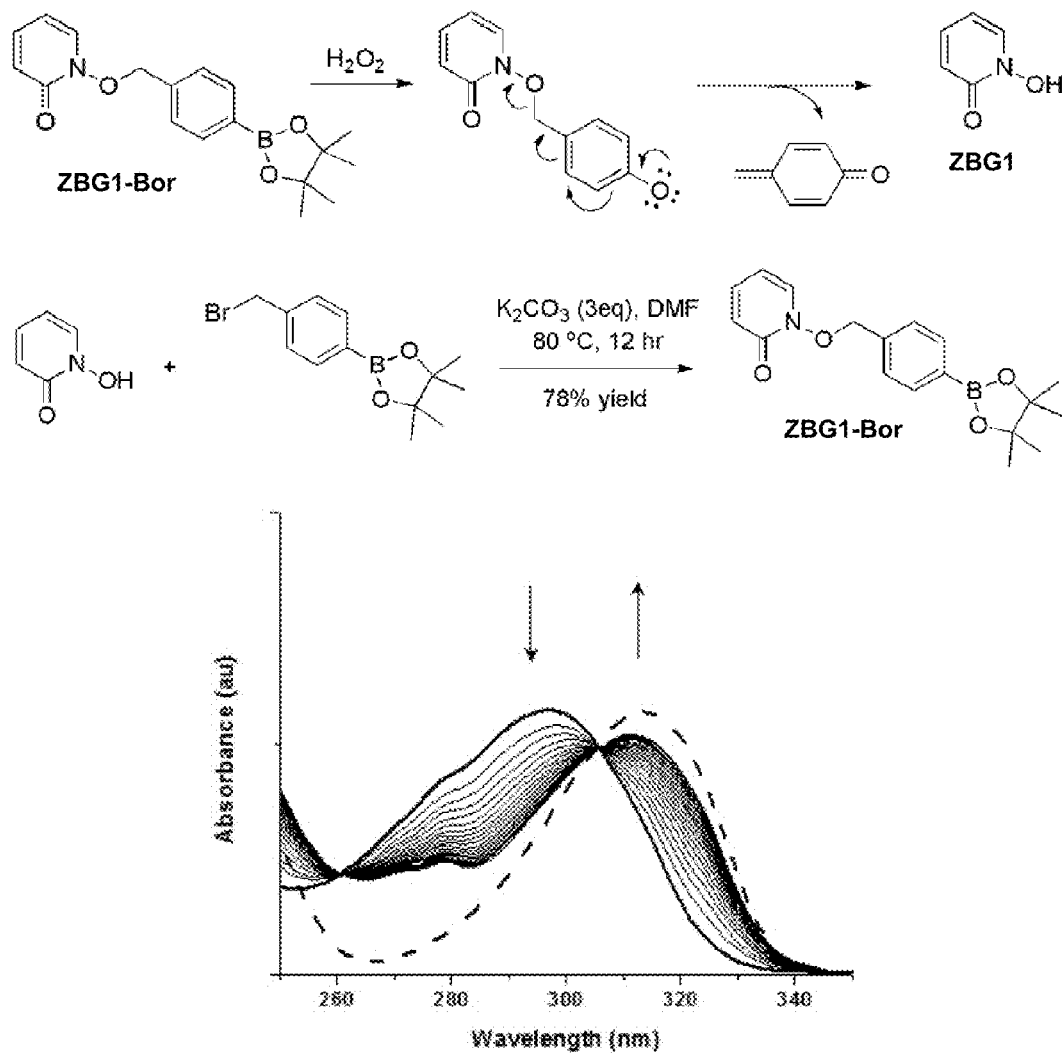
FIG. 18. Boronic Ester Protecting Strategy. A novel, self-immolative approach to the development of ROS-activated, boronic ester proinhibitors (oxidatively sensitive prodrugs comprising ROS-reactive boronic esters and metal binding moieties) (Top) has been discovered. The synthesis of protected B19 with a self-immolative linker and boronic ester trigger (Middle). UV-Visible spectroscopy (Bottom) shows clean conversion of B19 to ZBG1 upon exposure to $H_2O_2$.

The preparation of ZBGs with boronic ester protecting groups that can be selectively cleaved in the presence of H$_2$O$_2$ has been conducted. A representative synthesis of a ZBG with a boronic ester protecting group is shown in FIG. 18 (Top).

Methyl 2-((4-(4,4,5,5-tetramethyl-1,3,2-dioxaborolan-2-yl)benzyl)oxy)benzoate (B1). To 5 ml of acetonitrile was added methyl 2-hydroxybenzoate (85 µL, 0.66 mmol), K$_2$CO$_3$ (273 mg, 2.0 mmol), and 4-bromomethylphenyl boronic acid pinacol ester (217 mg, 0.73 mmol). The reaction was heated to 70° C. under nitrogen overnight. After removal of the solvent via rotary evaporation, the resulting oil was brought up in EtOAc and washed with a saturated sodium bicarbonate solution to remove starting materials. The organic layer was dried over MgSO$_4$, filtered and concentrated. The product was purified on a silica gel column eluting with 5% EtOAc in hexanes to yield B1 as a white solid in 77% yield (186 mg, 0.5 mmol). $^1$H NMR (400 MHz, CDCl$_3$) δ=7.85-7.81 (m, 3H), 7.49 (d, J=7.6 Hz, 2H), 7.40 (dt, J$_1$=8.4 Hz, J$_2$=1.8 Hz, 1H), 7.00-6.96 (m, 2H), 5.20 (s, 2H), 3.90 (s, 3H), 1.35 (s, 12H). $^{13}$C NMR (100 MHz, CDCl$_3$) δ=140.2, 135.2, 133.6, 132.0, 126.2, 121.0, 120.8, 114.0, 84.0, 70.7, 52.3, 25.1. ESI-MS(+): m/z 368.82 [M+H]$^+$, 385.69 [M+NH$_4$]$^+$.

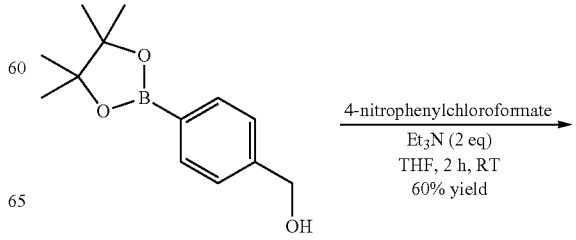

4-nitrophenylchloroformate
Et$_3$N (2 eq)
THF, 2 h, RT
60% yield

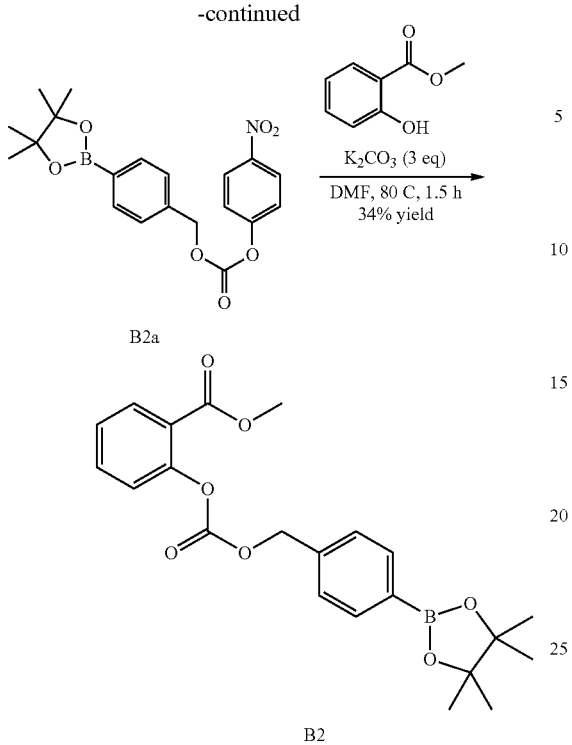

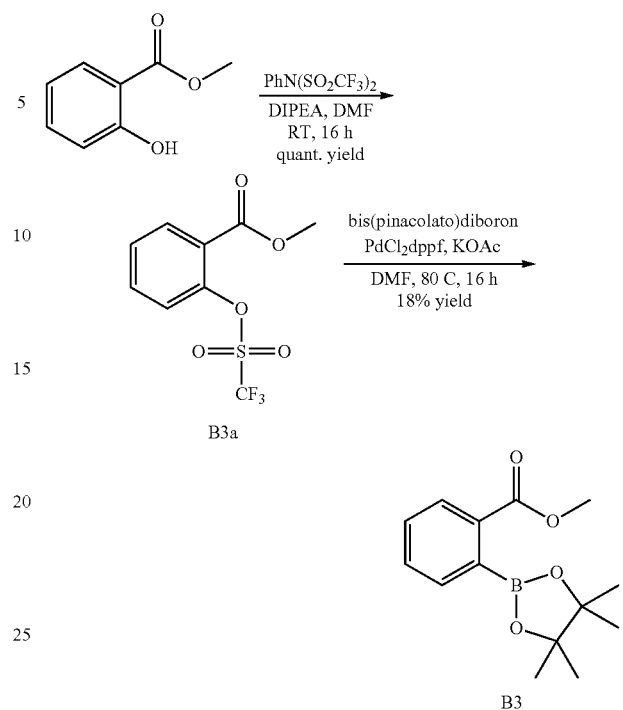

4-Nitrophenyl 4-(4,4,5,5-tetramethyl-1,3,2-dioxaborolan-2-yl)benzyl carbonate (B2a)

4-(Hydroxymethyl)phenylboronic acid pinacol ester (0.5 g, 2.1 mmol) was dissolved in 20 mL of dry THF. Triethylamine (0.6 mL, 4.3 mmol) was added followed by 4-nitrophenyl chloroformate (0.47 g, 2.3 mmol) and the reaction was allowed to stir at room temperature for 1 h. The reaction was diluted with EtOAc and washed with 1.0 M HCl followed by saturated $NaHCO_3$. The organic layer was dried over $MgSO_4$, filtered and concentrated. Compound B2a was purified on a silica gel column eluting with 5% EtOAc in hexanes to give 0.51 g (1.3 mmol, 60% yield) as a white solid. $^1$H NMR (400 MHz, $CDCl_3$) δ=8.25 (d, J=9.2 Hz, 2H), 7.85 (d, J=8.0 Hz, 2H), 7.43 (d, J=8.0 Hz, 2H), 7.36 (d, J=9.2 Hz, 2H), 5.31 (s, 2H), 1.35 (s, 12H). $^{13}$C NMR (100 MHz, $CDCl_3$) δ=155.7, 152.7, 145.6, 137.2, 135.4, 127.9, 125.5, 122.0, 84.2, 71.0, 25.1. ESI-MS(+): m/z 417.19 $[M+NH_4]^+$, 422.20 $[M+Na]^+$.

Methyl 2-((((4-(4,4,5,5-tetramethyl-1,3,2-dioxaborolan-2-yl)benzyl)oxy)carbonyl)oxy)benzoate (B2). In 5 mL of anhydrous DMF was dissolved methyl 2-hydroxybenzoate (42 μL, 0.32 mmol), B2a (100 mg, 0.25 mmol), and $K_2CO_3$ (104 mg, 0.75 mmol). The reaction was allowed to stir at 80° C. for 1.5 h. The solvent was removed by rotary evaporation and the residue was redissolved in EtOAc and washed three times with water and once with brine. The organic layer was dried over $MgSO_4$, filtered, and concentrated. Product was ran on a silica gel column and eluted with 10% EtOAc in hexanes yielding B2 in 34% yield (35 mg, 0.085 mmol). $^1$H NMR (400 MHz, $CDCl_3$) δ=8.02 (dd, $J_1$=7.8 Hz, $J_2$=1.7 Hz, 1H), 7.83 (d, J=8.0 Hz, 2H), 7.56 (td, $J_1$=7.7 Hz, $J_2$=1.4 Hz, 1H), 7.45 (d, J=7.6 Hz, 2H), 7.34 (td, $J_1$=7.7 Hz, $J_2$=1.2 Hz, 1H), 7.19 (dd, $J_1$=8.1 Hz, $J_2$=1.2 Hz, 1H), 5.32 (s, 2H), 3.76 (s, 3H), 1.35 (s, 12H). $^{13}$C NMR (100 MHz, $CDCl_3$)=153.6, 150.9, 138.0, 135.3, 134.2, 132.2, 127.8, 126.7, 125.5, 123.6, 123.4, 122.0, 84.2, 70.6, 52.5, 25.1. ESI-MS(+): m/z 429.94 $[M+NH_4]^+$, 434.94 $[M+Na]^+$.

Methyl 2-(((trifluoromethyl)sulfonyl)oxy)benzoate (B3a)

In 10 mL of anhydrous DMF was dissolved methyl 2-hydroxybenzoate (170 μL, 1.3 mmol), N-phenyl bis(trifluoromethanesulfonate) (0.56 g, 1.5 mmol), and DIPEA (680 μL, 3.9 mmol). The reaction was allowed to stir at room temperature overnight. The solvent was removed by rotary evaporation and the residue was redissolved in EtOAc and washed three times with water and once with brine. The organic layer was dried over $MgSO_4$, filtered, and concentrated. Product was ran on a silica gel column and eluted with 10% EtOAc in hexanes yielding B3a in quantitative yield (0.36 g, 1.3 mmol). $^1$H NMR (400 MHz, $CDCl_3$) δ=8.03 (dd, $J_1$=7.8 Hz, $J_2$=1.7 Hz, 1H), 7.58 (td, $J_1$=8.2 Hz, $J_2$=1.7 Hz, 1H), 7.42 (td, $J_1$=7.6 Hz, $J_2$=1.1 Hz, 1H), 7.28 (dd, $J_1$=7.8 Hz, $J_2$=2.0 Hz, 1H), 3.91 (s, 3H). $^{13}$C NMR (100 MHz, $CDCl_3$) δ=164.6, 148.5, 134.6, 132.3, 129.8, 128.7, 124.5, 117.3, 52.9. APCI-MS(+): m/z 284.88 $[M+H]^+$.

Methyl 2-(4,4,5,5-tetramethyl-1,3,2-dioxaborolan-2-yl)benzoate (B3). In 5 mL of anhydrous DMF was added B3a (150 mg, 0.5 mmol), $PdCl_2dppf \cdot CH_2Cl_2$ (40 mg, 0.05 mmol), bis(pinacolato)diboron (190 mg, 0.75 mmol) and KOAc (147 mg, 1.5 mmol). The reaction was allowed to stir at 80° C. for 16 h. Upon cooling to room temperature, the reaction was filtered twice through celite and the resulting filtrate was concentrated and purified on a silica gel column eluting with 5% EtOAc in hexanes yielding B3 in 18% yield (24 mg, 0.09 mmol). $^1$H NMR (400 MHz, $CDCl_3$) δ=7.93 (d, J=7.7 Hz, 1H), 7.50 (m, 2H), 7.40 (m, 1H), 3.91 (s, 3H), 1.42 (s, 12H). $^{13}$C NMR (100 MHz, $CDCl_3$) δ=133.8, 133.0, 132.5, 129.2, 128.9, 128.5, 84.4, 74.3, 25.6. ESI-MS(+): m/z 262.88 $[M+H]^+$.

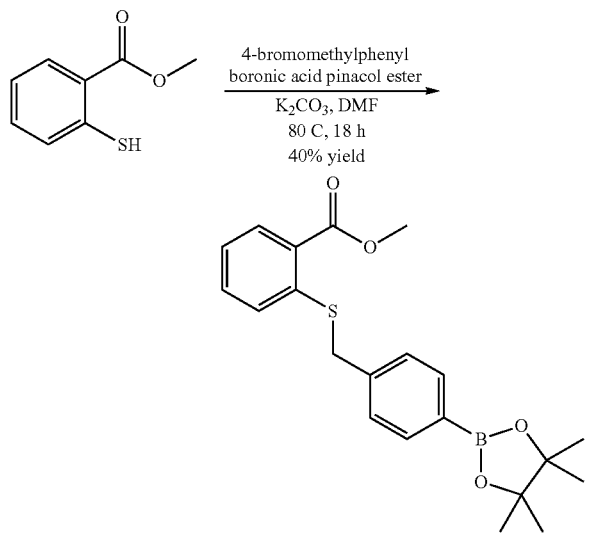

Methyl 2-((4-(4,4,5,5-tetramethyl-1,3,2-dioxaborolan-2-yl)benzyl)thio)benzoate (B4)

The synthesis of B4 was accomplished following the procedure outlined for B1 using methyl 2-mercaptobenzoate (0.32 g, 1.9 mmol), 4-bromomethylphenyl boronic acid pinacol ester (0.62 g, 2.1 mmol), and 780 mg of $K_2CO_3$ (5.7 mmol) in 8 mL of anhydrous DMF. B4 was collected as a white solid in 40% yield (0.29 g, 0.76 mmol). $^1$H NMR (400 MHz, CDCl$_3$) δ=7.95 (dd, $J_1$=7.9 Hz, $J_2$=1.4 Hz, 1H), 7.75 (d, J=8.1 Hz, 2H), 7.43 (d, J=8.1 Hz, 2H), 7.38 (td, $J_1$=7.2 Hz, $J_2$=1.6 Hz, 1H), 7.30 (dd, $J_1$=8.0 Hz, $J_2$=0.8 Hz, 1H), 7.15 (td, $J_1$=7.8 Hz, $J_2$=1.2 Hz, 1H), 4.17 (s, 2H), 3.90 (s, 3H), 1.34 (s, 12H). $^{13}$C (100 MHz, CDCl$_3$)=141.9, 139.7, 135.2, 132.6, 131.5, 128.6, 127.8, 126.3, 124.3, 84.0, 52.3, 37.6, 25.1. ESI-MS(+): m/z 384.87 [M+H]$^+$, 401.71 [M+NH$_4$]$^+$.

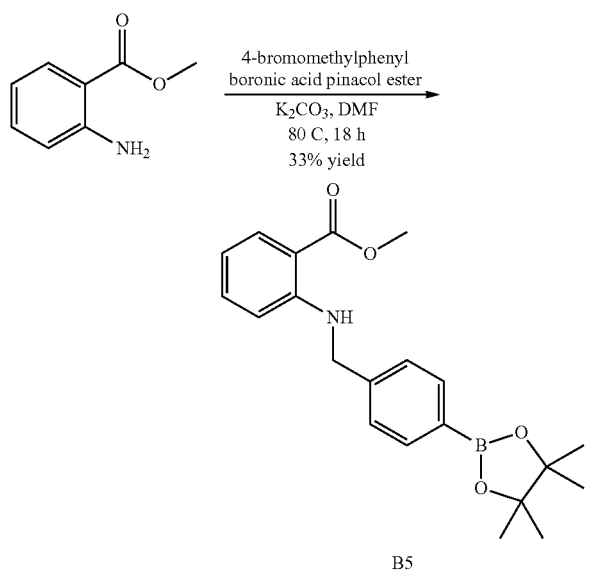

Methyl 2-((4-(4,4,5,5-tetramethyl-1,3,2-dioxaborolan-2-yl)benzyl)amino)benzoate (B5)

The synthesis of B5 was accomplished following the procedure outlined for B1 using methyl 2-aminobenzoate (86 μL, 0.6 mmol), 4-bromomethylphenyl boronic acid pinacol ester (0.22 g, 0.73 mmol), and $K_2CO_3$ (274 mg, 1.98 mmol) 5 mL of anhydrous DMF. B5 was collected in 33% (82 mg, 0.22 mmol) yield as a pale yellow solid. $^1$H NMR (400 MHz, CDCl$_3$) δ=8.20 (t, J=5.3 Hz, 1H, NH), 7.91 (dd, $J_1$=7.8 Hz, $J_2$=1.8 Hz, 1H), 7.78 (d, J=8.1 Hz, 2H), 7.35 (d, J=8.2 Hz, 2H), 7.26 (dt, $J_1$=7.2 Hz, $J_2$=1.6 Hz, 1H), 6.58 (m, 2H), 4.47 (d, J=5.8 Hz, 2H), 3.87 (s, 3H), 1.34 (s, 12H). $^{13}$C NMR (100 MHz, CDCl$_3$) δ=169.3, 151.3, 142.5, 135.4, 134.8, 131.8, 126.6, 115.1, 112.0, 110.5, 83.9, 51.7, 47.3, 25.1. ESI-MS(+): m/z 367.98 [M+H]$^+$.

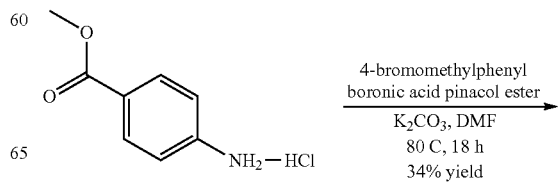

Methyl 4-((4-(4,4,5,5-tetramethyl-1,3,2-dioxaborolan-2-yl)benzyl)amino)benzoate (B6)

The synthesis of B6 was accomplished following the procedure outlined for B1 using methyl 4-aminobenzoate (75 mg, 0.5 mmol), 4-bromomethylphenyl boronic acid pinacol ester (0.15 g, 0.5 mmol), and $K_2CO_3$ (206 mg, 1.5 mmol) in 5 mL of anhydrous DMF.B6 was collected in 20% (38 mg, 0.1 mmol) yield as a pale yellow solid. $^1$H NMR (400 MHz, CDCl$_3$) δ=7.85 (d, J=7.0 Hz, 2H), 7.79 (d, J=8.0 Hz, 2H), 7.34 (d, J=8.0 Hz, 2H), 6.57 (d, J=8.8 Hz, 2H), 4.40 (s, 2H), 3.84 (s, 3H), 1.34 (s, 12H). $^{13}$C NMR (125 MHz, CDCl$_3$) δ=167.3, 151.7, 141.8, 135.4, 135.3, 131.6, 126.7, 118.8, 111.7, 83.9, 51.6, 47.8, 24.9. ESI-MS(+): m/z 368.02 [M+H]$^+$.

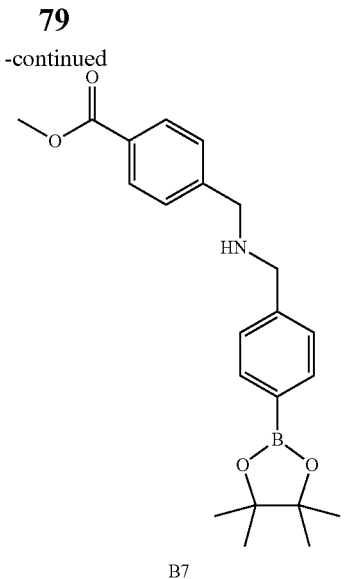

B7

Methyl 4-(((4-(4,4,5,5-tetramethyl-1,3,2-dioxaborolan-2-yl)benzyl)amino)methyl)benzoate (B7)

The synthesis of B7 was accomplished following the procedure outlined for B1 using methyl 4-(aminomethyl)benzoate hydrochloride (100 mg, 0.5 mmol), 4-bromomethylphenyl boronic acid pinacol ester (0.15 g, 0.5 mmol), and $K_2CO_3$ (207 mg, 1.5 mmol) in 7 mL of anhydrous DMF. The crude product was purified on a silica gel column eluting with 20% EtOAc in hexanes to give B7 in 34% (67 mg, 0.17 mmol) yield as a pale yellow solid. $^1$H NMR (400 MHz, $CDCl_3$) δ=8.01 (d, J=8.3 Hz, 2H), 7.78 (d, J=8.0 Hz, 2H), 7.40 (d, J=8.1 Hz, 2H), 7.34 (d, J=7.8 Hz, 2H), 3.91 (s, 3H), 3.83 (d, J=7.2 Hz, 4H), 1.35 (s, 12H). $^{13}$C NMR (100 MHz, $CDCl_3$) δ=167.3, 145.8, 143.4, 135.2, 130.0, 129.1, 128.3, 127.7, 84.0, 53.4, 52.8, 52.3, 25.1. ESI-MS(+): m/z 382.03 [M+H]$^+$.

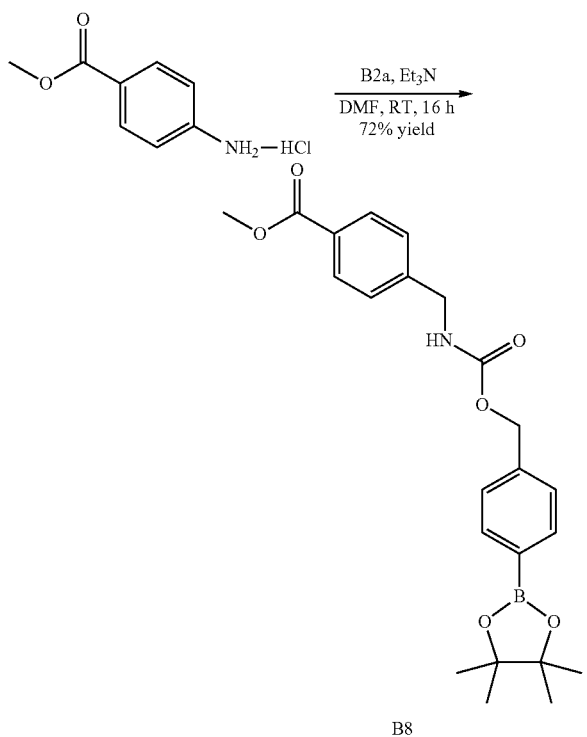

B8

Methyl 4(((((4-(4,4,5,5-tetramethyl-1,3,2-dioxaborolan-2-yl)benzyl)oxy)carbonyl)amino)methyl)benzoate (B8)

In 5 mL of anhydrous DMF was dissolved methyl 4-(aminomethyl)benzoate hydrochloride (65 mg, 0.32 mmol), B2a (100 mg, 0.25 mmol), and $Et_3N$ (105 μL, 0.75 mmol). The reaction was allowed to stir overnight at room temperature. The solvent was removed by rotary evaporation and the residue was redissolved in EtOAc and washed three times with water and once with brine. The organic layer was dried over $MgSO_4$, filtered, and concentrated. Product was ran on a silica gel column and eluted with 10% EtOAc in hexanes yielding B8 in 72% yield (77 mg, 0.18 mmol). $^1$H NMR (400 MHz, $CDCl_3$) δ=8.01 (d, J=7.3 Hz, 2H), 7.80 (d, J=7.5 Hz, 1H), 7.36-7.33 (m, 4H), 5.15 (s, 2H), 4.44 (d, J=6.1 Hz, 2H), 3.91 (s, 3H), 1.34 (s, 12H). $^{13}$C NMR (100 MHz, $CDCl_3$) δ=167.1, 156.6, 143.8, 139.5, 135.2, 130.2, 129.6, 127.2, 126.4, 84.1, 67.1, 52.4, 45.0, 25.1. ESI-MS(+): m/z 426.1 [M+H]$^+$, 443.08 [M+$NH_4$]$^+$.

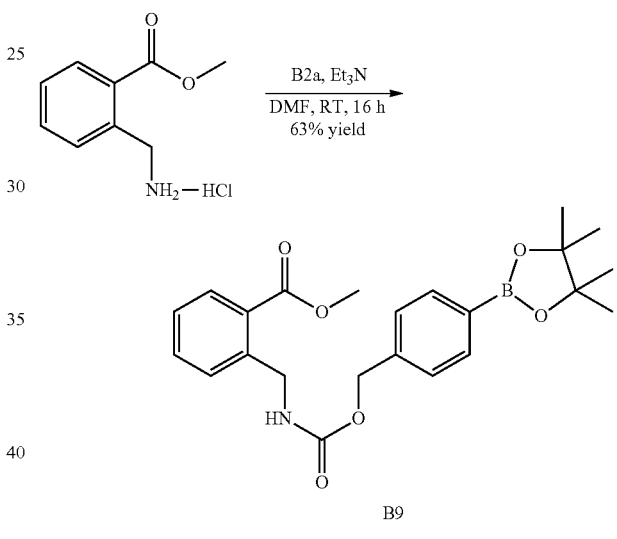

B9

Methyl 2-(((((4-(4,4,5,5-tetramethyl-1,3,2-dioxaborolan-2-yl)benzyl)oxy)carbonyl)amino) methyl) benzoate (B9)

In 5 mL of anhydrous DMF was dissolved 2-carbomethoxybenzylamine hydrochloride (65 mg, 0.32 mmol) and B2a (100 mg, 0.25 mmol) with triethylamine (105 μL, 0.75 mmol). The reaction was allowed to stir at room temperature for 16 h. The solvent was removed by rotary evaporation and the residue was redissolved in EtOAc and washed with a saturated solution of sodium bicarbonate. The organic layer was dried over $MgSO_4$, filtered, and concentrated for purification via silica gel column chromatography eluting with 8% EtOAc in hexanes. B9 was collected as a yellow oil in 63% yield (67 mg, 0.16 mmol). $^1$H NMR (400 MHz, $CDCl_3$) δ=7.9 (d, J=7.3 Hz, 1H), 7.77 (d, J=7.9 Hz, 2H), 7.57-7.46 (m, 2H), 7.36 (td, $J_1$=8.8 Hz, $J_2$=1.8 Hz, 1H), 7.32 (d, J=7.9 Hz, 2H), 5.9 (t, J=5.9 Hz, 1H, NH), 5.08 (s, 2H), 4.57 (d, J=6.7 Hz, 2H), 3.90 (s, 3H), 1.33 (s, 12H). $^{13}$C NMR (100 MHz, $CDCl_3$) δ=162.3, 157.0, 140.1, 139.6, 135.2, 133.3, 131.4, 128.2, 127.2, 126.4, 115.9, 84.2, 67.1, 52.6, 44.7, 25.1. ESI-MS(+): m/z 425.81 [M+H]$^+$, 442.72 [M+$NH_4$]$^+$.

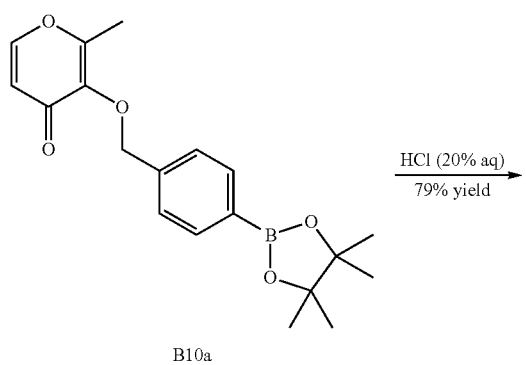

B10a

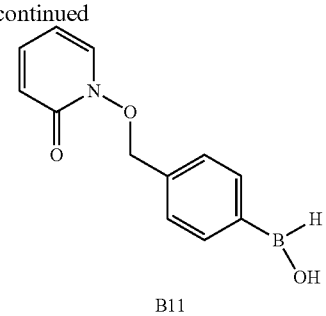

B11

(4-(((2-Oxopyridin-1(2H)-yl)oxy)methyl)phenyl)boronic acid (B11). 1-((4-(4,4,5,5-Tetramethyl-1,3,2-dioxaborolan-2-yl)benzyl)oxy)pyridin-2(1H)-one (B11a) was synthesized as previously described. 1 B11a (200 mg, 0.61 mmol) was dissolved in 20 mL of a 20% HCl aqueous solution and stirred vigorously for 3 h resulting in a thick, white slurry. The solids were filtered off and washed with a large amount of water yielding B11 in 77% yield (115 mg, 0.47 mmol) as a white solid. 1H NMR (400 MHz, DMSO) δ=7.79 (d, J=7.9 Hz, 2H), 7.74 (dd, J1=7.1 Hz, J2=2.0 Hz, 1H), 7.41 (d, J=7.8 Hz, 2H), 7.39 (td, J1=7.9 Hz, J2=2.4 Hz, 1H), 6.54 (dd, J1=9.2 Hz, J2=1.6 Hz, 1H), 6.11 (td, J1=8.4 Hz, J2=1.7 Hz, 1H), 5.18 (s, 2H). 13C NMR (100 MHz, CDCl3) δ=160.0, 140.2, 137.3, 134.1, 129.1, 121.3, 106.4, 78.7. ESI-MS (+): m/z 245.89 [M+H]+.

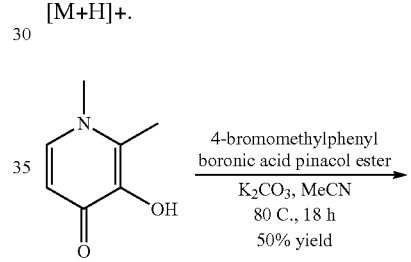

B10

(4-(((2-Methyl-4-oxo-4H-pyran-3-yl)oxy)methyl)phenyl)boronic acid B10)

2-Methyl-3-((4-(4,4,5,5-tetramethyl-1,3,2-dioxaborolan-2-yl)benzyl)oxy)-4H-pyran-4-one (B10a) was synthesized as previously described. ¹B10a (200 mg, 0.58 mmol) was dissolved in 20 mL of a 20% HCl aqueous solution and stirred vigorously for 3 h resulting in a thick, white slurry. The solids were filtered off and washed with a large amount of water yielding B10 in 79% (13 mg, 0.05 mmol) yield as a white solid. ¹H NMR (400 MHz, DMSO) δ=8.06 (s, 2H), 8.03 (dd, J₁=5.6 Hz, J₂=0.6 Hz, 1H), 7.76 (d, J=7.7 Hz, 2H), 7.33 (d, J=7.8 Hz, 2H), 6.35 (dd, J₁=5.6 Hz, J₂=0.6 Hz, 1H), 5.01 (s, 2H), 2.10 (s, 3H). ¹³C NMR (100 MHz, CDCl₃) δ=176.3, 161.7, 155.5, 143.6, 134.6, 133.9, 128.1, 116.3, 73.5, 13.8. ESI-MS(+): m/z 260.86 [M+H]⁺.

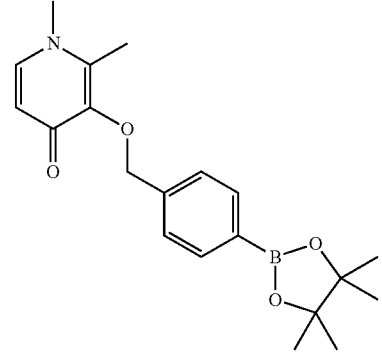

B12

1,2-Dimethyl-3-((4-(4,4,5,5-tetramethyl-1,3,2-dioxaborolan-2-yl)benzyl)oxy)pyridin-4(1H)-one (B12)

The synthesis of B12 was accomplished following the procedure outlined for B1 using 3-hydroxy-1,2-dimethylpyridin-4(1H)-one (80 mg, 0.54 mmol), 4-bromomethylphenyl boronic acid pinacol ester (180 mg, 0.59 mmol), and K₂CO₃ (223 mg, 1.6 mmol) in 8 mL of acetonitrile affording B12 in 50% yield (0.09 g, 0.26 mmol). ¹HNMR (400 MHz, CDCl₃) δ=7.70 (d, J=8.4 Hz, 2H), 7.36 (d, J=8.4 Hz, 2H), 7.11 (d, J=7.6 Hz, 1H), 6.27 (d, J=7.6 Hz, 1H), 5.18 (s, 2H), 3.44 (s, 3H), 2.02 (s, 3H), 1.29 (s, 12H). ¹³C NMR (100 MHz, CDCl₃)

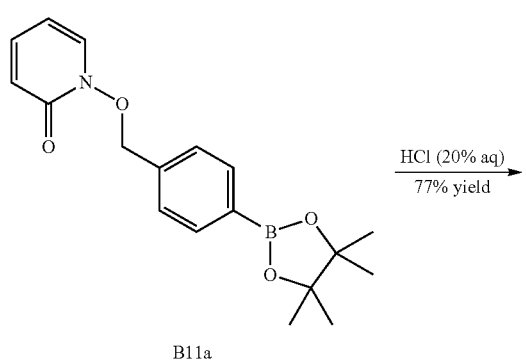

B11a

δ=173.55, 146.13, 141.63, 140.83, 139.19, 134.91, 128.46, 117.21, 84.05, 73.00, 41.80, 24.97, 13.15. ESI-MS(+): m/z 356.20 [M+H]+, 378.10 [M+Na]+.

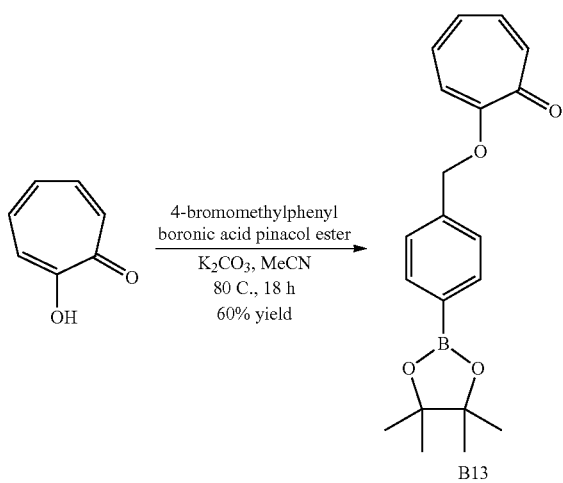

2-((4-(4,4,5,5-Tetramethyl-1,3,2-dioxaborolan-2-yl)benzyl)oxy)cyclohepta-2,4,6-trienone (B13)

The synthesis of B13 was accomplished following the procedure outlined for B1 using 2-hydroxycyclohepta-2,4,6-trienone (0.10 g, 0.82 mmol), bromomethylphenyl boronic acid pinacol ester (0.27 g, 0.90 mmol), and K$_2$CO$_3$ (340 mg, 2.46 mmol) in 10 mL of acetonitrile affording B13 in 60% yield (0.16 g, 0.48 mmol). $^1$H NMR (400 MHz, CDCl$_3$) δ=7.81 (d, J=8 Hz, 2H), 7.42 (d, J=8.4 Hz, 2H), 7.24-7.18 (m, 2H), 6.93 (td, J$_1$=9.6 Hz, J$_2$=1.2 Hz, 1H), 6.85-6.82 (m, 1H), 6.68 (d, J=9.6 Hz, 1H), 5.31 (s, 2H), 1.34 (s, 12H). $^{13}$C NMR (100 MHz, CDCl$_3$) δ=180.94, 164.48, 138.63, 137.62, 136.64, 135.41, 132.73, 128.50, 126.25, 115.09, 84.10, 70.96, 25.08. ESI-MS(+): m/z 338.82 [M+H]+.

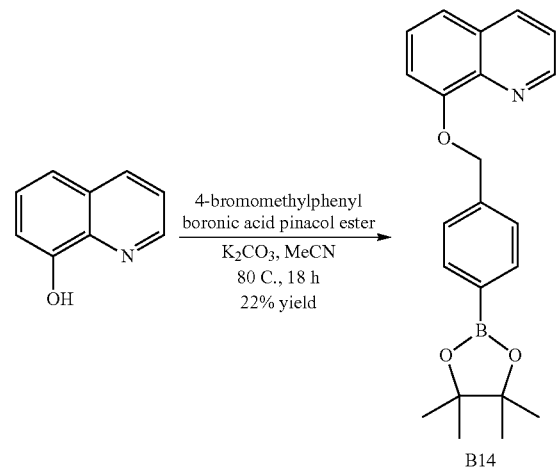

8-((4-(4,4,5,5-Tetramethyl-1,3,2-dioxaborolan-2-yl)benzyl)oxy)quinoline (B14)

The synthesis of B14 was accomplished following the procedure outlined for B1 using 8-hydroxyquinoline (0.12 g, 0.8 mmol), 4-bromomethylphenyl boronic acid pinacol ester (0.26 g, 0.88 mmol), and K$_2$CO$_3$ (0.33 g, 2.4 mmol) in 10 mL of acetonitrile affording B14 in 22% yield (0.06 g, 0.17 mmol). $^1$H NMR (400 MHz, CDCl$_3$) δ=8.96 (dd, J$_j$=4.4 Hz, J$_2$=1.2 Hz, 1H), 8.09 (dd, J$_1$=8.4 Hz, J$_2$=1.6 Hz, 1H), 7.79 (d, J=7.6 Hz, 2H), 7.49 (d, J=7.6 Hz, 2H), 7.40 (dd, J$_1$=8 Hz, J$_2$=4 Hz, 1H) 7.34-7.28 (m, 2H), 6.95 (dd, 7.79 J$_1$=7.2 Hz, J$_2$=1.6 Hz, 1H), 5.47 (s, 2H), 1.31 (s, 12H). $^{13}$C NMR (100 MHz, CDCl$_3$) δ=154.38, 149.60, 140.69, 140.42, 136.13, 135.32, 129.70. 126.77, 126.26, 121.84, 120.11, 110.25, 84.01, 70.87, 25.08. ESI-MS(+): m/z 362.02 [M+H]+.

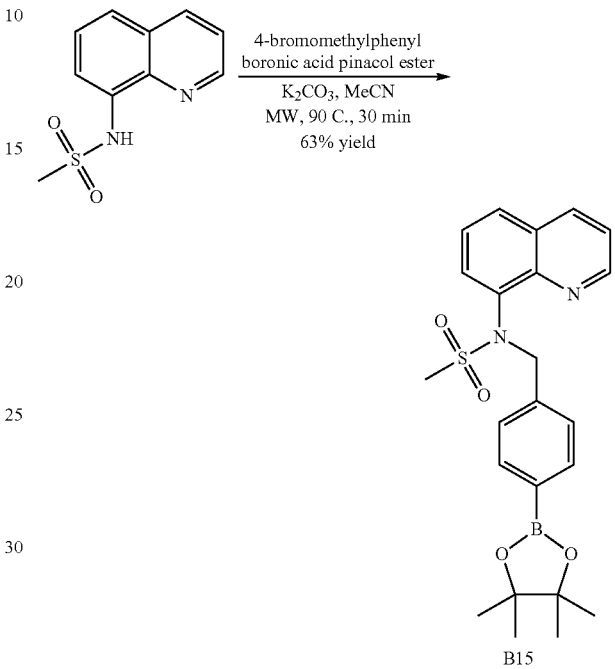

N-(Quinolin-8-yl)-N-(4-(4,4,5,5-tetramethyl-1,3,2-dioxaborolan-2-yl)benzyl)methanesulfonamide (B15)

N-(quinolin-8-yl)methanesulfonamide was synthesized as previously described. $^2$N-(quinolin-8-yl)methanesulfonamide (0.08 g, 0.34 mmol), was reacted with 4-bromomethylphenyl boronic acid pinacol ester (0.11 g, 0.37 mmol), in the presence of K$_2$CO$_3$ (0.14 g, 1.0 mmol) in 3 mL MeCN in a microwave reactor at 90° C. for 30 min affording B15 in 63% yield (0.09 g, 0.21 mmol). $^1$H NMR (400 MHz, CDCl$_3$) δ=8.97 (dd, J$_1$=4 Hz, J$_2$=1.6 Hz, 1H), 8.18 (dd, J$_1$=8.4 Hz, J$_2$=1.6 Hz, 1H), 7.74 (dd, J$_1$=8.4 Hz, J$_2$=1.2 Hz, 1H), 7.64 (d, J=8 Hz, 2H), 7.50 (dd, J$_1$=7.2 Hz, J$_2$=1.2 Hz, 1H), 7.46 (dd, J$_1$=8.4 Hz, J$_2$=4.4 Hz, 1H), 7.36 (t, J=7.6 Hz, 1H), 7.22 (d, J=8 Hz, 2H), 5.20 (s, 2H), 3.20 (s, 3H), 1.30 (s, 12H). $^{13}$C NMR (100 MHz, CDCl$_3$) δ=150.30, 145.18, 140.39, 137.00, 135.36, 135.17, 134.93, 129.74, 129.06, 128.25, 126.75, 121.68, 83.98, 55.08, 40.37, 25.08. ESI-MS(+): m/z 438.96 [M+H]+, 460.97 [M+Na]+.

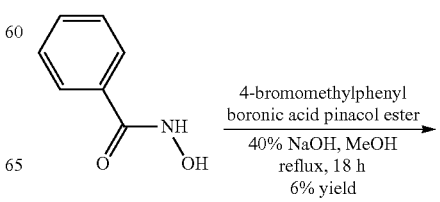

-continued

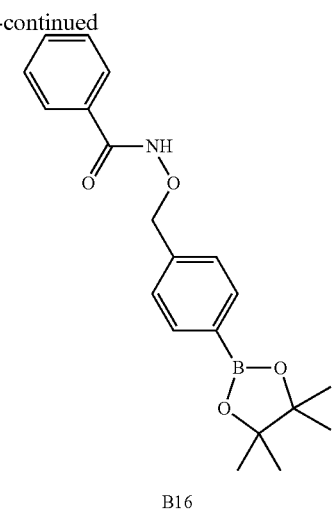

B16

N-((4-(4,4,5,5-Tetramethyl-1,3,2-dioxaborolan-2-yl)benzyl)oxy)benzamide (B16)

N-hydroxybenzamide (0.17 g, 1.2 mmol) was dissolved in 8 mL of MeOH followed by the addition of 4-bromomethylphenyl boronic acid pinacol ester (0.40 g, 1.30 mmol). A 40% aqueous solution of NaOH (2 mL) was then added dropwise and the reaction was left to stir at reflux overnight. After cooling to room temperature and concentrated, concentrated HCl was added until a pH of 1 was observed. The resulting solution was then extracted with EtOAc and washed with brine. The organic layer was collected and dried over MgSO$_4$ then purified via silica gel chromatography affording B16 in 6% yield (0.03 g, 0.07 mmol). $^1$HNMR (400 MHz, CDCl$_3$) δ=8.61 (br, 1H, NH), 7.83 (d, J=8 Hz, 2H), 7.64 (d, J=7.6 Hz, 2H), 7.51-7.37 (m, 5H), 5.04 (s, 2H), 1.35 (s, 12H). $^{13}$C NMR (100 MHz, CDCl$_3$) δ=166.67, 138.45, 135.32, 132.35, 132.10, 128.95, 128.72, 127.25, 84.18, 78.45, 25.10. ESI-MS(+): m/z 354.10 [M+H]$^+$, 376.10 [M+Na]$^+$.

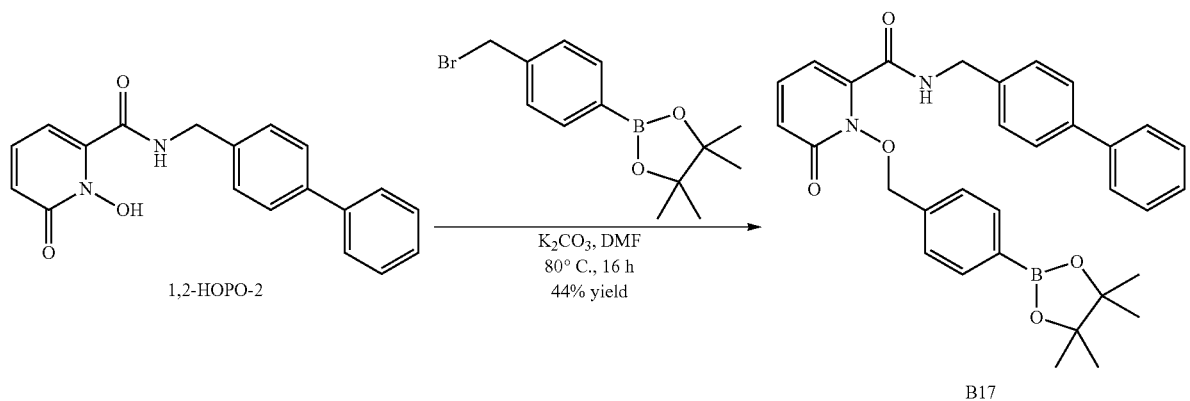

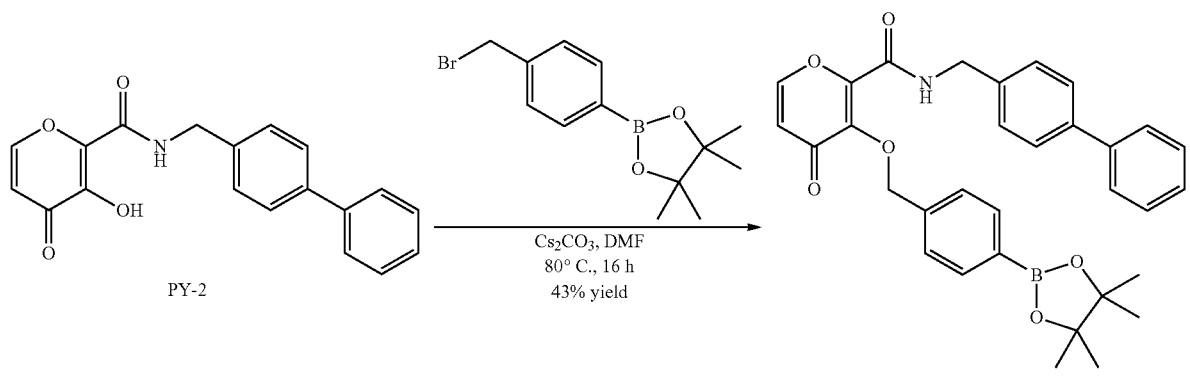

N-([1,1'-biphenyl]-4-ylmethyl)-6-oxo-1-((4-(4,4,5,5-tetramethyl-1,3,2-dioxaborolan-2-yl)benzyl)oxy)-1,6-dihydropyridine-2-carboxamide (B17). 1,2-HOPO-2 was prepared as previously reported.[111]. 1,2-HOPO-2 (0.20 g, 0.6 mmol) was dissolved in 15 mL of anhydrous DMF. To this was added K$_2$CO$_3$ (0.26 g, 1.8 mmol) followed by 4-bromomethylphenyl boronic acid pinacol ester (0.19 g, 0.6 mmol). The reaction was heated overnight at 80° C. under nitrogen. After cooling to room temperature, the solvent was evaporated and the resulting oil was brought up in dichloromethane (20 mL) then washed twice with H$_2$O (20 mL) and once with brine (20 mL). The organic layer was dried over MgSO$_4$, filtered and concentrated for silica gel column purification eluting with 1% MeOH in DCM to yield a white solid in 44% yield (0.15 g, 0.27 mmol). $^1$H NMR (500 MHz, CDCl$_3$) δ=7.99 (br, 1H, NH), 7.77 (d, J=8.0 Hz, 2H), 7.55 (d, J=7.45 Hz, 2H), 7.47 (d, J=8.0 Hz, 2H), 7.43 (d, J=8.0 Hz, 2H), 7.38 (d, J=8.0 Hz, 2H), 7.34 (t, J=7.45 Hz, 1H), 7.27-7.25 (m, 3H), 6.64 (dd, J$_1$=9.15 Hz, J$_2$=1.7 Hz, 1H), 6.57 (dd, J$_1$=6.9 Hz, J$_2$=1.75 Hz, 1H), 5.26 (s, 2H, OCH$_2$), 4.53 (d, J=5.75 Hz, 2H, NCH), 1.32 (s, 12H). $^{13}$C NMR (100 MHz, CDCl$_3$) δ=160.2, 158.7, 142.2, 141.1, 140.8, 138.3, 136.4, 136.0, 135.3, 129.6, 129.0, 128.7, 127.7, 127.6, 127.3, 124.6, 107.2, 84.2, 79.4, 44.0, 25.1. ESI-MS(+): m/z 537.30 [M+H]$^+$, 559.33 [M+Na]$^+$. Anal. calcd for C$_{32}$H$_{33}$BN$_2$O$_5$.0.25H$_2$O: C, 71.05; H, 6.24; N, 5.18. Found: C, 71.41; H, 6.65; N, 5.50.

N-([1,1'-biphenyl]-4-ylmethyl)-4-oxo-3-((4-(4,4,5,5-tetramethyl-1,3,2-dioxaborolan-2-yl)benzyl)oxy)-4H-pyran-2-carboxamide (B18). PY-2 was prepared as previously reported.[111] Proinhibitor 2 was synthesized and purified following the same procedure for 1 using PY-2 (0.20 g, 0.6 mmol), Cs$_2$CO$_3$ (0.61 g, 1.8 mmol), and 4-bromomethylphenyl boronic acid pinacol ester (0.37 g, 1.2 mmol) in 15 mL of anhydrous DMF. $^1$H NMR (400 MHz, CDCl$_3$) δ=8.13 (t, J=5.2 Hz, 1H, NH), 7.84 (d, J=5.6 Hz, 1H), 7.72 (d, J=8.0 Hz, 2H), 7.61 (dd, J=8.4 Hz, J$_2$=1.2 Hz, 2H), 7.54 (d, J=8.4 Hz, 2H), 7.45 (t, J=7.6 Hz, 2H), 7.37 (dd, J=7.2 Hz, J$_2$=1.6 Hz, 1H), 7.23 (d, J=7.6 Hz, 2H), 7.21 (d, J=8.0 Hz, 2H), 5.39 (s, 2H, OCH$_2$), 4.47 (d, J=5.6 Hz, 2H, NCH$_2$), 1.33 (s, 12H). $^{13}$C NMR (100 MHz, CDCl$_3$) δ=176.0, 159.0, 154.8, 147.2, 141.0, 140.9, 137.9, 136.2, 135.6, 135.3, 129.0, 128.7, 128.6, 127.8, 127.6, 127.4, 126.3, 117.8, 84.2, 75.4, 43.7, 25.1. ESI-MS(+): m/z 538.20 [M+H]$^+$, 560.26 [M+Na]$^+$. Anal. calcd. for C$_{32}$H$_{32}$BNO$_6$.0.30H$_2$O: C, 70.81; H, 6.05; N, 2.58. Found: C, 71.18; H, 6.49; N, 2.60.

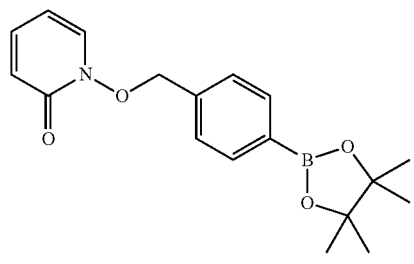

B19

1-((4-(4,4,5,5-tetramethyl-1,3,2-dioxaborolan-2-yl)benzyl)oxy)pyridin-2(1H)-one (B19)

2-hydroxypyridine-1-oxide (0.04 g, 0.34 mmol) was dissolved in 5 mL of anhydrous DMF. To this was added K$_2$CO$_3$ (0.14 g, 1.02 mmol) and 4-bromomethylphenyl boronic acid pinacol ester (0.10 g, 0.34 mmol). The reaction was heated to 80° C. and allowed to stir under nitrogen overnight. After cooling to room temperature, the solvent was evaporated and the resulting residue was brought up in dichloromethane and washed twice with water. The organic layer was dried over MgSO$_4$, filtered and concentrated for purification via silica gel chromatography eluting with 2% MeOH in DCM. The protected B19 was collected as an off-white solid in 87% yield (98 mg, 0.3 mmol). $^1$H NMR (400 MHz, CDCl$_3$) δ=7.79 (d, J=8.0 Hz, 2H), 7.38 (d, J=8.0 Hz, 2H), 7.24 (td, J=7.2 Hz, J$_2$=2.0 Hz, 1H), 7.05 (dd, J=7.2 Hz, J$_2$=2.0 Hz, 1H), 6.67 (dd, J=9.2 Hz, J$_2$=1.2 Hz, 1H), 5.89 (td, J=6.8 Hz, J$_2$=1.6 Hz, 1H), 5.29 (s, 2H), 1.35 (s, 12H). $^{13}$C NMR (100 MHz, CDCl$_3$) δ=159.2, 138.9, 137.0, 136.8, 135.3, 129.5, 122.9, 104.7, 84.3, 78.4, 25.1. ESI-MS(+): m/z 328.18 [M+H]$^+$. Anal. calcd. for C$_{18}$H$_{22}$BNO$_4$. 0.4 CH$_3$OH: C, 65.26; H, 6.94; N, 4.16. Found: C, 65.54; H, 7.20; N, 3.76.

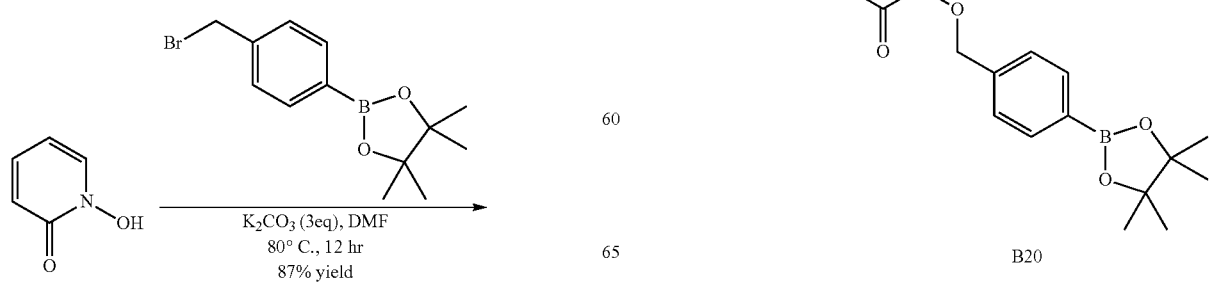

B20

2-methyl-3-((4-(4,4,5,5-tetramethyl-1,3,2-dioxaborolan-2-yl)benzyl)oxy)-4H-pyran-4-one (B20)

Maltol (0.50 g, 3.96 mmol) was dissolved in 25 mL of acetonitrile followed by the addition of 1.6 g (11.88 mmol) of $K_2CO_3$. The reaction was heated to reflux for 10 min before adding 4-bromomethylphenyl boronic acid pinacol ester (1.3 g, 4.4 mmol). The reaction was left stirring under refluxing conditions for 12 h then cooled to room temperature and filtered rinsing with DCM. The resulting filtrate was concentrated and purified via silica gel chromatography eluting with 0-2% MeOH in DCM. B20 (1.03 g, 3.0 mmol) was collected and dried yielding a pale yellow solid in 76% yield. $^1$H NMR (400 MHz, CDCl$_3$) δ=7.77 (d, J=7.6 Hz, 2H), 7.58 (d, J=5.2 Hz, 1H), 7.37 (d, J=7.6 Hz, 2H), 6.35 (d, J=5.6 Hz, 1H), 5.19 (s, 2H), 2.06 (s, 3H), 1.34 (s, 12H). $^{13}$C NMR (100 MHz, CDCl$_3$) δ=175.3, 160.0, 153.6, 143.9, 140.0, 135.1, 128.5, 117.4, 84.1, 73.6, 25.1, 15.2. ESI-MS(+): m/z 343.18 [M+H]$^+$. Anal. calcd. for $C_{19}H_{23}BO_5$: C, 66.69; H, 6.77. Found: C, 66.34; H, 6.67.

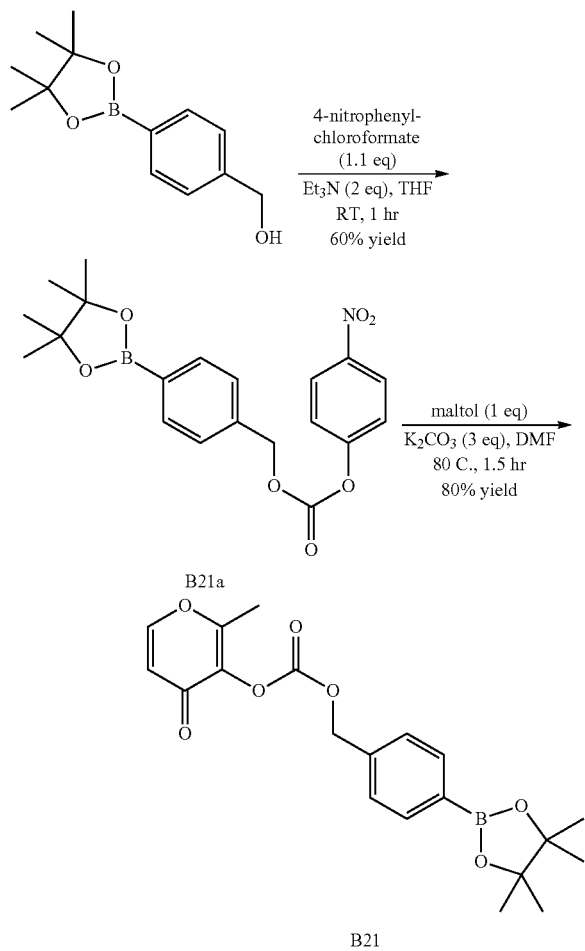

4-nitrophenyl 4-(4,4,5,5-tetramethyl-1,3,2-dioxaborolan-2-yl)benzyl carbonate (B21a)

4-(Hydroxymethyl)phenylboronic acid pinacol ester (0.5 g, 2.1 mmol) was dissolved in 20 mL of dry THF. Triethylamine (0.6 mL, 4.3 mmol) was added followed by 4-nitrophenyl chloroformate (0.47 g, 2.3 mmol) and the reaction was allowed to stir at room temperature for 1 h. The reaction was diluted with ethyl acetate and washed with 1.0 M HCl followed by saturated NaHCO$_3$. The organic layer was dried over MgSO$_4$, filtered and concentrated. Compound B21a was purified on a silica gel column eluting with 5% EtOAc in hexanes to give 0.51 g (1.3 mmol, 60% yield) as a white solid. $^1$H NMR (400 MHz, CDCl$_3$) δ=8.25 (d, J=9.2 Hz, 2H), 7.85 (d, J=8.0 Hz, 2H), 7.43 (d, J=8.0 Hz, 2H), 7.36 (d, J=9.2 Hz, 2H), 5.31 (s, 2H), 1.35 (s, 12H). $^{13}$C NMR (100 MHz, CDCl$_3$) δ=155.7, 152.7, 145.6, 137.2, 135.4, 127.9, 125.5, 122.0, 84.2, 71.0, 25.1. ESI-MS(+): m/z 417.19 [M+NH$_4$]$^+$, 422.20 [M+Na]$^+$.

2-methyl-4-oxo-4H-pyran-3-yl 4-(4,4,5-trimethyl-1,3,2-dioxaborolan-2-yl)benzyl carbonate (B21). Maltol (0.032 g, 0.25 mmol) was dissolved in 5 mL of dry DMF and K$_2$CO$_3$ (0.10 g, 0.75 mmol) was added. The reaction was heated to 80° C. for 10 minutes before adding B21a (0.10 g, 0.25 mmol). The reaction was allowed to go for 1.5 h. After cooling to room temperature, DMF was removed by rotary evaporation. The residue was brought up in EtOAc, washed with water (3×) and with brine. The organics were dried over MgSO$_4$, filtered and concentrated for column purification. B21 was eluted with 1% MeOH in DCM giving a pale orange compound in 80% yield (0.078 g, 0.2 mmol). $^1$H NMR (400 MHz, CDCl$_3$) δ=7.82 (d, J=8.0 Hz, 2H), 7.68 (d, J=6.0 Hz, 1H), 7.41 (d, J=8.0 Hz, 2H), 6.43 (d, J=5.6 Hz, 1H), 5.30 (s, 2H), 2.30 (s, 3H), 1.34 (s, 12H). $^{13}$C NMR (100 MHz, CDCl$_3$) δ=172.1, 159.6, 154.6, 152.2, 139.3, 137.6, 135.3, 127.6, 117.3, 115.9, 84.2, 71.1, 25.1, 15.2. ESI-MS(+): m/z 387.07 [M+H]$^+$, 409.13 [M+Na]$^+$. Anal. calcd. for $C_{20}H_{23}BO_7$: C, 62.20; H, 6.00. Found: C, 61.85; H, 6.40.

Synthesis of Control Compounds

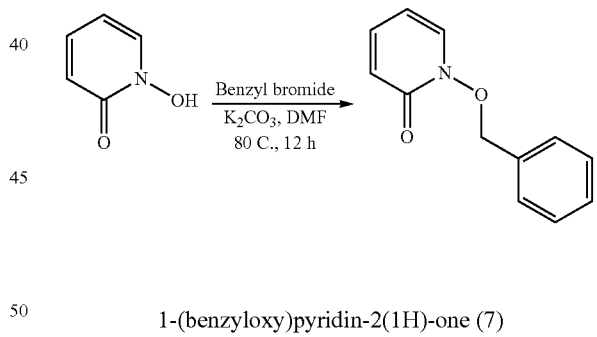

1-(benzyloxy)pyridin-2(1H)-one (7)

2-hydroxypyridine-1-oxide (0.50 g, 4.5 mmol) was reacted with benzyl bromide (0.64 mL, 5.4 mmol) in DMF (10 mL) in the presence of K$_2$CO$_3$ (1.8 g, 13.5 mmol) at 80° C. for 16 h. After cooling to room temperature, the solvent was removed by rotary evaporation. The crude product was redissolved in DCM and washed twice with water. The organic layer was then dried over MgSO$_4$, filtered, and concentrated resulting in 7 as a white solid in 84% yield (0.78 g, 3.8 mmol) without the need for further purification. $^1$H NMR (400 MHz, CDCl$_3$) δ=7.41-7.36 (m, 5H), 7.25 (td, J$_1$=6.8 Hz, J$_2$=2.0 Hz, 1H), 7.10 (dd, J$_1$=7.2 Hz, J$_2$=2.0 Hz, 1H), 6.68 (dd, J$_1$=9.2 Hz, J$_2$=1.6 Hz, 1H), 5.91 (td, J$_1$=6.8 Hz, J$_2$=1.6 Hz, 1H), 5.28 (s, 2H). $^{13}$C NMR (100 MHz, CDCl$_3$) δ=159.2, 138.9, 136.9, 133.9, 130.3, 129.6, 128.9, 122.9, 104.7, 78.6. ESI-MS(+): m/z 202.19 [M+H]$^+$, 224.29 [M+Na]$^+$.

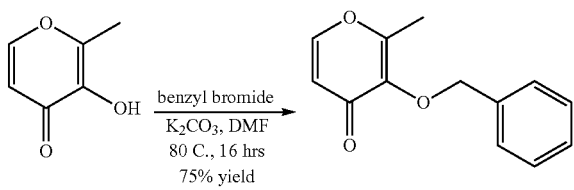

3-(benzyloxy)-2-methyl-4H-pyran-4-one (7)

To a 500 mL flask with 10.0 g (0.08 mol) of maltol (3-hydroxy-2-methyl-4H-pyran-4-one) in 120 mL of anhydrous DMF was added 14.1 mL (0.12 mol) of benzyl bromide and potassium carbonate (16.4 g, 0.12 mol) and heated at 80° C. overnight. After cooling to room temperature, the reaction was filtered and the solvents evaporated. The residual oil was brought up in 100 mL $CH_2Cl_2$ and washed twice with a saturated $NaHCO_3$ solution, water, and brine. The organic layer was dried over $MgSO_4$, filtered and concentrated. Product was purified on a silica gel column eluting with 0.5% MeOH in $CH_2Cl_2$ to yield a pale yellow solid in 75% yield (12.8 g, 59 mmol). $^1$H NMR (400 MHz, $CDCl_3$) δ=7.59 (d, J=5.6 Hz, 1H), 7.36 (m, 5H), 6.36 (d, J=5.6 Hz, 1H), 5.15 (s, 2H, $OCH_2$), 2.08 (s, 3H, $CH_3$). ESI-MS(+): m/z 217.03 [M+H]$^+$, 239.07 [M+Na]$^+$.

Example 4

Exemplary Methods Related to Prodrugs Comprising Carbohydrate Moieties

UV-Vis Spectroscopy.

Absorption spectra of compounds 1-8 were taken on a Perkin-Elmer Lambda 25 UV-visible spectrophotometer. To a 1.0 mL solution at 0.05-0.06 mM concentration in HEPES buffer (50 mM, pH 7.5) was added β-glucosidase (16 U for compounds 2, 4, and 6, and 100 U for compound 8). Spectra were monitored over time either at room temperature for compounds 1-7 or at 37° C. for compound 8.

Calculation of Km.

Figure 10:
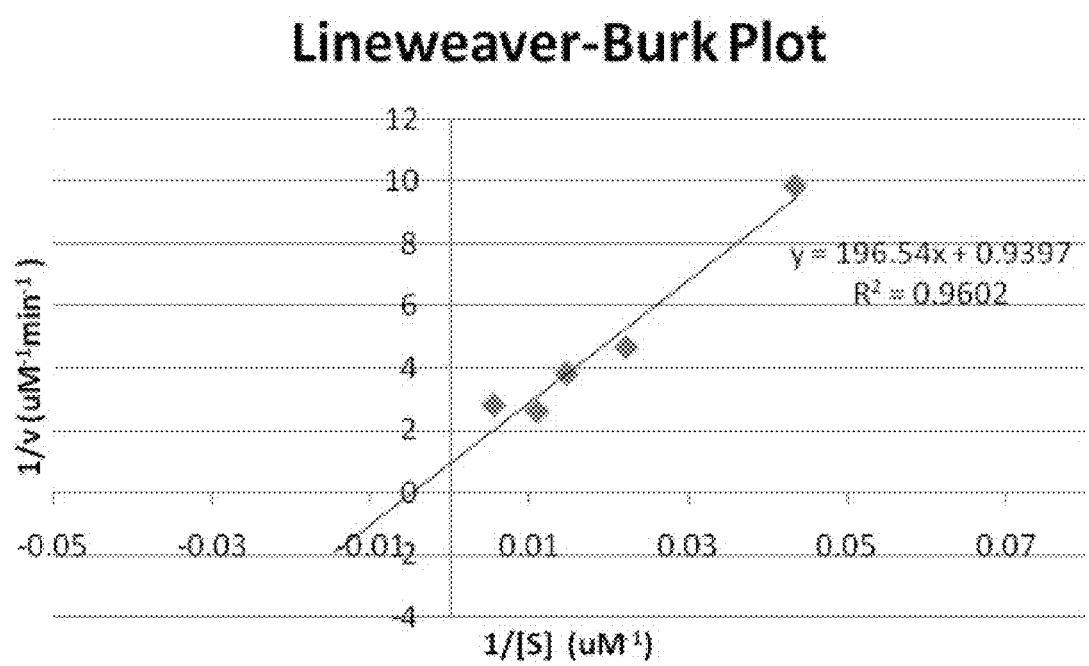
FIG. 10. Lineweaver-Burk plot of the initial velocity of β-glucosidase (100 U) cleavage with varying amounts of inhibitor 8. A K$_m$ of ~210 μM was obtained.

To a 1.0 mL solution of 8 in HEPES buffer at 25 μM, 50 μM, 75 μM, 100 μM, and 200 μM was added 100 U of β-glucosidase. Spectra were monitored over 4 h at 37° C. The concentration of product formed, 1,2-HOPO-2 (7), was determined using the extinction coefficient for 7 calculated at 346 nm (4279±372 M-1 cm-1) and was plotted versus time (min). The initial velocity (v) of each reaction was determined analyzing the linear slope of the first 50 min. The Km value was calculated from the Lineweaver-Burk plot (1/v vs. 1/[8]) where −1/Km equals the x-intercept (FIG. 10).

Acid Stability.

Figure 11:
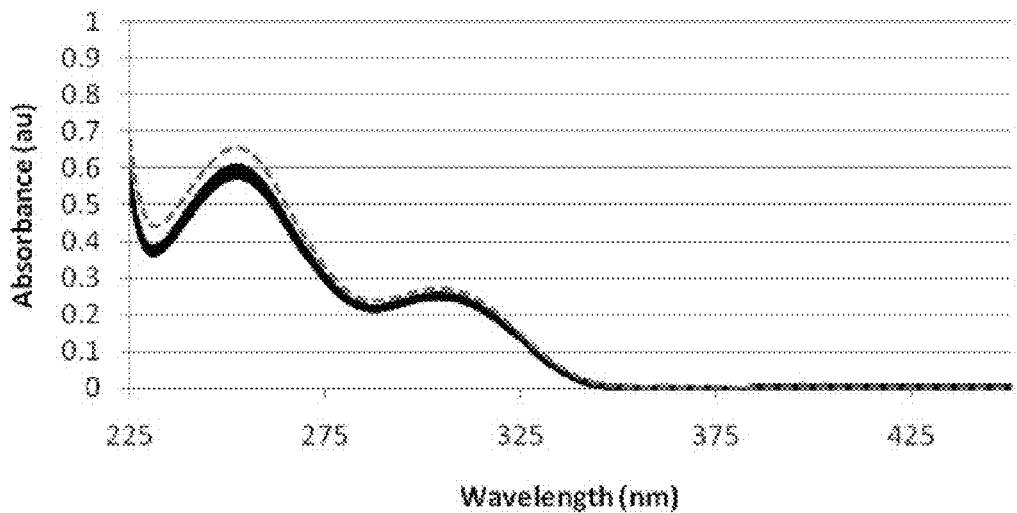
FIG. 11. Top: Absorption spectra of the glucose-protected full-length inhibitor 8 (0.05 mM) in 0.1 M HCl monitored every hour for 24 h (overlapping solid spectra). A sample of 8 (~0.05 mM) in HEPES buffer is also shown (dashed). The overlapping spectra indicate that compound 8 is stable to hydrolysis in the presence of acid. Bottom: Percent inhibition of MMP-8 with compounds 7 and 8 tested at 150 nM in the absence and presence of β-glucosidase. Results represent the average of two independent experiments run each in duplicate.
Figure 11:
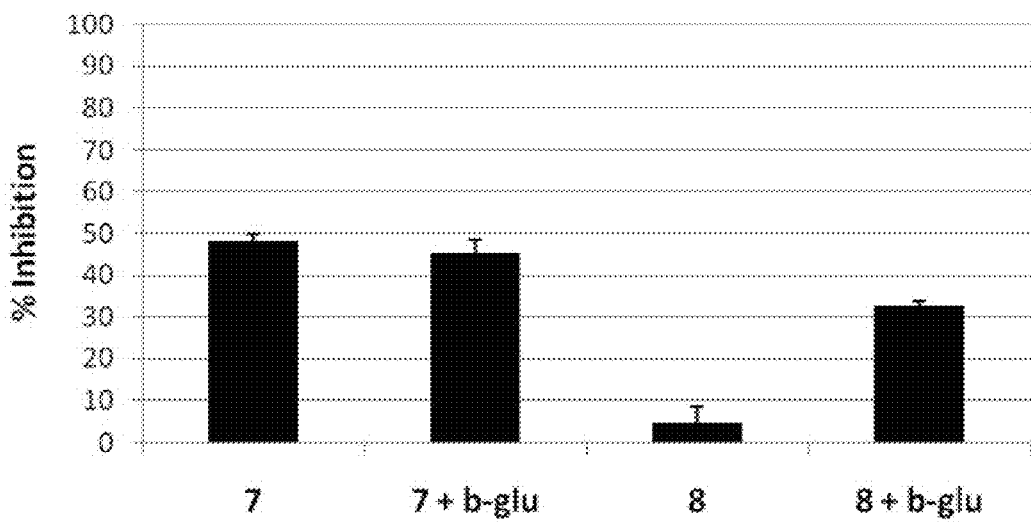

To examine the stability of compound 8 towards acid hydrolysis, the absorption spectra of a 0.05 mM solution of 8 in a 0.1 M aqueous solution of HCl was collected. Spectra were collected at room temperature every hour for a 24 h time period. No change in the spectra was observed (FIG. 11).

HPLC.

Analytical HPLC was performed on a HP Series 1050 system equipped with a Vydac® C18 reverse phase column (218 TP, 250×4.6 mm, 5 μm). Separation was achieved with a flow rate of 1 mL/min and the following solvents: solvent A is 5% MeOH and 0.1% formic acid in $H_2O$ and solvent B is 0.1% formic acid in MeOH. Starting with 95% A and 5% B, an isocratic gradient was run for 15 min to a final solvent mixture of 5% A and 95% B, which was held for 5 min before ramping back down to 95% A and 5% B in 2 min and holding for an additional 4 min. Compounds 1-6 were prepared in HEPES buffer (50 mM, pH 7.5) at a concentration of 1.6 mM and compounds 7-8 were prepared at a concentration of 1 mM. Retention times of compounds 1-8 were determined under identical HPLC conditions prior to evaluation of glucose cleavage of the protected compounds. To evaluate the efficiency of glucose cleavage for the protected ZBGs 2, 4, and 6, 1 mL samples of each compound were made up at a concentration of 1.6 mM in HEPES buffer (50 mM, pH 7.5). To each sample was added 50 U of β-glucosidase (1 U/μL) and incubated at 37° C. After 1 h, a 400 μL, aliquot was collected and filtered through a microcentrifuge filter (30 kDa MWCO, PLTK cellulosic membrane) to remove β-glucosidase prior to injection on the HPLC. For the full-length inhibitor 8, a 1 mL sample in HEPES buffer at a concentration of 1 mM was incubated at 37° C. with 250 U of β-glucosidase (1 U/μL) for 5 h. A 200 μL, aliquot was collected every hour and filtered through a microcentrifuge filter prior to injection on the HPLC.

Inhibition Assays.

MMP-9 (catalytic domain, human, recombinant), MMP-8 (catalytic domain, human, recombinant), and the assay kit were purchased from BIOMOL International. The assays were carried out according to the procedure provided with the kit. MMP activity was measured in 96-well plates using a Bio-Tek Flx 800 fluorescent plate reader. The ZBGs and their protected analogs were dissolved in DMSO and diluted in HEPES buffer (50 mM, pH 7.5) to a concentration of 10 mM for 1-2, 40 mM for 3-4, and 1.25 mM for 5-6. Each well contained 20 μL, of MMP-9 (0.45 U/mL), inhibitor (10 μL, of 1-6), 5 μL, of β-glucosidase (1 U/μL) when used, and buffer for a total volume of 99 μL. These were incubated for 1 h at 37° C. A control sample containing just β-glucosidase (5 μL at 5 U/μL) with MMP-9 (20 μL) was also prepared to confirm that the β-glucosidase did not inhibit of MMP-9. The reaction was initiated by the addition of 1 μL (400 μM) of the fluorescent substrate (Mca-Pro-Leu-Gly-Leu-Dpa-Ala-Arg-NH2 where Mca=(7-methoxycoumarin-4-yl)-acetyl and Dpa=N-3-(2,4-dinitrophenyl)-L-α-β-diaminopropionyl)) and kinetic activity was measured every minute for 30 min with excitation and emission wavelengths at 335 nm and 405 nm, respectively. Enzyme activity with inhibitor was calculated with respect to the control experiment (no inhibitor present). Measurements were performed in duplicate in two independent experiments.

For Cmpds 7 and 8, 1 mL sample in HEPES buffer at a concentration of 1 mM was incubated at 37° C. with 250 U of β-glucosidase (1 U/μL) for 4 h giving a final concentration of 0.8 mM of the inhibitor. After 4 h, a 200 μL aliquot was collected and filtered through a microcentrifuge filter. UV-Vis absorption spectroscopy was to verify that the concentration of 1,2-HOPO-2 was 0.71±0.2 mM in each of the samples using the extinction coefficient for 1,2-HOPO-2 (7) calculated at 346 nm (4,279.3±372 M-1 cm-1). Each well was made up with 20 μL of MMP-9 (0.45 U/mL), inhibitor (2 μL, for 7 and 8), and buffer for a total volume of 99 μL. These were incubated for 30 min at 37° C. For MMP-8 inhibition assays, each of the samples was diluted to 1 μM in HEPES buffer and 15 μL of each were added to 20 μL of MMP-8 (0.092 U/mL) and buffer for a total of 99 μL. The reaction was initiated by the addition of 1 μL (400 μM) of the fluorescent substrate and kinetic activity was measured every minute for 30 min with excitation and emission wavelengths at 335 nm and 405 nm, respectively. Enzyme activity with inhibitor was calculated with respect to the control experiment (no inhibitor present). A control sample was also performed, in which an aliquot of 250 U of β-glucosidase (1 U/μL) with 1 mL of HEPES buffer was incubated for 4 h at 37° C., filtered through a microcentrifuge filter, and evaluated in the MMP assay to confirm that no inhibition is observed with β-glucosidase. Measurements were performed in duplicate in two independent experiments.

was accomplished following a literature procedure used by Orvig and coworkers for enzyme-activated metal-binding chelators (Scheme 1 following).[9,34]. The ZBG was protected with acetobromo-α-D-glucose in a 1:1 solution of 1.0 M NaOH and $CH_2Cl_2$ in the presence of $(nBu)_4NBr$. The desired products were obtained by cleavage of the glucose acetate groups using NaOMe in MeOH.

Scheme 1. Synthesis of the glucose protected ZBGs 2, 4 and 6

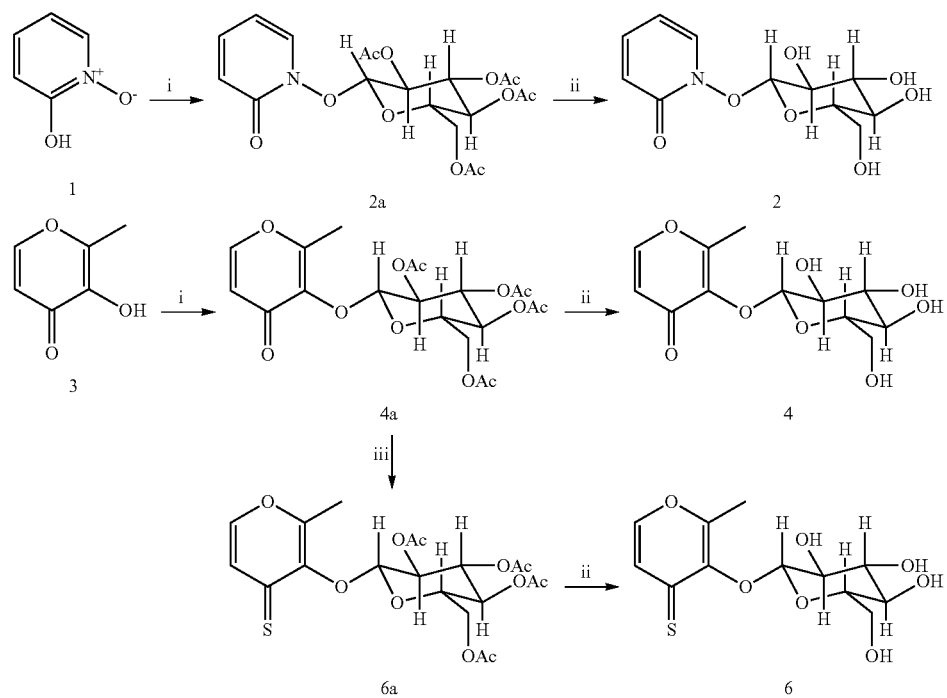

IC50 values were obtained for compounds 1-8 against MMP-9 and for compounds 7 and 8 against MMP-8. Serial dilutions of the compounds in DMSO were incubated at 37° C. for 30 minutes with 20 μL of the appropriate MMP (0.45 U/mL for MMP-9 and 0.092 U/mL for MMP-8) and HEPES buffer (50 mM, pH 7.5) for a total volume of 99 μL. The reaction was initiated by the addition of 1 μL (400 μM) of the fluorescent substrate and kinetic activity was measured every minute for 20 min with excitation and emission wavelengths at 335 nm and 405 nm, respectively. Enzyme activity with inhibitor was calculated with respect to the control experiment (no inhibitor present). Measurements were performed in duplicate. The percent inhibition is plotted versus the inhibitor concentration. A linear fit of the data for each experiment gives the 1050 value of the inhibitor where y=50%.

Example 5

Exemplary Prodrugs Comprising a Carbohydrate Moiety

Figure 1:
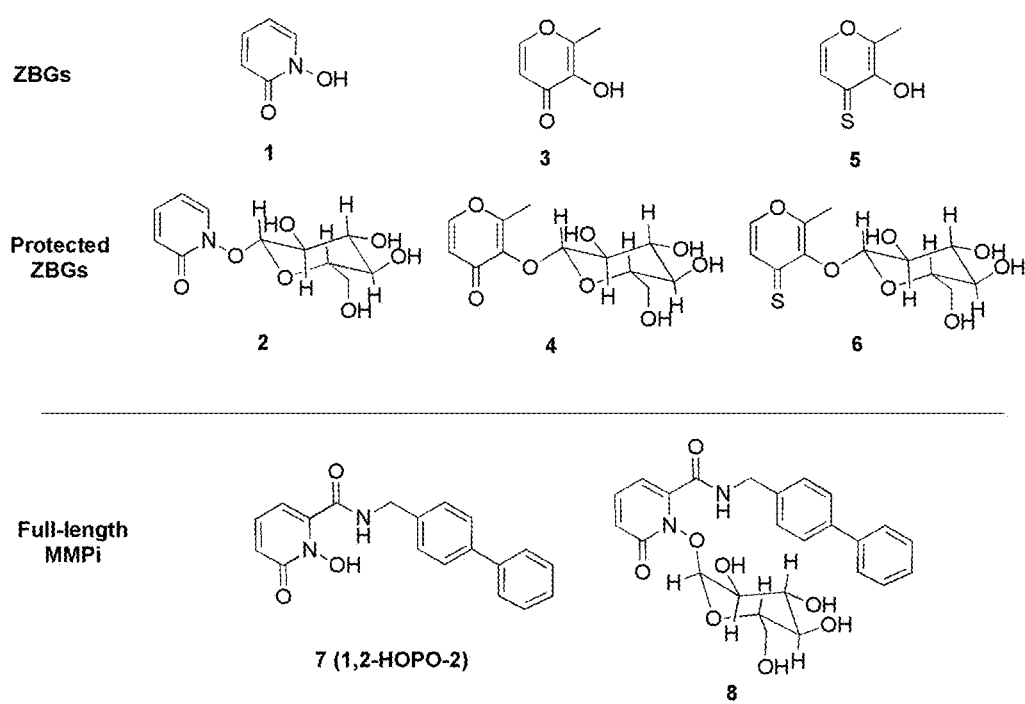
FIG. 1. Structures of inhibitors and proinhibitors tested in this study. Compounds include the ZBGs (examples of potential zinc binding drugs) 1-hydroxy-pyridin-2(1H)-one (1), 3-hydroxy-2-methyl-4-pyrone (3) and 3-hydroxy-2-methyl-4-pyrothione (5) as well as the full-length MMPi 1,2-HOPO-2 (7).

Building on the strategy of glycosidic protecting groups, we first focused our attention on the development of glucose-protected non-hydroxamate zinc-binding groups (ZBGs)[32,33] that can be activated by enzymatic cleavage of the protecting group with β-glucosidase to release the ZBG and glucose (FIG. 1). The synthesis of the protected ZBGs (2, 4, and 6)

The conditions for Scheme 1 are the following: (i) acetobromo-α-D-glucose, tetrabutylammonium bromide, CH2Cl2:1.0 M NaOH (1:1), 3 h, room temp; (ii) NaOMe, MeOH, 2-3 h, room temp; (iii) P4S10, HMDO, benzene, 100° C., 45 min.

Figure 2:
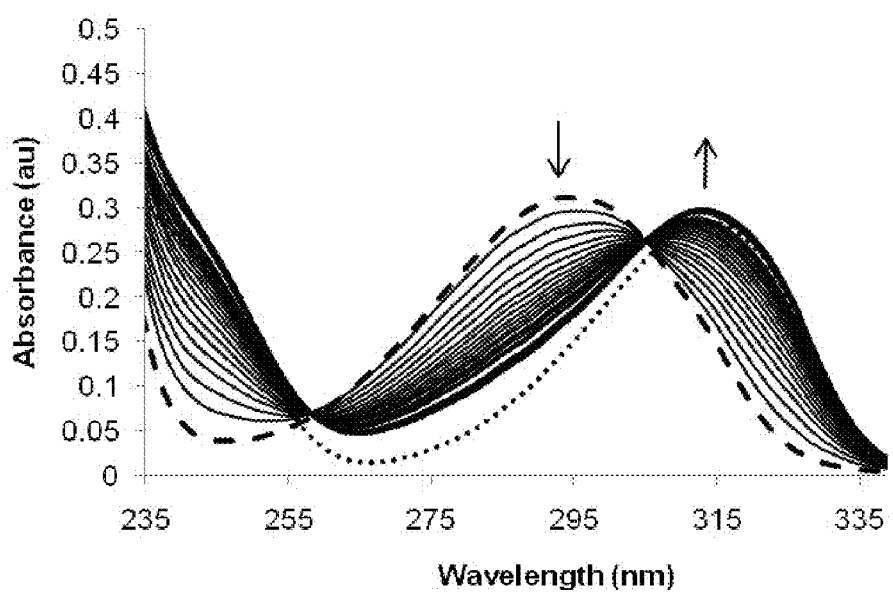
FIG. 2. Absorption spectra of the glucose-protected ZBG 2 (example of a potential prodrug comprising a carbohydrate moiety) (0.05 mM, HEPES buffer, pH=7.5) in the presence of β-glucosidase (16 U) monitored over time. The heavy lines are the initial (dashed) and final (solid) spectra and arrows indicate the change in spectra over time. The spectrum of an authentic sample of ZBG 1 (dotted) is also shown.
Figure 3:
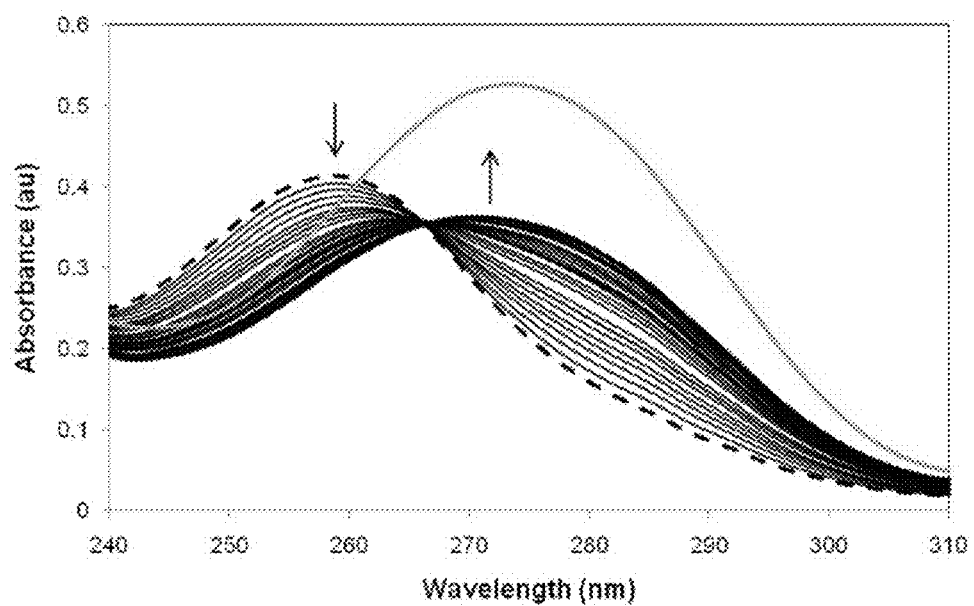
FIG. 3. Absorption spectra of the glucose-protected ZBG 4 (0.06 mM in HEPES buffer) in the presence of β-glucosidase (16 U) monitored every minute for one hour with spectra shown every 2 min. The heavy lines are the initial (dashed) and final (solid) spectra; arrows indicate change in spectra over time. An authentic sample of the ZBG (compound 3, ~0.1 mM) in HEPES buffer is also shown.
Figure 4:
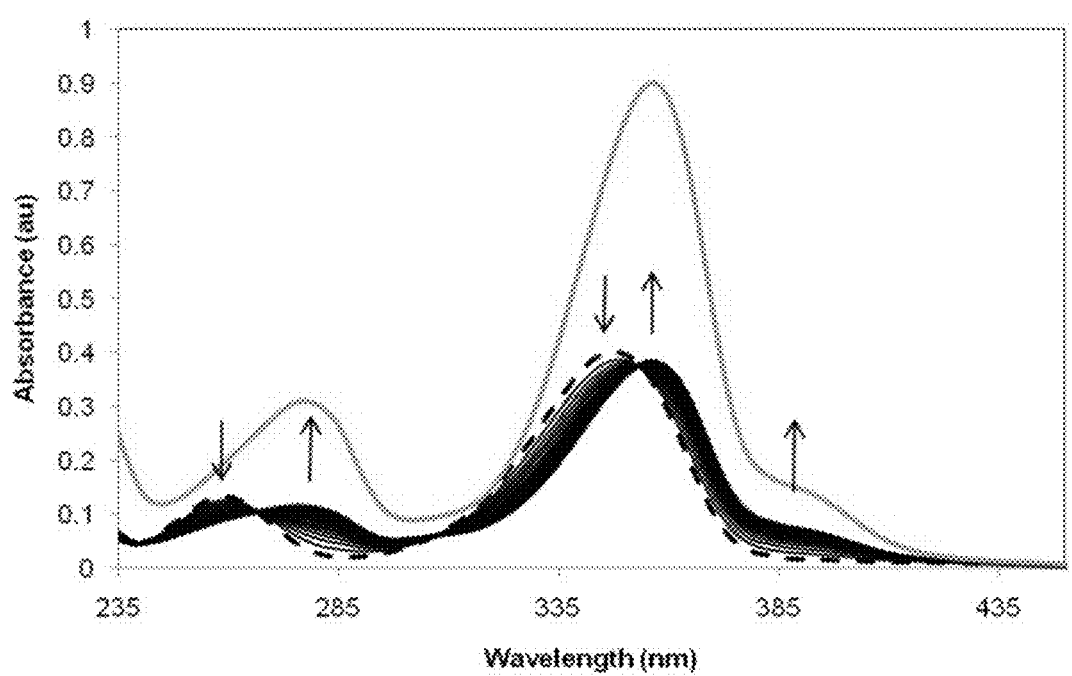
FIG. 4. Absorption spectra of the glucose-protected ZBG 6 (0.05 mM in HEPES buffer) in the presence of β-glucosidase (16 U) monitored every minute for one hour with spectra shown every 2 min. The heavy lines are the initial (dashed) and final (solid) spectra; arrows indicate change in spectra over time. An authentic sample of the ZBG (compound 5, ~0.1 mM) in HEPES buffer is also shown (light gray solid line).
Figure 5:
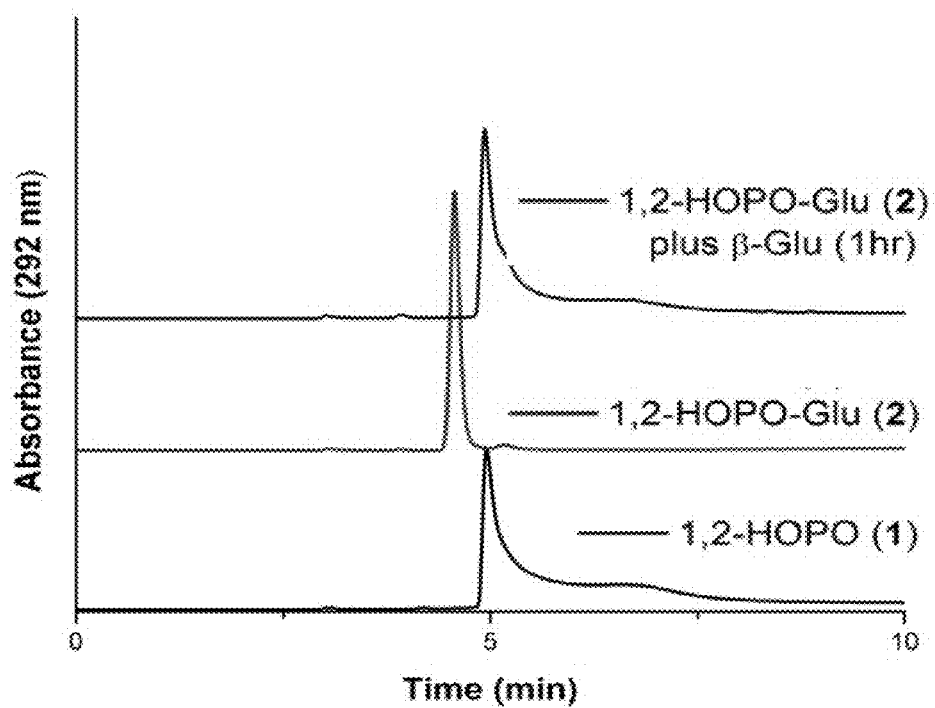
FIG. 5. HPLC traces of compounds 1 (bottom) and 2 (middle) and compound 2 after incubation with β-glucosidase (50 U, top) for 1 h. Retention times are 4.92 min for 1 and 4.42 min for 2.
Figure 6:
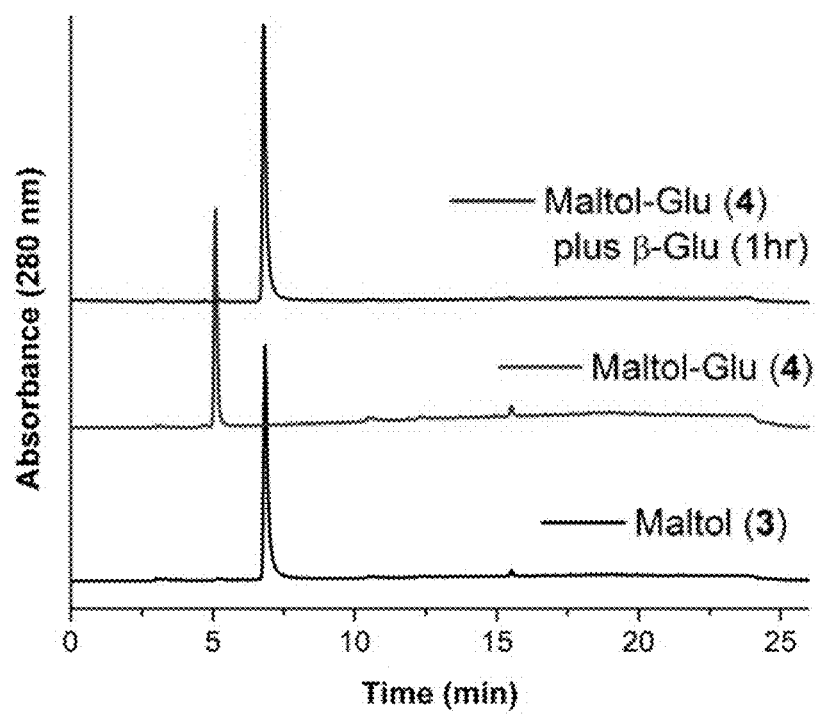
FIG. 6. HPLC traces of compounds 3 (bottom) and 4 (middle) and compound 4 after incubation with β-glucosidase (50 U, top) for 1 h. Retention times are 6.84 min for 3 and 5.07 min for 4.
Figure 7:
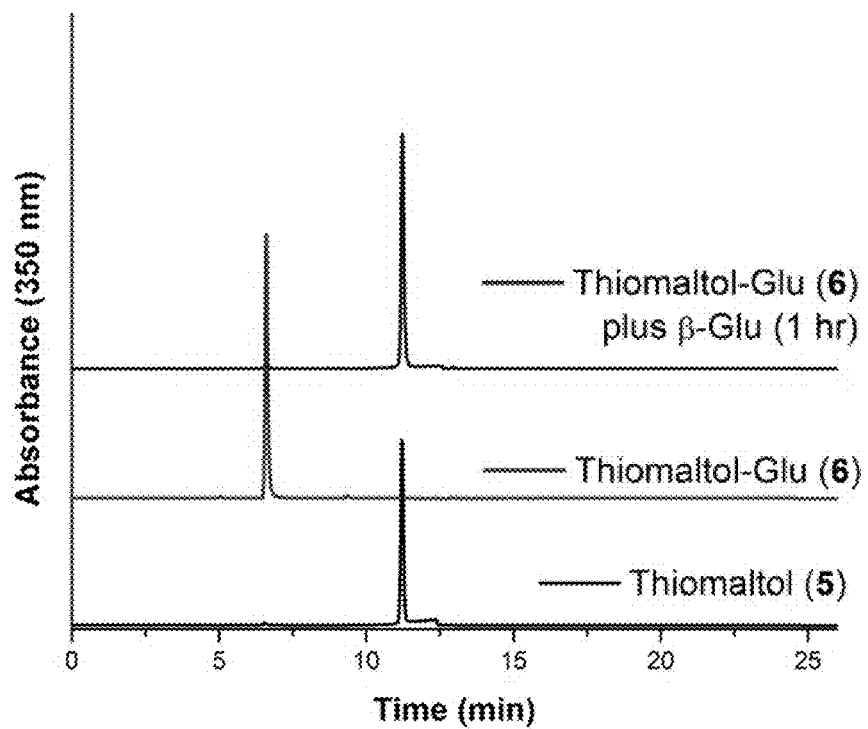
FIG. 7. HPLC traces of compounds 5 (bottom) and 6 (middle) and compound 6 after incubation with β-glucosidase (50 U, top) for 1 h. Retention times are 11.21 min for 5 and 6.60 min for 6.

To evaluate the ability of these compounds to be enzymatically activated, cleavage of the protected ZBGs in the presence of β-glucosidase (from almond extract, Fluka) was followed using electronic spectroscopy. To a solution of the protected ZBG in HEPES buffer was added β-glucosidase and the change in absorbance was monitored over time. As can be seen in FIG. 2 for compound 2, the absorbance over time shows a decrease at 292 nm while a band at 312 nm emerges, indicative of the deprotected ZBG 1-hydroxy-2-pyridin-2(1H)-one (1). Similar spectra were observed for the hydroxypyrone derivatives 4 and 6 (FIGS. 3-4). In addition, cleavage of the protected ZBGs was confirmed by HPLC analysis (FIGS. 5-7). These studies demonstrate that in aqueous buffer at room temperature, the glucose-protected ZBGs can be readily activated in the presence of β-glucosidase providing compelling evidence that hydroxypyridinone and hydroxypyrone ZBGs are well suited for the development of enzyme-activated MMP proinhibitors.

Having demonstrated the use of glucose as an effective protecting group for the aforementioned ZBGs, we aimed to incorporate a glucose protecting group into a full-length MMPi (matrix metalloprotease inhibitor) to develop an MMP proinhibitor. We selected the full-length inhibitor 1,2-HOPO-2 (7), a potent non-hydroxamate inhibitor of MMPs that uses a 1-hydroxy-2-pyridin-2(1H)-one (1) ZBG.[35] Synthesis of the MMP proinhibitor was achieved by addition of acetobromo-α-D-glucose and $Cs_2CO_3$ to 7 in DMF at room temperature to give 8a in high yields (>80%, Scheme 2). These reaction conditions were a vast improvement in yield over the aqueous reaction conditions used to protect the ZBGs. Surprisingly, these high-yield reaction conditions did not produce the desired products with the ZBGs (1, 3, and 5). The final proinhibitor (8) was obtained by deprotection of the glucose acetate groups with NaOMe in MeOH at 0° C. for one hour.

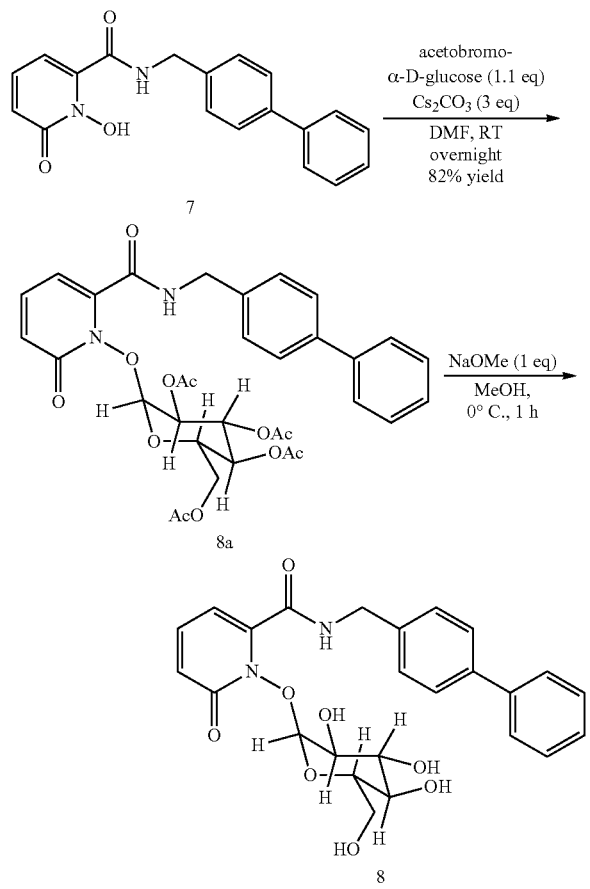

Figure 8:
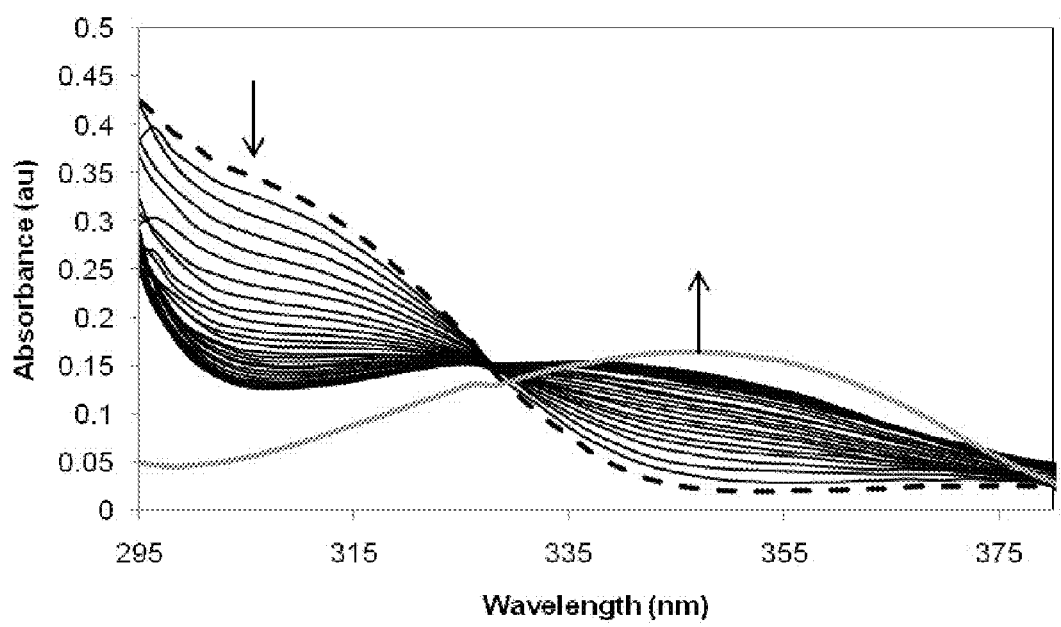
FIG. 8. Absorption spectra of the glucose-protected full-length inhibitor 1,2-HOPO-2 (8) (0.05 mM in HEPES buffer) in the presence of β-glucosidase (100 U) at 37° C. monitored every 5 min for 4 h with spectra shown every 10 min. The heavy lines are the initial (dashed) and final (solid) spectra; arrows indicate change in spectra over time. A sample of 1,2-HOPO-2 (7) (~0.05 mM) in HEPES buffer is also shown (light gray solid line).
Figure 9:
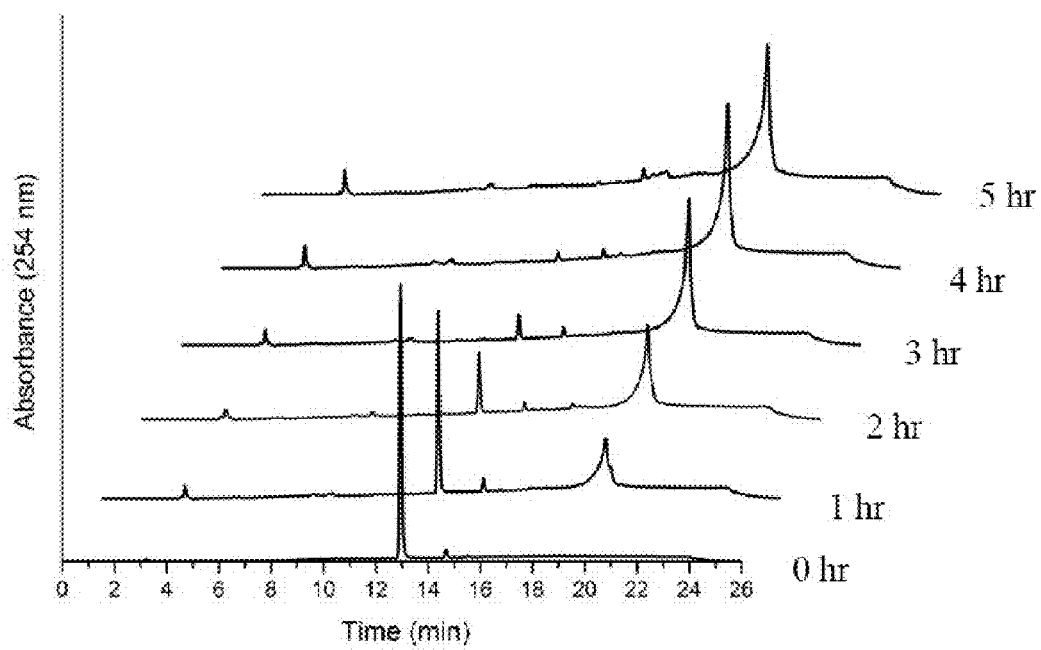
FIG. 9. HPLC traces of compound 8 (0.8 mM) over time in the presence of β-glucosidase (250 U). Retention times are 12.88 min for 8 and 19.39 min for the product 7.

The MMP proinhibitor 8 was first evaluated for activation by β-glucosidase using electronic spectroscopy and HPLC analysis (FIGS. 8-9). Results from these studies indicate that while cleavage of 8 to produce the active MMPi 1,2-HOPO-2 (7) goes to completion, the kinetics of the reaction are noticeably slower than that observed for the protected ZBGs. Complete conversion of 8 to 7 required ~4 h at 37° C.; a $K_m$ value of 210 μM was determined (FIG. 10). Notably, compound 8 was not cleaved under acidic conditions (0.1 M HCl) over 24 h (FIG. 11). Overall, this is the first example of a glucosidase proinhibitor that can be enzymatically cleaved to yield the active MMPi.

Figure 12:
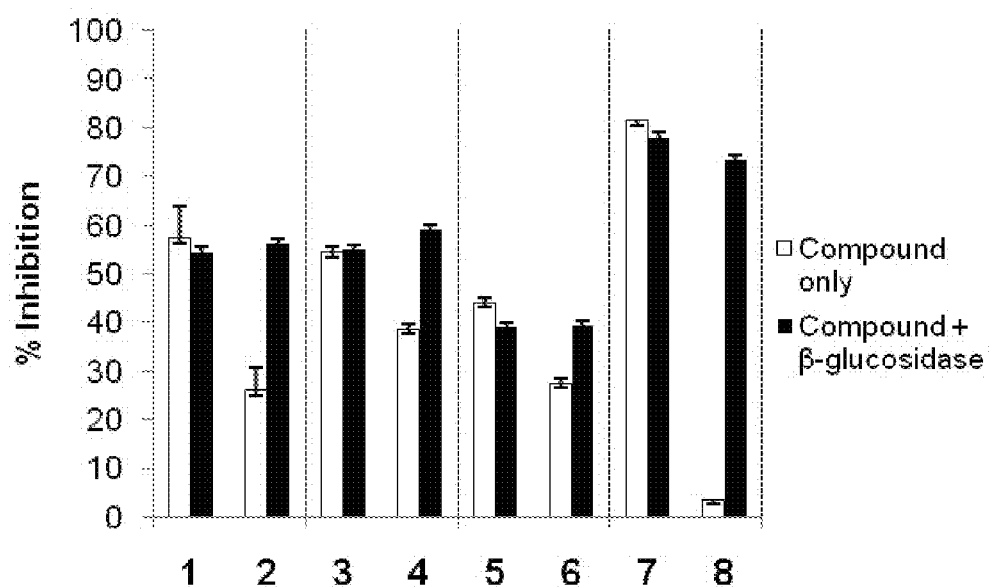
FIG. 12. Percent inhibition of MMP-9 with compounds 1-8 tested at 1 mM for 1 and 2, 4 mM for 3 and 4, 125 μM for 5 and 6, and 16 μM for 7 and 8, in the absence (white) and presence (black) of β-glucosidase.

The ability of the protected compounds to inhibit MMP-9 (gelatinase-B) in the presence of β-glucosidase was evaluated using a fluorescence-based assay.[36]. Compounds 1-8 were evaluated at a concentration close to their reported $IC_{50}$ values in the presence and absence of β-glucosidase (FIG. 12). The percent inhibition of MMP-9 with the ZBGs (1, 3, and 5) is close to 50% when tested with and without β-glucosidase indicating that the presence of low concentrations of β-glucosidase in the assay has little effect on MMP inhibition. The protected ZBGs (2, 4, and 6) show attenuated inhibition when evaluated without the activating enzyme and complete restoration of inhibition when exposed to β-glucosidase. Compounds 2, 4, and 6 do show some inhibition of MMP-9 which is likely due to non-specific binding at the high concentrations of the ZBGs (0.125-4 mM) used in these experiments.

In the absence of β-glucosidase, the complete MMPi 8 (16 μM) displays very little inhibition of MMP-9, but upon activation, MMP-9 activity is inhibited by 73%, which is essentially identical to an authentic sample of inhibitor 7. Even greater potency was observed against MMP-8, where MMPi 8 could be activated with β-glucosidase to obtain 33% inhibition at only 150 nM (FIG. 11), representing a >1000-fold increase in activity upon enzymatic activation. The factor of 1000 difference in the quotient $IC_{50}$ ($IC_{50}$ value of proinhibitor in the presence and absence of enzyme) has been reported as an optimal value for the ADEPT approach to targeted therapy,[11] and hence MMPi 8 exceeds this threshold with MMP-8. The higher activity against MMP-8 is consistent with the potency of the cleavage product (7) against this metalloenzyme.[35] The results for 8 show that incorporation of a ZBG protection strategy into an MMPi gives near complete abolition and recovery of inhibitory activity with these enzyme inhibitors.

In summary, there has been demonstrated passivation of an MMPi as a proinhibitor, activation thereof through an enzymatic reaction, and inhibition of MMPs in a controlled manner. We have shown that protection of the metal-binding moiety of MMPi can be achieved and enzymatically removed to release an active, intact MMPi.

REFERENCES

1. L. M. Coussens, B. Fingleton and L. M. Matrisian, Science, 2002, 295, 2387-2392.
2. M. Whittaker, C. D. Floyd, P. Brown and A. J. H. Gearing, Chem. Rev., 1999, 99, 2735-2776.
3. C. M. Overall and C. Lüpez-Otín, Nat. Rev. Cancer, 2002, 2, 657-672.
4. R. Renkiewicz, L. Qiu, C. Lesch, X. Sun, R. Devalaraja, T. Cody, E. Kaldjian, H. Welgus and V. Baragi, Arthritis Rheum., 2003, 48, 1742-1749.
5. B. Fingleton, Sem. Cell Dev. Biol., 2008, 19, 61-68.
6. W. A. Denny, Cancer Invest., 2004, 22, 604-619.
7. F. H. Fry and C. Jacob, Curr. Pharma. Des., 2006, 12, 4479-4499.
8. T. A. Houston, Curr. Drug Del., 2007, 4, 264-268.
9. H. Schugar, D. E. Green, M. L. Bowen, L. E. Scott, T. Storr, K. Bohmerle, F. Thomas, D. D. Allen, P. R. Lockman, M. Merkel, K. H. Thompson and C. Orvig, Angew. Chem. Int. Ed., 2007, 46, 1716-1718.
10. T. Storr, M. Merkel, G. X. Song-Zhao, L. E. Scott, D. E. Green, M. L. Bowen, K. H. Thompson, B. O. Patrick, H. Schugar and C. Orvig, J. Am. Chem. Soc., 2007, 129, 7453-7463.
11. L. F. Tietze and T. Feuerstein, Aus. J. Chem., 2003, 56, 841-854.
12. S. Wang, D. Liu, X. Zhang, S. Li, Y. Sun, J. Li, Y. Zhou and L. Zhang, Carbo. Res., 2007, 342, 1254-1260.
13. K. N. Syrigos, G. Rowlinson-Busza and A. A. Epenetos, Int. J. Cancer, 1998, 78, 712-719.

14. L. F. Tietze, H. J. Schuster, B. Krewer and I. Schuberth, J. Med. Chem., 2009, 52, 537-543.
15. I. Niculescu-Duvaz and C. J. Springer, Exp. Opin. Invest. Drugs, 1996, 3, 289-308.
16. K. D. Bagshawe, Curr. Durg. Tar., 2009, 10, 152-157.
17. K. D. Bagshawe and R. H. J. Begent, Adv. Drug Del. Rev., 1996, 22, 365-367.
18. Y. S. Tian, H. Y. Lee, C. S. Lim, J. Park, H. M. Kim, Y. N. Shin, E. S. Kim, H. J. Jeon, S. B. Park and B. R. Cho, Angew. Chem. Int. Ed., 2009, 48, 8027-8031.
19. R. J. Gillies, I. Robey and R. A. Gatenby, J. Nucl. Med., 2008, 49, 24S-42S.
20. Y.-S. Lin, R. Tungpradit, S. Sinchaikul, F.-M. An, D.-Z. Liu, S. Phutrakul and S.-T. Chen, J. Med. Chem., 2008, 51, 7428-7441.
21. C. Fernandez, O. Nieto, E. Rivas, G. Montenegro, J. A. Fontenla and A. Fernandez-Mayoralas, Carbo. Res., 2000, 327, 353-365.
22. G. De Simone, R. M. Vitale, A. Di Fiore, C. Pedone, A. Scozzafava, J.-L. Montero, J.-Y. Winum and C. T. Supuran, J. Med. Chem., 2006, 49, 5544-5551.
23. T. W. Failes, C. Cullinane, C. I. Diakos, N. Yamamoto, J. G. Lyons and T. W. Hambley, Chem. Eur. J., 2007, 13, 2974-2982.
24. T. W. Failes and T. W. Hambley, J. Inorg. Biochem., 2007, 101, 396-403.
25. T. Suzuki, S. Hisakawa, Y. Itoh, N. Suzuki, K. Takahashi, M. Kawahata, K. Yamaguchi, H. Nakagawa and N. Miyata, Bioorg. Med. Chem. Lett., 2007, 17, 4208-4212.
26. A. Bowers, N. West, J. Taunton, S. L. Schreiber, J. E. Bradner and R. M. Williams, J. Am. Chem. Soc., 2008, 130, 11219-11222.
27. M. B. Mitchell and I. W. A. Whitcombe, Tetrahedron Lett., 2000, 41, 8829-8834.
28. M. Thomas, F. Rivault, I. Tranoy-Opalinski, J. Roche, J.-P. Gesson and S. Papot, Bioorg. Med. Chem. Lett., 2007, 17, 983-986.
29. M. Thomas, J. Clarhaut, I. Tranoy-Opalinski, J.-P. Gesson, J. Roche and S. Papot, Bioorg. Med. Chem., 2008, 16, 8109-8116.
30. K. Liu, P. Wahlberg, G. Leonardsson, A.-C. Hägglund, A. Ny, I. Bodén, C. Wibom, L. R. Lund and T. Ny, Develop. Biol., 2006, 295, 615-622.
31. S. E. Gill, C. Pape and K. J. Leco, Develop. Biol., 2006, 298, 540-554.
32. D. T. Puerta, J. A. Lewis and S. M. Cohen, J. Am. Chem. Soc., 2004, 126, 8388-8389.
33. D. T. Puerta, M. O. Griffin, J. A. Lewis, D. Romero-Perez, R. Garcia, F. J. Villarreal and S. M. Cohen, J. Biol. Inorg. Chem., 2006, 11, 131-138.
34. L. E. Scott, B. D. G. Page, B. O. Patrick and C. Orvig, Dalton Trans., 2008, 6364-6367.
35. A. Agrawal, D. Romero-Perez, J. A. Jacobsen, F. J. Villarreal and S. M. Cohen, ChemMedChem, 2008, 3, 812-820.
36. C. G. Knight, F. Willenbrock and G. Murphy, FEBS Letters, 1992, 296, 263-266.

Example 6

Exemplary Methods Related to Prodrugs Including Sulfonate Ester Moieties

Proinhibitors for matrix metalloproteinases (MMPs), as described herein, have been synthesized. Specifically, MMP proinhibitors have been obtained that can be activated in the presence of reactive oxygen species (ROS). These findings show that the resultant compounds can be rapidly cleaved by ROS and hence may provide cardioprotection at an ischemic site. There is provided description of the use of two different ROS-activated protecting groups (aryl sulfonate esters and boronic esters) with the zinc-binding group (ZBG) warheads of MMP inhibitors.

General.

Starting materials and solvents were purchased from commercial suppliers (Sigma-Aldrich, Alfa Aesar, Fisher, and others) and used as received. $^1H/^{13}C$ NMR spectra were recorded at ambient temperature on a 400 or 500 MHz Varian FT-NMR instrument or a 500 MHz JEOL instrument, located in the Department of Chemistry and Biochemistry at the University of California San Diego. Mass spectra were obtained at the Molecular Mass Spectrometry Facility in the Department of Chemistry and Biochemistry at the University of California, San Diego. Elemental analysis was preformed by NuMega Resonance Labs, San Diego.

UV-Vis Spectroscopy.

Absorption spectra of compounds were taken on a Perkin-Elmer Lambda 25 UV-Visible Spectrophotometer. To a 1.0 mL solution at 0.05 mM concentration of each compound in HEPES buffer (50 mM, pH 7.5) was added $H_2O_2$ (10 µL, 0.09M in HEPES) and absorption spectra were monitored over time at room temperature. Hydrolytic stability was measured by monitoring each sample in HEPES buffer over a 24 hour time period.

Calculation of Rate Constant.

The pseudo-first order rate constant was calculated following literature procedure [20]. To a 1.0 mL solution of compounds PZBG-1a, PZBG-1b, PZBG-1e, PZBG-5a, and PZBG-5b in HEPES buffer at 50 µM was added $H_2O_2$ to final concentrations of 150 µM, 250 µM, 500 µM, 750 µM, and 900 µM. Spectra were monitored over 15-30 min at room temperature with at least 50 spectra recorded at every concentration. The change in absorption at 298 nm for PZBG-1a and PZBG-1b were monitored, while the change in absorption at 288 nm was recorded for PZBG-1e, and 310 nm for PZBG-5a and PZBG-5b. The rate constant ($k_{obs}$) was found from the linear slope of $\ln[(A-A_{ZBG})/(A_o-A_{ZBG})]$ vs. time where $A_{ZBG}$ is the absorbance of a 50 µM sample of the ZBG or full-length inhibitor and $A_O$ is the initial absorbance of PZBG-1a, PZBG-1b, PZBG-1e, PZBG-5a, and PZBG-5b. The rate of conversion was determined from the slope of the line of $k_{obs}$ vs. $[H_2O_2]$.

HPLC.

Analytical HPLC was performed on a HP Series 1050 system equipped with a Vydac® C18 reverse phase column (218 TP, 250×4.6 mm, 5 µm). Separation was achieved with a flow rate of 1 mL/min and the following solvents: solvent A is 5% MeOH and 0.1% formic acid in $H_2O$ and solvent B is 0.1% formic acid in MeOH. Starting with 95% A and 5% B, an isocratic gradient was run for 15 min to a final solvent mixture of 5% A and 95% B, which was held for 5 min before ramping back down to 95% A and 5% B in 2 min and holding for an additional 4 min. Compounds ZBG-1a and PZBG-1a were prepared in HEPES buffer (50 mM, pH 7.5) at a concentration of 1 mM and retention times were determined. To evaluate cleavage by $H_2O_2$, a 1 mM solution of PZBG-1a in HEPES buffer was reacted with a 20-fold excess of $H_2O_2$ before analyzing under identical HPLC conditions as before.

Inhibition Assays.

MMP-12 (catalytic domain, human recombinant) was purchased from Enzo Life Sciences. The assays were carried out in a 96-well plate using a Bio-Tex Flx 800 plate reader. The activity of MMP-12 was evaluated after a 30 min incubation in the presence of $H_2O_2$ and proMMPi. The concentration of proMMPi used was selected to be close to the $IC_{50}$ value of the parent full-length inhibitors, 1,2-HOPO-2 and PY-2[38]. In each well, 1 μL of proinhibitors PZBG-5a, PZGB-5b, and PZBG-6a and the inhibitors 1,2-HOPO-2 and PY-2 in DMSO (5 μM) were incubated for 30 min at 37° C. with 20 μL of MMP-12 (0.35 U/mL), 10 μL $H_2O_2$ (1 mM in HEPES buffer, pH 7.5), and MMP assay buffer (50 mM HEPES, 10 mM $CaCl_2$, 0.10% Brij-35, pH 7.5) for a total volume of 99 μL. A control sample containing 10 μL $H_2O_2$ (1 mM in HEPES buffer, pH 7.5) in MMP assay buffer was also prepared to confirm that $H_2O_2$ did not inhibit MMP-12. The reaction was initiated by the addition of 1 μL (400 μM) of the fluorescent substrate (Mca-Pro-Leu-Gly-Leu-Dpa-Ala-Arg-$NH_2$ where Mca=(7-methoxycoumarin-4-yl)-acetyl and Dpa=N-3-(2,4-dinitrophenyl)-L-α-β-diaminopropionyl)) after the 30 minute incubation period and kinetic activity was measured every minute for 20 minutes with excitation and emission wavelengths at 335 nm and 405 nm, respectively. Enzyme activity with inhibitor was calculated with respect to the control experiment—no inhibitor present. Measurements were performed in duplicate in two independent experiments. (1 mM

Example 7

Exemplary Prodrugs Including Sulfonylaryls/Sulfonate Esters

Figure 13:
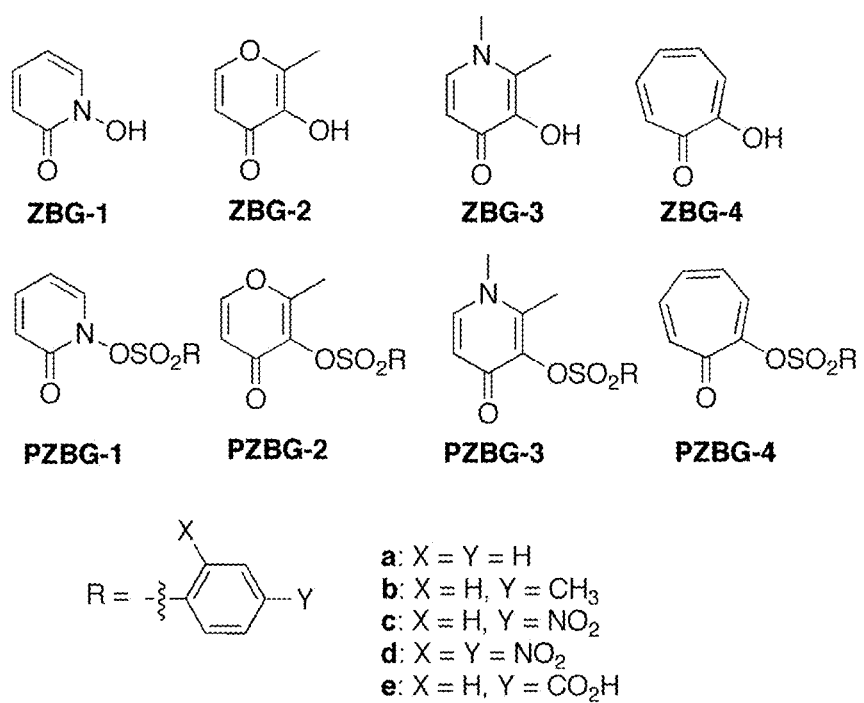
FIG. 13. ZBGs and their sulfonate ester derivatives (PZBGs) (examples of potential oxidatively sensitive prodrugs and potential zinc binding moieties) examined in this study.

Assessment of Sulfonate Esters as Suitable Protecting Groups for ZBGs. Previous studies utilizing fluorescent probes have shown sulfonate esters to be suitable protecting groups of hydroxyl groups that show a turn-on response upon exposure to ROS, including $H_2O_2$ and superoxide anion [35-37]. To investigate the use of sulfonate ester protecting groups for the development of ROS-activated proMMPi, a small library of compounds was synthesized. As shown in FIG. 13, sulfonate esters with varying substituents were appended to 1,2-hydroxypyridinone (1,2-HOPO, ZBG-1), 3-hydroxy-2-methyl-4H-pyran-4-one (maltol, ZBG-2), 3-hydroxy-1,2-dimethylpyridin-4(1H)-one (3,4-HOPO, ZBG-3), and tropolone (ZBG-4) to evaluate which protected ZBGs provided efficient activation in the presence of $H_2O_2$. These protected ZBGs (PZBGs) were readily prepared by combining a ZBG with the appropriate sulfonyl chloride in pyridine. In total, 17 PZBGs (1a-e, 2a-d, 3a-d, and 4a-d) were prepared and tested for cleavage in the presence of $H_2O_2$.

Figure 14:
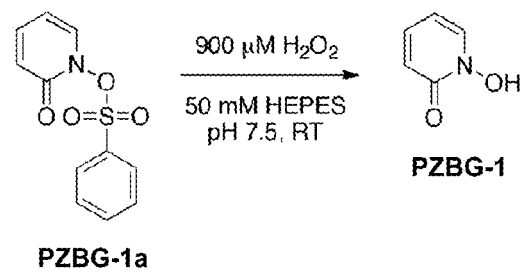
FIG. 14. Analysis of PZBGs in the presence of H$_2$O$_2$. Top. PZBG-1a and ZBG-1. Middle. Absorption spectra of PZBG-1a (0.05 mM, 50 mM HEPES buffer, pH=7.5) in the presence of H$_2$O$_2$ (0.9 mM, 18 equiv) monitored every 5 min for 60 min. The dashed line represents the initial spectrum, and an authentic sample of ZBG-1 is shown as a heavy line. The arrows indicate change in spectra over time. Bottom. HPLC chromatogram of PZBG-1a, PZBG-1a+H$_2$O$_2$, and ZBG-1. Retention times are 11.5 min for PZBG-1a and 5.0 min for ZBG-1.
Figure 14:
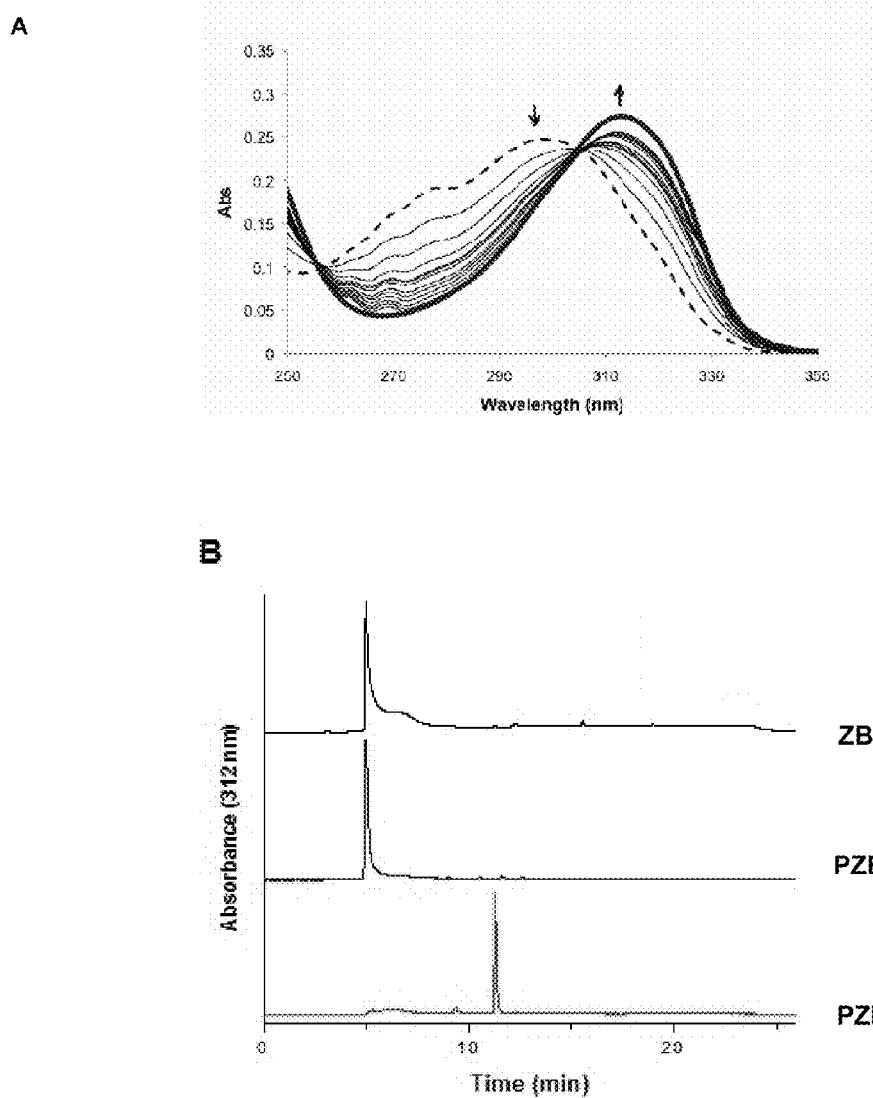

To evaluate cleavage of the compounds by ROS, a sample of each PZBG in HEPES buffer (50 mM, pH 7.5) was activated with excess $H_2O_2$ (0.9 M, 18 equiv) and the change in absorbance was monitored over time via electronic spectroscopy. Surprisingly, only compounds derived from ZBG-1 (1,2-HOPO) showed a change in absorption (corresponding to the formation of the free ZBG) upon exposure to $H_2O_2$. The fact that only the five PZBG-1 derivatives (out of 17 total combinations) were cleaved in the presence of $H_2O_2$ suggests that the N—O group is important for the observed reactivity. FIG. 14 shows representative absorption spectra of PZBG-1a in the presence of $H_2O_2$. A decrease in absorption at 298 nm over time is noted, representing the disappearance of the PZBG-1a and a gradual increase in absorption at 312 nm is observed, indicating the emergence of ZBG-1. In addition, analytical HPLC was used to confirm that ZBG-1 was the product after reaction with $H_2O_2$ (FIG. 14). Upon the addition of $H_2O_2$ to PZBG-1a for 60 min, a peak with a retention time of 5.0 min was observed, which is identical to an authentic sample of ZBG-1. Similarly, treatment of PZBG-1b with $H_2O_2$ resulted in nearly identical spectra as found with PZBG-1a, while PZBG-1c showed rapid hydrolysis upon the addition of $H_2O_2$ (data not shown). It should be noted that the absorption spectra of PZBG-1d was not readily interpreted, due to the overlapping of absorption profiles of the protecting group and the free ZBG; however, thin-layer chromatography showed the emergence of the free ZBG, demonstrating rapid hydrolytic cleavage of the protecting group (even in the absence of $H_2O_2$). These findings taken together prompted the synthesis of PZBG-1e, a more water-soluble alternative to PZBG-1c, with a carboxylic acid attached to the para position of the sulfonate ester. A substantial increase in solubility in buffered solution was noted, and the cleavage behavior was similar to the other compounds reported (see below), making PZBG-1e an attractive candidate for development into a full length proMMPi. As mentioned above, sulfonate ester derivatives of ZBG-2a-d, ZBG-3a-d, and ZBG-4-a-d did not show any change in absorbance over a period of 1 h with an 18 molar excess of $H_2O_2$. These findings suggest that the N—O bond in ZBG-1 is important for facile cleavage of the sulfonate ester group in this series of ligands, although this will require verification by additional studies. It is interesting to note that the compounds tested that did not contain the N—O moiety (those based off of PZBG-2, PZBG-3, and PZBG-4) appeared to be stable in aqueous buffer (over at least a 1 h time period).

One key factor for any prodrug approach is the stability of the protecting group in the absence of the triggering stimuli. In order to test the stability of the sulfonate esters in buffer, absorption spectra for PZBG-1a, b, and e were collected over 24 h. These stability studies showed ~50% cleavage of PZBG-1a and PZBG-1e in 6 h, while PZBG-1b was ~30% cleaved in 24 h. The rates of conversion of PZBG-1a, b, and e were determined by monitoring the change in absorption using pseudo-first order reaction conditions with an excess of $H_2O_2$ as previously reported [20]. The calculated rate constants indicate that PZBG-1e had the fastest rate constant at 1.3 $M^{-1}$ $sec^{-1}$, while rate constants of 0.7 $M^{-1}$ $sec^{-1}$ and 0.3 $M^{-1}$ $sec^{-1}$ were determined for PZBG-1a and b, respectively. It should be noted that the determined rate constants do take into account background hydrolysis and reactivity with $H_2O_2$; however, all kinetic experiments were taken over a 15-30 min time period, which is before a measurable amount of hydrolysis was observed. Experiments with PZBG-1c and PZBG-1d showed the fastest cleavage kinetics upon exposure to $H_2O_2$, with complete dissociation achieved in <3 min (no rate constants determined). The rates of conversion for the PZBG-1 compounds are consistent with the nature of the respective substituents on the leaving groups. When substituents are varied on an aromatic ring, the change in free energy of activation for a given reaction is proportional to the change in Gibbs free energy, as summarized by the Hammett equation [39]. Of the molecules for which rate constants were obtained, PZBG-1e that contains an electron-withdrawing group (—$CO_2H$) in the para position, dissociates the fastest. PZBG-1b, on the other hand, with an electron-donating group (—$CH_3$) in the para position had the slowest rate of the compounds tested. PZBG-1a, with no substituents had a cleavage rate falling between the others, consistent with the Hammett relationship. The results with PZBG-1c and PZBG-1d are also consistent with this relationship, with the strongly electron withdrawing nitro groups producing the fastest rates, resulting in the inability to acquire precise values.

Development of Full-Length proMMPi.

Figure 15:
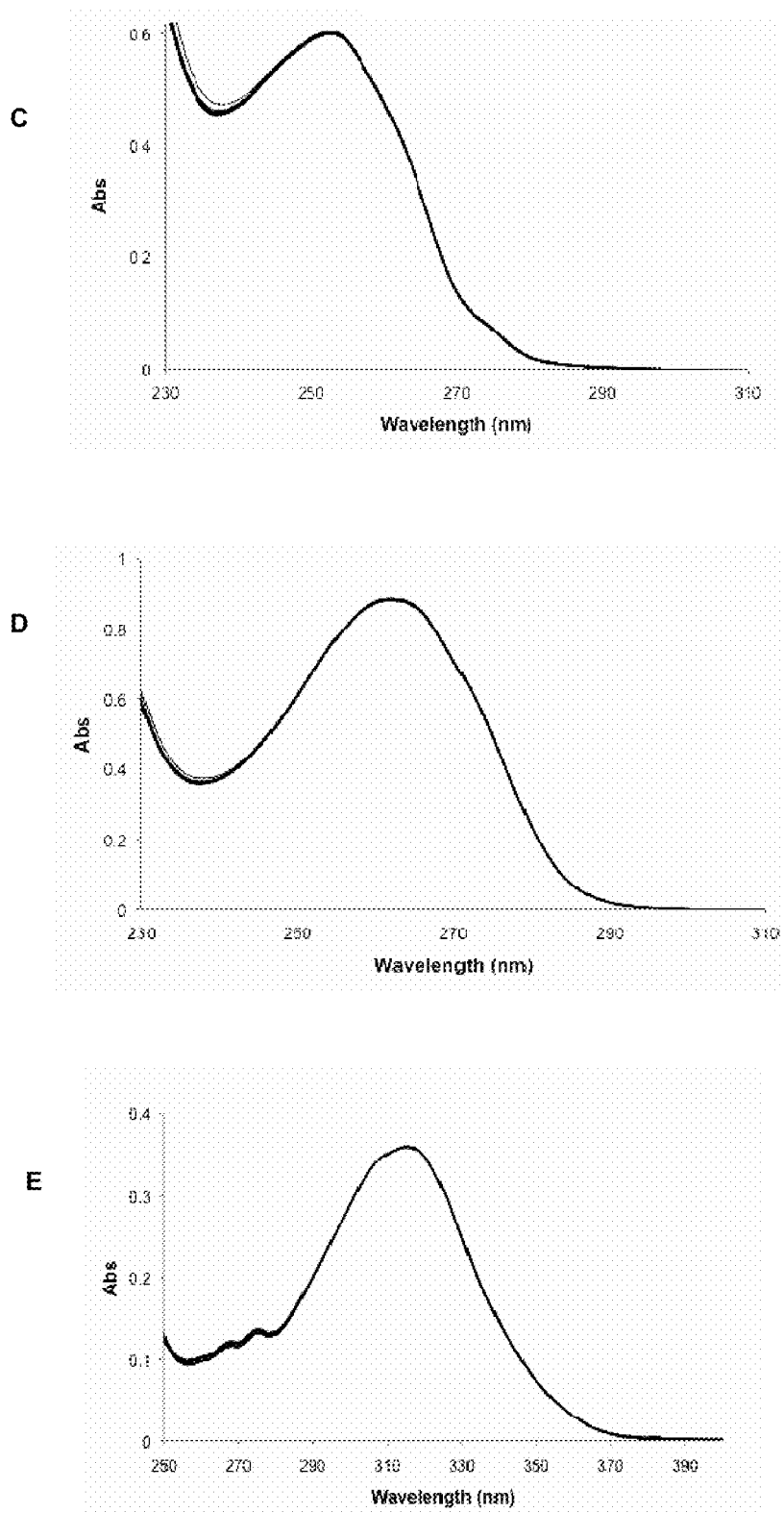
FIG. 15. Absorption spectra (Top to Bottom) of PZBG-2a, PZBG-3a, and PZBG-4-a, respectively (0.05 mM, 50 mM HEPES buffer, pH=7.5) in the presence of H$_2$O$_2$ (0.9 mM, 18 equiv) monitored every 5 min for 60 min. The overlapping spectra indicate that no cleavage of the protecting group is occurring in the presence of H$_2$O$_2$.
Figure 16:
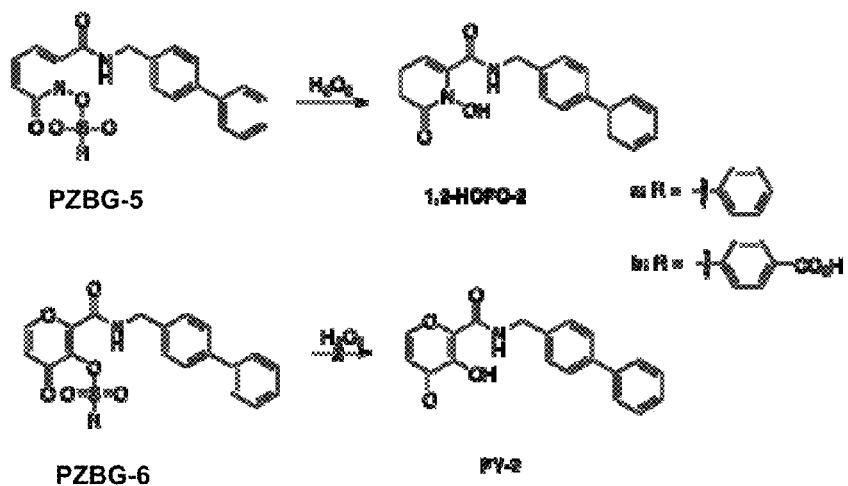
FIG. 16. Top panel: Scheme 1. Activation of proinhibitor PZBG-5a or PZBG-5b with H$_2$O$_2$ results in generation of the inhibitor 1,2-HOPO-2. In contrast, treatment of proinhibitor PZBG-6a with H$_2$O$_2$ did not result in production of the inhibitor PY-2. Bottom panel: Absorption spectra of PZBG-5b (0.05 mM, 50 mM HEPES buffer, pH=7.5) in the presence of H$_2$O$_2$ (0.9 mM, 18 equiv excess) monitored every 5 min for 60 min. The dashed line represents the initial spectrum, and an authentic sample of 1,2-HOPO-2 is shown as a heavy line. The arrows indicate change in spectra over time.
Figure 16:
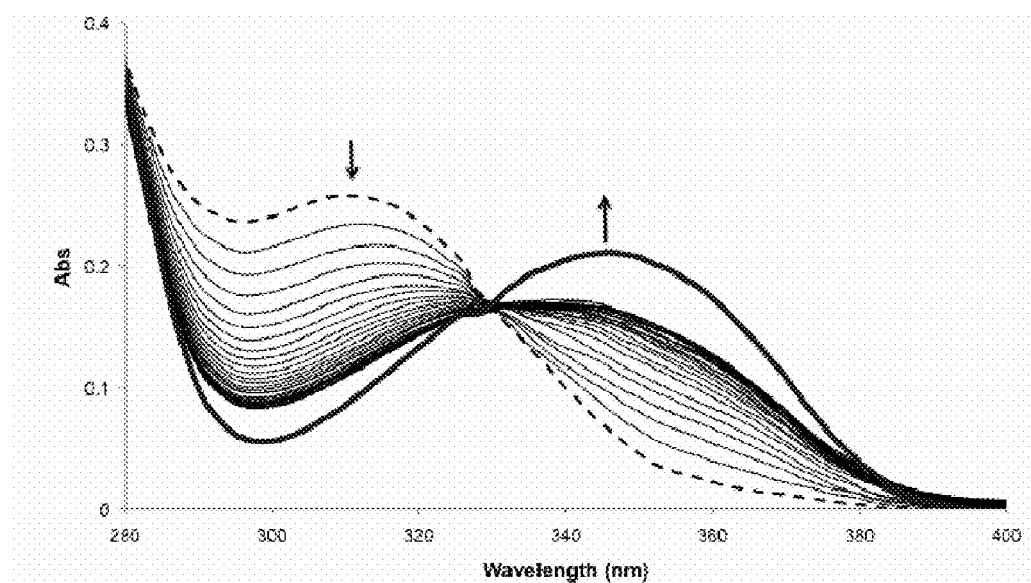

Having demonstrated the ability of sulfonate esters to act as cleavable protecting groups for ZBG-1, this chelator was incorporated into a full-length proMMPi. The corresponding full-length inhibitor of ZBG-1 with a hydrophobic biphenyl backbone, 1,2-HOPO-2, has been previously prepared and studied [38]. 1,2-HOPO-2 is an effective inhibitor of MMP-3, MMP-8 and MMP-12 with $IC_{50}$ values under 100 nM [38]. Two full length MMPi (1,2-HOPO-2 and PY-2) were prepared by previously reported procedures and then protected in pyridine with an excess of the appropriate sulfonyl chloride to generate proMMPi PZBG5a, PZBG5b, and PZBG6a. The products were generally purified via silica gel chromatography affording the desired product. The proMMPi PZBG5a and PZBG5b were evaluated for activation by $H_2O_2$ via electronic spectroscopy in the same manner as with the PZBG compounds. As shown in FIG. 15 (Top), the activation of PZBG5a and PZBG5b to the known MMPi 1,2-HOPO-2 is achieved upon the addition of $H_2O_2$. FIG. 16 shows the absorption spectra of PZGB5b in which a decrease at 310 nm over time is observed, indicating the disappearance of the protected MMPi while a gradual increase in absorption at 350 nm is observed, demonstrating the emergence of 1,2-HOPO-2. Pseudo-first order rate constants were determined with an excess of $H_2O_2$ as described above. Rate constants of 0.3 $M^{-1}$ $s^{-1}$ and 1.1 $M^{-1}$ $s^{-1}$ were obtained for PZBG5a and PZBG5, respectively, which is in good agreement with the rate constants determined for the protected chelators PZBG-1a and PZBG-1e. To evaluate the stability of the sulfonate esters, absorption spectra of PZBG5a and PZBG5 were collected in buffer alone. Compounds PZBG5a and PZBG5 showed ~50% hydrolysis after 9 h and 3 h, respectively.

In order to further confirm that the behavior of the protected chelators (PZBG) was readily translated to a complete proMMPi, a proinhibitor based on PZBG-2a was synthesized. Compound PZBG6a, which contains a biphenyl backbone like PZBG5a, was prepared. Upon cleavage of the protecting group, PZBG6a should produce PY-2, a known inhibitor of several MMPs [38]. Treatment of PZBG6a with excess $H_2O_2$ over the course of 60 min did not result in cleavage of the sulfonate ester (Scheme 1), as evidenced by absorption spectroscopy (data not shown). This negative result is consistent with all of the findings described above, showing that the cleavage behavior of the PZBG is retained in its full-length proMMPi.

MMP Inhibition Studies.

Figure 17:
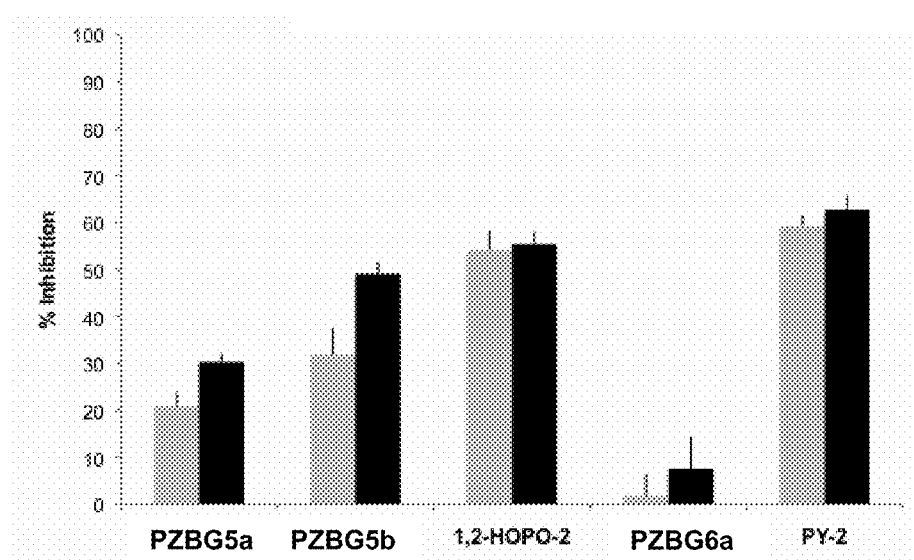
FIG. 17. Percent inhibition of MMP-12 with proinhibitors PZBG-5a, PZBG-5b, and PZBG-6a tested at 50 nM in the absence (gray) and presence (black) of $H_2O_2$ after 30 min of activation.

To monitor the ability of the protected compounds to inhibit MMP-12 in the presence of $H_2O_2$, a fluorescence-based assay was used [40]. Compounds PZBG-5a, PZBG-5b, and PZBG-6a were tested at concentrations close to the $IC_{50}$ values of their active parent molecules, 1,2-HOPO-2 and PY-2, against MMP-12. The percent inhibition of proinhibitors PZBG-5a, PZBG-5b, and PZBG-6a at 50 nM were evaluated after 30 min of incubation with and without $H_2O_2$ (FIG. 17). Before treatment with $H_2O_2$, PZBG5a and PZBG5 were shown to exhibit ~20% and ~30% inhibition of MMP-12, respectively. This significant level of inhibition is likely due to the hydrolysis of these compounds to the active MMPi during the incubation period, as described in the stability studies above. In addition, the inhibition assays are performed at a higher temperature then our kinetic experiments, which may result in an increase in the rate of hydrolysis and therefore lead to higher inhibition than might otherwise be expected. After treatment with 100 µM $H_2O_2$, the percent inhibition by proinhibitors PZBG5a and PZBG5 increased to ~30% and ~50% respectively, indicative of activation to 1,2-HOPO-2. Proinhibitor PZBG6a was used as a negative control, and as expected, displayed no significant change in inhibitory activity upon exposure to $H_2O_2$.

In an effort to develop broadly applicable methods to metalloprotein prodrugs, we have focused on developing 'proinhibitors' of the zinc(II)-dependent matrix metalloproteinases (MMPs), a canonical metalloprotein target of medicinal interest.[11, 12] MMP inhibitors (MMPi), like most metalloprotein inhibitors, generally employ a metal-binding group (MBG), which if blocked abolishes inhibitory activity. Prodrug matrix metalloproteinase inhibitors ('proMMPi') have been developed using enzymatic activation or activation by reactive oxygen species (ROS).[13-15] The development of ROS-activated proMMPi proved particularly intriguing, because: a) these were the first ROS-activated prodrugs of any kind reported, and b) these proMMPi can simultaneously result in targeted delivery of an MMPi while scavenging tissue-damaging ROS.[15] This 'dual mode' of action is particularly relevant to ischemia-reperfusion injury associated with stroke, where an increase in ROS (e.g. $H_2O_2$) and the concurrent activation of MMPs during the inflammatory response leads to the breakdown of the protective blood-brain barrier.[16-18]

REFERENCES

1. Whittaker M, Flyod C D, Brown P, Gearing A J H (1999) Chemical Rev. 99:2735-2776
2. Coussens L, Fingelton B, Matrisian L M (2002) Science 295:2387-2392
3. Jacobsen J A, Major Jourden J L, Miller M T, Cohen S M (2010) Biochim. Biophys. Acta 1803:72-94
4. Fingleton B (2008) Semin. Cell Dev. Biol. 19:61-68
5. Renkiewicz R, Qiu L, Lesch C, Sun X, Devalaraja R, Cody T, Kaldjian E, Welgus H, Baragi V (2003) Arthritis & Rheum. 48:1742-1749
6. Basset P, Bellocq J P, Wolf C, Stoll I, Hutin P, Limacher J M, Podhajcer O L, Chenard M P, Rio M C, Chambon P (1990) Nature 348:699-704
7. Wang J, Tsirka S E (2005) Brain 128:1622-1633
8. Wang Q, Tang X N, Yenari M A (2007) J. Neuroimmunol. 184:53-68
9. Rosenberg G A, Cunningham L A, Wallace J, Alexander S, Estrada E Y, Grossetete M, Razhagi A, Miller K, Gearing A (2001) Brain Res. 893:104-112
10. Mun-Bryce S, Rosenberg G A (1998) J. Cereb. Blood F. Met. 18:1163-1172
11. Fishman R (1975) N. Engl. J. Med. 293:706-711
12. Haorah J, Ramirez S H, Schall K, Smith D, Pandya R, Persidsky Y (2007) J. Neurochem. 101:566-576
13. Copin J-C, Merlani P, Sugawara T, Chan P H, Gasche Y (2008) Exp. Neurology 213:196-201
14. Yang Y, Estrada E Y, Thompson J F, Liu W, Rosenberg G A (2007) J. Cereb. Blood F. Met. 27
15. Overall C M, Kleifeld O (2006) Br J Cancer 94:941-946
16. Nagase H, Woessner Jr. J F (1999) J. Biol. Chem. 274: 21491-21494
17. Nelson A R, Fingleton B, Rothenberg M L, Matrisian L M (2000) J. Clin. Oncol. 18:1135-1149
18. Peterson J T (2006) Cardiovasc. Res. 69:677-687
19. Jin R, Yang G, Li G (2010) Neurobio. Disease 38:376-385
20. Dickens M G, Franz K J (2010) ChemBioChem 11:59-62
21. Perez L R, Franz K J (2010) Dalton Trans. 39:2177-2187
22. Schugar H, Green D E, Bowen M L, Scott L E, Storr T, Bohmerle K, Thomas F, Allen D D, Lockman P R, Merkel M, Thompson K H, Orvig C (2007) Angew. Chem. Intl. Ed 46:1716-1718
23. Storr T, Merkel M, Song-Zhao G X, Scott L E, Green D E, Bowen M L, Thompson K H, Patrick B O, Schugar H, Orvig C (2007) J. Am. Chem. Soc. 129:7453-7463
24. Wei Y, Guo M (2007) Angew. Chem. Intl. Ed 46:4722-4725

25. Wei Y, Zhang Y, Liu Z, Guo M (2010) ChemComm 46:4472-4474
26. Failes T W, Cullinane C, Diakos N, Yamamoto N, Lyons J G, Hambley T W (2007) Chem.—Eur. J. 13:2974-2982
27. Failes T W, Hambley T W (2006) Dalton Trans. 15:1895-1901
28. Failes T W, Hambley T W (2007) J. Inorg. Biochem. 101:396-403
29. Mitchell M B, Whitcombe I W A (2000) Tetrahedron Lett. 41:8829-8834
30. Major Jourden J L, Cohen S M (2010) Chem. Commun. 46:1241-1243
31. Major Jourden J L, Cohen S M (2010) Angew. Chem. Intl. Ed 49: Online Contents
32. Tietze L F, Feuerstein T (2003) Aust. J. Chem. 56:841-854
33. Miller E W, Tulyathan O, Isacoff E Y, Chang C J (2007) Nat. Chem. Biol. 3:263-267
34. Miller E W, Albers A E, Pralle A, Isacoff E Y, Chang C J (2005) J. Am. Chem. Soc. 127:16652-16659
35. Maeda H, Fukuyasu Y, Yoshida S, Fukuda M, Saeki K, Matsuno H, Yamauchi Y, Yoshida K, Hirata K, Miyamoto K (2004) Angew. Chem. Intl. Ed 43:2389-2391
36. Maeda H, Yamamoto K, Nomura Y, Kohno I, Hafsi L, Ueda N, Yoshida S, Fukuda M, Fukuyasu Y, Yamauchi Y, Itoh N (2005) J. Am. Chem. Soc. 127:68-69
37. Xu K, Tang B, Huang H, Yang G, Chen Z, Li P, An L (2005) ChemComm 48:5974-5976
38. Agrawal A, Romero-Perez D, Jacobsen J A, Villarreal F J, Cohen S M (2008) ChemMedChem 3:812-820
39. Hammett L P (1937) J. Am. Chem. Soc. 59:96-103
40. Knight C G, Willenbrock, F., Murphy, G. (1992) FEBS Lett. 296:263-266
41. Haba K, Papkov M, Shamis M, Lerner R A, Barbas III C F, Shabat D (2005) Angew. Chem., Int. Ed. 44:716-720
42. Weinstain R, Baran P S, Shabat D (2009) Bioconjugate Chem. 20:1783-1791

Example 8

Exemplary Methods Related to Oxidatively-Sensitive Prodrugs

UV-Vis Spectroscopy.

Absorption spectra of compounds B1-B16 were taken on a Perkin-Elmer Lambda 25 UV-visible spectrophotometer. To a 1.0 mL solution at 0.05 mM concentration in HEPES buffer (50 mM, pH 7.5) was added $H_2O_2$ (10 uL (0.09 M) in HEPES for compounds B1-B12 and B14-B16, 10 uL (0.9 M) in HEPES for compound B3, and 2.8 uL (0.09 M) in HEPES for compound B13). Spectra were monitored over time at room temperature. Absorption spectra of compounds B17-B21 were taken on a Perkin-Elmer Lambda 25 UV-visible spectrophotometer. To a 1.0 mL solution at 0.05 mM concentration of compounds 1-7 in HEPES buffer (50 mM, pH=7.5) was added $H_2O_2$ (10 uL, 0.09 M in HEPES) or $KO_2$ (0.10 mM) with catalase (5 U). Hydrolytic stability was measured by monitoring samples of B19-B21 in HEPES buffer for a 24 h time period. Spectra were monitored over time at room temperature.

Calculation of Rate Constant.

The pseudo-first order rate constant was calculated by monitoring the absorption spectra over time in the presence of excess hydrogen peroxide. To a 1.0 mL solution of compounds B1-B3 and B10-B14 in HEPES buffer (50 mM, pH 7.5) at 50 µM was added $H_2O_2$ to final concentrations of 150 µM, 250 µM, 500 µM, 750 µM, and 900 µM. Spectra were monitored over 15-30 min at room temperature with at least 50 spectra recorded. The change in absorption at 302 nm for B1-B3, 272 nm for B10, 312 nm for B11, 268 for B12, 306 nm for B13, and 303 nm for B14 were monitored. For compounds B1-B3 and B10-B11, the rate constant ($k_{obs}$) was found from monitoring the appearance of the monitored absorption peak by plotting the linear slope of ln $[(A_\infty-A_t)/(A_\infty)]$ vs. time (where $A_\infty$ is the absorbance of a 50 µM sample of the methyl salicylate for B1-B3, maltol for B10, and 1,2-HOPO for B11). For compounds B12-B14 the rate constant ($k_{obs}$) was found from monitoring the disappearance of the monitored absorption peak by plotting the linear slope of ln $[(A-A_{ZBG})/(A_0-A_{ZBG})]$ vs. time (where $A_{ZBG}$ is the absorbance of a 50 µM sample of the ZBG and $A_0$ is the initial absorbance of B3-B5).[3] The rate of conversion was determined from the slope of the line of $k_{obs}$ vs. $[H_2O_2]$. The pseudo-first order rate constant was calculated following literature procedure.[15] To a 1.0 mL solution of compounds B19-B21 in HEPES buffer at 50 µM was added $H_2O_2$ to final concentrations of 150 µM, 250 µM, 500 µM, 750 µM, and 900 µM. Spectra were monitored over 15-30 min at room temperature with at least 50 spectra recorded. The change in absorption at 292 nm for B19 and 252 nm for B20 and B21 were monitored. The rate constant ($k_{obs}$) was found from the linear slope of ln $[(A-A_{ZBG})/(A_0-A_{ZBG})]$ vs. time (where $A_{ZBG}$ is the absorbance of a 50 µM sample of the ZBG and $A_0$ is the initial absorbance of B19-B21). The rate of conversion was determined from the slope of the line of $k_{obs}$ vs. $[H_2O_2]$.

HPLC.

Analytical HPLC was performed on a HP Series 1050 system equipped with a Vydac® C18 reverse phase column (218 TP, 250×4.6 mm, 5 µm). Separation was achieved with a flow rate of 1 mL/min and the following solvents: solvent A is 5% MeOH and 0.1% formic acid in $H_2O$ and solvent B is 0.1% formic acid in MeOH. Starting with 95% A and 5% B, an isocratic gradient was run for 15 min to a final solvent mixture of 5% A and 95% B, which was held for 5 min before ramping back down to 95% A and 5% B in 2 min and holding for an additional 4 min. Compounds were prepared in HEPES buffer (50 mM, pH 7.5) at a concentration of 1 mM. Retention times of compounds were determined under identical HPLC conditions prior to and after reaction with $H_2O_2$. LC-MS(+) was performed on compounds B6, B15 and B16 to confirm cleavage of the boronic ester to the phenolic moiety.

Inhibition Assays.

MMP-9 (catalytic domain, human, recombinant) and MMP-12 (catalytic domain, human, recombinant) were purchased from Enzo Life Sciences. The assays were carried out in 96-well plates using a Bio-Tek Flx 800 plate reader. $IC_{50}$ values were obtained for proinhibitors B17 and B18 against MMP-9 and MMP-12. Serial dilutions of the compounds dissolved in DMSO were incubated at 37° C. for 30 minutes with 20 µL of the appropriate MMP (0.45 U/mL for MMP-9 and 0.35 U/mL for MMP-12) in MMP assay buffer (50 mM HEPES, 10 mM $CaCl_2$, 0.10% Brij-35, pH 7.5), for a total volume of 99 pt. The reaction was initiated by the addition of 1 µL (400 µM) of the fluorescent substrate (Mca-Pro-Leu-Gly-Leu-Dpa-Ala-Arg-$NH_2$ where Mca=(7-methoxycoumarin-4-yl)-acetyl and Dpa=N-3-(2,4-dinitrophenyl)-L-α-β-diaminopropionyl)) and kinetic activity was measured every minute for 20 min with excitation and emission wavelengths at 335 nm and 405 nm, respectively. Measurements were performed in duplicate. The percent inhibition was plotted versus the inhibitor concentration. A linear fit of the data for each experiment gives the $IC_{50}$ value of the inhibitor where y=50%.

MMP activity in the presence of $H_2O_2$ was evaluated with both MMP-9 and MMP-12 with 1 h of activation at concentrations close to their $IC_{50}$ values. Using the calculated rate constants for the protected ZBGs B19 and B20, it was determined that 1 h of activation time for each proinhibitor with 100 µM $H_2O_2$ will provide enough 1,2-HOPO-2 or PY-2 to inhibit the MMPs at 50%. For example, for proinhibitor B17 with MMP-9, if the rate=k[B17][$H_2O_2$] and k=3.9 $M^{-1}s^{-1}$, [B17]=10 µM, and [$H_2O_2$]=100 µM, the rate of conversion would be $3.9 \times 10^{-9}$ M/s. Therefore, activation for 1 h would release 14 µM 1,2-HOPO-2, or enough inhibitor to provide approximately 50% inhibition of MMP-9 ($IC_{50}$ value for 1,2-HOPO-2 against MMP-9 is ~6 µM).

In each well, 1 µL of proinhibitors B17 and B18 and the inhibitors 1,2-HOPO-2 and PY-2 in DMSO (1 mM for MMP-9 or 5 µM for MMP-12) were incubated for 1 h at 37° C. with 10 µL $H_2O_2$ (1 mM in HEPES buffer, pH 7.5) in MMP assay buffer for a total volume of 79 pt. A control sample containing 10 µL $H_2O_2$ (1 mM in HEPES buffer, pH 7.5) in MMP assay buffer was also prepared to confirm that $H_2O_2$ did not inhibit MMP-9 or MMP-12. After activation of the proinhibitors, 20 µL of the appropriate MMP (0.45 U/mL for MMP-9 and 0.35 U/mL for MMP-12) was added and incubated for an additional 30 min. The reaction was initiated by the addition of 1 pt (400 µM) of the fluorescent substrate and kinetic activity was measured every minute for 20 min with excitation and emission wavelengths at 335 nm and 405 nm, respectively. Enzyme activity with inhibitor was calculated with respect to the control experiment (no inhibitor present). Measurements were performed in duplicate in two independent experiments.

Example 9

Exemplary Oxidatively-Sensitive Prodrugs

Figure 19:
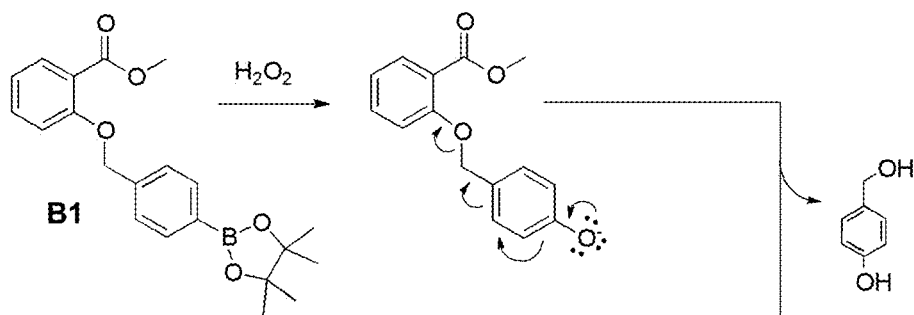
FIG. 19. Three approaches to the development of ROS-activated boronic ester proMMPi demonstrated with the methyl salicylate derivatives B1-B3 using either an ether or ester linked self-immolative linker or through direct linkage of the protecting group.
Figure 19:
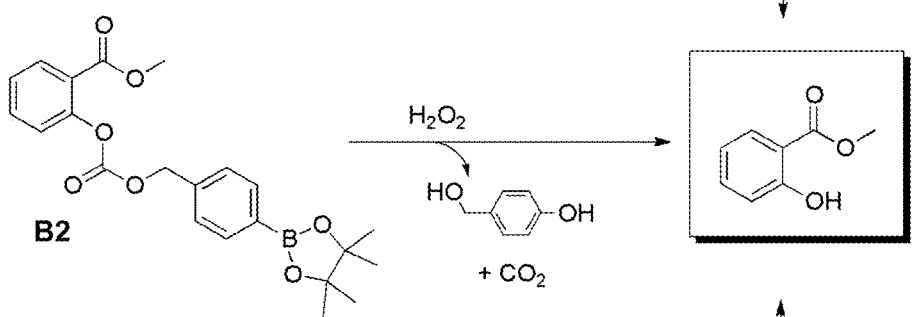
Figure 19:
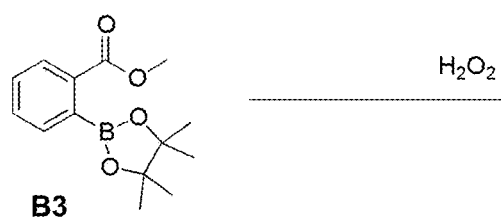

In the development of ROS-activated proMMPi, we employed a relatively underutilized self-immolative protecting group with several apparent advantages over previously described systems. The use of self-immolative linkers has become increasingly popular in drug development, molecular sensors, and polymeric delivery systems.[1, 19-21] Linkers that undergo self-immolative elimination upon removal of the protecting group can release an active species through a 1,6-benzyl elimination (FIG. 19). This reaction is thermodynamically driven by the release of $CO_2$ when a carbonate or carbamate ester linkage is employed.[21-23] However, in the development of proMMPi, it was found that the use of an ether linkage between the activating group and the inhibitor was preferred over the more commonly used carbonate ester linkage (compare compound B1 vs. B2 in FIG. 19) due to better synthetic accessibility, superior hydrolytic stability, and comparably fast cleavage kinetics. Recently, this ether linkage was utilized in studies on ROS-sensitive luciferase probes[24] and protease-sensitive fluorophores.[22] Nonetheless, there are essentially no studies on the generality and utility of this promising linking strategy. This report investigates the scope of this ether-connected, self-immolative proinhibitor strategy with a variety of functional groups and MBGs.

Figure 20:
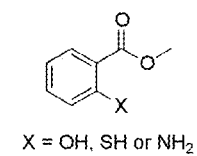
FIG. 20. Methyl salicylate derivatives B4-B9 investigated in this study with varying leaving groups and linkage strategies.
Figure 20:
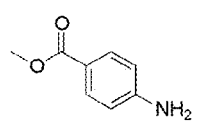
Figure 20:
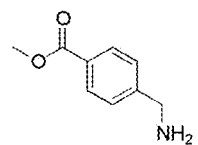
Figure 20:
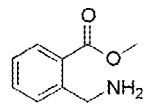
Figure 20:
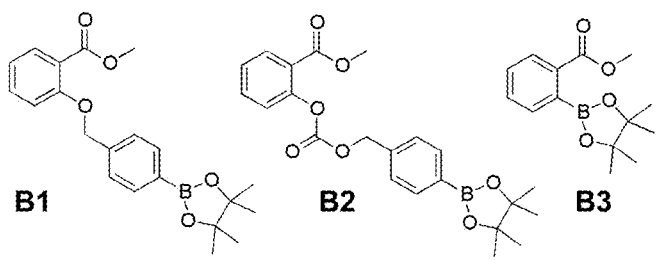
Figure 20:
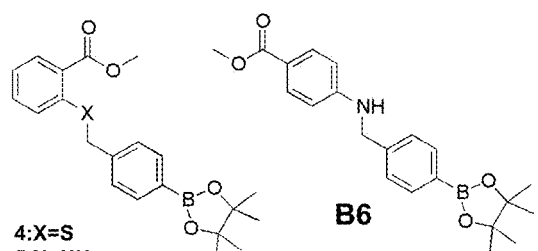
Figure 20:
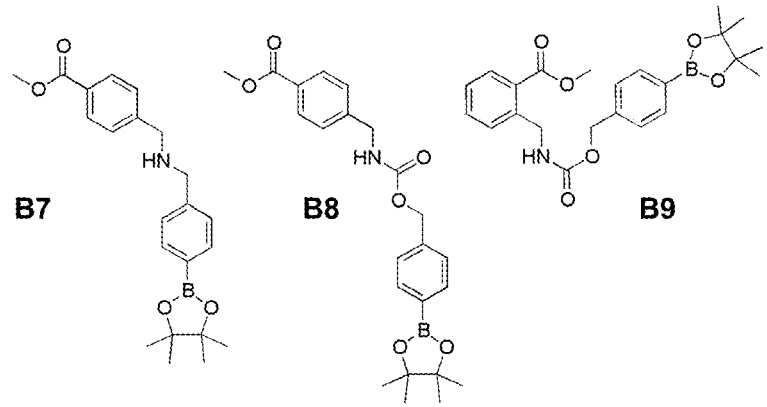
Figure 21:
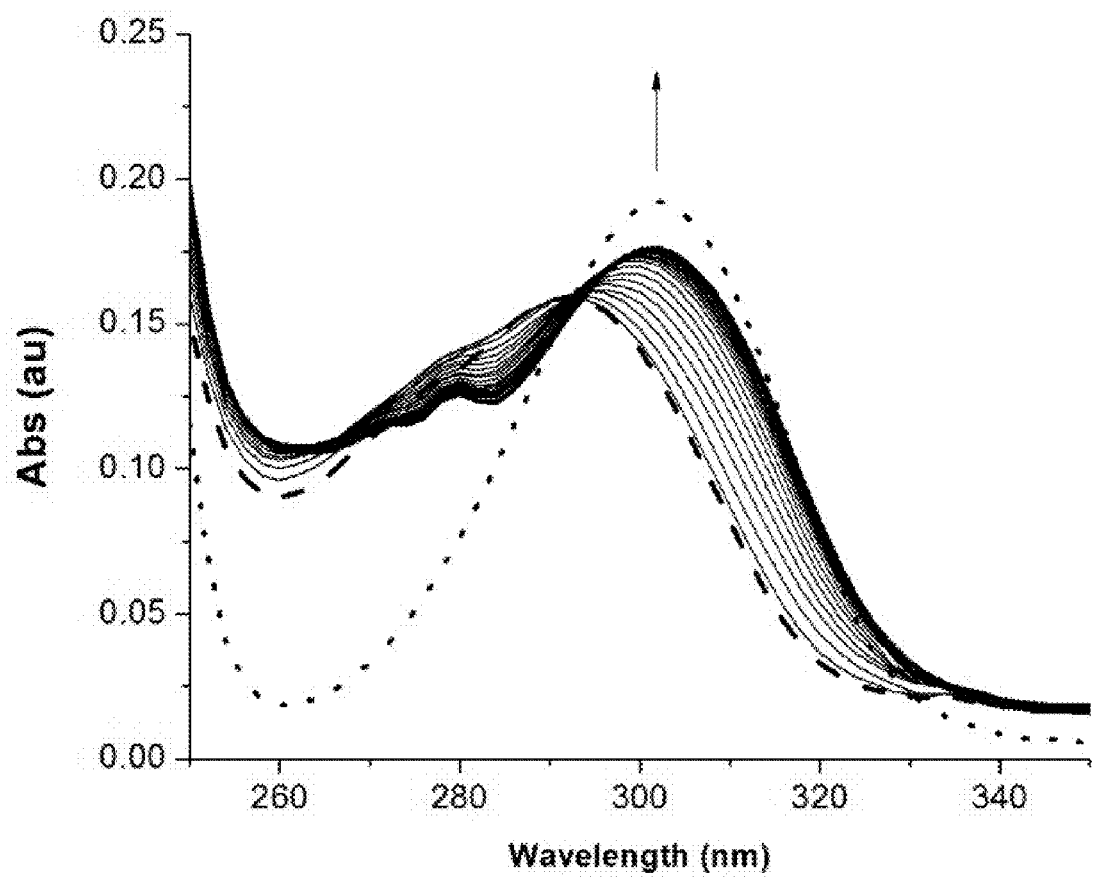
FIG. 21. Absorption spectra of B1 (50 μM in HEPES buffer, pH 7.5) in the presence of $H_2O_2$ (18 eq) monitored every 2 min over 60 min. The dashed line is the starting spectrum and the bold solid line is the final spectrum. A sample of methyl salicylate is shown as a dotted line. The arrow represents the change in absorption over time.

Here we further investigate the behavior of different activation strategies using related, but distinct self-immolative linkers for coupling to the MBGs. All of the strategies studied here use boronic ester protecting groups that can be selectively removed by $H_2O_2$. A series of methyl salicylate derivatives containing phenol, thiophenol, aniline, and benzylamine leaving groups were investigated using either an ether linkage, a carbonate/carbamate ester linker, or no linker to the boronic ester protecting group (FIG. 19 and FIG. 20). In addition, we looked at a variety of MBGs protected with a boronic ester self-immolative leaving group to expand our inventory of MBGs for use in novel metalloprotein prodrugs.

Figure 24:
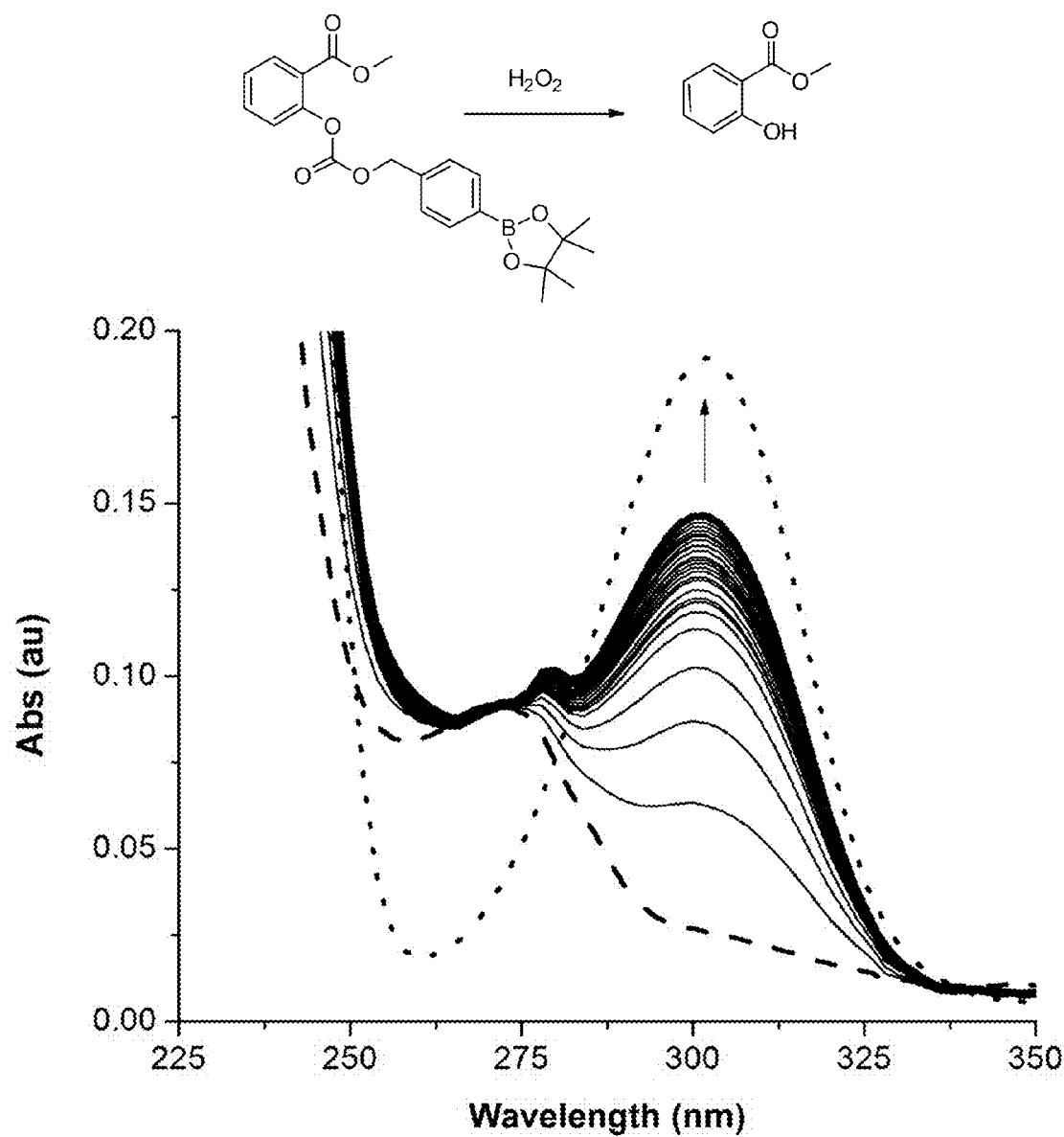
FIG. 24. Absorption spectra of B2 (0.05 mM in HEPES buffer (50 mM, pH 7.5)) in the presence of $H_2O_2$ (18 eq) monitored every minute for 30 min. The dashed line is the initial spectra and the bold solid line is the final spectra; the arrow indicates the change in spectra over time. An authentic sample of methyl 2-hydroxybenzoate (0.05 mM in HEPES buffer (50 mM, pH 7.5)) is shown as a dotted line.
Figure 25:
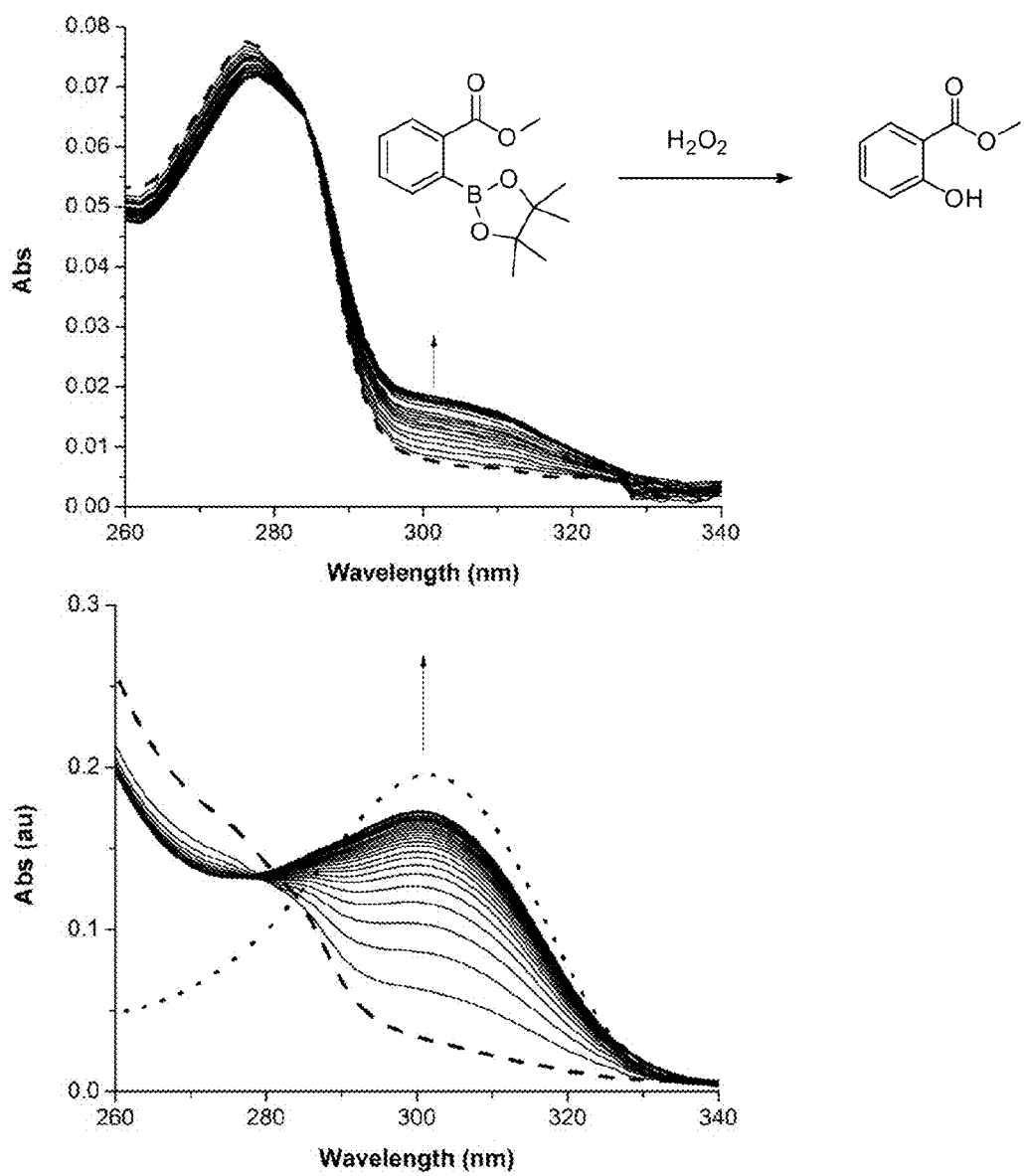
FIG. 25. Top. Absorption spectra of B3 (0.05 mM in HEPES buffer (50 mM, pH 7.5)) in the presence of $H_2O_2$ (18 eq) monitored every minute for 1 hr with spectra shown every 2 min. The dashed line is the initial spectra and the bold solid line is the final spectra; the arrow indicates the change in spectra over time. Bottom. Absorption spectra of B3 (0.05 mM in HEPES buffer (50 mM, pH 7.5)) in the presence of $H_2O_2$ (180 eq) monitored every minute for 1 hr with spectra shown every 2 min. The dashed line is the initial spectra and the bold solid line is the final spectra; the arrow indicates the change in spectra over time. An authentic sample of methyl 2-hydroxybenzoate (0.05 mM in HEPES buffer (50 mM, pH 7.5)) is shown as a dotted line.
Figure 26:
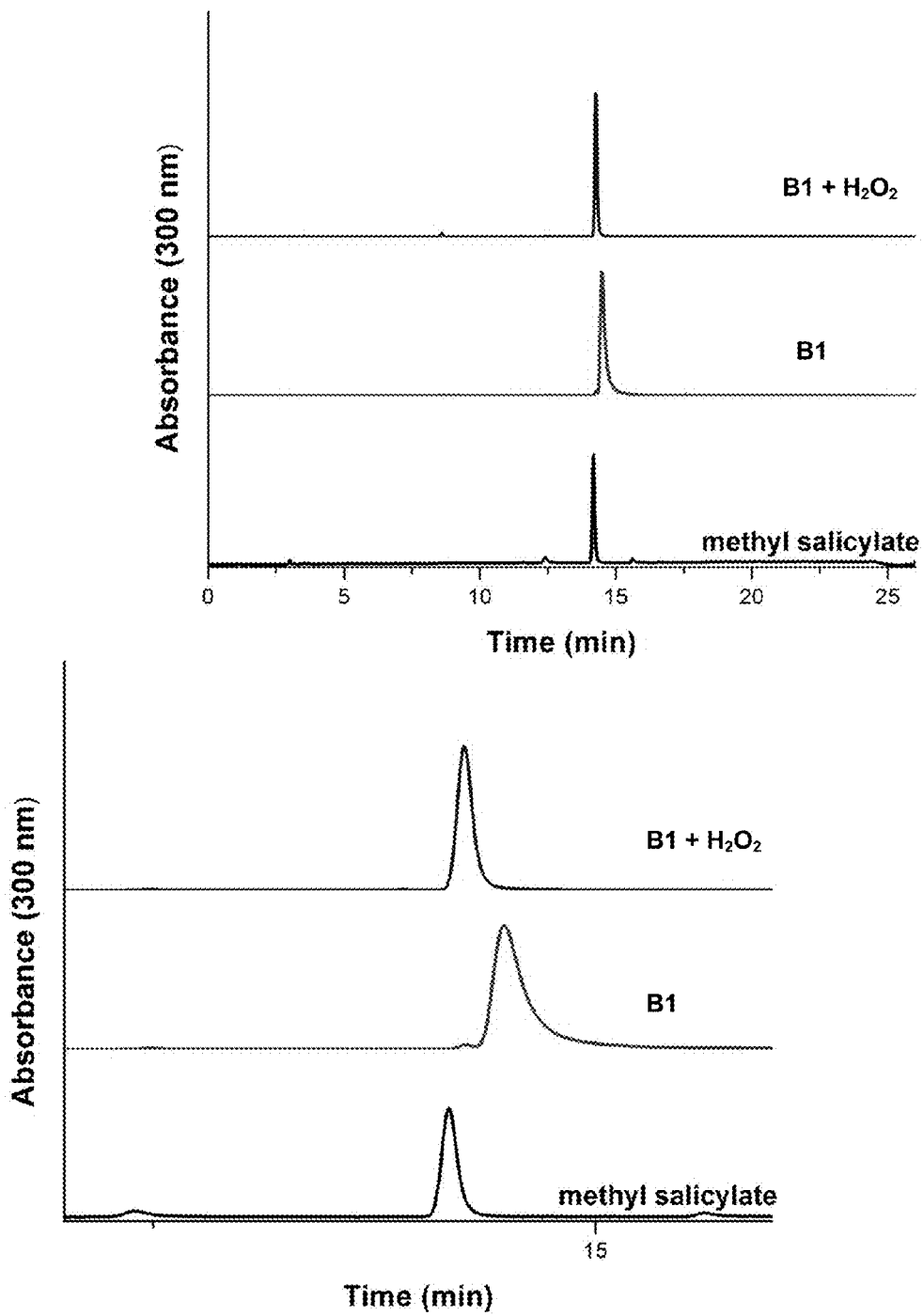
FIG. 26. Top. HPLC traces of compounds methyl salicylate, B1 and compound B1 after reaction with $H_2O_2$ (1.8 eq) for 30 min. Bottom. Zoomed in view of chromatograms. Retention times are 14.2 min for methyl salicylate and 14.5 min for B1.
Figure 27:
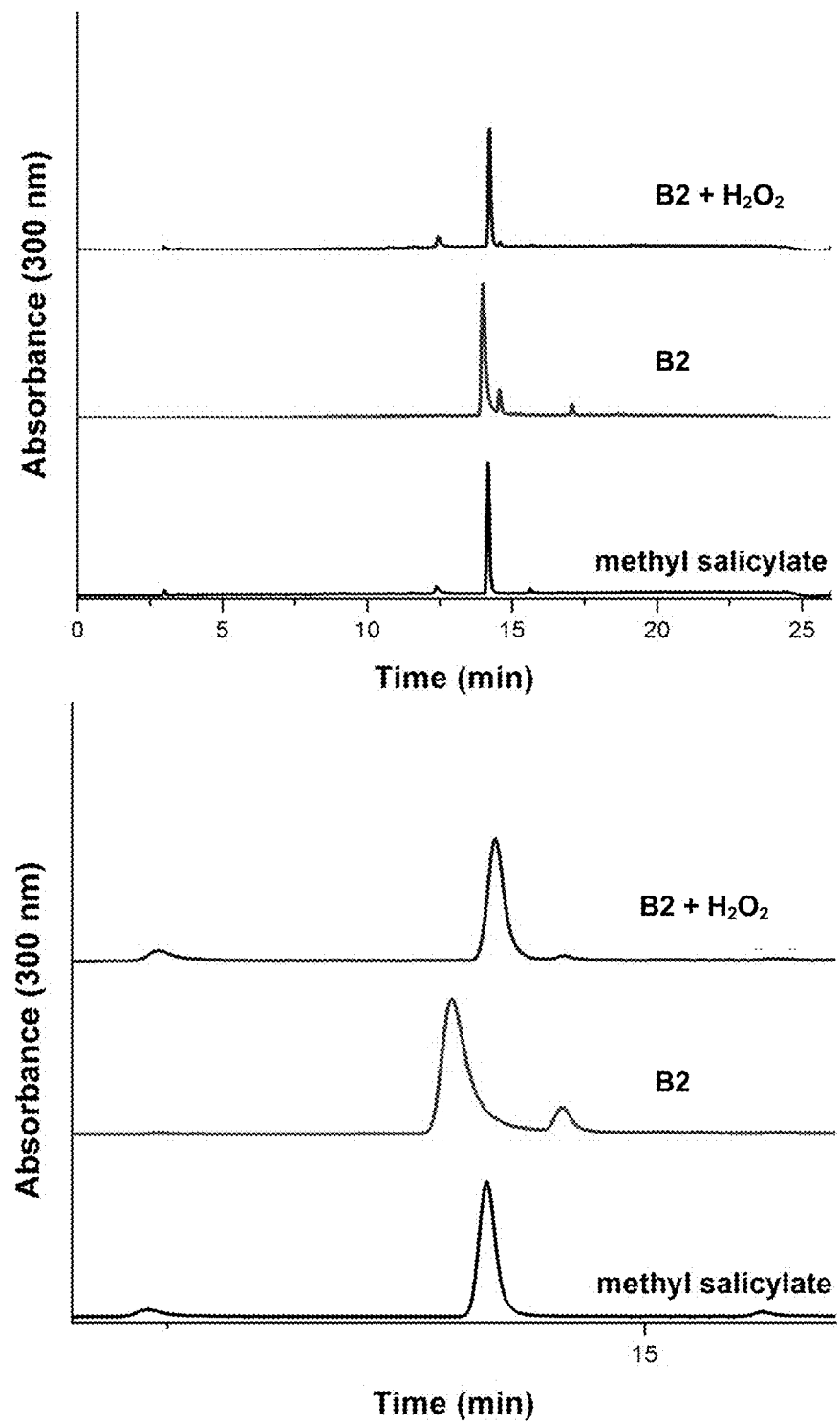
FIG. 27. Top. HPLC traces of compounds methyl salicylate, B2 and compound B2 after reaction with $H_2O_2$ (1.8 eq) for 30 min. Bottom. Zoomed in view of chromatograms. Retention times are 14.2 min for methyl salicylate and 13.9 min for B2.
Figure 28:
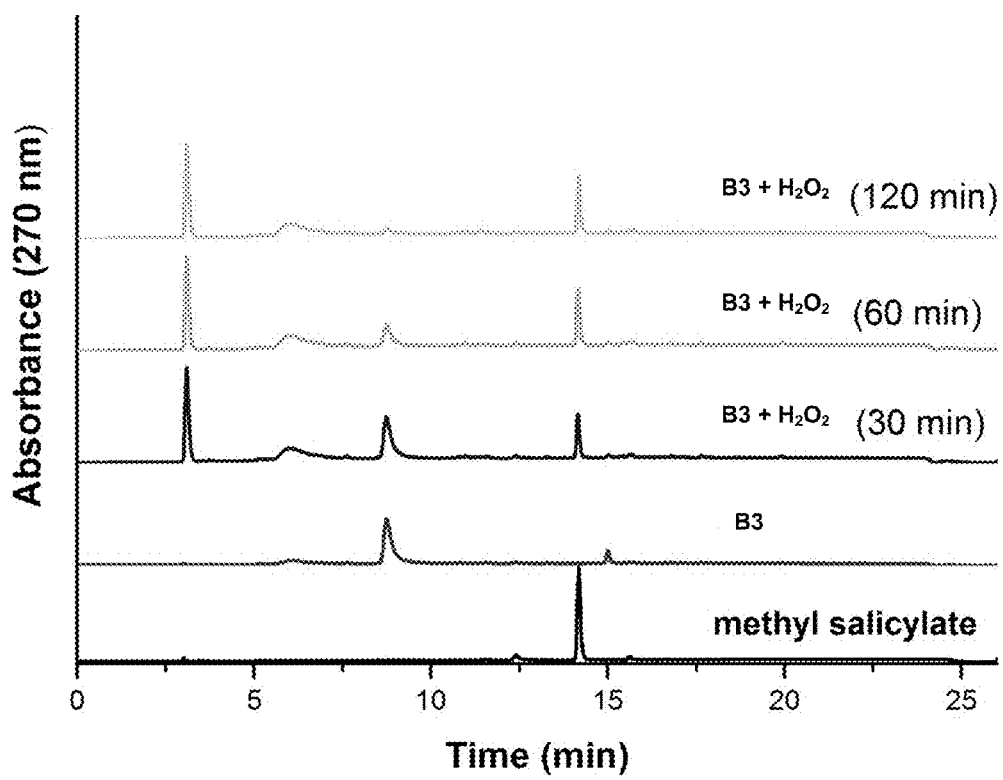
FIG. 28. HPLC traces of compounds methyl salicylate, B3, and compound B3 after reaction with $H_2O_2$ (18 eq) for 30 min, 60 min and 120 min. Retention times are 14.2 min for methyl salicylate and 8.7 min for B3.
Figure 29:
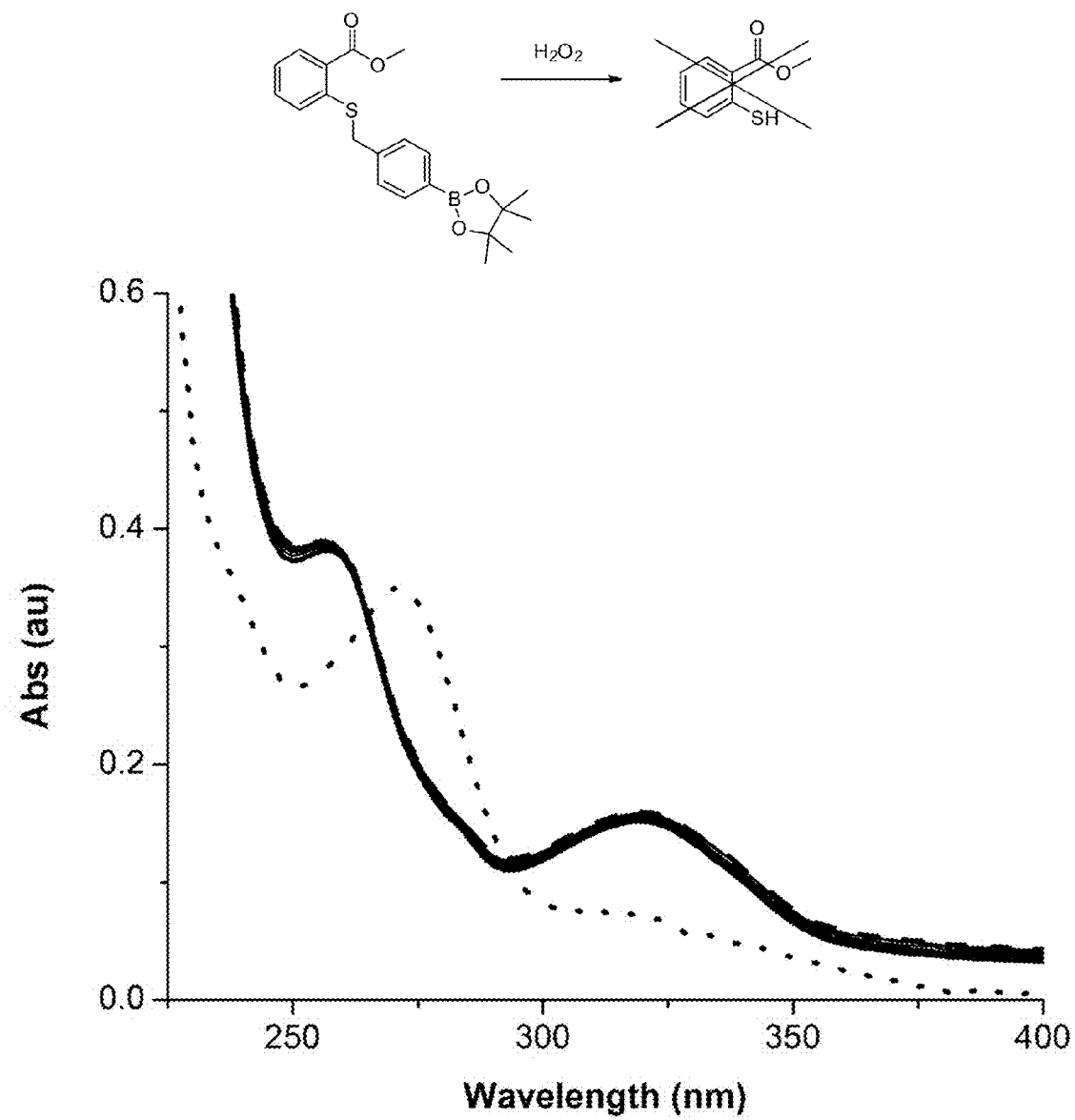
FIG. 29. Absorption spectra of B4 (0.05 mM in HEPES buffer (50 mM, pH 7.5)) in the presence of $H_2O_2$ (18 eq) monitored every two minutes for 30 min. The dashed line is the initial spectra and the bold solid line is the final spectra. An authentic sample of methyl 2-mercaptobenzoate (0.05 mM in HEPES buffer (50 mM, pH 7.5)) is shown as a dotted line. The overlapping spectra indicate there is no cleavage of the protecting group in the presence of $H_2O_2$.
Figure 30:
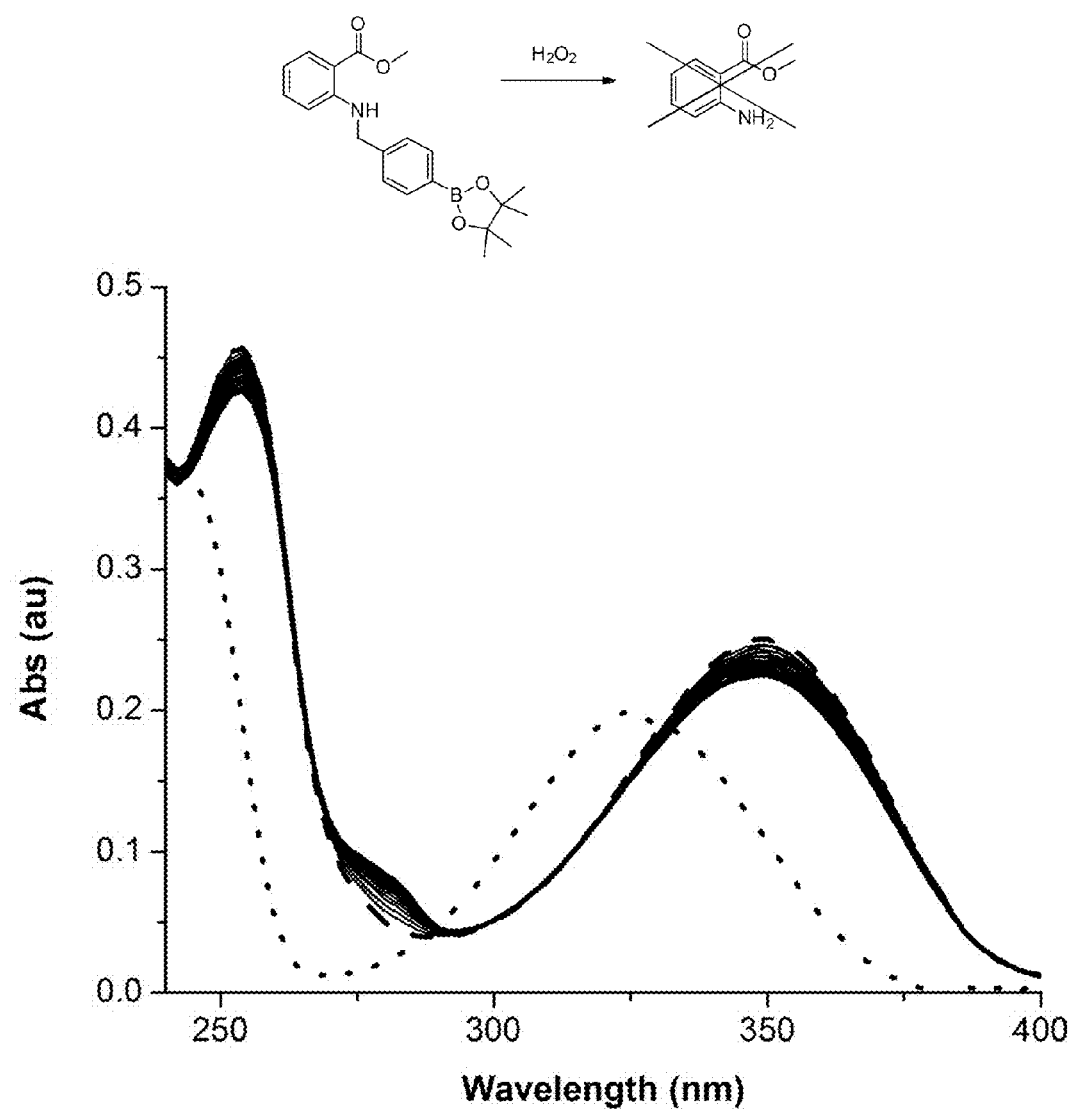
FIG. 30. Absorption spectra of B5 (0.05 mM in HEPES buffer (50 mM, pH 7.5)) in the presence of $H_2O_2$ (18 eq) monitored every two minutes for 1 h. The dashed line is the initial spectra and the bold solid line is the final spectra. An authentic sample of methyl 2-aminobenzoate (0.05 mM in HEPES buffer (50 mM, pH 7.5)) is shown as a dotted line. The minimal change in spectra over time indicates that there is no formation of 2-aminobenzoate in the presence of $H_2O_2$.
Figure 31:
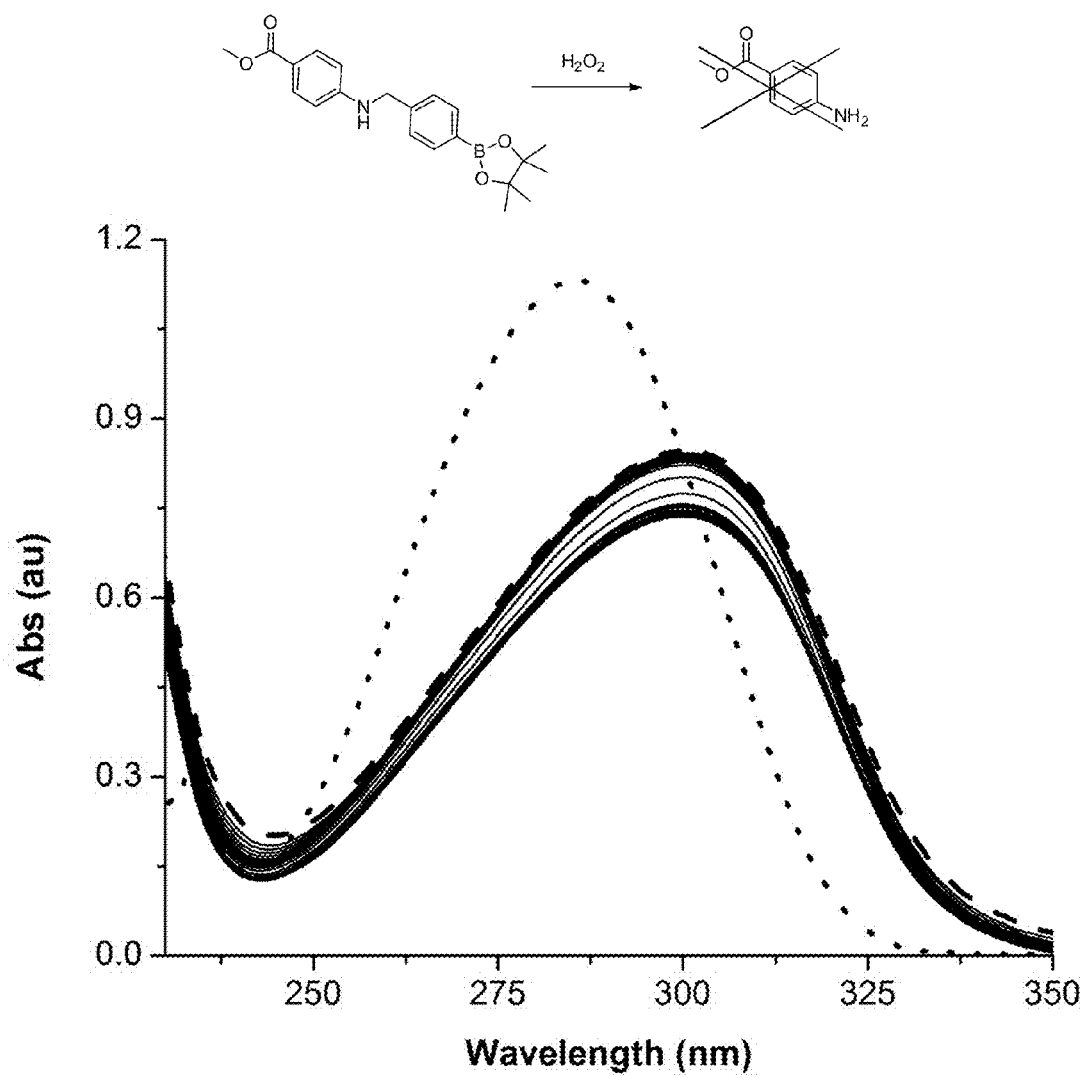
FIG. 31. Absorption spectra of B6 (0.05 mM in HEPES buffer (50 mM, pH 7.5)) in the presence of $H_2O_2$ (18 eq) monitored every two minutes for 1 h. The dashed line is the initial spectra and the bold solid line is the final spectra. An authentic sample of methyl 4-aminobenzoate (0.05 mM in HEPES buffer (50 mM, pH 7.5)) is shown as a dotted line. The minimal change in spectra over time indicates that there is no formation of 4-aminobenzoate in the presence of $H_2O_2$.
Figure 32:
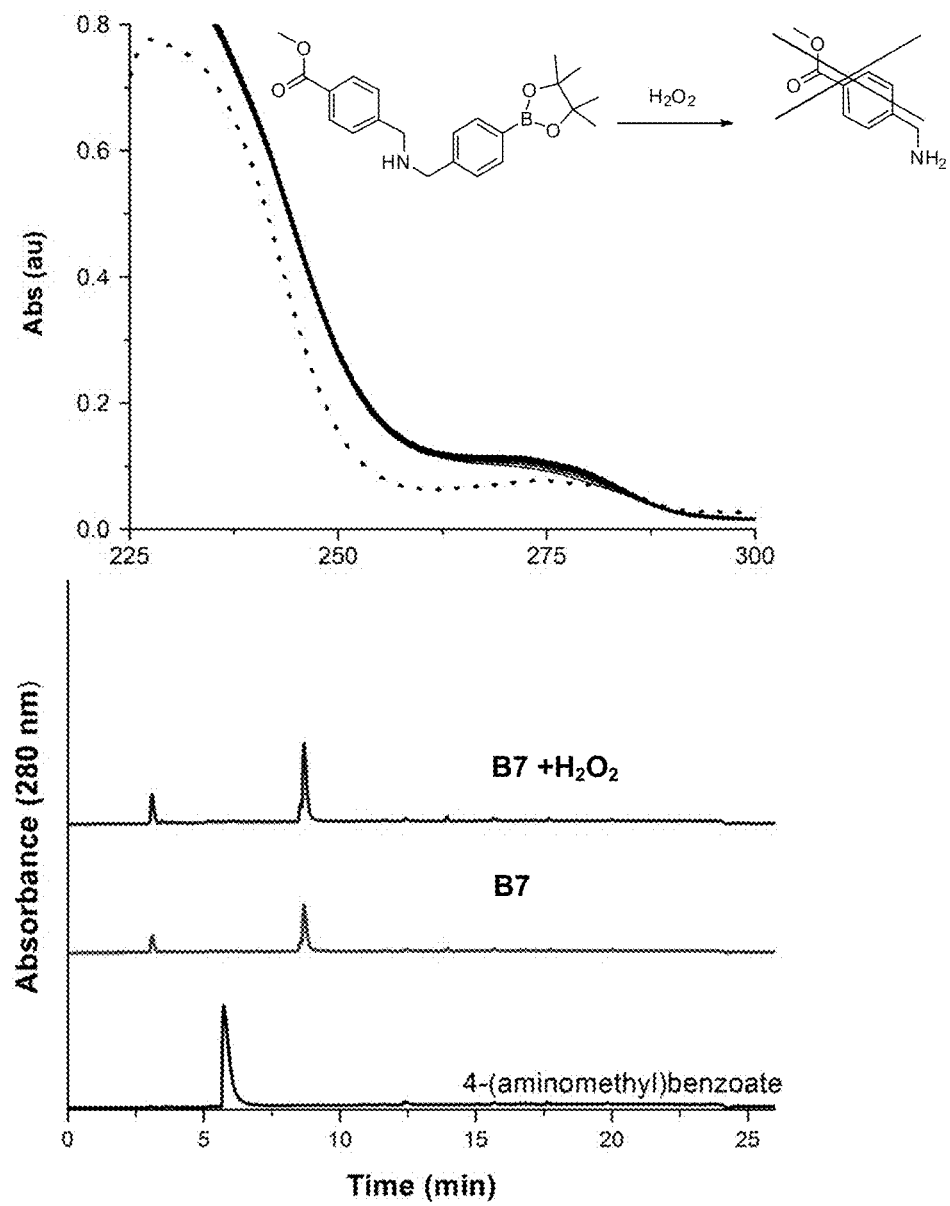
FIG. 32. Top. Absorption spectra of B7 (0.05 mM in HEPES buffer (50 mM, pH 7.5)) in the presence of $H_2O_2$ (18 eq) monitored every minute for 30 min. The dashed line (hidden) is the initial spectra and the bold solid line is the final spectra. An authentic sample of 4-(aminomethyl)benzoate (0.05 mM in HEPES buffer (50 mM, pH 7.5)) is shown as a dotted line. The overlapping spectra indicate there is no cleavage of the protecting group in the presence of $H_2O_2$. Bottom. HPLC traces of compounds 4-(aminomethyl)benzoate, B7 and compound B7 after reaction with $H_2O_2$ (22 eq) for 30 min. Retention times are 5.8 min for 4-(aminomethyl)benzoate and 8.6 min for B7.

Compounds B1-B3 were designed to release methyl salicylate in the presence of $H_2O_2$ using a self-immolative ether linkage (B1), a carbonate ester linkage (B2), or no self-immolative linker (B3) to directly compare three possible designs of a prodrug scaffold. The syntheses of these compounds are described in Example 3. Compounds B1-B3 were first examined for activation in the presence of $H_2O_2$ using UV-Vis spectroscopy. To a solution of the boronic ester derivative in HEPES buffer (50 mM, pH 7.5) was added $H_2O_2$ and the change in absorbance was monitored over time. As shown in FIG. 20 for compound B1, the absorbance over time shows an increase at 302 nm indicative of the emergence of methyl salicylate with a clear isobestic point at 293 nm. Similar results were obtained with compounds B2 and B3. While compounds B1 and B2 achieved >90% cleavage within 45 min using an 18-fold excess of $H_2O_2$ (FIG. 24-25), deprotection of compound B3 required a 180-fold excess of $H_2O_2$ to realize cleavage in a comparable time frame. Release of methyl salicylate for all three compounds was confirmed by HPLC (FIG. 26-27).

The rates of conversion to methyl salicylate were determined by monitoring the change in absorbance under pseudo first-order reaction conditions with an excess of $H_2O_2$. The calculated rate constants are presented in Table 2. Consistent with earlier reports, the carbonate ester derivative B2 displayed the fastest rate of conversion, but B2 also underwent spontaneous hydrolytic cleavage in buffer, whereas compound B1 was stable in buffer over a 4 h period (data not shown). Introduction of the carbonate group into the self-immolative linker of B2 leads to hydrolytic instability facilitated by nucleophilic attack of water at the carbonyl position which is not possible in compound B1.[25] Interestingly, while the hydrolytic stability of B3 was comparable to the ether linkage used in B1, the rate of conversion for B3 was about two orders of magnitude slower than either B1 or B2, suggesting that use of self-immolative linker facilitates conversion to the desired active compound.

TABLE 2

Pseudo first-order rate constants calculated with an excess of $H_2O_2$.

| Compound | k ($M^{-1}s^{-1}$) |
| --- | --- |
| B1 | 1.12 ± 0.04 |
| B2 | 2.7 ± 0.1 |
| B3 | 0.031 ± 0.002 |
| B10 | 3.1 ± 0.5 |
| B11 | 5.9 ± 0.2 |
| B12 | 3.5 ± 0.3 |
| B13 | 2.9 ± 0.1 |
| B14 | 4.1 ± 0.2 |

Figure 33:
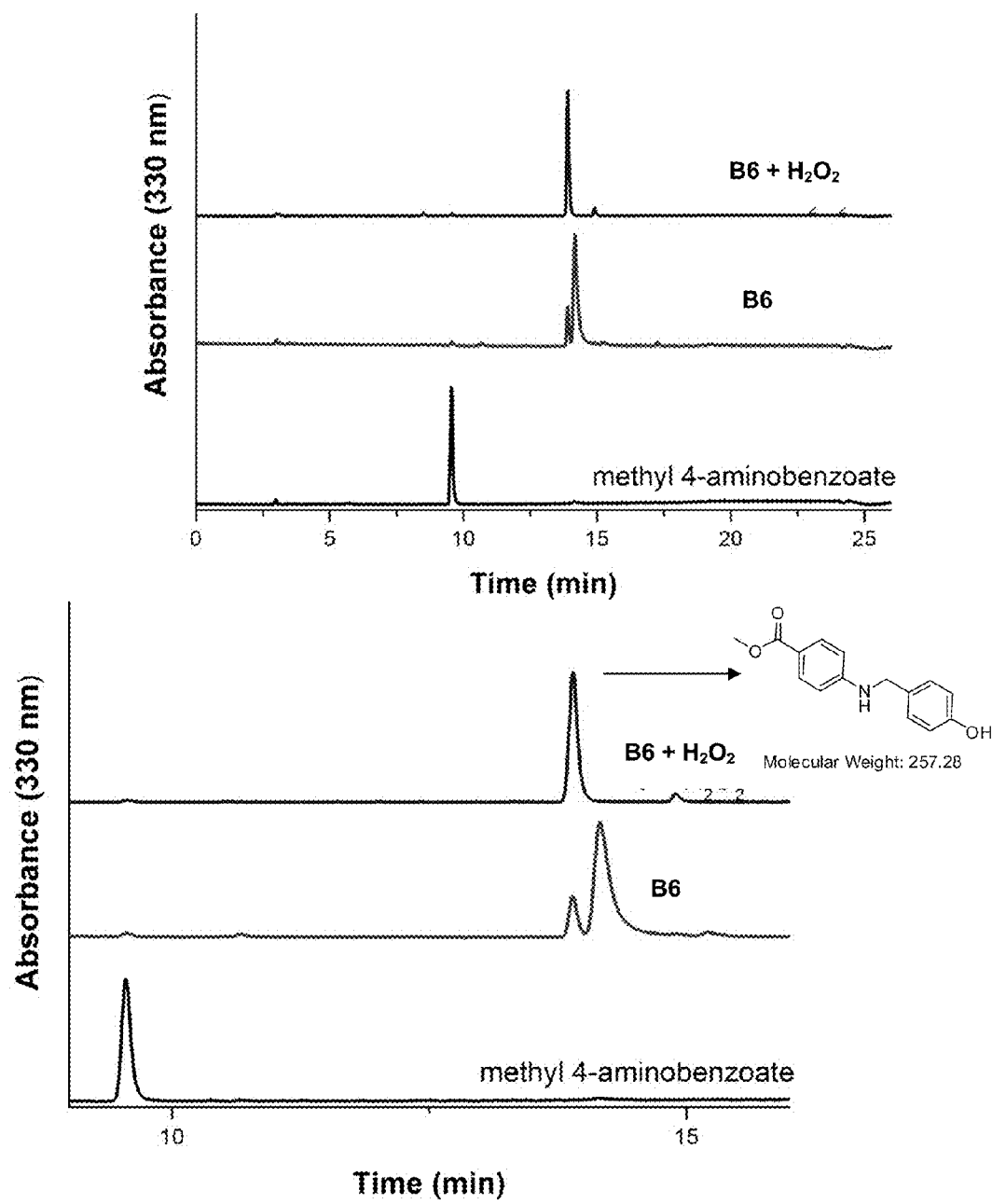
FIG. 33. HPLC traces of compounds methyl 4-aminobenzoate, B6 and compound B6 after reaction with $H_2O_2$ (22 eq) for 30 min. Retention times are 10.2 min for methyl 4-aminobenzoate, 14.5 min for B6, and 14.3 for B6 after reaction with $H_2O_2$. LC-MS(+) gave an m/z peak at 258.1 confirming the release of the boronic ester to the phenolic moiety.
Figure 34:
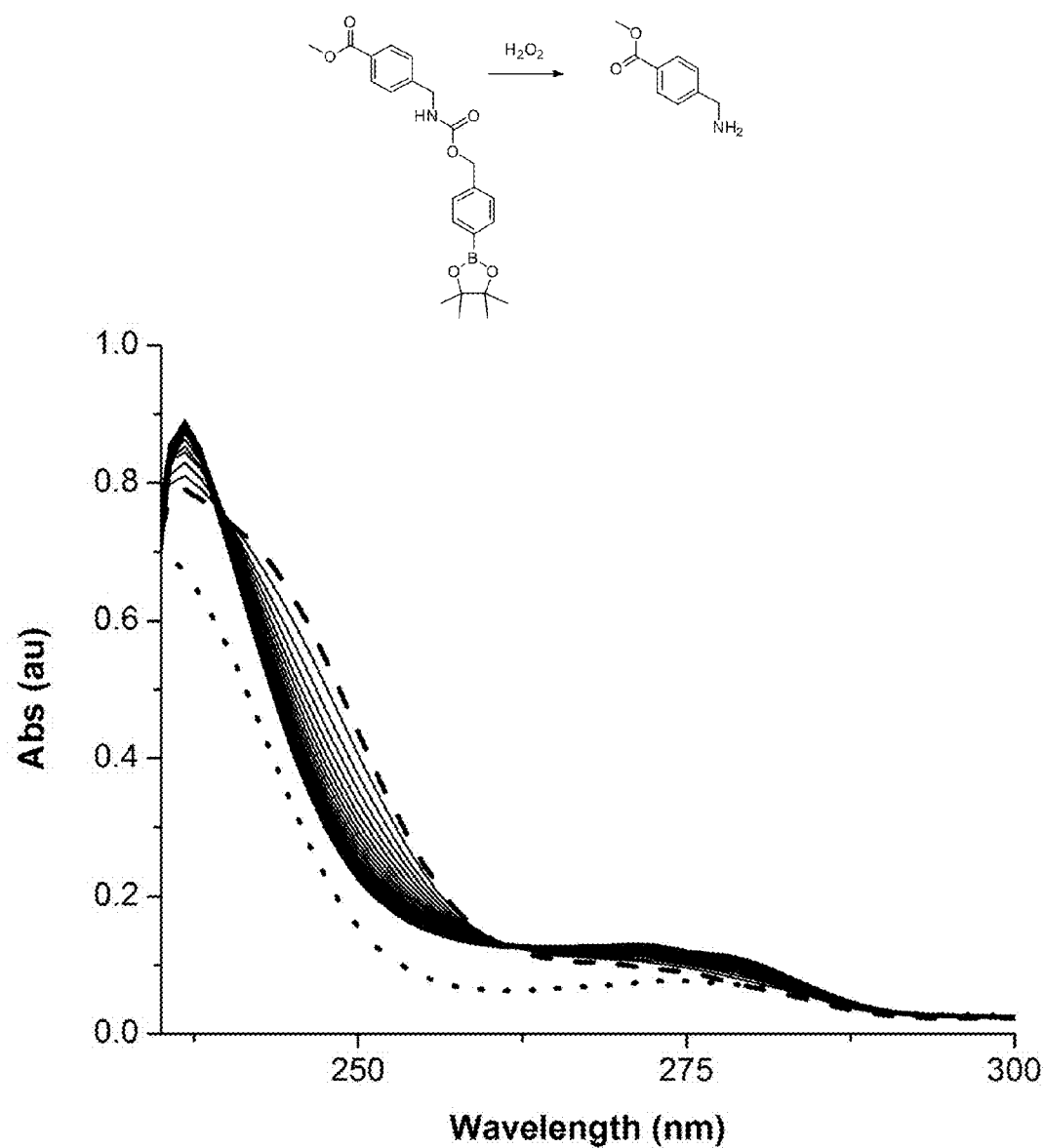
FIG. 34. Absorption spectra of B8 (0.05 mM in HEPES buffer (50 mM, pH 7.5)) in the presence of $H_2O_2$ (18 eq) monitored every two minutes for 50 min. The dashed line is the initial spectra and the bold solid line is the final spectra. An authentic sample of 4-(aminomethyl)benzoate (0.05 mM in HEPES buffer (50 mM, pH 7.5)) is shown as a dotted line.
Figure 35:
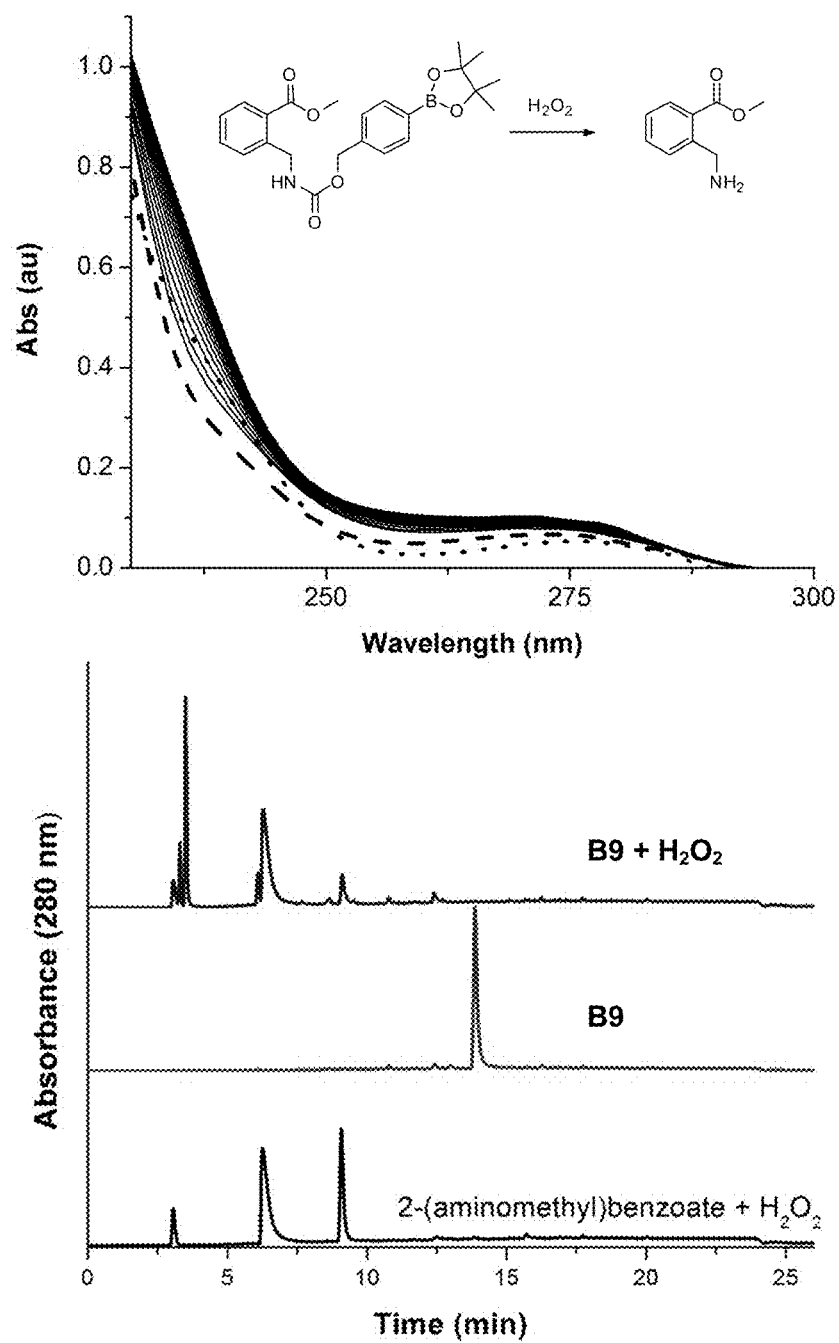
FIG. 35. Top. Absorption spectra of B9 (0.05 mM in HEPES buffer (50 mM, pH 7.5)) in the presence of $H_2O_2$ (18 eq) monitored every minute for 30 min. The dashed line is the initial spectra and the bold solid line is the final spectra. An authentic sample of 4-(aminomethyl)benzoate (0.05 mM in HEPES buffer (50 mM, pH 7.5)) is shown as a dotted line. Bottom. HPLC traces of compounds 2-(aminomethyl)benzoate with $H_2O_2$ (22 eq), B9 and B9 after reaction with $H_2O_2$ (22 eq) for 30 min. Retention times are 6.3 min and 9.1 min for 2-(aminomethyl)benzoate and 13.9 min for B9.
Figure 36:
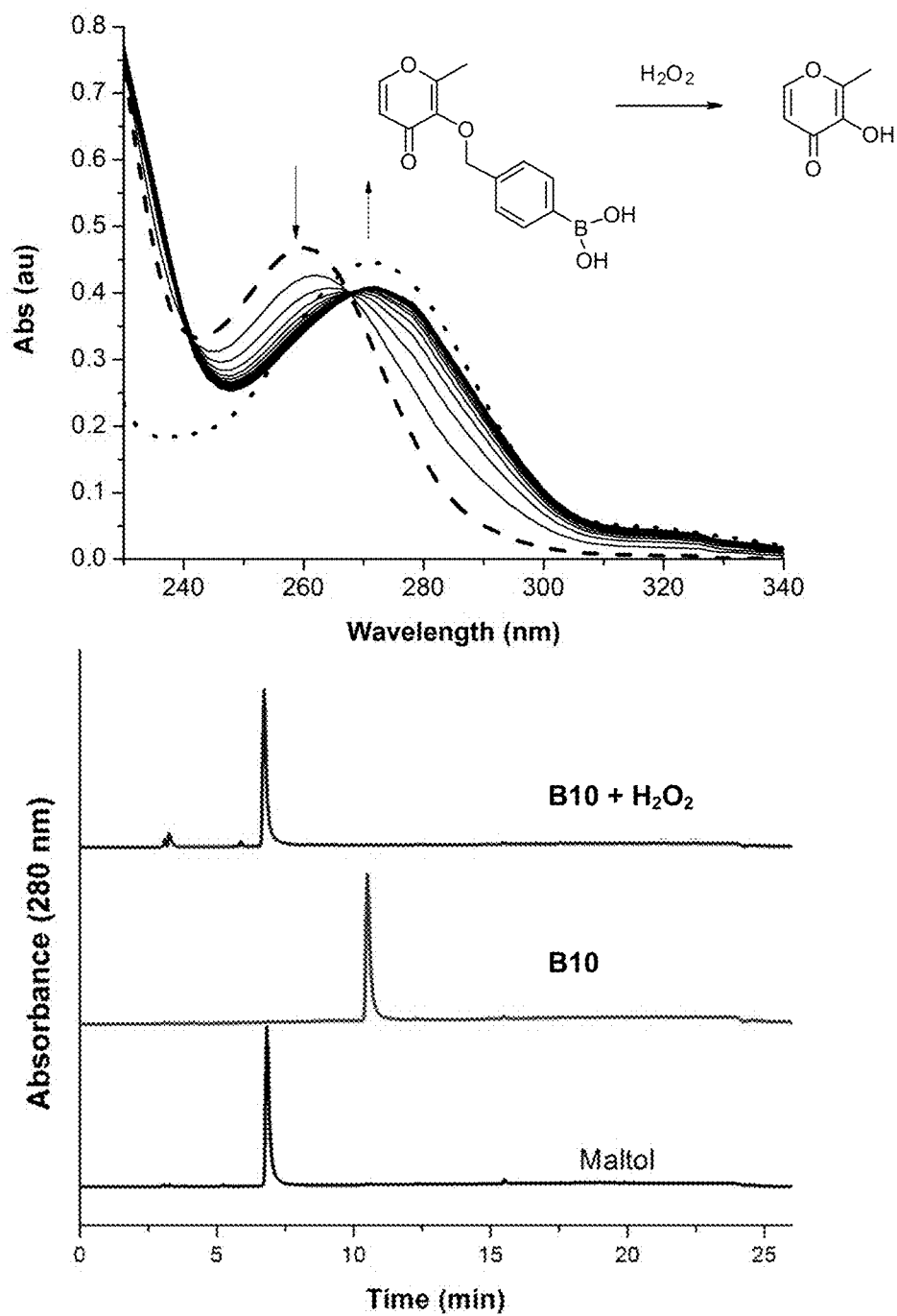
FIG. 36. Top. Absorption spectra of B10 (0.05 mM in HEPES buffer (50 mM, pH 7.5)) in the presence of $H_2O_2$ (18 eq) monitored every two minutes for 30 min. The dashed line is the initial spectra and the bold solid line is the final spectra. An authentic sample of maltol (0.05 mM in HEPES buffer (50 mM, pH 7.5)) is shown as a dotted line. Bottom. HPLC traces of compounds maltol, B10 and B10 after reaction with $H_2O_2$ (1.8 eq) for 30 min. Retention times are 6.8 min for maltol and 10.8 min for B10.
Figure 37:
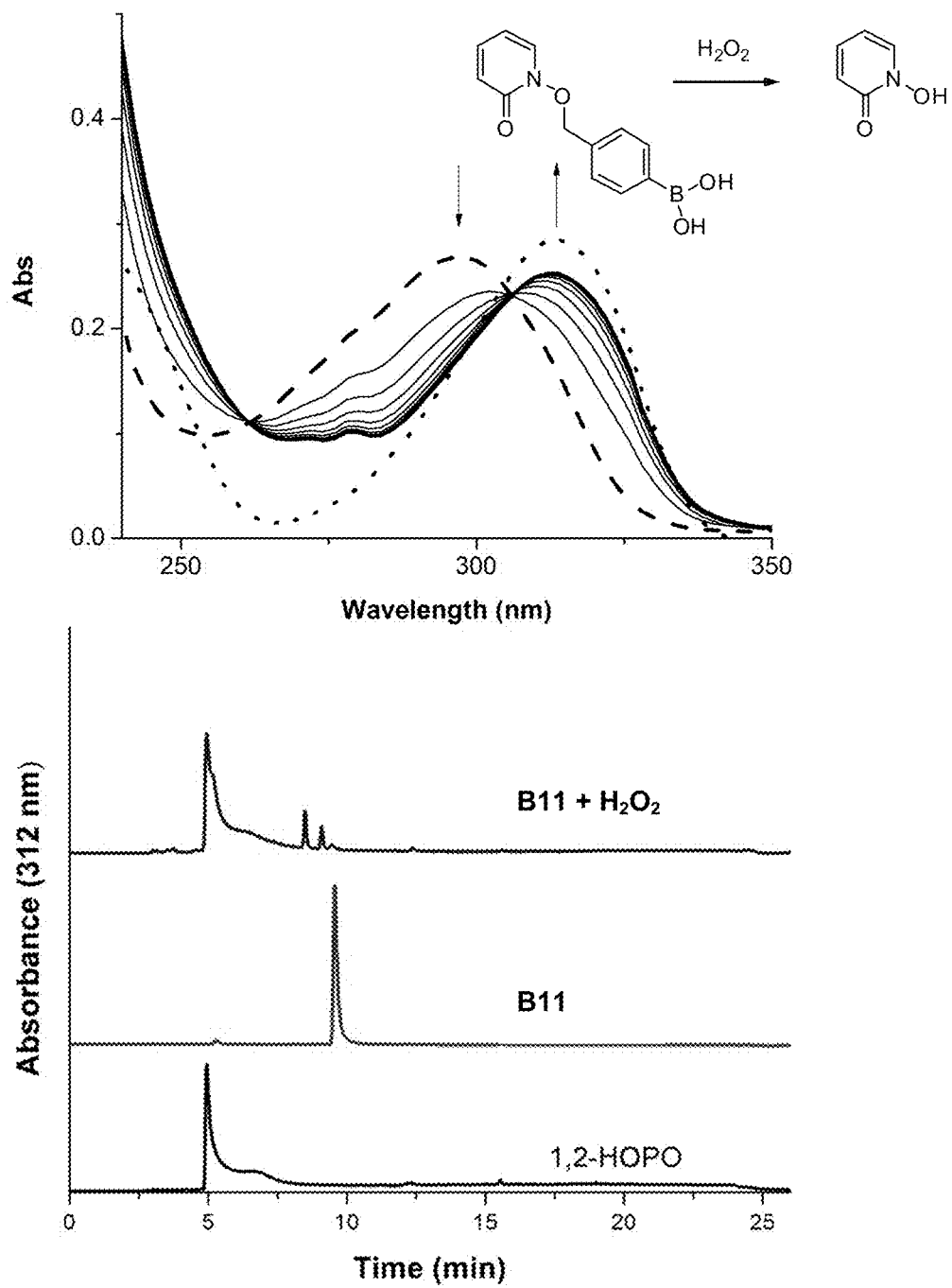

Based on the behavior of compounds B1-B3, the most promising linking strategy is the benzyl ether linkage seen in compound B1. The benzyl ether linkage shows excellent stability in buffer while maintaining rapid cleavage kinetics upon activation. Therefore, we investigated the use of this motif with other leaving groups. Compounds B4-B7 were synthesized to study the effects of using sulfur (B4), aniline (B5-B6), or benzyl amine (B7) leaving groups. Evaluation with UV-Vis absorption spectroscopy of B4-B7 in the presence of $H_2O_2$ showed no cleavage of the protecting group (FIG. 29-32). Further evaluation with LC-MS showed that the boronic ester of compound 6 was cleaved to the phenol group, but that the cascade reaction did not proceed as expected to release the aniline group (FIG. 33). This may reflect the general robustness of these amine derivatives and their ionization potential.[26] Compounds B8 and B9 were then evaluated to investigate the use of a carbamate ester linkage. Unlike compound B7, the carbamate self-immolative linkers in B8 and B9 showed that the desired benzyl amine is released in the presence of $H_2O_2$, thermodynamically driven by the release of $CO_2$ (FIG. 34-35). This suggests that for the release of nitrogen-derived leaving groups, the carbamate linkage may still be preferable for prodrug development.[1]

Figure 23:
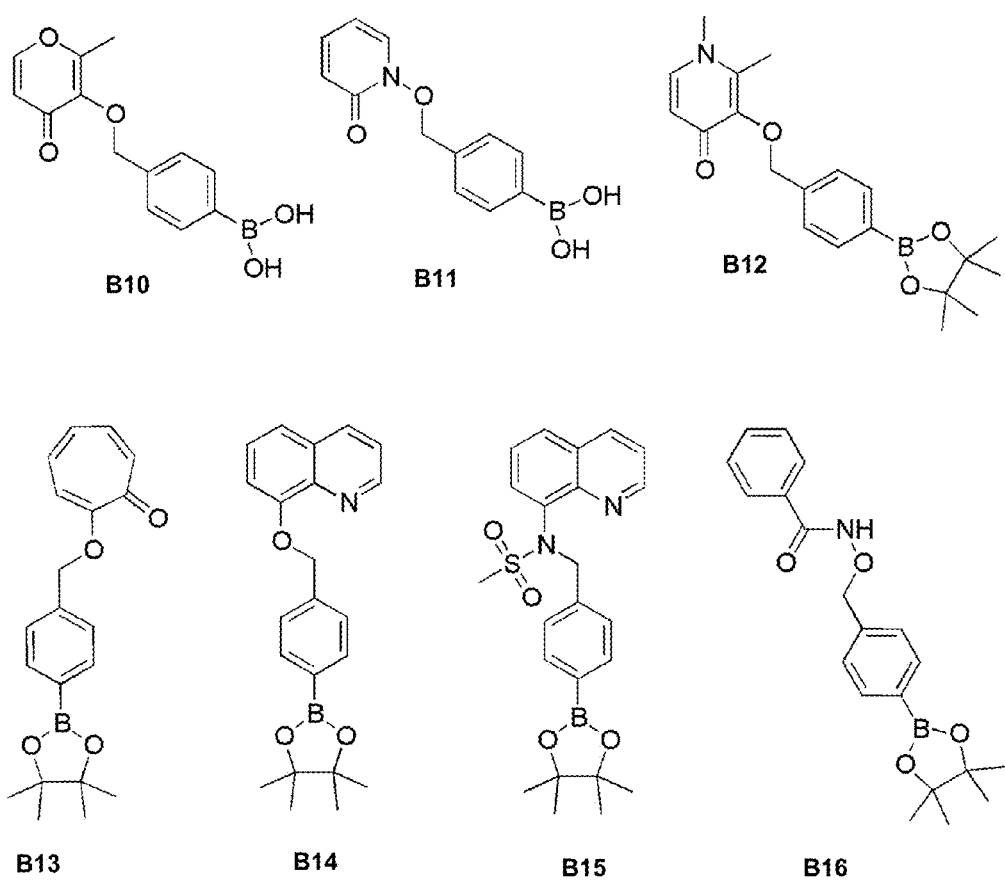
FIG. 23. Protected MBGs (prochelators) (potential oxidatively sensitive prodrugs comprising metal binding moieties) designed with a benzyl-ether self-immolative linker.

To validate our observations in the context of MBGs, a series of activatable MBGs (prochelators)[27] were synthesized (compounds B10-B14, FIG. 23) and evaluated. Compounds B10 and B11 were designed with a boronic acid protecting group to improve water solubility of the protected MBGs.[15] Several other protected MBGs were examined including the oxygen-binding 3-hydroxy-1,2-dimethylpyridin-4(1H)-one (B12), tropolone (B13), and 8-hydroxyquinoline (B14). Compounds B10-B14 showed rapid cleavage to the desired MBG in the presence of $H_2O_2$, as determined by absorption spectroscopy (Table 2), thus confirming the broader utility of the benzyl ether self-immolative strategy for designing metalloprotein proinhibitors (FIG. 36-40). Additionally, use of the boronic acid derivative in B10 and B11 shows both improved solubility and an increase in the rate of cleavage when compared to their boronic ester counterparts.[15] The pinacol boronic ester analog of B10 had a rate constant of 2.9 $M^{-1}s^{-1}$, which is comparable to B10. However; compound B11 showed a notable improvement in rate, increasing from 4.0 $M^{-1}s^{-1}$ for the pinacol boronic ester to 5.9 $M^{-1}s^{-1}$ for B11. This rate approaches that of the reported rate of 6.7 $M^{-1}s^{-1}$ for the carbonate ester-linked boronic ester protected MBG.[15] Compound B15 was synthesized and did not show cleavage in the presence of $H_2O_2$, confirming that this protection strategy is not effective with nitrogen-based MBGs.[28] In the presence of $H_2O_2$, B15 shows similar deprotection of the boronic ester to the phenolic group as B6 and B7, but does not undergo release of the protecting group (FIG. 41). Overall, the results validate our findings that benzyl-ether linkages are best suited for oxygen-based MBGs.

Hydroxamic acid MBGs are the most prevalent metal chelators in metalloprotein inhibitors, including MMPi, yet attempts to develop proMMPi using hydroxamic acid MBGs have not generally been successful.[29] Therefore, compound B16, which is comprised of phenyl hydroxamic acid protected with the boronic-ester self-immolative linker, was synthesized and evaluated. In the presence of $H_2O_2$ compound B16 showed no release of the desired hydroxamic acid ligand. HPLC indicates exposure to $H_2O_2$ results in boronic ester cleavage to a phenol group, but no further cascade reaction occurs to release the hydroxamic acid (vide supra, FIG. 42).

A thorough investigation of boronic ester prochelators shows that the use of benzyl ether self-immolative linkers provides a superior platform for the development of metalloprotein proinhibitors with oxygen-based leaving groups. These compounds show excellent hydrolytic stability as well as fast rates of cleavage to the active compounds in the presence of $H_2O_2$. The use of boronic acids (instead of esters) results in even faster cleavage and better aqueous solubility with no loss in hydroylic stability. These findings are significant in the development of triggered metalloprotein proinhibitors, $H_2O_2$-activated prodrugs.

1. F. Kratz, I. A. Muller, C. Ryppa and A. Warnecke, ChemMedChem, 2008, 3, 20-53.
2. J. Rautio, H. Kumpulainen, T. Heimbach, R. Oliyai, D. Oh, T. Jarvinen and J. Savolainen, Nat. Rev. Drug Disc., 2008, 7, 255-270.
3. N. Tarasneko, A. Nudelman, I. Tarasneko, M. Entin-Meer, D. Hass-Kogan, A. Inbal and A. Rephaeli, Clin. Exp. Metastasis, 2008, 25, 703-716.
4. A. Rephaeli, R. Zhuk and A. Nudelman, Drug Dev. Res., 2000, 50, 379-391.
5. T. Reid, F. Valone, W. Lipera, D. Irwin, W. Paroly, R. Natale, S. Sreedharan, H. Keer, B. Lum, F. Scappaticci and A. Bhatnagar, Lung Cancer, 2004, 45, 381-386.
6. R. Furumai, A. Matsuyama, N. Kobashi, K.-H. Lee, H. Nishiyama, A. Tanaka, Y. Komatsu, N. Nishino, M. Yoshida and S. Horinouchi, Cancer Res., 2002, 62, 4916-4921.
7. A. Bowers, N. West, J. Taunton, S. L. Schreiber, J. E. Bradner and R. M. Williams, J. Am. Chem. Soc., 2008, 130, 11219-11222.
8. T. W. Failes, C. Cullinane, C. I. Diakos, N. Yamamoto, J. G. Lyons and T. W. Hambley, Chemistry A European Journal, 2007, 13, 2974-2982.
9. T. W. Failes and T. W. Hambley, Journal of Inorganic Biochemistry, 2007, 101, 396-403.
10. G. De Simone, R. M. Vitale, A. Di Fiore, C. Pedone, A. Scozzafava, J.-L. Montero, J.-Y. Winum and C. T. Supuran, Journal of Medicinal Chemistry, 2006, 49, 5544-5551.
11. M. Whittaker, C. D. Flyod, P. Brown and A. J. H. Gearing, Chem. Rev., 1999, 99, 2735-2776.
12. L. M. Coussens, B. Fingleton and L. M. Matrisian, Science, 2002, 295, 2387-2392.
13. J. L. Major Jourden and S. M. Cohen, Chem. Commun., 2010, 46, 1241-1243.
14. K. B. Daniel, J. L. Major Jourden, K. E. Negoescu and S. M. Cohen, J. Biol. Inorg. Chem., 2011, 16, 313-323.
15. J. L. Major Jourden and S. M. Cohen, Angew. Chem. Int. Ed., 2010, 49, 6795-6797.
16. Q. Wang, X. N. Tang and M. A. Yenari, J. Neuroimmunol., 2007, 184, 53-68.
17. G. A. Rosenberg, L. A. Cunningham, J. Wallace, S. Alexander, E. Y. Estrada, M. Grossetete, A. Razhagi, K. Miller and A. Gearing, Brain Res., 2001, 893, 104-112.
18. R. Jin, G. Yang and G. Li, Neurobio. Disease, 2010, 38, 376-385.
19. E. Sella and D. Shabat, Chem. Commun., 2008, 5701-5703.
20. R. Weinstain, P. S. Baran and D. Shabat, Bioconjugate Chem., 2009, 20, 1783-1791.
21. C. A. Blencowe, A. T. Russell, F. Greco, W. Hayes and Thornthwaite, Polym. Chem., 2011, 2, 773-790.
22. Y. Meyer, J.-A. Richard, B. Delest, P. Noack, P.-Y. Renard and A. Romieu, Org. Biomol. Chem., 2010, 8, 1777-1780.
23. H. Y. Lee, X. Jiang and D. Lee, Org. Lett., 2009, 11, 2065-2068.
24. G. C. Van de Bittner, E. A. Dubikovskaya, C. R. Bertozzi and C. J. Chang, Proc. Nat. Acad. Sci. USA, 2010, 107, 21316-21321.
25. J. Ostergaar and C. Larsen, Molecules, 2007, 12, 2396-2412.
26. A. L. Simplicio, J. M. Clancy and J. F. Gilmer, Molecules, 2008, 13, 519-547.
27. L. K. Charkoudian, D. M. Pham and K. J. Franz, J. Am. Chem. Soc., 2006, 128, 12424-12425.
28. M. Rouffet, C. A. F. de Oliveira, Y. Udi, A. Agrawal, I. Sagi, J. A. McCammon and S. M. Cohen, J. Am. Chem. Soc., 2010, 132, 8232-8233.
29. M. B. Mitchell and I. W. A. Whitcombe, Tet. Lett., 2000, 41, 8829-8834.

A promising strategy in MMPi is through the development of MMP prodrugs or 'proinhibitors' that offer the ability to selectively control inhibitory activity. Metalloenzyme inhibitors such as MMPi are particularly suitable to the proinhibitor approach because such compounds generally contain a metal-binding group that can be blocked, which strongly attenuates their inhibitory activity. In the presence of the appropriate stimuli, the protecting group can be removed from the metal-binding group to release the MMPi at the site of activation, and thereby avoiding systemic inhibition of MMPs (which are necessary for normal physiological processes).[8, 9] However, metalloenzyme proinhibitors have not been widely investigated, especially in the case of MMP proinhibitors. MMP proinhibitors are shown to be activated by $H_2O_2$ for use as protective therapeutics following ischemia and reperfusion injury during stroke (FIG. 43). As described below, the proinhibitors reported can protect the blood brain barrier (BBB) in two ways, taking advantage of both the triggering mechanism and the resulting MMPi. First, the proinhibitors will consume damaging ROS (e.g. $H_2O_2$), which would otherwise directly attack the BBB and also activate pathogenic MMPs. Second, the resulting active MMPi serves to inhibit any remaining MMP activity that might damage the BBB. Thus, this unprecedented class of proinhibitors has a dual mode of action: reducing the amount of ROS available to activate MMPs, while also generating an active MMPi.

Two MMPi, the pyridinone-based molecule 1,2-HOPO-2 and the pyrone-based molecule PY-2, were selected for this study. Both compounds are potent, semi-selective MMPi that have been previously described.[11] The hydroxyl group of the zinc-binding group (ZBG) of each inhibitor was protected with a self-immolative protecting group containing a boronic ester as the ROS-sensitive trigger (FIG. 44). In the presence of $H_2O_2$, the boronic ester is cleaved by nucleophilic attack of $H_2O_2$, facilitating a spontaneous reaction to release the active MMPi through a 1,6-benzyl elimination (FIG. 43). Boronic esters as $H_2O_2$-reactive protecting groups has been well documented in the literature for $H_2O_2$-activated fluorophores[12, 13] and in the generation of triggered Fe(III) and Cu(II) chelates.[14, 15]

The ROS-triggered self-immolative protecting group can be attached to the MMPi by using either an ether (B19, B20) or carbonate ester (B21) linkage at the hydroxyl group of the ZBG (FIG. 44). To determine which linker strategy provided the best overall approach, both the cleavage kinetics and solution stability of protected B19, B20, B21 were examined. The ability of these compounds to be activated by $H_2O_2$ was evaluated by using electronic spectroscopy. A sample of each compound in HEPES buffer (50 mM, pH 7.5) was activated with an excess (18 equiv)[12-15] of $H_2O_2$ and the change in absorbance was monitored over time. In all cases, the spectra of the protected ZBG compounds decreased over time while the spectra of the free ZBG appeared, demonstrating the expected cleavage reaction. To confirm that the boronic ester moiety was necessary for $H_2O_2$ cleavage, the ZBGs were prepared with benzyl protecting groups without the boronic ester. For these compounds, no change in absorbance was observed over time in the presence of $H_2O_2$. Additionally, the selectivity of the boronic ester towards $H_2O_2$ was confirmed by examining cleavage in the presence of $KO_2$ and catalase. As expected,[12, 20] the superoxide anion was unable to activate the protected ZBGs.

The rates of conversion of compounds B19-B21 their respective activated ZBGs were then determined by monitoring the change in absorption using pseudo-first order reaction conditions with an excess of $H_2O_2$. The calculated rate constants indicated that the carbonate ester linkage in compound B21 provided the fastest conversion with a rate constant of 6.7 $M^{-1}s^{-1}$, while rate constants of 4.0 $M^{-1}s^{-1}$ and 2.9 $M^{-1}s^{-1}$ were found for compounds B19 and B20, respectively. Upon examination of the solution stability of these compounds, B19 and B20 were stable in buffer over a 24 h time period, while B21 showed >50% hydrolysis. Although the use of carbonate and carbamate ester linkages in self-immolative systems are more common (due to the additional thermodynamic driving force from the release of $CO_2$ in the cascade reaction).

After establishing a strategy for the addition of $H_2O_2$ activated protecting groups to the appropriate ZBGs, the full-length inhibitors 1,2-HOPO-2 and PY-2 were protected with 4-bromomethylphenyl boronic acid pinacol ester in the presence of $K_2CO_3$ in DMF to yield compounds B17 and B18, respectively. Activation of B17 and B18 by $H_2O_2$ to release 1,2-HOPO-2 and PY-2 was confirmed by absorption spectroscopy. Similar spectra were obtained under the same reaction conditions as those used for compounds B19 and B20 indicating that the cleavage rates for the proinhibitors B17 and B18 would have comparable rate constants. The $IC_{50}$ values of the proinhibitors B17 and B18 against MMP-9 were found to be greater than 1 mM, representing a >100 fold-increase than the active inhibitor (FIG. 45). When B17 and B18 were tested against MMP-12, their $IC_{50}$ values were found to be in the micromolar range (FIG. 25), which was again >100-fold less effective than their activated counterparts. Both sets of experiments show that when the ZBG of the inhibitor is protected, the ability of the compounds to inhibit MMPs is severely attenuated.

Having established that proinhibitors B17 and B18 could be effectively protected and activated in the presence of $H_2O_2$, the ability of these compounds to inhibit MMPs after activation was evaluated. Using a fluorescence-based assay, compounds B17 and B18 were tested with MMP-9 and MMP-12 in the presence of $H_2O_2$ at concentrations close to their reported $IC_{50}$ values.[11] MMP-9 is considered a high-value MMP target in the context of ischemia-reperfusion injury associated with stroke.[7] The percent inhibition of proinhibitors B17 and B18 were evaluated after one hour of activation with and without $H_2O_2$. As expected, when there is no hydrogen peroxide present, there is little inhibition observed for the proinhibitors (FIG. 46). However, after activation with 100 μM $H_2O_2$, the percent inhibition observed for B17 was similar to that observed for the active inhibitor 1,2-HOPO-2. Assuming that the rate constants found for the cleavage of B19 and B20 are essentially the same when incorporated into B17 and B18, then the 50% inhibition observed is consistent with the calculated amount of active inhibitor present when exposed to 100 μM $H_2O_2$ for 1 h.

The proinhibitors introduced in this work demonstrate an effective means to passivate MMPi and activate them in the presence of $H_2O_2$. Through addition of a boronic ester protecting group to the metal-binding moiety of MMPi via a self-immolative linker, proinhibitors based on two different ZBGs were developed. These compounds were found to be sufficiently stable in buffer and were found to have high rates of cleavage allowing for efficient activation with $H_2O_2$. These compounds should display a dual mode of action in the prevention of reperfusion injury, by neutralizing ROS and generating an active MMPi. To the best of our knowledge, this is the first example of a $H_2O_2$ activated prodrug which offers a novel way to provide both spatial and temporal control over MMP inhibition for use in reperfusion injury.

[1] M. Whittaker, C. D. Flyod, P. Brown, A. J. H. Gearing, *Chemical Rev.* 1999, 99, 2735.
[2] Q. Wang, X. N. Tang, M. A. Yenari, *J. Neuroimmunol.* 2007, 184, 53.
[3] R. Fishman, N. *Engl. J. Med.* 1975, 293, 706.

[4] Haorah, S. H. Ramirez, K. Schall, D. Smith, R. Pandya, Y. Persidsky, *J. Neurochem.* 2007, 101, 566.
[5] G. A. Rosenberg, L. A. Cunningham, J. Wallace, S. Alexander, E. Y. Estrada, M. Grossetete, A. Razhagi, K. Miller, A. Gearing, *Brain Res.* 2001, 893, 104.
[6] J.-C. Copin, P. Merlani, T. Sugawara, P. H. Chan, Y. Gasche, *Exp. Neurology* 2008, 213, 196.
[7] R. Jin, G. Yang, G. Li, *Neurobio. Disease* 2010, 38, 376.
[8] R. Renkiewicz, L. Qiu, C. Lesch, X. Sun, R. Devalaraja, T. Cody, E. Kaldjian, H. Welgus, V. Baragi, *Arthritis & Rheum.* 2003, 48, 1742.
[9] B. Fingleton, *Semin. Cell Dev. Biol.* 2008, 19, 61.
[10] J. L. Major Jourden, S. M. Cohen, *Chem. Commun.* 2010, 46, 1241.
[11] A. Agrawal, D. Romero-Perez, J. A. Jacobsen, F. J. Villarreal, S. M. Cohen, *ChemMedChem* 2008, 3, 812.
[12] M. C. Y. Chang, A. Pralle, E. Y. Isacoff, C. J. Chang, *J. Am. Chem. Soc.* 2004, 126, 15392.
[13] E. W. Miller, O. Tulyathan, E. Y. Isacoff, C. J. Chang, *Nature Chemical Biology* 2007, 3, 263.
[14] L. R. Perez, K. J. Franz, *Dalton Trans.* 2010, 39, 2177.
[15] M. G. Dickens, K. J. Franz, *ChemBioChem* 2010, 11, 59.
[16] R. Weinstain, P. S. Baran, D. Shabat, *Bioconjugate Chem.* 2009, 20, 1783.
[17] D. Srikun, E. W. Miller, D. W. Domaille, C. J. Chang, *J. Am. Chem. Soc.* 2008, 130, 4596.
[18] L.-C. Lo, C.-Y. Chu, *Chem. Commun.* 2003, 2728.
[19] E. Sella, D. Shabat, *Chem. Commun.* 2008, 5701.
[20] H. G. Kuivila, A. G. Armour, *J. Am. Chem. Soc.* 1957, 79, 5659.
[21] H. Y. Lee, X. Jiang, D. Lee, *Org. Lett.* 2009, 11, 2065.
[22] Y. Meyer, J.-A. Richard, B. Delest, P. Noack, P.-Y. Renard, A. Romieu, *Org. Biomol. Chem.* 2010, 8, 1777.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of the formula:

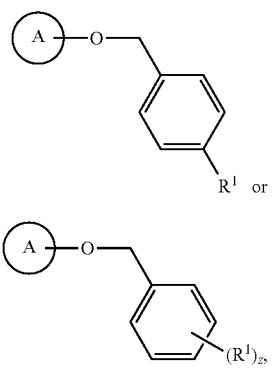

wherein,
A is an anticancer drug moiety;
$R^1$ is —B(OH)$_2$ or an ROS-reactive boronic ester; and
z is an integer from 1 to 5.

2. The compound of claim 1, comprising a metal binding moiety.

3. The compound of claim 2, wherein said metal binding moiety is a zinc binding moiety.

4. The compound of claim 1, wherein said ROS-reactive boronic ester is capable of reacting with hydrogen peroxide.

5. The compound of claim 1 of formula (I) or (Ia), wherein A is

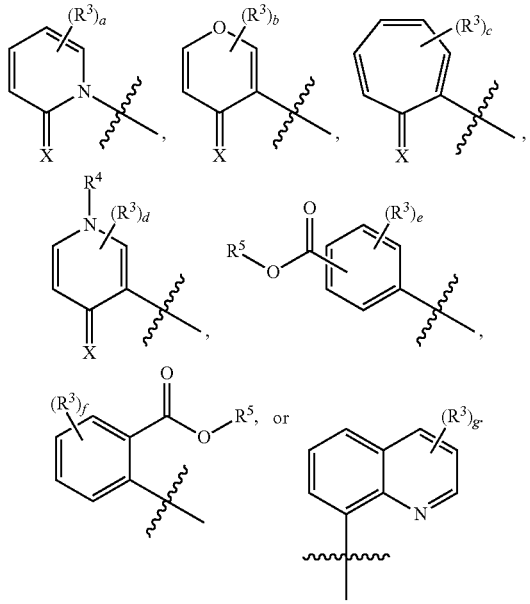

wherein
$R^3$ is independently halogen, —CN, —N(O)$_m$, —NR$^7$R$^8$, —C(O)R$^9$, —C(O)—OR$^{10}$, —C(O)NR$^{11}$R$^{12}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
m is an integer from 1 to 2;
$R^7$, $R^8$, $R^9$, $R^{10}$, $R^{11}$, $R^{12}$, and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is independently hydrogen, or substituted or unsubstituted alkyl;
$R^5$ is independently hydrogen, or substituted or unsubstituted alkyl;
a, e, and f are independently an integer from 0 to 4;
b and d are independently an integer from 0 to 3;
c is an integer from 0 to 5;
g is an integer from 0 to 6;
and
X is =O or =S.

6. A pharmaceutical composition comprising the compound of claim 1 and a pharmaceutically acceptable excipient.

7. The compound of claim 1, wherein A is not covalently bound to —B(OH)$_2$ or an ROS-reactive boronic ester or salts thereof.

* * * * *